United States Patent
Schreiber et al.

(10) Patent No.: US 11,332,509 B2
(45) Date of Patent: May 17, 2022

(54) METHODS OF MAKING AND USING EXTRACELLULAR DOMAIN-BASED CHIMERIC PROTEINS

(71) Applicant: Shattuck Labs, Inc., Austin, TX (US)

(72) Inventors: Taylor Schreiber, Austin, TX (US); George Fromm, Austin, TX (US); Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 275 days.

(21) Appl. No.: 16/484,852

(22) PCT Filed: Feb. 27, 2018

(86) PCT No.: PCT/US2018/020040
§ 371 (c)(1),
(2) Date: Aug. 9, 2019

(87) PCT Pub. No.: WO2018/157165
PCT Pub. Date: Aug. 30, 2018

(65) Prior Publication Data
US 2020/0222503 A1 Jul. 16, 2020

Related U.S. Application Data

(60) Provisional application No. 62/464,002, filed on Feb. 27, 2017.

(51) Int. Cl.
| | | |
|---|---|---|
| *A61K 38/17* | (2006.01) | |
| *A61K 38/00* | (2006.01) | |
| *C07K 14/705* | (2006.01) | |
| *C07K 14/525* | (2006.01) | |
| *A61P 35/00* | (2006.01) | |

(52) U.S. Cl.
CPC .......... *C07K 14/705* (2013.01); *A61K 38/177* (2013.01); *A61K 38/1774* (2013.01); *A61K 38/1793* (2013.01); *A61P 35/00* (2018.01); *C07K 14/525* (2013.01); *C07K 14/70578* (2013.01); *C07K 14/70596* (2013.01); *A61K 38/00* (2013.01); *C07K 2319/30* (2013.01)

(58) Field of Classification Search
CPC .................. A61K 38/177; A61K 38/1774
See application file for complete search history.

(56) References Cited

U.S. PATENT DOCUMENTS

| | | | |
|---|---|---|---|
| 5,844,095 A | 12/1998 | Linsley et al. | |
| 7,569,663 B2 | 8/2009 | Tykocinski et al. | |
| 7,696,168 B2 | 4/2010 | Kuliopulos et al. | |
| 8,039,437 B2 | 10/2011 | Tykocinksi et al. | |
| 8,080,246 B2 | 12/2011 | Lin et al. | |
| 8,329,657 B2 | 12/2012 | Tykocinksi et al. | |
| 8,735,553 B1 | 5/2014 | Li et al. | |
| 9,029,315 B2 | 5/2015 | Chen et al. | |
| 9,221,895 B2 | 12/2015 | Tykocinski | |
| 9,352,037 B2 | 5/2016 | Van Den Berg | |
| 9,388,230 B2 | 7/2016 | Elhalel | |
| 9,493,575 B2 | 11/2016 | Jaiswal et al. | |
| 9,657,082 B2 | 5/2017 | Tykocinski | |
| 9,845,345 B2 | 12/2017 | Ring et al. | |
| 9,969,789 B2 | 5/2018 | Uger et al. | |
| 2003/0232323 A1 | 12/2003 | Freeman et al. | |
| 2005/0191721 A1 | 9/2005 | Kuchroo et al. | |
| 2007/0036783 A1 | 2/2007 | Humeau et al. | |
| 2008/0131431 A1 | 6/2008 | Smith et al. | |
| 2009/0226435 A1 | 9/2009 | Khare | |
| 2010/0136006 A1 | 6/2010 | Lin et al. | |
| 2010/0136007 A1 | 6/2010 | Lin et al. | |
| 2011/0041190 A1 | 2/2011 | Tykocinksi et al. | |
| 2013/0039911 A1 | 2/2013 | Bedi et al. | |
| 2013/0065815 A1 | 3/2013 | Tykocinski et al. | |
| 2013/0243697 A1 | 9/2013 | Tykocinski et al. | |
| 2014/0113370 A1 | 4/2014 | Camphausen et al. | |
| 2014/0154252 A1 | 6/2014 | Thompson et al. | |
| 2014/0227315 A1 | 8/2014 | Tykocinski et al. | |
| 2014/0242077 A1 | 8/2014 | Choi et al. | |
| 2014/0286858 A1 | 9/2014 | Zimmerman et al. | |
| 2015/0098942 A1 | 4/2015 | Curti et al. | |
| 2015/0174268 A1 | 6/2015 | Li | |
| 2015/0183881 A1 | 7/2015 | Bedi et al. | |
| 2015/0190506 A1 | 7/2015 | Cheung et al. | |
| 2015/0191525 A1 | 7/2015 | Epstein et al. | |
| 2015/0266942 A1 | 9/2015 | Tian | |
| 2015/0353642 A1 | 12/2015 | Tykocinski | |
| 2015/0368350 A1 | 12/2015 | Tykocinski et al. | |
| 2015/0376260 A1 | 12/2015 | Elhalel et al. | |
| 2016/0024176 A1 | 1/2016 | Damschroder et al. | |
| 2016/0159927 A1 | 6/2016 | Molloy et al. | |

(Continued)

FOREIGN PATENT DOCUMENTS

| | | |
|---|---|---|
| WO | WO 93/08207 | 4/1993 |
| WO | WO 01/49318 A1 | 7/2001 |

(Continued)

OTHER PUBLICATIONS

Ali, et al., "Anti-tumour therapeutic efficacy of OX40L in murine tumour model," Vaccine, 22, 2004, pp. 3585-3594.
Anderson, et al., "Lag-3, Tim-3, and TIGIT: Co-inhibitory Receptors with Specialized Functions in Immune Regulation," Immunity, 44, May 17, 2016, pp. 989-1004.
Barclay, "Signal regulatory protein alpha (SIRPα)/CD47 interaction and function," Current Opinion in Immunology, 21, 2009, pp. 47-52.
Barclay, et al., "The Interation Between Signal Regulatory Protein Alpha (SIRPα) and CD47: Structure, Function, and Therapeutic Target," Annu. Rev. Immunol., 32, 2014, pp. 25-50.

(Continued)

*Primary Examiner* — Prema M Mertz
(74) *Attorney, Agent, or Firm* — Morgan, Lewis & Bockius LLP

(57) ABSTRACT

The present invention relates, inter alia, to compositions and methods, including chimeric proteins and combination therapies that find use in the treatment of disease, such as cancer and/or an inflammatory disease.

20 Claims, 62 Drawing Sheets

Specification includes a Sequence Listing.

(56) References Cited

U.S. PATENT DOCUMENTS

| | | |
|---|---|---|
| 2016/0166685 A1 | 6/2016 | Cheung et al. |
| 2016/0177276 A1 | 6/2016 | Lo et al. |
| 2016/0186150 A1 | 6/2016 | Deming et al. |
| 2016/0250322 A1 | 9/2016 | Schreiber et al. |
| 2016/0256527 A1 | 9/2016 | Gurney |
| 2016/0340409 A1 | 11/2016 | Dranitzki-Elhalel |
| 2016/0340430 A1 | 11/2016 | Bedi et al. |
| 2016/0347846 A1 | 12/2016 | Tykocinski |
| 2017/0095531 A1 | 4/2017 | Scheriber et al. |
| 2017/0107270 A1 | 4/2017 | Pons et al. |
| 2018/0142019 A1 | 5/2018 | Manning et al. |

FOREIGN PATENT DOCUMENTS

| | | | |
|---|---|---|---|
| WO | WO 2005/047334 A1 | 5/2005 |
| WO | WO 2007/149880 A2 | 12/2007 |
| WO | WO 2008/061377 A1 | 5/2008 |
| WO | WO 2010/003118 A1 | 1/2010 |
| WO | WO 2010/005519 A1 | 1/2010 |
| WO | WO 2010/062401 A1 | 6/2010 |
| WO | WO 2010/070047 A1 | 6/2010 |
| WO | WO 2010/105068 A1 | 9/2010 |
| WO | WO 2012/042480 A1 | 4/2012 |
| WO | WO 2013/000234 A1 | 1/2013 |
| WO | WO 2013/019615 A2 | 2/2013 |
| WO | WO 2013/164694 A1 | 11/2013 |
| WO | WO 2013/173820 A2 | 11/2013 |
| WO | WO 2014/094122 A1 | 6/2014 |
| WO | WO 2014/106839 A1 | 7/2014 |
| WO | WO 2014/121085 A1 | 8/2014 |
| WO | WO 2014/121093 A1 | 8/2014 |
| WO | WO 2014/121099 A1 | 8/2014 |
| WO | WO 2014/134165 A1 | 9/2014 |
| WO | WO 2014/164427 A1 | 10/2014 |
| WO | WO 2015/095423 A2 | 6/2015 |
| WO | WO 2015/104406 A2 | 7/2015 |
| WO | WO 2015/112534 A2 | 7/2015 |
| WO | WO 2015/116178 A1 | 8/2015 |
| WO | WO 2015/183902 A1 | 12/2015 |
| WO | WO 2015/200828 A1 | 12/2015 |
| WO | WO 2016/025385 A1 | 2/2016 |
| WO | WO 2016/126608 A1 | 8/2016 |
| WO | WO 2016/166139 A1 | 10/2016 |
| WO | WO 2017/059168 A1 | 4/2017 |

OTHER PUBLICATIONS

Bartkowiak, et al., "4-1 BB agonists: multi-potent potentiators of tumor immunity," Frontiers in Oncology, vol. 5, Article 117, Jun. 8, 2015, pp. 1-16.

Batlevi, et al., "Novel immunotherapies in lymphoid malignancies," Nature Reviews, Clinical Oncology, vol. 13, 2016, pp. 25-40.

Baum, et al., Molecular characterization of murine and human OX40/OX40 ligand systems: identification of a human OX40 ligand as the HTLV-1-regulated protein gp34.

Callahan, et al., "Targeting T Cell Co-receptors for Cancer Therapy," Immunity Review, vol. 44, May 17, 2016, pp. 1069-1078.

Cao, et al., "T Cell Immunoglobulin Mucin-3 Crystal Structure Reveals a Galectin-9-lndependent Ligand-Binding Surface," Immunity, 26, Mar. 2007, pp. 311-321.

Chao, et al., "The CD47-SIRPα pathway in cancer immune evasion and potential therapeutic implications," Current Opinion in Immunology, 24, 2012, pp. 225-232.

Chen, et al., "Structure of macrophage colony stimulating factor bound to FMS: Diverse signaling assemblies of class III receptor tyrosine kinases," PNAS, vol. 105, No. 47, Nov. 25, 2008, pp. 18267-18272.

Compaan, et al., "The Crystal Structure of the Costimulatory OX40-OX40L Complex," Structure, 14, Aug. 2006, pp. 1321-1330.

Croft, et al., "The Significance of OX40 and OX40L to T cell Biology and Immune Disease," Immunol Rev., 229(1), 2009, pp. 173-191.

Curran, et al., "Editorial: Advances in combination tumor immunotherapy," Frontiers in Oncology, vol. 5, Article 198, Sep. 20105, pp. 1-2.

De Visser, et al., "The interplay between innate and adaptive immunity regulates cancer development," Cancer Immunol, Immunotherapy, vol. 54, No. 11, May 12, 2005, pp. 1143-1152.

De Visser, et al., "Paradoxical roles of the immune system during cancer development," Nature Reviews Cancer, vol. 6, Jan. 2006, pp. 24-37.

Freeman, et al., "TIM genes: a family of cell surface phosphatidylserine receptors that regulate innate and adaptive immunity," Immunol Rev., 235(1), 2010, pp. 172-189.

Fromm, et al., "Agonist redirected checkpoint, PD1-Fc-OX40L, for cancer immunotherapy," Journal for ImmunoTherapy of Cancer, (2018) 6:149, 16 pages.

Guo, et al., "PD-1 Blockade and OX40 Triggering Synergistically Protects against Tumor Growth in a Murine Model of Ovarian Cancer," PLOS ONE, vol. 9. No. 2, 2014, pp. 1-10.

Hatherley, et al., "The Structure of the Macrophage Signal Regulatory Protein α (SIRPα) Inhibitory Receptor Reveals a Binding Face Reminiscent of That Used by T Cell Receptors," The Journal of Biological Chemistry, vol. 82, No. 19, 2007, pp. 14567-14575.

Hirano, et al., "Inhibition of Human Breast Carcinoma Growth by a Soluble Recombinant Human CD40 Ligand," Blood, vol. 43, No. 9, May 1, 1999, pp. 2999-3007.

Huang, et al., "CTLA-4-Fas ligand functions as a trans signal converter protein in bridging antigen-presenting cells and T cells," International Immunology, vol. 13, No. 4, 2001, pp. 529-539.

International Search Report and Written Opinion, International Application No. PCT/US2016/054598, dated Jan. 9, 2017, 18 pages.

International Search Report and Written Opinion, International Application No. PCT/US2018/020039, dated Jun. 11, 2018, 10 pages.

Karman, et al., "Ligation of Cytotoxic T Lymphocyte Antigen-4 to T Cell Receptor Inhibits T Cell Activation and Directs Differentiation into Foxp3+ Regulatory T Cells," The Journal of Biological Chemistry, vol. 287, No. 14, 2012, pp. 11098-11107.

Karpusas, et al., "2 Å crystal structure of an extracellular fragment of human CD40 ligand," Structure, 3, Oct. 15, 1995, pp. 1031-1039.

Kermer, et al., "An Antibody Fusion Protein for Cancer Immunotherapy Mimicking IL-15 trans-Presentation at the Tumor Site," Molecular Therapeutics, vol. 11, No. 6, 2012, pp. 1279-1288.

Khalil, et al., "The future of cancer treatment: immunomodulation, CARs and combination immunotherapy," Nature Reviews Clinical Oncology, 2016, pp. 1-18.

Ledford, "The Perfect Blend," Nature, vol. 532, Apr. 14, 2016, pp. 162-164.

Lee, et al., "Novel Structural Determinants on SIRPαthat mediate Binding to CD47," The Journal of Immunology, 179, 2007, pp. 7741-7750.

Linch, et al., "OX40 agonists and combination immunotherapy: putting the pedal to the metal," Frontiers in Oncology, vol. 5, Article 34, Feb. 2015, pp. 1-14.

Ma, et al., "The role of CD40 and CD154.CD40L in dendritic cells," Seminars in Immunology, 21, 2009, pp. 265-272.

Mahoney, et al., "Combination cancer immunotherapy and new immunomodulatory targets," Nature Reviews Drug Discovery, vol. 14, 2015, pp. 561-585.

Marcus, et al., "Recognition of tumors by the innate immune system and natural killer cells," Advances in Immunology, vol. 122, Jan. 1, 2015, pp. 91-128.

Munroe, et al., "A Costimulatory Function for T Cell CD40," Journal of Immunology, 178, 2007, pp. 671-682.

Orbach, et al., "CD40«FasL and CTLA-4«FasL Fusion Proteins Induce Apoptosis in Malignant Cell Lines by Dual Signaling," The American Journal of Pathology, vol. 177, No. 6, 2010, pp. 3159-3168.

Pardoll, et al., "The blockade of immune checkpoints in cancer immunotherapy," Nature Reviews Cancer, vol. 12, 2012, pp. 252-264.

Schildberg, et al., "Coinhibitory Pathways in the B7-CD28 Ligand-Receptor Family," Immunity, vol. 44, 2016, pp. 955-972.

(56) References Cited

OTHER PUBLICATIONS

Scott, et al., "Antibody therapy of cancer," Nature Reviews Cancer, vol. 12, 2012, pp. 278-287.
Spiess, et al., "Alternative molecular formats and therapeutic applications for bispecific antibodies," Molecular Immunology, vol. 67, 2015, pp. 95-106.
Ward-Kavanaugh, et al., "The TNF Receptor Superfamily in Co-stimulating and Co-inhibitory Responses," Immunity, vol. 44, 2016, pp. 1005-1019.
Zhang, et al.,"Targeted and Untargeted CD137L Fusion Proteins for the Immunotherapy of Experimental Solid Tumors," Clin Cancer Res, vol. 13, No. 9, 20017, pp. 2758-2767.
Zhao, et al., "A Bispecific Protein Capable of Engaging CTLA-4 and MHCII Protects Non-Obese Diabetic Mice from Autoimmune Diabetes," PLOS ONE, vol. 8, Issue 5, 2013, pp. 1-11.
De Visser, et al., "The interplay between innate and adaptive immunity regulates cancer development," Cancer Immunology, Immunotherapy, vol. 54, No. 11, May 12, 2005 pp. 1143-1152.
International Search Report & Written Opinion PCT. Application No. PCT/US18/20040, dated May 23, 2018, 10 pages.

FIG. 5A

| | Gene Id | Protein Name | Accession | Primary Screen | | Confirmation Screen | | Comment |
|---|---|---|---|---|---|---|---|---|
| | | | | Rep 1 | Rep 2 | Rep 1 | Rep2 | |
| | PDL1 (CD274) | CD274 Molecule | NM_014143.3 | strong | strong | strong | strong | isoform 1 |
| | PDCD1LG2 | Programmed Cell Death 1 Ligand 2 | BC113678 | strong | strong | strong | strong | |
| | OX40 | TNF Receptor Superfamily Member 4 | | n/a | n/a | strong | strong | |
| PD1-Fc-OX40L | PDL1 | CD274 Molecule | | n/a | n/a | strong | strong | |
| | TNFRSF4 | TNF Receptor Superfamily Member 4 | NM_003327.3 | n/a | n/a | medium | medium | canonical isoform |
| | LGALS1 | Galectin 1 | BC001693 | med/strong | med/strong | medium | medium | soluble; seen with other Fc fusion proteins |

FIG. 5B

| | Gene Id | Protein Name | Accession | Primary Screen | | Confirmation Screen | | Comment |
|---|---|---|---|---|---|---|---|---|
| | | | | Rep 1 | Rep 2 | Rep 1 | Rep2 | |
| CSF1R-Fc-CD40L | CD40 | CD40 Molecule | BC012419 | strong | strong | strong | strong | canonical isoform |
| | CSF1 | Colony Stimulating Factor 1 | NM_000757.4 | med/strong | med/strong | strong | strong | canonical isoform |
| | CSF1 | Colony Stimulating Factor 1 | NM_172210.2 | strong | strong | strong | strong | isoform 2 |
| | LGALS1 | Galectin 1 | BC001693 | med/strong | med/strong | weak/med | weak/med | soluble; seen with other Fc fusion proteins |
| | SLC51B | Solute Carrier Family 51 Beta Subunit | BC103822.1 | v. weak | v. weak | weak | weak | |

FIG. 5C

| | Gene Id | Protein Name | Accession | Primary Screen | | Confirmation Screen | | Comment |
|---|---|---|---|---|---|---|---|---|
| | | | | Rep 1 | Rep 2 | Rep 1 | Rep2 | |
| mCD172a(SIRPα)-Fc-CD40L | CD47 | CD 47 Molecule | BC012884 | medium | medium | strong | strong | isoform OA3-305 |
| | CD47 | CD 47 Molecule | BC037306 | medium | medium | strong | strong | isoform OA3-305 |
| | CD40 | CD40 Molecule | BC012419 | strong | strong | strong | strong | canonical isoform |
| | CD47 | CD 47 Molecule | NM_001777.3 | med/strong | med/strong | med/strong | med/strong | canonical isoform |
| | SIRPA | Signal Regulatory Protein Alpha | BC033092.1 | inverse | inverse | inverse | inverse | binding partner of CD47 |
| | LGALS1 | Galectin 1 | BC001693 | med/strong | med/strong | weak/med | weak/med | soluble; seen with other Fc fusion proteins |

| | Sample | Ka (on-rate; 1/Ms) | Kd (off-rate; 1/s) | KD (binding; M) |
|---|---|---|---|---|
| Human Binding to: CD47 | CD172a-Fc | 7.56 E+5 | 2.39 E-3 | 3.16 nM |
| | CD172a-Fc-CD40L | 2.42 E+5 | 8.61 E-4 | 3.59 nM |
| FcγR1A | IgG1 | 2.49 E+4 | 4.40 E-4 | 17.7 nM |
| | CD172a-Fc-CD40L | ND | ND | ND |
| FcRn | IgG1 | 9.45 E+5 | 4.60 E-3 | 4.87 nM |
| | CD172a-Fc-CD40L | 9.56 E+3 | 7.56 E-3 | 790 nM |

Mouse CD172-Fc-CD40L

| | Sample | Ka (on-rate; 1/Ms) | Kd (off-rate; 1/s) | KD (binding; M) |
|---|---|---|---|---|
| Mouse Binding to: mCD40 | mCD40L-Fc | 3.04 E+4 | 9.81 E-5 | 3.23 nM |
| | CD172a-Fc-CD40L | 7.28 E+4 | 5.51 E-5 | .756 nM |

| Group | Total, N | Short-Term, N (Immune Profiling) | Long-Term, N (Tumor Growth/Survival) | % Rejection (Primary Tumor) | % Rejection (Re-challenge) |
|---|---|---|---|---|---|
| Untreated | 33 | 12 | 21 | 0.0 | 0.0 |
| αCD47 (MIAP301) | 5 | / | 5 | 0.0 | N/A |
| αCD40 (FGK4.5) | 12 | / | 12 | 8.3 | N/A |
| αCD47 (CD40) | 10 | 4 | 6 | 33.3 | 0.0 |
| CD172a-Fc-CD40L (150μg x2) | 11 | 6 | 5 | 80.0 | 75.0 |
| CD172a-Fc-CD40L (350μg x2) | 8 | 4 | 4 | 75.0 | 33.3 |

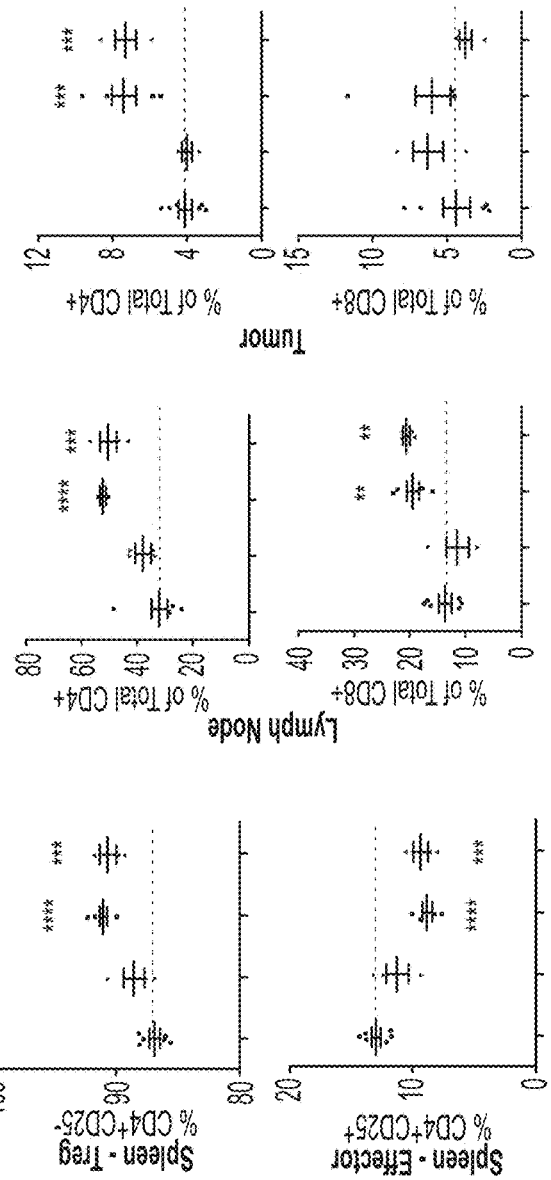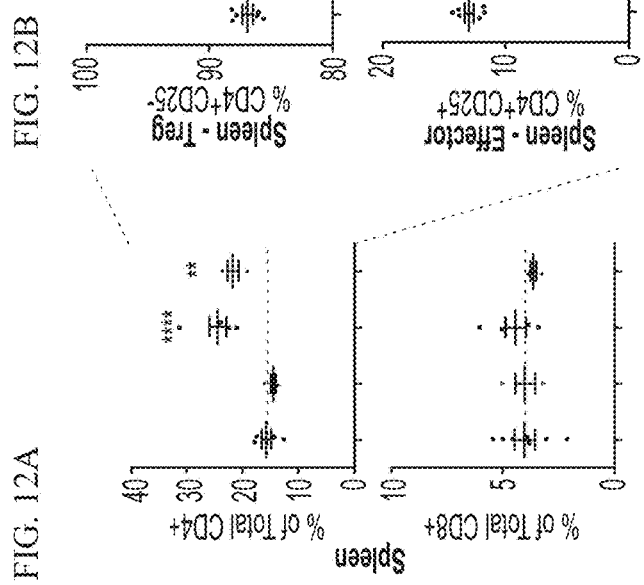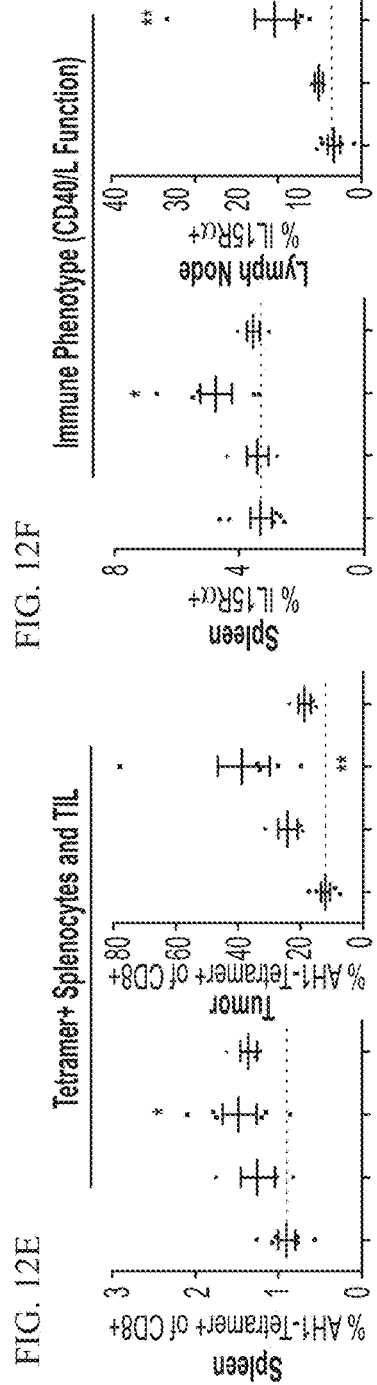

FIG. 27C

| CT26 Tumor Survival Statistics | |
|---|---:|
| Mantel-Cox p-value | |
| Untr. vs OX40 | <.0001 |
| Untr. vs PD-L1 | <.0001 |
| Untr. vs PD1 (RMP1-14) | <.0001 |
| Untr. vs OX40/PD-L1 | <.0001 |
| Untr. vs OX40/PD1 (RMP1-14) | .0001 |
| Untr. vs mPD1-Fc-OX40L (100 μg x2) | <.0001 |
| Untr. vs mPD1-Fc-OX40L (150 μg x2) | .0001 |
| Untr. vs mPD1-Fc-OX40L (300 μg x2) | <.0001 |

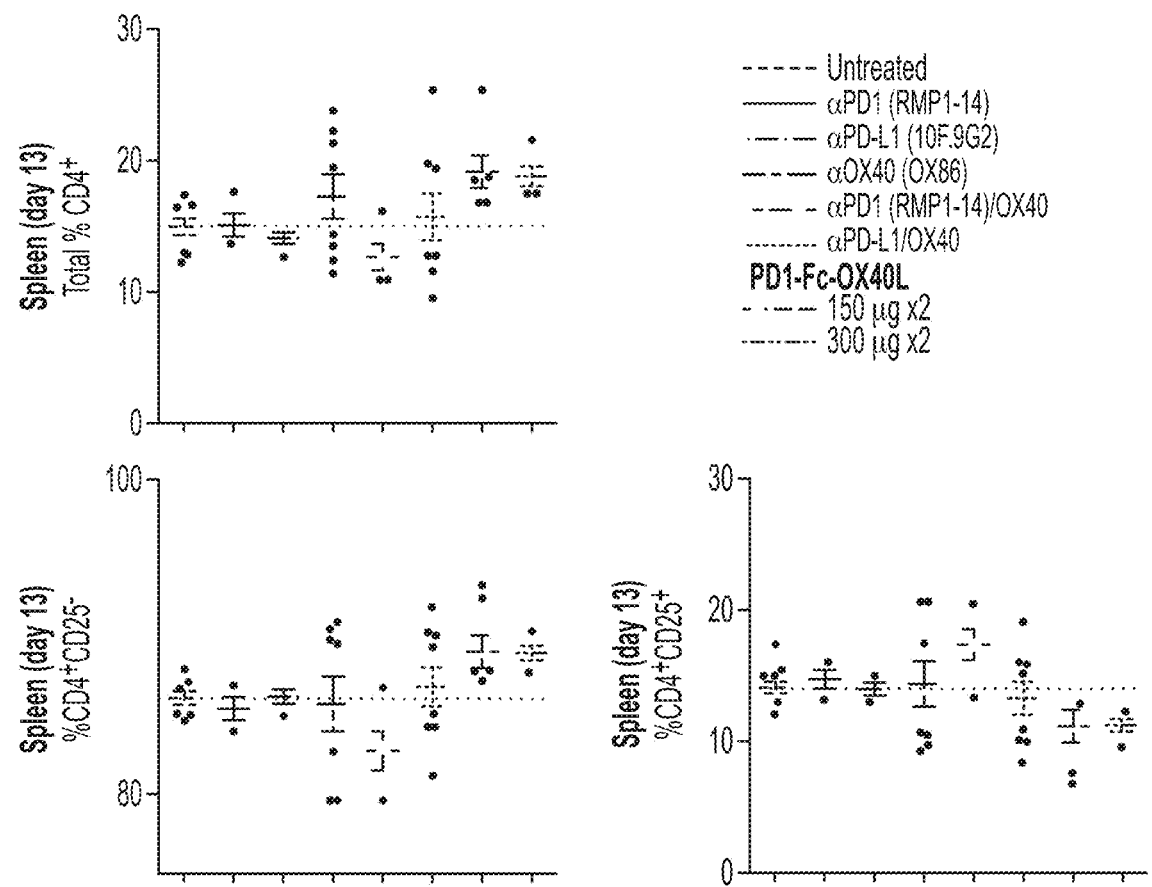

| Group | Total, N | Short-Term, N (Immune Profiling) | Long-Term, N (Tumor Growth/Survival) | % Rejection (Primary Tumor) | % Rejection (Re-challenge) | Serum Cytokine Response Total N | % |
|---|---|---|---|---|---|---|---|
| Untreated | 33 | 12 | 21 | 0.0 | 0.0 | 0/20 | 0 |
| αPD1 (RMP1-14) | 14 | 12 | 2 | 0.0 | N/A | 0/9 | 0 |
| αPD-L1 (10F.9G2) | 14 | 12 | 2 | 20.0 | 0.0 | 4/8 | 50 |
| αOX40 (OX86) | 29 | 8 | 21 | 19.1 | 0.0 | 12/20 | 60 |
| αPD-L1/OX40 | 17 | 9 | 8 | 37.5 | 66.6 | 10/10 | 100 |
| αPD1 (RMP1-14)/OX40 | 10 | 5 | 5 | 20.0 | 0.0 | 3/5 | 60 |
| PD1-Fc-OX40L (100μg x2) | 8 | 7 | 8 | 0.0 | NA | 2/8 | 25 |
| PD1-Fc-OX40L (150μg x2) | 12 | 7 | 5 | 60.0 | 71.4 | 5/12 | 42 |
| PD1-Fc-OX40L (300μg x2) | 11 | 5 | 6 | 16.7 | 75.0 | 7/11 | 64 |

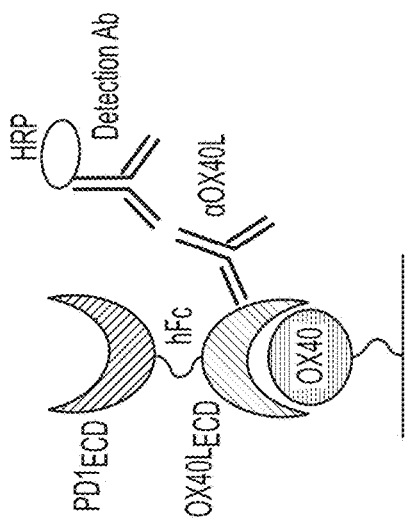
FIG. 28A
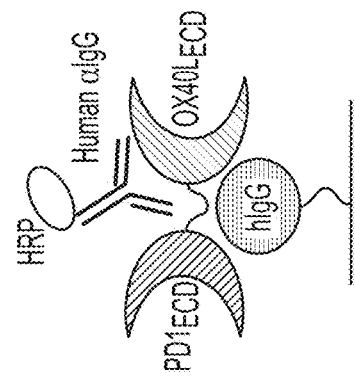
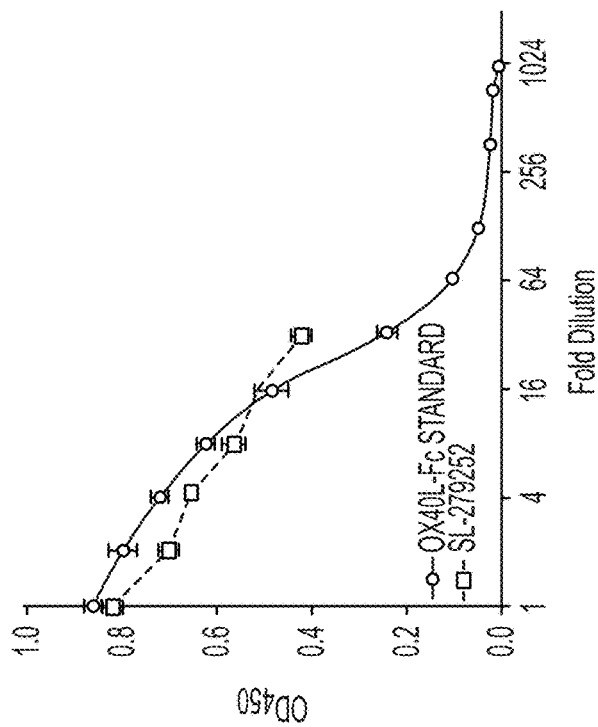
FIG. 28B
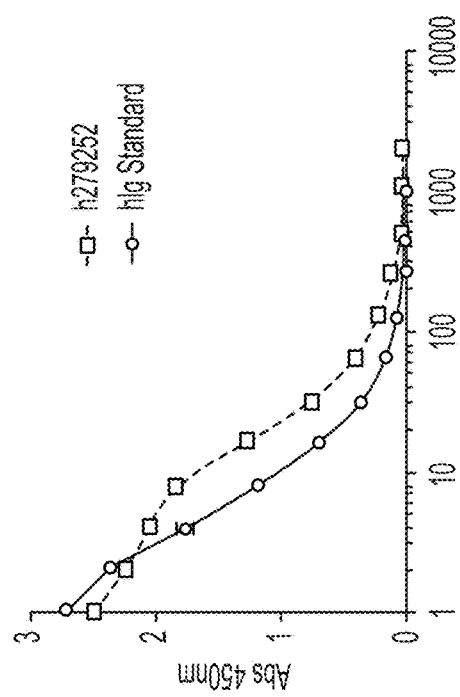

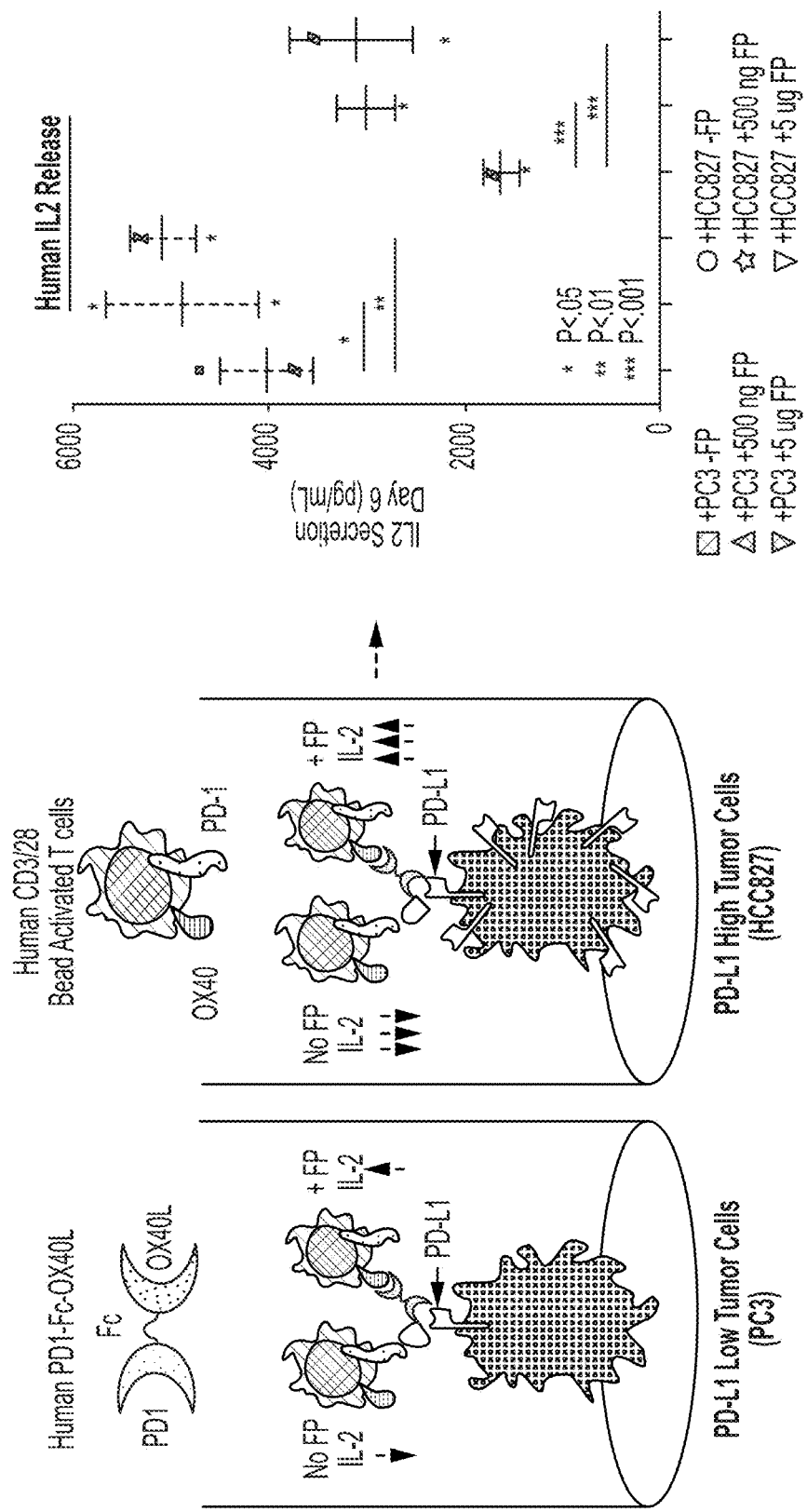

FIG. 38A
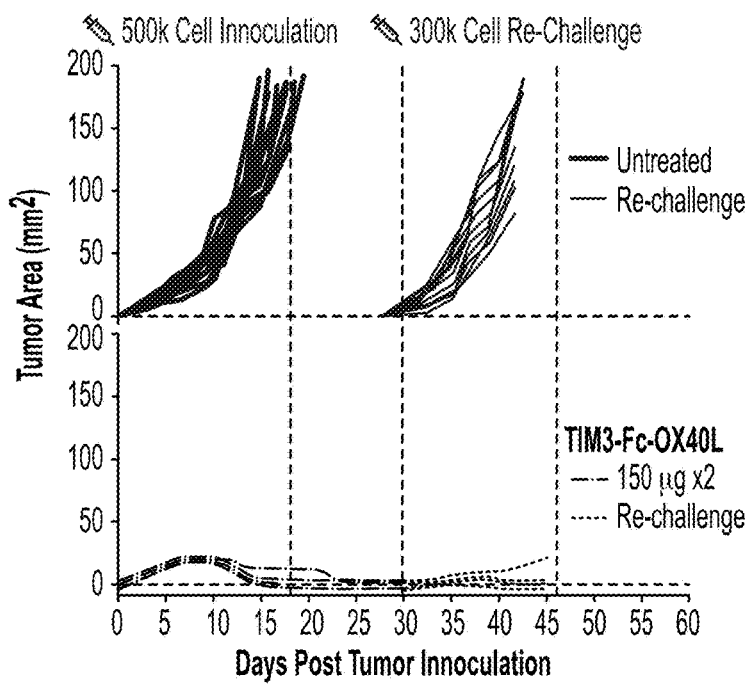
FIG. 38B
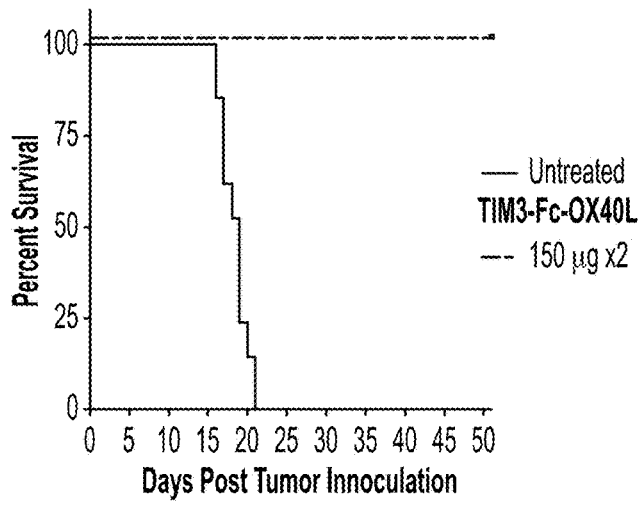
FIG. 38C
| Group | Total, N | Short-Term, N (Immune Profiling) | Long-Term, N (Tumor Growth/Survival) | % Rejection (Primary Tumor) | % Rejection (Re-challenge) |
|---|---|---|---|---|---|
| Untreated | 33 | 12 | 21 | 0.0 | 0.0 |
| TIM3-Fc-OX40L (150μg x2) | 9 | 5 | 4 | 100.0 | 75 |

FIG. 39

| Joining Linker 1 | Fc | Joining Linker 2 | Linker Module = Joining Linker 1 + Fc + Joining Linker 2 |
|---|---|---|---|
| SKYGPPCPSCP (SEQ ID NO: 48) | APEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 45) | IEGRMD (SEQ ID NO: 51) | SKYGPPCPSCPAPEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKIEGRMD (SEQ ID NO: 95) |
| SKYGPPCPSCP (SEQ ID NO: 48) | APEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK (SEQ ID NO: 46) | IEGRMD (SEQ ID NO: 51) | SKYGPPCPSCPAPEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGKIEGRMD (SEQ ID NO: 96) |
| SKYGPPCPSCP (SEQ ID NO: 48) | APEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK (SEQ ID NO: 47) | IEGRMD (SEQ ID NO: 51) | SKYGPPCPSCPAPEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGKIEGRMD (SEQ ID NO: 97) |
| SKYGPPCPPCP (SEQ ID NO: 49) | APEFLGGPSVFLFPPKPKDTLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 45) | IEGRMD (SEQ ID NO: 51) | SKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKIEGRMD (SEQ ID NO: 98) |
| SKYGPPCPPCP (SEQ ID NO: 49) | APEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK (SEQ ID NO: 46) | IEGRMD (SEQ ID NO: 51) | SKYGPPCPPCPAPEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGKIEGRMD (SEQ ID NO: 99) |
| SKYGPPCPPCP (SEQ ID NO: 49) | APEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK (SEQ ID NO: 47) | IEGRMD (SEQ ID NO: 51) | SKYGPPCPPCPAPEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGKIEGRMD (SEQ ID NO: 100) |

SEQUENCE LISTING

<160> NUMBER OF SEQ ID NOS: 100

<210> SEQ ID NO 1
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 1

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly
        195                 200

<210> SEQ ID NO 2
<211> LENGTH: 181
<212> TYPE: PRT
<213> ORGANISM: Artificial Sequence
<220> FEATURE:
<223> OTHER INFORMATION: Synthetic Polypeptide

<400> SEQUENCE: 2

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

```
Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
        130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180

<210> SEQ ID NO 3
<211> LENGTH: 183
<212> TYPE: PRT
<213> ORGANISM: Artificial Sequence
<220> FEATURE:
<223> OTHER INFORMATION: Synthetic Polypeptide

<400> SEQUENCE: 3

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 4
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 4

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30
```

Asp Glu Ile Met Lys Val Gln Asn Asn Ser Val Ile Ile Asn Cys Asp
         35                  40                  45

Gly Phe Tyr Leu Ile Ser Leu Lys Gly Tyr Phe Ser Gln Glu Val Asn
     50                  55                  60

Ile Ser Leu His Tyr Gln Lys Asp Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
                100                 105                 110

Phe His Val Asn Gly Gly Glu Leu Ile Leu Ile His Gln Asn Pro Gly
                115                 120                 125

Glu Phe Cys Val Leu
        130

<210> SEQ ID NO 5
<211> LENGTH: 548
<212> TYPE: PRT
<213> ORGANISM: Artificial Sequence
<220> FEATURE:
<223> OTHER INFORMATION: Synthetic Polypeptide

<400> SEQUENCE: 5

Ser Glu Val Glu Tyr Arg Ala Glu Val Gly Gln Asn Ala Tyr Leu Pro
 1               5                  10                  15

Cys Phe Tyr Thr Pro Ala Ala Pro Gly Asn Leu Val Pro Val Cys Trp
                 20                  25                  30

Gly Lys Gly Ala Cys Pro Val Phe Glu Cys Gly Asn Val Val Leu Arg
             35                  40                  45

Thr Asp Glu Arg Asp Val Asn Tyr Trp Thr Ser Arg Tyr Trp Leu Asn
 50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
                115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ser Lys Tyr Gly Pro Pro Cys Pro Ser Cys Pro
                180                 185                 190

Ala Pro Glu Phe Leu Gly Gly Pro Ser Val Phe Leu Phe Pro Pro Lys
                195                 200                 205

Pro Lys Asp Thr Leu Met Ile Ser Arg Thr Pro Glu Val Thr Cys Val
    210                 215                 220

Val Val Asp Val Ser Gln Glu Asp Pro Glu Val Gln Phe Asn Trp Tyr
225                 230                 235                 240

Val Asp Gly Val Glu Val His Asn Ala Lys Thr Lys Pro Arg Glu Glu
                245                 250                 255

Gln Phe Asn Ser Thr Tyr Arg Val Val Ser Val Leu Thr Val Leu His
            260                 265                 270

Gln Asp Trp Leu Ser Gly Lys Glu Tyr Lys Cys Lys Val Ser Ser Lys
        275                 280                 285

Gly Leu Pro Ser Ser Ile Glu Lys Thr Ile Ser Asn Ala Thr Gly Gln
    290                 295                 300

Pro Arg Glu Pro Gln Val Tyr Thr Leu Pro Pro Ser Gln Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
            340                 345                 350

Tyr Lys Thr Thr Pro Pro Val Leu Asp Ser Asp Gly Ser Phe Phe Leu
        355                 360                 365

Tyr Ser Arg Leu Thr Val Asp Lys Ser Ser Trp Gln Glu Gly Asn Val
    370                 375                 380

Phe Ser Cys Ser Val Met His Glu Ala Leu His Asn His Tyr Thr Gln
385                 390                 395                 400

Lys Ser Leu Ser Leu Ser Leu Gly Lys Ile Glu Gly Arg Met Asp Gln
                405                 410                 415

Val Ser His Arg Tyr Pro Arg Ile Gln Ser Ile Lys Val Gln Phe Thr
            420                 425                 430

Glu Tyr Lys Lys Glu Lys Gly Phe Ile Leu Thr Ser Gln Lys Glu Asp
        435                 440                 445

Glu Ile Met Lys Val Gln Asn Asn Ser Val Ile Ile Asn Cys Asp Gly
    450                 455                 460

Phe Tyr Leu Ile Ser Leu Lys Gly Tyr Phe Ser Gln Glu Val Asn Ile
465                 470                 475                 480

Ser Leu His Tyr Gln Lys Asp Glu Glu Pro Leu Phe Gln Leu Lys Lys
                485                 490                 495

Val Arg Ser Val Asn Ser Leu Met Val Ala Ser Leu Thr Tyr Lys Asp
            500                 505                 510

Lys Val Tyr Leu Asn Val Thr Thr Asp Asn Thr Ser Leu Asp Asp Phe
        515                 520                 525

His Val Asn Gly Gly Glu Leu Ile Leu Ile His Gln Asn Pro Gly Glu
    530                 535                 540

Phe Cys Val Leu
545

<210> SEQ ID NO 6
<211> LENGTH: 167
<212> TYPE: PRT
<213> ORGANISM: Artificial Sequence
<220> FEATURE:
<223> OTHER INFORMATION: Synthetic Polypeptide

<400> SEQUENCE: 6

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
        100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln
                165

<210> SEQ ID NO 7
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 7

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln
145

<210> SEQ ID NO 8
<211> LENGTH: 510
<212> TYPE: PRT
<213> ORGANISM: Artificial Sequence
<220> FEATURE:
<223> OTHER INFORMATION: Synthetic Polypeptide

<400> SEQUENCE: 8

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro

-continued

```
                35                  40                  45
Ser Asn Gln Thr Asp Lys Leu Ala Ala Phe Pro Glu Asp Arg Ser Gln
 50                  55                  60
Pro Gly Gln Asp Cys Arg Phe Arg Val Thr Gln Leu Pro Asn Gly Arg
 65                  70                  75                  80
Asp Phe His Met Ser Val Val Arg Ala Arg Arg Asn Asp Ser Gly Thr
                 85                  90                  95
Tyr Leu Cys Gly Ala Ile Ser Leu Ala Pro Lys Ala Gln Ile Lys Glu
            100                 105                 110
Ser Leu Arg Ala Glu Leu Arg Val Thr Glu Arg Arg Ala Glu Val Pro
        115                 120                 125
Thr Ala His Pro Ser Pro Ser Pro Arg Pro Ala Gly Gln Phe Gln Ser
    130                 135                 140
Lys Tyr Gly Pro Pro Cys Pro Ser Cys Pro Ala Pro Glu Phe Leu Gly
145                 150                 155                 160
Gly Pro Ser Val Phe Leu Phe Pro Pro Lys Pro Lys Asp Thr Leu Met
                165                 170                 175
Ile Ser Arg Thr Pro Glu Val Thr Cys Val Val Val Asp Val Ser Gln
            180                 185                 190
Glu Asp Pro Glu Val Gln Phe Asn Trp Tyr Val Asp Gly Val Glu Val
        195                 200                 205
His Asn Ala Lys Thr Lys Pro Arg Glu Glu Gln Phe Asn Ser Thr Tyr
    210                 215                 220
Arg Val Val Ser Val Leu Thr Val Leu His Gln Asp Trp Leu Ser Gly
225                 230                 235                 240
Lys Glu Tyr Lys Cys Lys Val Ser Ser Lys Gly Leu Pro Ser Ser Ile
                245                 250                 255
Glu Lys Thr Ile Ser Asn Ala Thr Gly Gln Pro Arg Glu Pro Gln Val
            260                 265                 270
Tyr Thr Leu Pro Pro Ser Gln Glu Glu Met Thr Lys Asn Gln Val Ser
        275                 280                 285
Leu Thr Cys Leu Val Lys Gly Phe Tyr Pro Ser Asp Ile Ala Val Glu
    290                 295                 300
Trp Glu Ser Asn Gly Gln Pro Glu Asn Asn Tyr Lys Thr Thr Pro Pro
305                 310                 315                 320
Val Leu Asp Ser Asp Gly Ser Phe Phe Leu Tyr Ser Arg Leu Thr Val
                325                 330                 335
Asp Lys Ser Ser Trp Gln Glu Gly Asn Val Phe Ser Cys Ser Val Met
            340                 345                 350
His Glu Ala Leu His Asn His Tyr Thr Gln Lys Ser Leu Ser Leu Ser
        355                 360                 365
Leu Gly Lys Ile Glu Gly Arg Met Asp Gln Val Ser His Arg Tyr Pro
    370                 375                 380
Arg Ile Gln Ser Ile Lys Val Gln Phe Thr Glu Tyr Lys Lys Glu Lys
385                 390                 395                 400
Gly Phe Ile Leu Thr Ser Gln Lys Glu Asp Glu Ile Met Lys Val Gln
                405                 410                 415
Asn Asn Ser Val Ile Ile Asn Cys Asp Gly Phe Tyr Leu Ile Ser Leu
            420                 425                 430
Lys Gly Tyr Phe Ser Gln Glu Val Asn Ile Ser Leu His Tyr Gln Lys
        435                 440                 445
Asp Glu Glu Pro Leu Phe Gln Leu Lys Lys Val Arg Ser Val Asn Ser
    450                 455                 460
```

```
Leu Met Val Ala Ser Leu Thr Tyr Lys Asp Lys Val Tyr Leu Asn Val
465                 470                 475                 480

Thr Thr Asp Asn Thr Ser Leu Asp Asp Phe His Val Asn Gly Gly Glu
                485                 490                 495

Leu Ile Leu Ile His Gln Asn Pro Gly Glu Phe Cys Val Leu
            500                 505                 510

<210> SEQ ID NO 9
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 9

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65              70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320
```

Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
        340                 345                 350

Pro Lys Glu Gln Gly Ser Asn Thr Ala Ala Glu Asn Thr Gly Ser Asn
    355                 360                 365

Glu Arg Asn Ile Tyr
    370

<210> SEQ ID NO 10
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 10

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr
            340

<210> SEQ ID NO 11
<211> LENGTH: 261
<212> TYPE: PRT
<213> ORGANISM: Artificial Sequence
<220> FEATURE:
<223> OTHER INFORMATION: Synthetic Polypeptide

<400> SEQUENCE: 11

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 12
<211> LENGTH: 215
<212> TYPE: PRT
<213> ORGANISM: Artificial Sequence
<220> FEATURE:
<223> OTHER INFORMATION: Synthetic Polypeptide

```
<400> SEQUENCE: 12

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30

Leu Ser Leu Leu Asn Cys Glu Ile Lys Ser Gln Phe Glu Gly Phe
        35                  40                  45

Val Lys Asp Ile Met Leu Asn Lys Glu Thr Lys Lys Glu Asn Ser
    50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
        115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
        210                 215

<210> SEQ ID NO 13
<211> LENGTH: 792
<212> TYPE: PRT
<213> ORGANISM: Artificial Sequence
<220> FEATURE:
<223> OTHER INFORMATION: Synthetic Polypeptide

<400> SEQUENCE: 13

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
```

-continued

```
            130                 135                 140
Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
                195                 200                 205

Pro Leu Arg Gly Thr Ala Asn Leu Ser Glu Thr Ile Arg Val Pro Pro
        210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
                275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ser Lys Tyr Gly Pro Pro Cys Pro Pro
                340                 345                 350

Cys Pro Ala Pro Glu Phe Leu Gly Gly Pro Ser Val Phe Leu Phe Pro
                355                 360                 365

Pro Lys Pro Lys Asp Gln Leu Met Ile Ser Arg Thr Pro Glu Val Thr
        370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
                420                 425                 430

Leu His Gln Asp Trp Leu Ser Gly Lys Glu Tyr Lys Cys Lys Val Ser
                435                 440                 445

Ser Lys Gly Leu Pro Ser Ser Ile Glu Lys Thr Ile Ser Asn Ala Thr
        450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Tyr Ser Arg Leu Thr Val Asp Lys Ser Arg Trp Gln Glu Gly
        530                 535                 540

Asn Val Phe Ser Cys Ser Val Leu His Glu Ala Leu His Asn His Tyr
545                 550                 555                 560
```

```
Thr Gln Lys Ser Leu Ser Leu Ser Leu Gly Lys Ile Glu Gly Arg Met
                565                 570                 575

Asp His Arg Arg Leu Asp Lys Ile Glu Asp Glu Arg Asn Leu His Glu
            580                 585                 590

Asp Phe Val Phe Met Lys Thr Ile Gln Arg Cys Asn Thr Gly Glu Arg
        595                 600                 605

Ser Leu Ser Leu Leu Asn Cys Glu Glu Ile Lys Ser Gln Phe Glu Gly
    610                 615                 620

Phe Val Lys Asp Ile Met Leu Asn Lys Glu Glu Thr Lys Lys Glu Asn
625                 630                 635                 640

Ser Phe Glu Met Gln Lys Gly Asp Gln Asn Pro Gln Ile Ala Ala His
                645                 650                 655

Val Ile Ser Glu Ala Ser Ser Lys Thr Thr Ser Val Leu Gln Trp Ala
            660                 665                 670

Glu Lys Gly Tyr Tyr Thr Met Ser Asn Asn Leu Val Thr Leu Glu Asn
        675                 680                 685

Gly Lys Gln Leu Thr Val Lys Arg Gln Gly Leu Tyr Tyr Ile Tyr Ala
    690                 695                 700

Gln Val Thr Phe Cys Ser Asn Arg Glu Ala Ser Ser Gln Ala Pro Phe
705                 710                 715                 720

Ile Ala Ser Leu Cys Leu Lys Ser Pro Gly Arg Phe Glu Arg Ile Leu
                725                 730                 735

Leu Arg Ala Ala Asn Thr His Ser Ser Ala Lys Pro Cys Gly Gln Gln
            740                 745                 750

Ser Ile His Leu Gly Gly Val Phe Glu Leu Gln Pro Gly Ala Ser Val
        755                 760                 765

Phe Val Asn Val Thr Asp Pro Ser Gln Val Ser His Gly Thr Gly Phe
    770                 775                 780

Thr Ser Phe Gly Leu Leu Lys Leu
785                 790

<210> SEQ ID NO 14
<211> LENGTH: 251
<212> TYPE: PRT
<213> ORGANISM: Artificial Sequence
<220> FEATURE:
<223> OTHER INFORMATION: Synthetic Polypeptide

<400> SEQUENCE: 14

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125
```

```
Lys Asn Arg Met Asn Tyr Thr Asn Lys Phe Leu Leu Ile Pro Glu Ser
            130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
            195                 200                 205

Phe Gln Pro Ile Tyr Leu Gly Ala Met Phe Ser Leu Glu Gly Asp
210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
            245                 250

<210> SEQ ID NO 15
<211> LENGTH: 192
<212> TYPE: PRT
<213> ORGANISM: Artificial Sequence
<220> FEATURE:
<223> OTHER INFORMATION: Synthetic Polypeptide

<400> SEQUENCE: 15

Arg Ala Gln Gly Glu Ala Cys Val Gln Phe Gln Ala Leu Lys Gly Gln
1               5                   10                  15

Glu Phe Ala Pro Ser His Gln Gln Val Tyr Ala Pro Leu Arg Ala Asp
                20                  25                  30

Gly Asp Lys Pro Arg Ala His Leu Thr Val Val Arg Gln Thr Pro Thr
            35                  40                  45

Gln His Phe Lys Asn Gln Phe Pro Ala Leu His Trp Glu His Glu Leu
        50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110

Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
    130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
                165                 170                 175

Val Asp Tyr Thr Lys Glu Asp Lys Thr Phe Phe Gly Ala Phe Leu Leu
            180                 185                 190

<210> SEQ ID NO 16
<211> LENGTH: 569
<212> TYPE: PRT
<213> ORGANISM: Artificial Sequence
<220> FEATURE:
<223> OTHER INFORMATION: Synthetic Polypeptide
```

<400> SEQUENCE: 16

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ser
    130                 135                 140

Lys Tyr Gly Pro Pro Cys Pro Ser Cys Pro Ala Pro Glu Phe Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
        195                 200                 205

His Asn Ala Lys Thr Lys Pro Arg Glu Glu Gln Phe Asn Ser Thr Tyr
    210                 215                 220

Arg Val Val Ser Val Leu Thr Val Leu His Gln Asp Trp Leu Ser Gly
225                 230                 235                 240

Lys Glu Tyr Lys Cys Lys Val Ser Ser Lys Gly Leu Pro Ser Ser Ile
                245                 250                 255

Glu Lys Thr Ile Ser Asn Ala Thr Gly Gln Pro Arg Glu Pro Gln Val
            260                 265                 270

Tyr Thr Leu Pro Pro Ser Gln Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
                325                 330                 335

Asp Lys Ser Ser Trp Gln Glu Gly Asn Val Phe Ser Cys Ser Val Met
            340                 345                 350

His Glu Ala Leu His Asn His Tyr Thr Gln Lys Ser Leu Ser Leu Ser
        355                 360                 365

Leu Gly Lys Ile Glu Gly Arg Met Asp Arg Ala Gln Gly Glu Ala Cys
    370                 375                 380

Val Gln Phe Gln Ala Leu Lys Gly Gln Glu Phe Ala Pro Ser His Gln
385                 390                 395                 400

Gln Val Tyr Ala Pro Leu Arg Ala Asp Gly Asp Lys Pro Arg Ala His
                405                 410                 415
```

Leu Thr Val Val Arg Gln Thr Pro Thr Gln His Phe Lys Asn Gln Phe
            420                 425                 430

Pro Ala Leu His Trp Glu His Glu Leu Gly Leu Ala Phe Thr Lys Asn
            435                 440                 445

Arg Met Asn Tyr Thr Asn Lys Phe Leu Leu Ile Pro Glu Ser Gly Asp
450                 455                 460

Tyr Phe Ile Tyr Ser Gln Val Thr Phe Arg Gly Met Thr Ser Glu Cys
465                 470                 475                 480

Ser Glu Ile Arg Gln Ala Gly Arg Pro Asn Lys Pro Asp Ser Ile Thr
            485                 490                 495

Val Val Ile Thr Lys Val Thr Asp Ser Tyr Pro Glu Pro Thr Gln Leu
            500                 505                 510

Leu Met Gly Thr Lys Ser Val Cys Glu Val Gly Ser Asn Trp Phe Gln
            515                 520                 525

Pro Ile Tyr Leu Gly Ala Met Phe Ser Leu Glu Gly Asp Lys Leu
            530                 535                 540

Met Val Asn Val Ser Asp Ile Ser Leu Val Asp Tyr Thr Lys Glu Asp
545                 550                 555                 560

Lys Thr Phe Phe Gly Ala Phe Leu Leu
            565

<210> SEQ ID NO 17
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 17

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser
145                 150

<210> SEQ ID NO 18
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 18

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
                20                  25                  30

Cys Ala Asn Arg Pro His Val Thr Trp Cys Lys Leu Asn Gly Thr Thr
            35                  40                  45

Cys Val Lys Leu Glu Asp Arg Gln Thr Ser Trp Lys Glu Glu Lys Asn
        50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125

<210> SEQ ID NO 19
<211> LENGTH: 487
<212> TYPE: PRT
<213> ORGANISM: Artificial Sequence
<220> FEATURE:
<223> OTHER INFORMATION: Synthetic Polypeptide

<400> SEQUENCE: 19

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
                20                  25                  30

Cys Ala Asn Arg Pro His Val Thr Trp Cys Lys Leu Asn Gly Thr Thr
            35                  40                  45

Cys Val Lys Leu Glu Asp Arg Gln Thr Ser Trp Lys Glu Glu Lys Asn
        50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Ser Lys Tyr Gly Pro Pro Cys Pro
        115                 120                 125

Ser Cys Pro Ala Pro Glu Phe Leu Gly Gly Pro Ser Val Phe Leu Phe
130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Ser Gly Lys Glu Tyr Lys Cys Lys Val
210                 215                 220

Ser Ser Lys Gly Leu Pro Ser Ser Ile Glu Lys Thr Ile Ser Asn Ala

```
                225                 230                 235                 240
Thr Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
                260                 265                 270

Phe Tyr Pro Ser Asp Ile Ala Val Glu Trp Glu Ser Asn Gly Gln Pro
                275                 280                 285

Glu Asn Asn Tyr Lys Thr Thr Pro Pro Val Leu Asp Ser Asp Gly Ser
            290                 295                 300

Phe Phe Leu Tyr Ser Arg Leu Thr Val Asp Lys Ser Ser Trp Gln Glu
305                 310                 315                 320

Gly Asn Val Phe Ser Cys Ser Val Met His Glu Ala Leu His Asn His
                    325                 330                 335

Tyr Thr Gln Lys Ser Leu Ser Leu Ser Leu Gly Lys Ile Glu Gly Arg
                340                 345                 350

Met Asp Gln Val Ser His Arg Tyr Pro Arg Ile Gln Ser Ile Lys Val
                355                 360                 365

Gln Phe Thr Glu Tyr Lys Lys Glu Lys Gly Phe Ile Leu Thr Ser Gln
        370                 375                 380

Lys Glu Asp Glu Ile Met Lys Val Gln Asn Asn Ser Val Ile Ile Asn
385                 390                 395                 400

Cys Asp Gly Phe Tyr Leu Ile Ser Leu Lys Gly Tyr Phe Ser Gln Glu
                405                 410                 415

Val Asn Ile Ser Leu His Tyr Gln Lys Asp Glu Glu Pro Leu Phe Gln
                420                 425                 430

Leu Lys Lys Val Arg Ser Val Asn Ser Leu Met Val Ala Ser Leu Thr
            435                 440                 445

Tyr Lys Asp Lys Val Tyr Leu Asn Val Thr Thr Asp Asn Thr Ser Leu
        450                 455                 460

Asp Asp Phe His Val Asn Gly Gly Glu Leu Ile Leu Ile His Gln Asn
465                 470                 475                 480

Pro Gly Glu Phe Cys Val Leu
                485

<210> SEQ ID NO 20
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 20

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
```

```
                100                 105                 110
Trp Ala Ala Val Glu Ile Pro Glu Leu Glu Glu Ala Glu Gly Asn Ile
            115                 120                 125

Thr Arg Leu Phe Val Asp Pro Asp Pro Thr Gln Asn Arg Asn Arg
            130                 135                 140

Ile Ala Ser Phe Pro Gly
145                 150

<210> SEQ ID NO 21
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 21

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
            20                  25                  30

Leu Arg Val Lys Trp Thr Lys Asp Gly Ala Ile Leu Cys Gln Pro Tyr
        35                  40                  45

Ile Thr Asn Gly Ser Leu Ser Leu Gly Val Cys Gly Pro Gln Gly Arg
50                  55                  60

Leu Ser Trp Gln Ala Pro Ser His Leu Thr Leu Gln Leu Asp Pro Val
65                  70                  75                  80

Ser Leu Asn His Ser Gly Ala Tyr Val Cys Trp Ala Ala Val Glu Ile
                85                  90                  95

Pro Glu Leu Glu Glu Ala Glu Gly Asn Ile Thr Arg Leu Phe Val Asp
            100                 105                 110

Pro Asp Pro Thr Gln Asn Arg Asn Arg Ile Ala Ser Phe Pro Gly
            115                 120                 125

<210> SEQ ID NO 22
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 22

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
            20                  25                  30

Leu Arg Val Lys Trp Thr Lys Asp Gly Ala Ile Leu Cys Gln Pro Tyr
        35                  40                  45

Ile Thr Asn Gly Ser Leu Ser Leu Gly Val Cys Gly Pro Gln Gly Arg
50                  55                  60

Leu Ser Trp Gln Ala Pro Ser His Leu Thr Leu Gln Leu Asp Pro Val
65                  70                  75                  80

Ser Leu Asn His Ser Gly Ala Tyr Val Cys Trp Ala Ala Val Glu Ile
                85                  90                  95

Pro Glu Leu Glu Glu Ala Glu Gly Asn Ile Thr Arg Leu Phe Val Asp
            100                 105                 110

Pro Asp Pro Thr Gln Asn Arg Asn Arg Ile Ala Ser Phe Pro Gly
            115                 120                 125
```

```
Ser Lys Tyr Gly Pro Pro Cys Pro Ser Cys Pro Ala Pro Glu Phe Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Ser
210                 215                 220

Gly Lys Glu Tyr Lys Cys Lys Val Ser Ser Lys Gly Leu Pro Ser Ser
225                 230                 235                 240

Ile Glu Lys Thr Ile Ser Asn Ala Thr Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Arg Leu Thr
305                 310                 315                 320

Val Asp Lys Ser Ser Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys Ile Glu Gly Arg Met Asp Gln Val Ser His Arg Tyr
        355                 360                 365

Pro Arg Ile Gln Ser Ile Lys Val Gln Phe Thr Glu Tyr Lys Lys Glu
370                 375                 380

Lys Gly Phe Ile Leu Thr Ser Gln Lys Glu Asp Glu Ile Met Lys Val
385                 390                 395                 400

Gln Asn Asn Ser Val Ile Ile Asn Cys Asp Gly Phe Tyr Leu Ile Ser
                405                 410                 415

Leu Lys Gly Tyr Phe Ser Gln Glu Val Asn Ile Ser Leu His Tyr Gln
            420                 425                 430

Lys Asp Glu Glu Pro Leu Phe Gln Leu Lys Lys Val Arg Ser Val Asn
        435                 440                 445

Ser Leu Met Val Ala Ser Leu Thr Tyr Lys Asp Lys Val Tyr Leu Asn
450                 455                 460

Val Thr Thr Asp Asn Thr Ser Leu Asp Asp Phe His Val Asn Gly Gly
465                 470                 475                 480

Glu Leu Ile Leu Ile His Gln Asn Pro Gly Glu Phe Cys Val Leu
                485                 490                 495

<210> SEQ ID NO 23
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 23
```

```
Met Glu Glu Ser Val Val Arg Pro Ser Val Phe Val Asp Gly Gln
1               5                   10                  15

Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
            35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
            130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
            165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
            195                 200                 205

Leu Glu Ala Gly Glu Lys Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240
```

<210> SEQ ID NO 24
<211> LENGTH: 182
<212> TYPE: PRT
<213> ORGANISM: Artificial Sequence
<220> FEATURE:
<223> OTHER INFORMATION: Synthetic Polypeptide

<400> SEQUENCE: 24

```
Leu Gln Leu His Trp Arg Leu Gly Glu Met Val Thr Arg Leu Pro Asp
1               5                   10                  15

Gly Pro Ala Gly Ser Trp Glu Gln Leu Ile Gln Glu Arg Ser His
            20                  25                  30

Glu Val Asn Pro Ala Ala His Leu Thr Gly Ala Asn Ser Ser Leu Thr
            35                  40                  45

Gly Ser Gly Gly Pro Leu Leu Trp Glu Thr Gln Leu Gly Leu Ala Phe
50                  55                  60

Leu Arg Gly Leu Ser Tyr His Asp Gly Ala Leu Val Val Thr Lys Ala
65                  70                  75                  80

Gly Tyr Tyr Tyr Ile Tyr Ser Lys Val Gln Leu Gly Gly Val Gly Cys
                85                  90                  95

Pro Leu Gly Leu Ala Ser Thr Ile Thr His Gly Leu Tyr Lys Arg Thr
            100                 105                 110

Pro Arg Tyr Pro Glu Glu Leu Glu Leu Leu Val Ser Gln Gln Ser Pro
            115                 120                 125
```

```
Cys Gly Arg Ala Thr Ser Ser Ser Arg Val Trp Trp Asp Ser Ser Phe
130                 135                 140

Leu Gly Gly Val Val His Leu Glu Ala Gly Glu Lys Val Val Val Arg
145                 150                 155                 160

Val Leu Asp Glu Arg Leu Val Arg Leu Arg Asp Gly Thr Arg Ser Tyr
                165                 170                 175

Phe Gly Ala Phe Met Val
            180

<210> SEQ ID NO 25
<211> LENGTH: 759
<212> TYPE: PRT
<213> ORGANISM: Artificial Sequence
<220> FEATURE:
<223> OTHER INFORMATION: Synthetic Polypeptide

<400> SEQUENCE: 25

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
            290                 295                 300
```

```
His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ser Lys Tyr Gly Pro Cys Pro Pro
            340                 345                 350

Cys Pro Ala Pro Glu Phe Leu Gly Gly Pro Ser Val Phe Leu Phe Pro
        355                 360                 365

Pro Lys Pro Lys Asp Gln Leu Met Ile Ser Arg Thr Pro Glu Val Thr
    370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
                420                 425                 430

Leu His Gln Asp Trp Leu Ser Gly Lys Glu Tyr Lys Cys Lys Val Ser
            435                 440                 445

Ser Lys Gly Leu Pro Ser Ser Ile Glu Lys Thr Ile Ser Asn Ala Thr
450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Arg Leu Thr Val Asp Lys Ser Arg Trp Gln Glu Gly
530                 535                 540

Asn Val Phe Ser Cys Ser Val Leu His Glu Ala Leu His Asn His Tyr
545                 550                 555                 560

Thr Gln Lys Ser Leu Ser Leu Ser Leu Gly Lys Ile Glu Gly Arg Met
                565                 570                 575

Asp Leu Gln Leu His Trp Arg Leu Gly Glu Met Val Thr Arg Leu Pro
            580                 585                 590

Asp Gly Pro Ala Gly Ser Trp Glu Gln Leu Ile Gln Glu Arg Arg Ser
            595                 600                 605

His Glu Val Asn Pro Ala Ala His Leu Thr Gly Ala Asn Ser Ser Leu
610                 615                 620

Thr Gly Ser Gly Gly Pro Leu Leu Trp Glu Thr Gln Leu Gly Leu Ala
625                 630                 635                 640

Phe Leu Arg Gly Leu Ser Tyr His Asp Gly Ala Leu Val Val Thr Lys
                645                 650                 655

Ala Gly Tyr Tyr Tyr Ile Tyr Ser Lys Val Gln Leu Gly Gly Val Gly
                660                 665                 670

Cys Pro Leu Gly Leu Ala Ser Thr Ile Thr His Gly Leu Tyr Lys Arg
                675                 680                 685

Thr Pro Arg Tyr Pro Glu Glu Leu Glu Leu Leu Val Ser Gln Gln Ser
            690                 695                 700

Pro Cys Gly Arg Ala Thr Ser Ser Ser Arg Val Trp Trp Asp Ser Ser
705                 710                 715                 720

Phe Leu Gly Gly Val Val His Leu Glu Ala Gly Glu Lys Val Val Val
```

```
                    725                 730                 735
Arg Val Leu Asp Glu Arg Leu Val Arg Leu Arg Asp Gly Thr Arg Ser
                740                 745                 750
Tyr Phe Gly Ala Phe Met Val
            755

<210> SEQ ID NO 26
<211> LENGTH: 710
<212> TYPE: PRT
<213> ORGANISM: Artificial Sequence
<220> FEATURE:
<223> OTHER INFORMATION: Synthetic Polypeptide

<400> SEQUENCE: 26

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
```

325                 330                 335
Ser Asn Glu Arg Asn Ile Tyr Ser Lys Tyr Gly Pro Pro Cys Pro Ser
                340                 345                 350

Cys Pro Ala Pro Glu Phe Leu Gly Gly Pro Ser Val Phe Leu Phe Pro
            355                 360                 365

Pro Lys Pro Lys Asp Thr Leu Met Ile Ser Arg Thr Pro Glu Val Thr
        370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
            420                 425                 430

Leu His Gln Asp Trp Leu Ser Gly Lys Glu Tyr Lys Cys Lys Val Ser
        435                 440                 445

Ser Lys Gly Leu Pro Ser Ser Ile Glu Lys Thr Ile Ser Asn Ala Thr
    450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Arg Leu Thr Val Asp Lys Ser Ser Trp Gln Glu Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly Lys Ile Glu Gly Arg Met
                565                 570                 575

Asp Gln Val Ser His Arg Tyr Pro Arg Ile Gln Ser Ile Lys Val Gln
            580                 585                 590

Phe Thr Glu Tyr Lys Lys Glu Lys Gly Phe Ile Leu Thr Ser Gln Lys
        595                 600                 605

Glu Asp Glu Ile Met Lys Val Gln Asn Asn Ser Val Ile Ile Asn Cys
    610                 615                 620

Asp Gly Phe Tyr Leu Ile Ser Leu Lys Gly Tyr Phe Ser Gln Glu Val
625                 630                 635                 640

Asn Ile Ser Leu His Tyr Gln Lys Asp Glu Glu Pro Leu Phe Gln Leu
                645                 650                 655

Lys Lys Val Arg Ser Val Asn Ser Leu Met Val Ala Ser Leu Thr Tyr
            660                 665                 670

Lys Asp Lys Val Tyr Leu Asn Val Thr Thr Asp Asn Thr Ser Leu Asp
        675                 680                 685

Asp Phe His Val Asn Gly Gly Glu Leu Ile Leu Ile His Gln Asn Pro
    690                 695                 700

Gly Glu Phe Cys Val Leu
705                 710

<210> SEQ ID NO 27
<211> LENGTH: 559
<212> TYPE: PRT
<213> ORGANISM: Artificial Sequence
<220> FEATURE:
<223> OTHER INFORMATION: Synthetic Polypeptide

<400> SEQUENCE: 27

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ser
    130                 135                 140

Lys Tyr Gly Pro Pro Cys Pro Pro Cys Pro Ala Pro Glu Phe Leu Gly
145                 150                 155                 160

Gly Pro Ser Val Phe Leu Phe Pro Pro Lys Pro Lys Asp Gln Leu Met
                165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
        195                 200                 205

His Asn Ala Lys Thr Lys Pro Arg Glu Glu Gln Phe Asn Ser Thr Tyr
    210                 215                 220

Arg Val Val Ser Val Leu Thr Val Leu His Gln Asp Trp Leu Ser Gly
225                 230                 235                 240

Lys Glu Tyr Lys Cys Lys Val Ser Ser Lys Gly Leu Pro Ser Ser Ile
                245                 250                 255

Glu Lys Thr Ile Ser Asn Ala Thr Gly Gln Pro Arg Glu Pro Gln Val
            260                 265                 270

Tyr Thr Leu Pro Pro Ser Gln Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
                325                 330                 335

Asp Lys Ser Arg Trp Gln Glu Gly Asn Val Phe Ser Cys Ser Val Leu
            340                 345                 350

His Glu Ala Leu His Asn His Tyr Thr Gln Lys Ser Leu Ser Leu Ser
        355                 360                 365

Leu Gly Lys Ile Glu Gly Arg Met Asp Leu Gln Leu His Trp Arg Leu
    370                 375                 380

Gly Glu Met Val Thr Arg Leu Pro Asp Gly Pro Ala Gly Ser Trp Glu
385                 390                 395                 400
```

```
Gln Leu Ile Gln Glu Arg Arg Ser His Glu Val Asn Pro Ala Ala His
                405                 410                 415

Leu Thr Gly Ala Asn Ser Ser Leu Thr Gly Ser Gly Pro Leu Leu
            420                 425                 430

Trp Glu Thr Gln Leu Gly Leu Ala Phe Leu Arg Gly Leu Ser Tyr His
            435                 440                 445

Asp Gly Ala Leu Val Val Thr Lys Ala Gly Tyr Tyr Tyr Ile Tyr Ser
        450                 455                 460

Lys Val Gln Leu Gly Gly Val Gly Cys Pro Leu Gly Leu Ala Ser Thr
465                 470                 475                 480

Ile Thr His Gly Leu Tyr Lys Arg Thr Pro Arg Tyr Pro Glu Glu Leu
                485                 490                 495

Glu Leu Leu Val Ser Gln Gln Ser Pro Cys Gly Arg Ala Thr Ser Ser
            500                 505                 510

Ser Arg Val Trp Trp Asp Ser Ser Phe Leu Gly Gly Val Val His Leu
        515                 520                 525

Glu Ala Gly Glu Lys Val Val Val Arg Val Leu Asp Glu Arg Leu Val
    530                 535                 540

Arg Leu Arg Asp Gly Thr Arg Ser Tyr Phe Gly Ala Phe Met Val
545                 550                 555
```

<210> SEQ ID NO 28
<211> LENGTH: 953
<212> TYPE: PRT
<213> ORGANISM: Artificial Sequence
<220> FEATURE:
<223> OTHER INFORMATION: Synthetic Polypeptide

<400> SEQUENCE: 28

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205
```

```
Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                    245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                    325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                    405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                    485                 490                 495

Thr Pro Val Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
        515                 520                 525

Val Arg Trp Lys Ile Ile Glu Ser Tyr Glu Gly Asn Ser Tyr Thr Phe
530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
                    565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
        595                 600                 605

Glu Ala Leu Met Ser Glu Leu Lys Ile Met Ser His Leu Gly Gln His
610                 615                 620
```

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
            645                 650                 655

Arg Arg Lys Ala Glu Ala Met Leu Gly Pro Ser Leu Ser Pro Gly Gln
        660                 665                 670

Asp Pro Glu Gly Gly Val Asp Tyr Lys Asn Ile His Leu Glu Lys Lys
    675                 680                 685

Tyr Val Arg Arg Asp Ser Gly Phe Ser Ser Gln Gly Val Asp Thr Tyr
690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
            725                 730                 735

Leu His Phe Ser Ser Gln Val Ala Gln Gly Met Ala Phe Leu Ala Ser
        740                 745                 750

Lys Asn Cys Ile His Arg Asp Val Ala Ala Arg Asn Val Leu Leu Thr
    755                 760                 765

Asn Gly His Val Ala Lys Ile Gly Asp Phe Gly Leu Ala Arg Asp Ile
770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
            805                 810                 815

Ser Asp Val Trp Ser Tyr Gly Ile Leu Leu Trp Glu Ile Phe Ser Leu
        820                 825                 830

Gly Leu Asn Pro Tyr Pro Gly Ile Leu Val Asn Ser Lys Phe Tyr Lys
    835                 840                 845

Leu Val Lys Asp Gly Tyr Gln Met Ala Gln Pro Ala Phe Ala Pro Lys
850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
            885                 890                 895

Glu Asp Arg Arg Glu Arg Asp Tyr Thr Asn Leu Pro Ser Ser Ser Arg
        900                 905                 910

Ser Gly Gly Ser Gly Ser Ser Ser Glu Leu Glu Glu Ser Ser
    915                 920                 925

Ser Glu His Leu Thr Cys Cys Glu Gln Gly Asp Ile Ala Gln Pro Leu
930                 935                 940

Leu Gln Pro Asn Asn Tyr Gln Phe Cys
945                 950

<210> SEQ ID NO 29
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 29

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

-continued

Gly Pro Pro Ser Pro His Trp Thr Leu Tyr Ser Asp Gly Ser Ser Ser
                35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
                115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
                195                 200                 205

Ser Val Asp Val Asn Phe Asp Val Phe Leu Gln His Asn Asn Thr Lys
                210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
                275                 280                 285

Asn Leu Ile Gln Glu Val Thr Val Gly Glu Gly Leu Asn Leu Lys Val
                290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
                370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr

```
            450                 455                 460
Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro

<210> SEQ ID NO 30
<211> LENGTH: 947
<212> TYPE: PRT
<213> ORGANISM: Artificial Sequence
<220> FEATURE:
<223> OTHER INFORMATION: Synthetic Polypeptide

<400> SEQUENCE: 30

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
        290                 295                 300

Met Val Glu Ala Tyr Pro Gly Leu Gln Gly Phe Asn Trp Thr Tyr Leu
305                 310                 315                 320
```

```
Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro Ser Lys Tyr Gly Pro Pro Cys Pro Pro Cys Pro Ala Pro Glu
            500                 505                 510

Phe Leu Gly Gly Pro Ser Val Phe Leu Phe Pro Pro Lys Pro Lys Asp
        515                 520                 525

Gln Leu Met Ile Ser Arg Thr Pro Glu Val Thr Cys Val Val Val Asp
    530                 535                 540

Val Ser Gln Glu Asp Pro Glu Val Gln Phe Asn Trp Tyr Val Asp Gly
545                 550                 555                 560

Val Glu Val His Asn Ala Lys Thr Lys Pro Arg Glu Glu Gln Phe Asn
                565                 570                 575

Ser Thr Tyr Arg Val Val Ser Val Leu Thr Val Leu His Gln Asp Trp
            580                 585                 590

Leu Ser Gly Lys Glu Tyr Lys Cys Lys Val Ser Ser Lys Gly Leu Pro
        595                 600                 605

Ser Ser Ile Glu Lys Thr Ile Ser Asn Ala Thr Gly Gln Pro Arg Glu
    610                 615                 620

Pro Gln Val Tyr Thr Leu Pro Pro Ser Gln Glu Met Thr Lys Asn
625                 630                 635                 640

Gln Val Ser Leu Thr Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Arg
        675                 680                 685

Leu Thr Val Asp Lys Ser Arg Trp Gln Glu Gly Asn Val Phe Ser Cys
    690                 695                 700

Ser Val Leu His Glu Ala Leu His Asn His Tyr Thr Gln Lys Ser Leu
705                 710                 715                 720

Ser Leu Ser Leu Gly Lys Ile Glu Gly Arg Met Asp His Arg Arg Leu
                725                 730                 735
```

Asp Lys Ile Glu Asp Glu Arg Asn Leu His Glu Asp Phe Val Phe Met
             740                 745                 750

Lys Thr Ile Gln Arg Cys Asn Thr Gly Glu Arg Ser Leu Ser Leu Leu
         755                 760                 765

Asn Cys Glu Glu Ile Lys Ser Gln Phe Glu Gly Phe Val Lys Asp Ile
         770                 775                 780

Met Leu Asn Lys Glu Glu Thr Lys Lys Glu Asn Ser Phe Glu Met Gln
785                 790                 795                 800

Lys Gly Asp Gln Asn Pro Gln Ile Ala Ala His Val Ile Ser Glu Ala
                 805                 810                 815

Ser Ser Lys Thr Thr Ser Val Leu Gln Trp Ala Glu Lys Gly Tyr Tyr
             820                 825                 830

Thr Met Ser Asn Asn Leu Val Thr Leu Glu Asn Gly Lys Gln Leu Thr
             835                 840                 845

Val Lys Arg Gln Gly Leu Tyr Tyr Ile Tyr Ala Gln Val Thr Phe Cys
         850                 855                 860

Ser Asn Arg Glu Ala Ser Ser Gln Ala Pro Phe Ile Ala Ser Leu Cys
865                 870                 875                 880

Leu Lys Ser Pro Gly Arg Phe Glu Arg Ile Leu Leu Arg Ala Ala Asn
                 885                 890                 895

Thr His Ser Ser Ala Lys Pro Cys Gly Gln Gln Ser Ile His Leu Gly
             900                 905                 910

Gly Val Phe Glu Leu Gln Pro Gly Ala Ser Val Phe Val Asn Val Thr
             915                 920                 925

Asp Pro Ser Gln Val Ser His Gly Thr Gly Phe Thr Ser Phe Gly Leu
930                 935                 940

Leu Lys Leu
945

<210> SEQ ID NO 31
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 31

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
             35                  40                  45

Leu Ala Cys Pro Trp Ala Val Ser Gly Ala Arg Ala Ser Pro Gly Ser
         50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

```
Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 32
<211> LENGTH: 205
<212> TYPE: PRT
<213> ORGANISM: Artificial Sequence
<220> FEATURE:
<223> OTHER INFORMATION: Synthetic Polypeptide

<400> SEQUENCE: 32

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Ser Glu Ala Arg
130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205
```

<210> SEQ ID NO 33
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 33

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
            35                  40                  45

Cys Leu Val Phe Thr Val Ala Thr Ile Met Val Leu Val Val Gln Arg
50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
            115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
            195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 34
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 34

Gln Arg Thr Asp Ser Ile Pro Asn Ser Pro Asp Asn Val Pro Leu Lys
1               5                   10                  15

Gly Gly Asn Cys Ser Glu Asp Leu Leu Cys Ile Leu Lys Arg Ala Pro
            20                  25                  30

Phe Lys Lys Ser Trp Ala Tyr Leu Gln Val Ala Lys His Leu Asn Lys
            35                  40                  45

Thr Lys Leu Ser Trp Asn Lys Asp Gly Ile Leu His Gly Val Arg Tyr
        50                  55                  60

Gln Asp Gly Asn Leu Val Ile Gln Phe Pro Gly Leu Tyr Phe Ile Ile
65                  70                  75                  80

Cys Gln Leu Gln Phe Leu Val Gln Cys Pro Asn Asn Ser Val Asp Leu
                85                  90                  95

Lys Leu Glu Leu Leu Ile Asn Lys His Ile Lys Lys Gln Ala Leu Val
            100                 105                 110

Thr Val Cys Glu Ser Gly Met Gln Thr Lys His Val Tyr Gln Asn Leu
            115                 120                 125
```

```
Ser Gln Phe Leu Leu Asp Tyr Leu Gln Val Asn Thr Thr Ile Ser Val
    130                 135                 140

Asn Val Asp Thr Phe Gln Tyr Ile Asp Thr Ser Thr Phe Pro Leu Glu
145                 150                 155                 160

Asn Val Leu Ser Ile Phe Leu Tyr Ser Asn Ser Asp
                165                 170

<210> SEQ ID NO 35
<211> LENGTH: 199
<212> TYPE: PRT
<213> ORGANISM: Artificial Sequence
<220> FEATURE:
<223> OTHER INFORMATION: Synthetic Polypeptide

<400> SEQUENCE: 35

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
    50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 36
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 36

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
```

```
            50                  55                  60
Glu Val Arg Leu Tyr Lys Asn Lys Asp Met Ile Gln Thr Leu Thr Asn
 65                  70                  75                  80

Lys Ser Lys Ile Gln Asn Val Gly Gly Thr Tyr Glu Leu His Val Gly
                 85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125
```

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 41

```
Met Arg Trp Cys Leu Leu Leu Ile Trp Ala Gln Gly Leu Arg Gln Ala
 1               5                  10                  15

Pro Leu Ala Ser Gly Met Met Thr Gly Thr Ile Glu Thr Thr Gly Asn
                20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
             50                  55                  60

Leu Leu Ala Ile Cys Asn Ala Asp Leu Gly Trp His Ile Ser Pro Ser
 65                  70                  75                  80

Phe Lys Asp Arg Val Ala Pro Gly Pro Gly Leu Gly Leu Thr Leu Gln
                 85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro
            130                 135                 140
```

```
<210> SEQ ID NO 42
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 42

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
            115                 120

<210> SEQ ID NO 43
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 43

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190
```

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 44
<211> LENGTH: 243
<212> TYPE: PRT
<213> ORGANISM: Artificial Sequence
<220> FEATURE:
<223> OTHER INFORMATION: Synthetic Polypeptide

<400> SEQUENCE: 44

Thr Asn Glu Leu Lys Gln Met Gln Asp Lys Tyr Ser Lys Ser Gly Ile
1               5                   10                  15

Ala Cys Phe Leu Lys Glu Asp Asp Ser Tyr Trp Asp Pro Asn Asp Glu
            20                  25                  30

Glu Ser Met Asn Ser Pro Cys Trp Gln Val Lys Trp Gln Leu Arg Gln
        35                  40                  45

Leu Val Arg Lys Met Ile Leu Arg Thr Ser Glu Glu Thr Ile Ser Thr
    50                  55                  60

Val Gln Glu Lys Gln Gln Asn Ile Ser Pro Leu Val Arg Glu Arg Gly
65                  70                  75                  80

Pro Gln Arg Val Ala Ala His Ile Thr Gly Thr Arg Gly Arg Ser Asn
                85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
        115                 120                 125

Leu His Leu Arg Asn Gly Glu Leu Val Ile His Glu Lys Gly Phe Tyr
    130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
        195                 200                 205

Ile Phe Glu Leu Lys Glu Asn Asp Arg Ile Phe Val Ser Val Thr Asn
    210                 215                 220

Glu His Leu Ile Asp Met Asp His Glu Ala Ser Phe Phe Gly Ala Phe
225                 230                 235                 240

Leu Val Gly

<210> SEQ ID NO 45
<211> LENGTH: 217

<212> TYPE: PRT
<213> ORGANISM: Artificial Sequence
<220> FEATURE:
<223> OTHER INFORMATION: Synthetic Polypeptide

<400> SEQUENCE: 45

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
210                 215
```

<210> SEQ ID NO 46
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 46

```
Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Thr Pro His
65                  70                  75                  80

Ser Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110
```

```
Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
                180                 185                 190

Phe Ser Cys Ser Val Leu His Glu Ala Leu His Asn His Tyr Thr Gln
            195                 200                 205

Lys Ser Leu Ser Leu Ser Leu Gly Lys
    210                 215
```

<210> SEQ ID NO 47
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 47

```
Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
                180                 185                 190

Phe Ser Cys Ser Val Leu His Glu Ala Leu His Asn His Tyr Thr Gln
            195                 200                 205

Lys Ser Leu Ser Leu Ser Leu Gly Lys
    210                 215
```

<210> SEQ ID NO 48
<211> LENGTH: 11
<212> TYPE: PRT
<213> ORGANISM: Artificial Sequence -continued

```
<220> FEATURE:
<223> OTHER INFORMATION: Synthetic Polypeptide

<400> SEQUENCE: 48

Ser Lys Tyr Gly Pro Pro Cys Pro Ser Cys Pro
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 49

Ser Lys Tyr Gly Pro Pro Cys Pro Pro Cys Pro
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 50

Ser Lys Tyr Gly Pro Pro
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 51

Ile Glu Gly Arg Met Asp
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Gly Gly Gly Val Pro Arg Asp Cys Gly
1               5

<210> SEQ ID NO 53
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 53

Ile Glu Gly Arg Met Asp Gly Gly Gly Ala Gly Gly Gly Gly
1               5                   10                  15

<210> SEQ ID NO 54
<211> LENGTH: 8
<212> TYPE: PRT
<213> ORGANISM: Artificial Sequence
<220> FEATURE:
```

```
<223> OTHER INFORMATION: Synthetic Polypeptide

<400> SEQUENCE: 54

Gly Gly Gly Ser Gly Gly Gly Ser
1               5

<210> SEQ ID NO 55
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 55

Gly Gly Gly Ser Gly Gly Gly Ser Gly Gly Gly
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 56

Glu Gly Lys Ser Ser Gly Ser Gly Ser Glu Ser Lys Ser Thr
1               5                   10

<210> SEQ ID NO 57
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Gly Gly Ser Gly
1

<210> SEQ ID NO 58
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 58

Gly Gly Ser Gly Gly Gly Ser Gly Gly Gly Ser Gly
1               5                   10

<210> SEQ ID NO 59
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 59

Glu Ala Ala Ala Lys Glu Ala Ala Ala Lys Glu Ala Ala Ala Lys
1               5                   10                  15

<210> SEQ ID NO 60
<211> LENGTH: 20
<212> TYPE: PRT
<213> ORGANISM: Artificial Sequence
<220> FEATURE:
<223> OTHER INFORMATION: Synthetic Polypeptide
```

<400> SEQUENCE: 60

Glu Ala Ala Arg Glu Ala Ala Arg Glu Ala Ala Arg Glu
1               5                   10                  15

Ala Ala Ala Arg
            20

<210> SEQ ID NO 61
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 61

Gly Gly Gly Gly Ser Gly Gly Gly Ser Gly Gly Gly Gly Ser Ala
1               5                   10                  15

Ser

<210> SEQ ID NO 62
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 62

Gly Gly Gly Gly Ala Gly Gly Gly Gly
1               5

<210> SEQ ID NO 63

<400> SEQUENCE: 63

000

<210> SEQ ID NO 64
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 64

Gly Ser Gly Ser Gly Ser
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 65

Gly Ser Gly Ser Gly Ser Gly Ser Gly Ser
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 66

```
Gly Gly Gly Gly Ser Ala Ser
1               5

<210> SEQ ID NO 67
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 67

Ala Pro Ala Pro Ala Pro Ala Pro Ala Pro Ala Pro Ala Pro Ala Pro
1               5                   10                  15

Ala Pro Ala Pro
            20

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 68

Cys Pro Pro Cys
1

<210> SEQ ID NO 69
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 69

Gly Gly Gly Gly Ser
1               5

<210> SEQ ID NO 70
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 70

Gly Gly Gly Gly Ser Gly Gly Gly Gly Ser
1               5                   10

<210> SEQ ID NO 71
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: Synthetic Polypeptide
```

<400> SEQUENCE: 72

Gly Gly Gly Gly Ser Gly Gly Gly Ser Gly Gly Gly Gly Ser Gly
1               5                   10                  15

Gly Gly Gly Ser
            20

<210> SEQ ID NO 73
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 73

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 74
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 74

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 75
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 75

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly Gly
            20                  25                  30

Gly Gly Ser
        35

<210> SEQ ID NO 76
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 76

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly Gly
            20                  25                  30

Gly Gly Ser Gly Gly Gly Gly Ser
        35                  40

<210> SEQ ID NO 77
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 77

```
Gly Gly Ser Gly Gly Ser Gly Gly Gly Ser Gly Gly Gly Ser
1               5                   10                  15
```

<210> SEQ ID NO 78
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 78

```
Gly Gly Gly Gly Gly Gly Gly Gly
1               5
```

<210> SEQ ID NO 79
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 79

```
Gly Gly Gly Gly Gly Gly
1               5
```

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

```
Glu Ala Ala Ala Lys
1               5
```

<210> SEQ ID NO 81
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 81

```
Glu Ala Ala Ala Lys Glu Ala Ala Ala Lys
1               5                   10
```

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

```
Glu Ala Ala Ala Lys Glu Ala Ala Ala Lys Glu Ala Ala Ala Lys
1               5                   10                  15
```

```
<210> SEQ ID NO 83
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 83

Ala Glu Ala Ala Ala Lys Glu Ala Ala Ala Lys Ala
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 84

Ala Glu Ala Ala Ala Lys Glu Ala Ala Ala Lys Glu Ala Ala Ala Lys
1               5                   10                  15

Ala

<210> SEQ ID NO 85
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 85

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 86
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 86

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 87
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 87

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45
```

```
<210> SEQ ID NO 88
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 88

Pro Ala Pro Ala Pro
1               5

<210> SEQ ID NO 89
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 89

Lys Glu Ser Gly Ser Val Ser Ser Glu Gln Leu Ala Gln Phe Arg Ser
1               5                   10                  15

Leu Asp

<210> SEQ ID NO 90
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 90

Gly Ser Ala Gly Ser Ala Ala Gly Ser Gly Glu Phe
1               5                   10

<210> SEQ ID NO 91
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 91

Gly Gly Gly Ser Glu
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 92

Gly Ser Glu Ser Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 93

Gly Ser Glu Gly Ser
1               5
```

<210> SEQ ID NO 94
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 94

```
Gly Glu Gly Gly Ser Gly Glu Gly Ser Ser Gly Glu Gly Ser Ser
1               5                   10                  15

Glu Gly Gly Ser Glu Gly Gly Ser Glu Gly Gly Ser Glu
            20                  25                  30

Gly Gly Ser
        35
```

<210> SEQ ID NO 95
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 95

```
Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Ile Glu Gly Arg Met Asp
225                 230
```

<210> SEQ ID NO 96
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 96

```
Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230
```

<210> SEQ ID NO 97
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 97

```
Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
```

```
                100                 105                 110
Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 98
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 98

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Ile Glu Gly Arg Met Asp
```

```
<210> SEQ ID NO 99
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 99
```

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

```
<210> SEQ ID NO 100
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 100
```

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

-continued

```
Val His Asn Ala Lys Thr Lys Pro Arg Glu Glu Gln Phe Asn Ser Thr
65              70              75                  80

Tyr Arg Val Val Ser Val Leu Thr Val Leu His Gln Asp Trp Leu Ser
            85              90                  95

Gly Lys Glu Tyr Lys Cys Lys Val Ser Ser Lys Gly Leu Pro Ser Ser
            100             105             110

Ile Glu Lys Thr Ile Ser Asn Ala Thr Gly Gln Pro Arg Glu Pro Gln
        115             120             125

Val Tyr Thr Leu Pro Pro Ser Gln Glu Glu Met Thr Lys Asn Gln Val
    130             135             140

Ser Leu Thr Cys Leu Val Lys Gly Phe Tyr Pro Ser Asp Ile Ala Val
145             150             155             160

Glu Trp Glu Ser Asn Gly Gln Pro Glu Asn Asn Tyr Lys Thr Thr Pro
                165             170             175

Pro Val Leu Asp Ser Asp Gly Ser Phe Phe Leu Tyr Ser Arg Leu Thr
            180             185             190

Val Asp Lys Ser Arg Trp Gln Glu Gly Asn Val Phe Ser Cys Ser Val
        195             200             205

Leu His Glu Ala Leu His Asn His Tyr Thr Gln Lys Ser Leu Ser Leu
    210             215             220

Ser Leu Gly Lys Ile Glu Gly Arg Met Asp
225             230
```

METHODS OF MAKING AND USING EXTRACELLULAR DOMAIN-BASED CHIMERIC PROTEINS

PRIORITY

This application is a 371 national stage application of PCT/US18/20040 filed Feb. 27, 2018, which claims the benefit of, and priority to, U.S. Provisional Application No. 62/464,002, filed Feb. 27, 2017, the contents of both of which are hereby incorporated by reference in its entirety.

DESCRIPTION OF THE TEXT FILE SUBMITTED ELECTRONICALLY

This application contains a sequence listing. It has been submitted electronically via EFS-Web as an ASCII text file entitled "SHK-001PC2_SequenceListing_ST25". The sequence listing is 149,084 bytes in size, and was created on or about Feb. 27, 2018. The sequence listing is hereby incorporated by reference in its entirety.

TECHNICAL FIELD

The present invention relates to, inter alia, compositions and methods, including chimeric proteins that find use in the treatment of disease, such as immunotherapies for cancer and autoimmunity.

BACKGROUND

Exceptional treatment for cancer have been evasive despite years of efforts. This is so, in part, because many cancers have developed mechanisms to avoid the immune system. Thus, there remains a need to develop therapeutics and treatment regimens that adequate engage multiple arms of the immune system to generate an anti-cancer immune response.

SUMMARY

Accordingly, in various aspects, the present invention provides for compositions and methods that are useful for cancer immunotherapy. For instance, the present invention, in part, relates to specific chimeric proteins that reverse or suppresses immune inhibitory signals while providing immune activating or co-stimulatory signals. Importantly, inter alia, the present invention provides for improved chimeric proteins that can maintain a stable and producible multimeric state based on, without wishing to be bound by theory, stabilization in a linker region including one or more disulfide bonds. Accordingly, the present compositions and methods overcome various deficiencies in producing bi-specific agents.

In some aspects, the chimeric protein is of a general structure of: N terminus-(a)-(b)-(c)-C terminus, where (a) is a first domain comprising an extracellular domain of a Type I transmembrane protein, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, where the linker connects the first domain and the second domain and optionally comprises one or more joining linkers as described herein.

Further, in various aspects, the present invention relates to methods of treating cancer by using a combination of the present chimeric proteins. For example, the present methods allow for regimens that modulate specific arms of the immune system, such as innate and adaptive immune responses, optionally in order.

In some aspects, there is provided a method of treating cancer, comprising administering to a subject in need thereof: (i) a first chimeric protein comprising a general structure of N terminus-(a)-(b)-(c)-C terminus, where: (a) is a first domain comprising an extracellular domain of a Type I transmembrane protein, (b) is a linker comprising at least one cysteine residue capable of forming a disulfide bond, and (c) is a second domain comprising an extracellular domain of a Type II transmembrane protein, and the first chimeric protein modulates the innate immune system; and (ii) a second chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the second chimeric protein modulates the adaptive immune system.

In some aspects, there is provided a method of treating cancer, comprising administering to a subject in need thereof: a second chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the second chimeric protein modulates the adaptive immune system, where the subject is undergoing or has undergone treatment with a first chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the first chimeric protein modulates the innate immune system.

In embodiments, first chimeric protein is administered before the second chimeric protein.

In embodiments, the first chimeric protein is administered after the second chimeric protein.

In embodiments, the first chimeric protein comprises at least one of: TIGIT, CSF1R, CD172a(SIRP1α), VSIG8, TIM3, 41BBL, CD40L, SIGLEC7, SIGLEC9, and LIGHT.

In embodiments, the second chimeric protein comprises at least one of: PD-1, TIM3, VSIG8, CD172a(SIRP1α), OX40L, GITRL, TL1A, and IL-2

In embodiments, the first chimeric protein and the second chimeric protein are independently selected from TIM3-Fc-OX40L, CD172a(SIRP1α)-Fc-CD40L, and CSF1R-Fc-CD40L.

In embodiments, TIM3-Fc-OX40L is administered before CD172a(SIRP1α)-Fc-CD40L. In embodiments, TIM3-Fc-OX40L is administered before CSF1R-Fc-CD40L. In embodiments, CD172a(SIRP1α)-Fc-CD40L is administered before TIM3-Fc-OX40L. In embodiments, CSF1R-Fc-CD40L is administered before TIM3-Fc-OX40L.

Any aspect or embodiment described herein can be combined with any other aspect or embodiment as disclosed herein.

BRIEF DESCRIPTION OF THE DRAWINGS

1C) may be engineered with transmembrane and intracellular domains removed and adjoined using a linker sequence (FIG. 1B) to generate a single chimeric protein wherein the extracellular domains of the Type I and Type II membrane proteins each face outward in a single chimeric protein. FIG. 1B depicts the linkage of a Type I and Type II membrane protein by removal of the transmembrane and intracellular domains of each protein, and where the liberated extracellular domains (ECD) from each protein have been adjoined by a linker sequence. The ECD in this depiction may include the entire amino acid sequence of a candidate Type I or Type II protein which is typically localized outside the cell membrane, or any portion thereof which retains binding to the intended receptor or ligand. FIG. 1D depicts adjoined extracellular domains in a linear construct wherein the extracellular domain of the Type I membrane protein faces the "left" side of the construct and the extracellular domain of the Type II membrane protein faces the "right" side of the construct.

FIG. 5A to FIG. 5C are tables of results showing the identified binding partners of human PD1-Fc-OX40L (FIG. 5A), of human CSF1R-Fc-CD40L (FIG. 5B), or of human CD172a(SIRPα)-Fc-CD40L (FIG. 5C) from a microarray containing about 6,000 human membrane proteins. In each case, the expected binding partners for each candidate molecule were identified by the screen. There was no evidence of non-specific binding to other human proteins, and binding to Galectin-1 is seen in the screen for all Fc-containing fusion proteins.

FIG. 7A shows binding of the human CD172a(SIRPα)-Fc-CD40L chimeric protein to hCD47 (top curve is HeLa/hCD47, bottom is HeLa Parental). FIG. 7B shows binding of the murine CD172a(SIRPα)-Fc-CD40L chimeric protein to mCD40 (top curve is CHOK1/mCD40, bottom curve is CHOK1 Parental).

FIG. 8A shows binding of the hCD172a(SIRPα)-Fc-CD40L chimeric protein to hCD47 (top curve is CD172A-Fc-CD40L (250 nM), bottom curve is CD172A-Fc-Cntl (250 nM)). FIG. 8B shows binding of the hCD172a(SIRPα)-Fc-CD40L chimeric protein to hFcγR1A (bottom curve is CD172a-Fc-CD40L (250 nM), top curve is CD172a-Fc-Cntl (250 nM)). FIG. 8C shows binding of the hCD172a(SIRPα)-Fc-CD40L chimeric protein to hFcRn (bottom curve is CD172a-Fc-CD40L (250 nM), top curve is CD172A-Fc-Cntl (250 nM)). FIG. 8D summarizes the affinity results in FIG. 8A to FIG. 8C. FIG. 8E shows binding affinity of the murine CD172a(SIRPα)-Fc-CD40L chimeric protein to mCD40.

FIG. 9A shows an ELISA-based blocking assay demonstrating the binding of hCD172a(SIRPα)-Fc-CD40L to cells overexpressing hCD47. FIG. 9B shows a schematic representation of the mode of action of a macrophage engulfment assay. FIG. 9C shows increased levels of double positive cells (phagocytosis) in response to CD172a(SIRPα)-Fc-CD40L chimeric protein in a concentration dependent manner.

FIG. 10A shows the detection of each individual domain of the mCD172a(SIRPα)-Fc-CD40L fusion construct using an anti-CD172a, anti-Fc, or anti-CD40L antibody. Untreated samples of the mCD172a(SIRPα)-Fc-CD40L chimeric protein, e.g., control, were loaded into lane 2 in all the blots (no β-mercaptoethanol or PNGase). Samples in lane 3 were treated with the reducing agent, β-mercaptoethanol, while samples in lane 4 were treated with PNGase. FIG. 10B shows ELISA assays to demonstrate the binding affinity of the different domains of mCD172a(SIRPα)-Fc-CD40L chimeric protein for their respective binding partners. In binding to CD47 (FIG. 10B, left side) the binding and detection of the mCD172a(SIRPα)-Fc-CD40L chimeric protein to CD47, the binding partner for CD172a (square symbols) were demonstrated. Recombinant mCD172a-mFc was used to generate a standard curve (circle symbols). In binding to CD40 (FIG. 10B, right side) the binding and detection of the mCD172a(SIRPα)-Fc-CD40L chimeric protein to the receptor CD40, the binding partner for CD40L (square symbols) were demonstrated. Recombinant mCD40L was used to generate a standard curve (circle symbols).

FIG. 11A shows the evolution of tumor size over forty-five days after tumor inoculation for each group. FIG. 11B shows the overall survival percentage of mice through fifty days after tumor inoculation (at day 50, the curves top to bottom are: CD172a-Fc-CD40L (150 μg×2), CD172a-Fc-CD40L (300 μg×2), αCD47/CD40, αCD40, αCD47 (0% survival by between days 30-35) and untreated (0% survival by between days 20-25). FIG. 11C summarizes the group sizes and treatment outcomes for each group.

FIG. 12A to FIG. 12F show in vivo functional assays of the mCD172a(SIRPα)-Fc-CD40L chimeric protein. Immune profiling was performed on tumor-bearing mice treated with the mCD172a(SIRPα)-Fc-CD40L chimeric protein. FIG. 12A shows changes in the CD4+ and CD8+ T-cell populations in the spleen in mice treated with the chimeric protein. FIG. 12B shows changes in the CD4+CD25− effector T cells or CD4+CD25+ regulatory T cells in the spleen of mice treated with the chimeric protein. FIG. 12C and FIG. 12D show changes in the CD4+ and CD8+ T-cell populations in the peripheral lymph nodes and tumor, respectively, in mice treated with the chimeric protein. FIG. 12E shows tetramer staining for determining the fraction of CD8+ T cells within splenocytes or tumor infiltrated lymphocytes (TIL) that recognized the AH1 tumor antigen natively expressed by CT26 tumors. FIG. 12F shows changes in the proportion of cells which upregulate IL-15 receptor alpha (IL15Rα), which is an indicator of CD40 activation. In each of FIG. 12A to FIG. 12F, the conditions from left to right are: untreated, αCD40/CD47, mCD172a (SIRPα)-Fc-CD40L (150 μg×2), mCD172a(SIRPα)-Fc-CD40L (300 μg×2).

In FIG. 26C and FIG. 26D, curves top to bottom at x axis point 2.5 are: PD1-Fc-OX40L, PD1-Fc/OX40L, OX40L-Fc, PD1-Fc/OX40L-Fc, PD1-Fc, and IgG control.

FIG. 27B and FIG. 27C show the overall survival percentage, and statistics, of mice and tumor rejection through forty days after tumor inoculation. In FIG. 27B, the different treatment conditions are identified as: untreated: "a", "e", and "h"; αPD-L1 (10F.9G2): "b"; αPD-1 (RMP1-14): "c"; αOX40 (OX86): "d"; PD-L1/OX40: "f"; αPD-1 (RMP1-14)/OX40: "g"; PD-1-Fc-OX40L (100 µg×2): "i"; PD-1-Fc-OX40L (150 µg×2): "j"; and PD-1-Fc-OX40L (300 µg×2): "k". FIG. 27D and FIG. 27E show immune profiling performed on CT26-tumor bearing mice treated with the murine PD-1-Fc-OX40L chimeric protein or antibodies (as monotherapies of αPD-1, αPD-L1, or αOX40 or as combination therapy of αPD-L1 and αOX40 or αPD-1 and αOX40). In both FIG. 27D and FIG. 27E, the order of test articles from left to right is: untreated, αPD-1 (RMP1-14), αPD-L1 (10F.9G2), αOX40 (OX86), αPD-1 (RMP1-14)/OX40, PD-L1/OX40, PD-1-Fc-OX40L (150 µg×2), and PD-1-Fc-OX40L (300 µg×2). In FIG. 27G, left two panels: untreated is the top curve. In FIG. 27G, third panel from left: curves top to bottom are untreated, αPD1 (2×100 µg), αPD-L1 (1×100 µg), and αPD-L1 (2×100 µg). In FIG. 27G, rightmost panel: curves top to bottom are untreated, αOX40/αPD-L1 (1×100 µg), αOX40/αPD-L1 (2×100 µg), αOX40/αPD1 (2×100 µg). In FIG. 27H, panel labelled "ARC Fusion Protein," curves are, top to bottom: untreated, PD1-Fc-OX40L (300 µg×2), and PD1-Fc-OX40L (150 µg×2). In FIG. 27H, panel labelled "OX40 Agonist," curves are, top to bottom: untreated and aOX86. In FIG. 27H, panel labelled "PD-1/L1 Blockade," curves are, top to bottom: untreated, aPD1, aPD-L1. In FIG. 27H, panel labelled "Antibody Combinations," curves are, top to bottom: untreated, aPD1/aOX86, aPD-L1/aOX86.

FIG. 28A to FIG. 28C show ELISA assays demonstrating binding affinity of the different domains of human PD-1-Fc-OX40L chimeric protein (also referred to as SL-279252) for their respective binding histograms partners. In FIG. 28C, for each concentration, left is OX40-His and right is HVEM-His.

FIG. 32A to 32G show in vitro functional assays of human PD-1-Fc-OX40L fusion protein. In FIG. 32C, the hPD-1-Fc-OX40L induced higher levels of secreted IL2 in PC3 cells (FIG. 32C, left bundle) than in HCC827 cells (FIG. 32C, right bundle). FIG. 32D is a flow cytometry analysis of cells taken from the T cell/tumor cell co-culture assays outlined in FIG. 32C. The left-most bars indicate the proportion of CD4+ or CD8+ cells expressing Ki67 (as an indicator of proliferation) in the absence of tumor cells. The second from left bars indicates the proportion of CD4+ or CD8+ cells expressing Ki67 in the presence of tumor cells but without ARC, whereas the third-from left and right-most bars indicate the proportion of CD4+ or CD8+ cells expressing Ki67 in the presence of 500 ng or 5 µg of ARC, respectively. FIG. 32F and FIG. 32G, the order of test articles in the inset histograms, left to right: media control, IgG control, PD1-Fc, OX40L-Fc, PD-1-Fc/OX40L-Fc, and PD-1-Fc-Ox40L.

FIG. 37A shows changes in the CD4+ and CD8+ T-cell populations in mice treated with the chimeric protein. FIG. 37B shows changes in the CD4+CD25− effector T cells or CD4+CD25+ regulatory T cells in mice treated with the chimeric protein. FIG. 37C shows tetramer staining to analyze the fraction of CD8+ T cells within splenocytes or tumor infiltrated lymphocytes (TIL) that recognized the AH1 tumor antigen natively expressed by CT26 tumors. In all of the panels, the left condition is untreated and the right condition is mTIM3-Fc-OX40L (150 µg×2).

FIG. 38A to FIG. 38C show results from in vivo tumor studies demonstrating that mTIM3-Fc-OX40L chimeric protein had significant anti-tumor activity in the CT26 mouse model. Mice were inoculated with CT26 tumors. When tumors reached 4-5 mm, mice were treated twice with 150 µg of mTIM3-Fc-OX40L chimeric protein or with control antibodies. FIG. 38A shows the evolution of tumor size over forty-five days after tumor inoculation for each group. FIG. 38B shows the overall survival percentage of mice through fifty days after tumor inoculation (TIM3-Fc-OX40L is the top curve). FIG. 38C summarizes the group sizes and treatment outcomes for each group.

FIG. 39 is a table showing joining linkers and Fc linkers that can be combined into exemplary modular linkers. The exemplary modular linkers shown can be combined with any herein-described Type I and Type II proteins and/or extracellular domains of a herein described Type I and Type II proteins to form a chimeric protein of the present invention.

DETAILED DESCRIPTION

Figure 1B:
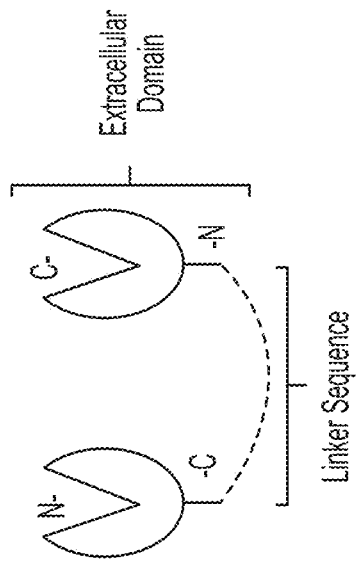
FIG. 1A to FIG. 1D show schematic illustrations of how a Type I and Type II membrane protein (FIG. 1A and FIG.

The present invention is based, in part, on the discovery that chimeric proteins can be engineered from the extracellular, or effector, regions of immune-modulating transmembrane proteins in a manner that exploits the orientations of these proteins (e.g., Type I versus Type II) and therefore allows the delivery of immune stimulatory and/or immune inhibitory signals, including, for example, masking an immune inhibitory signal and replacing it with an immune stimulatory signal in the treatment of cancer.

Chimeric Proteins

In some aspects, the chimeric protein is of a general structure of: N terminus-(a)-(b)-(c)-C terminus, where (a) is a first domain comprising an extracellular domain of a Type I transmembrane protein, (b) is a linker having at least one cysteine residue capable of forming a disulfide bond (including without limitation, hinge-CH2-CH3 Fc domain is derived from human IgG4), and (c) is a second domain comprising an extracellular domain of Type II transmembrane protein, where the linker connects the first domain and the second domain and optionally comprises one or more joining linkers as described herein, where one of the first and second extracellular domains is an immune inhibitory signal and one of the first and second extracellular domains is an immune stimulatory signal.

In embodiments, chimeric protein refers to a recombinant fusion protein, e.g., a single polypeptide having the extracellular domains described herein. For example, in embodiments, the chimeric protein is translated as a single unit in a cell. In embodiments, chimeric protein refers to a recombinant protein of multiple polypeptides, e.g., multiple extracellular domains described herein, that are linked to yield a single unit, e.g., in vitro (e.g., with one or more synthetic linkers described herein). In embodiments, the chimeric protein is chemically synthesized as one polypeptide or each domain may be chemically synthesized separately and then combined. In embodiments, a portion of the chimeric protein is translated and a portion is chemically synthesized.

In embodiments, an extracellular domain refers to a portion of a transmembrane protein which is capable of interacting with the extracellular environment. In embodiments, an extracellular domain refers to a portion of a transmembrane protein which is sufficient to bind to a ligand or receptor and effective transmit a signal to a cell. In embodiments, an extracellular domain is the entire amino acid sequence of a transmembrane protein which is external of a cell or the cell membrane. In embodiments, an extracellular domain is the that portion of an amino acid sequence of a transmembrane protein which is external of a cell or the cell membrane and is needed for signal transduction and/or ligand binding as may be assayed using methods know in the art (e.g., in vitro ligand binding and/or cellular activation assays).

In embodiments, an immune inhibitory signal refers to a signal that diminishes or eliminates an immune response. For example, in the context of oncology, such signals may diminish or eliminate antitumor immunity. Under normal physiological conditions, inhibitory signals are useful in the maintenance of self-tolerance (e.g., prevention of autoimmunity) and also to protect tissues from damage when the immune system is responding to pathogenic infection. For instance, without limitation, immune inhibitory signal may be identified by detecting an increase in cellular proliferation, cytokine production, cell killing activity or phagocytic activity when such an inhibitory signal is blocked.

In embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes. Specific examples include direct stimulation of TNF superfamily receptors such as OX40, LTbR, 4-1BB or TNFRSF25 using either receptor agonist antibodies or using chimeric proteins encoding the ligands for such receptors (OX40L, LIGHT, 4-1BBL, TL1A, respectively). Stimulation from any one of these receptors may directly stimulate the proliferation and cytokine production of individual T cell subsets. Another example includes direct stimulation of an immune inhibitory cell with through a receptor that inhibits the activity of such an immune suppressor cell. This would include, for example, stimulation of CD4+FoxP3+ regulatory T cells with a GITR agonist antibody or GITRL containing chimeric protein, which would reduce the ability of those regulatory T cells to suppress the proliferation of conventional CD4+ or CD8+ T cells. In another example, this would include stimulation of CD40 on the surface of an antigen presenting cell using a CD40 agonist antibody or a chimeric protein containing CD40L, causing activation of antigen presenting cells including enhanced ability of those cells to present antigen in the context of appropriate native costimulatory molecules, including those in the B7 or TNF superfamily. In another example, this would include stimulation of LTBR on the surface of a lymphoid or stromal cell using a LIGHT containing chimeric protein, causing activation of the lymphoid cell and/or production of pro-inflammatory cytokines or chemokines to further stimulate an immune response, optionally within a tumor.

Membrane proteins typically consist of an extracellular domain, one or a series of trans-membrane domains, and an intracellular domain. Without wishing to be bound by theory, the extracellular domain of a membrane protein is responsible for interacting with a soluble or membrane bound receptor or ligand. Without wishing to be bound by theory, the trans-membrane domain(s) are responsible for localizing a protein to the plasma membrane. Without wishing to be bound by theory, the intracellular domain of a membrane protein is responsible for coordinating interactions with cellular signaling molecules to coordinate intracellular responses with the extracellular environment (or visa-versa). There are two types of single-pass membrane proteins, those with an extracellular amino terminus and intracellular carboxy terminus (Type I) and those with an extracellular carboxy terminus and intracellular amino terminus (Type II). Both Type I and Type II membrane proteins can be either receptors or ligands. For Type I membrane proteins, the amino terminus of the protein faces outside the cell, and therefore contains the functional domains that are responsible for interacting with other binding partners (either ligands or receptors) in the extracellular environment. For Type II membrane proteins, the carboxy terminus of the protein faces outside the cell, and therefore contains the functional domains that are responsible for interacting with other binding partners (either ligands or receptors) in the extracellular environment. Thus, these two types of proteins have opposite orientations to each other.

Figure 1D:
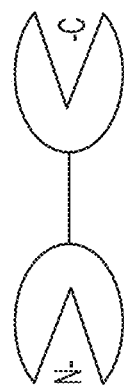
Figure 1A:
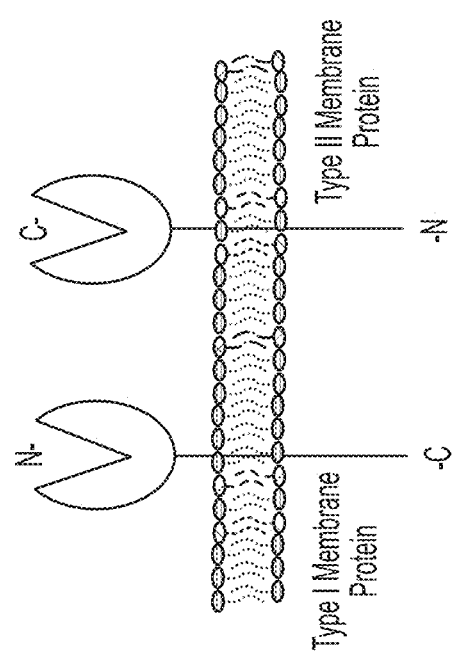
Figure 1C:
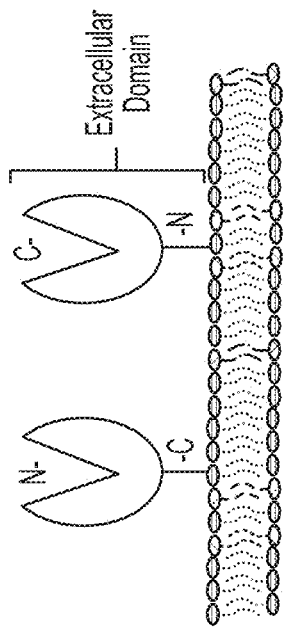

Because the outward facing domains of Type I and Type II membrane proteins are opposite, it is possible to link the extracellular domains of a Type I and Type II membrane protein such that the 'outward facing' domains of the molecules are also in opposing orientation to each other (FIG. 1D). The resulting construct would therefore consist of the extracellular domain of a Type I membrane protein on the 'left' side of the molecule, connected to the extracellular domain of a Type II membrane protein on the 'right' side of the molecule using a linker sequence. This construct could be produced by cloning of these three fragments (the extracellular domain of a Type I protein, followed by a linker sequence, followed by the extracellular domain of a Type II protein) into a vector (plasmid, viral or other) wherein the amino terminus of the complete sequence corresponded to the 'left' side of the molecule containing the Type I protein and the carboxy terminus of the complete sequence corresponded to the 'right' side of the molecule containing the Type II protein. Accordingly, in embodiments, the present chimeric proteins are engineered as such.

In embodiments, the extracellular domain may be used to produce a soluble protein to competitively inhibit signaling by that receptor's ligand. In embodiments, the extracellular domain may be used to provide artificial signaling.

In embodiments, the extracellular domain of a Type I transmembrane protein is an immune inhibitory signal. In embodiments, the extracellular domain of a Type II transmembrane protein is an immune stimulatory signal.

In embodiments, the present chimeric proteins comprise an extracellular domain of a Type I transmembrane protein, or a functional fragment thereof. In embodiments, the present chimeric proteins comprise an extracellular domain of a Type II transmembrane protein, or a functional fragment thereof. In embodiments, the present chimeric proteins comprise an extracellular domain of a Type I transmembrane protein, or a functional fragment thereof, and an extracellular domain of a Type II transmembrane protein, or a functional fragment thereof.

In embodiments, the present chimeric proteins may be engineered to target one or more molecules that reside on human leukocytes including, without limitation, the extracellular domains (where applicable) of SLAMF4, IL-2 R α, 4-1BB/TNFRSF9, IL-2 R β, ALCAM, BTLA, B7-1, IL-4 R, B7-H3, BLAME/SLAMFS, CEACAM1, IL-6 R, IL-7 Rα, IL-10R α, IL-1 0 R β, IL-12 R β1, IL-12 R β2, CD2, IL-13 R α1, IL-13, CD3, CD4, ILT2/CDS5j, ILT3/CDS5k, ILT4/CDS5d, ILT5/CDS5a, Integrin α 4/CD49d, CDS, Integrin α E/CD103, CD6, Integrin α M/CD 11 b, CDS, Integrin α X/CD11c, Integrin β2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R β, Osteopontin, CRACC/SLAMF7, PD-1, CRTAM, PSGL-1, CTLA-4, RANK/TNFRSF11A, CX3CR1, CX3CL1, L-Selectin, SIRPβ1, SLAM, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γR2, TSLP, IL-1 R1, LIGHT, LTBR (TNFRSF3) and TSLP R.

The activation of regulatory T cells is critically influenced by costimulatory and coinhibitory signals. Two major families of costimulatory molecules include the B7 and the tumor necrosis factor (TNF) families. These molecules bind to receptors on T cells belonging to the CD28 or TNF receptor families, respectively. Many well-defined coinhibitors and their receptors belong to the B7 and CD28 families.

In embodiments, the present chimeric proteins may be engineered to target one or more molecules involved in immune inhibition, including for example: CSF1R, CTLA-4, PD-L1, PD-L2, PD-1, BTLA, HVEM, TIM3, GAL9, VISTA/VSIG8, KIR, 2B4, TIGIT, CD160 (also referred to as BY55), CHK 1 and CHK2 kinases, A2aR, CEACAM (e.g., CEACAM-1, CEACAM-3 and/or CEACAM-5), and various B-7 family ligands (including, but are not limited to, B7-1, B7-2, B7-DC, B7-H1, B7-H2, B7-H3, B7-H4, B7-H5, B7-H6 and B7-H7).

In embodiments, the chimeric protein of the present invention comprises an extracellular domain of an immune inhibitory agent, including without limitation, one or more of TIM-3, BTLA, PD-1, CSF1R, CTLA-4, CD244, CD160, TIGIT, CD172a(SIRP1α), 2B4, VISTA, VSIG8, CD200 and TMIGD2.

In embodiments, the chimeric protein of the present invention comprises an extracellular domain of a Type I membrane protein which has immune inhibitory properties. In embodiments, the chimeric protein is engineered to disrupt, block, reduce, and/or inhibit the transmission of an immune inhibitory signal.

In embodiments, the chimeric protein of the present invention comprises an extracellular domain of an immune stimulatory signal is one or more of 4-1BBL, OX-40 ligand (OX-40L), LIGHT (CD258), GITR ligand (GITRL), CD70, CD30 ligand, CD40 ligand (CD40L), CD137 ligand, TRAIL, and TL1A.

In embodiments, the chimeric protein simulates binding of an inhibitory signal ligand to its cognate receptor (e.g., PD-1 to PD-L1 or PD-L2; e.g., CD172a(SIRP1α) to CD47; e.g., CD115 to CSF1; e.g., TIM-3 to galectin-9 or phosphatidylserine) but inhibits the inhibitory signal transmission to an immune cell (e.g., a T cell, macrophage or other leukocyte).

In embodiments, the chimeric protein comprises an immune inhibitory receptor extracellular domain and an immune stimulatory ligand extracellular domain which can, without limitation, deliver an immune stimulation to a T cell while masking a tumor cell's immune inhibitory signals. In embodiments, the chimeric protein delivers a signal that has the net result of T cell activation.

In embodiments, the chimeric protein comprises an immune inhibitory signal which is an ECD of a receptor of an immune inhibitory signal and this acts on a tumor cell that bears a cognate ligand of the immune inhibitory signal. In embodiments, the chimeric protein comprises an immune stimulatory signal which is an ECD of a ligand of an immune stimulatory signal and this acts on a T cell that bears a cognate receptor of the immune stimulatory signal. In embodiments, the chimeric protein comprises both (i) an immune inhibitory signal which is a receptor of an immune inhibitory signal and this acts on a tumor cell that bears a cognate ligand of the immune inhibitory signal and (ii) an immune stimulatory signal which is a ligand of an immune stimulatory signal and this acts on a T cell that bears a cognate receptor of the immune stimulatory signal.

In embodiments, the chimeric protein of the present invention comprises an extracellular domain of one or more of the immune-modulating agents described in Mahoney, *Nature Reviews Drug Discovery* 2015:14; 561-585, the entire contents of which are hereby incorporated by reference.

In embodiments, a chimeric protein is capable of binding murine ligand(s)/receptor(s).

In embodiments, a chimeric protein is capable of binding human ligand(s)/receptor(s)

In embodiments, the chimeric protein of the present invention comprises an extracellular domain of a Type II membrane protein which has immune stimulatory properties. In embodiments, the chimeric protein is engineered to enhance, increase, and/or stimulate the transmission of an immune stimulatory signal.

In embodiments, the chimeric protein comprises the extracellular domain of the immune inhibitory agent PD-1 and is paired with an immune stimulatory agent as follows: PD-1/4-1BBL; PD-1/OX-40L; PD-1/LIGHT; PD-1/GITRL; PD-1/CD70; PD-1/CD30L; PD-1/CD40L; and PD-1/TL1A. In embodiments the chimeric protein is PD-1-Fc-LIGHT or PD-1-Fc-OX40L, in which the Fc represents a linker that comprises at least a portion of an Fc domain of an antibody and which comprises at least one cysteine residue capable of forming a disulfide bond.

In an embodiment, the chimeric protein comprises the extracellular domain of the immune inhibitory agent PD-1 and is paired with the immune stimulatory agent OX-40L. In embodiments, the chimeric protein binds to human PD-L1 or PD-L2 with a $K_D$ of about 1 nM to about 5 nM, for example, about 1 nM, about 1.5 nM, about 2 nM, about 2.5 nM, about 3 nM, about 3.5 nM, about 4 nM, about 4.5 nM, or about 5 nM. In embodiments, the chimeric protein binds to human PD-L1 with a $K_D$ of about 5 nM to about 15 nM, for example, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 10.5 nM, about 11 nM, about 11.5 nM, about 12 nM, about 12.5 nM, about 13 nM, about 13.5 nM, about 14 nM, about 14.5 nM, or about 15 nM.

In embodiments, the chimeric protein exhibits enhanced stability and protein half-life. In embodiments, the chimeric protein binds to FcRn with high affinity. In embodiments, the chimeric protein may bind to FcRn with a $K_D$ of about 1 nM to about 80 nM. For example, the chimeric protein may bind to FcRn with a $K_D$ of about 1 nM, about 2 nM, about 3 nM, about 4 nM, about 5 nM, about 6 nM, about 7 nM, about 8 nM, about 9 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 71 nM, about 72 nM, about 73 nM, about 74 nM, about 75 nM, about 76 nM, about 77 nM, about 78 nM, about 79 nM, or about 80 nM. In an embodiment, the chimeric protein may bind to FcRn with a $K_D$ of about 9 nM. In embodiments, the chimeric protein does not substantially bind to other Fc receptors (i.e. other than FcRn) with effector function.

In embodiments, the chimeric protein comprises the extracellular domain of the immune inhibitory agent PD-L1 or PD-L2 and is paired with an immune stimulatory receptor as follows: PD-L1/4-1BB; PD-L1/OX-40; PD-L1/HVEM; PD-L1/GITR; PD-L1/CD27; PD-L1/CD28; PD-L1/CD30; PD-L1/CD40 and PD-L1/CD137.

In embodiments, the chimeric protein comprises the extracellular domain of the immune inhibitory agent PD-L2 and is paired with an immune stimulatory receptor as follows: PD-L2/4-1BB; PD-L2/OX-40; PD-L2/HVEM; PD-L2/GITR; PD-L2/CD27; PD-L2/CD28; PD-L2/CD30; PD-L2/CD40 and PD-L2/CD137.

In embodiments, the chimeric protein comprises the extracellular domain of the immune inhibitory agent TIM-3 and is paired with an immune stimulatory agent as follows: TIM-3/OX-40L; TIM-3/LIGHT; TIM-3/GITRL; TIM-3/CD70; TIM-3/CD30L; TIM-3/CD40L; TIM-3/CD137L; TIM-3/TL1A; and TIM-3/OX40L. In embodiments the chimeric protein is TIM3-Fc-OX40L, in which the Fc represents a linker that comprises at least a portion of an Fc domain of an antibody and which comprises at least one cysteine residue capable of forming a disulfide bond.

In embodiments, there is provided a method of treating a cancer or an inflammatory disease (e.g., any one of those described elsewhere herein) by administering to a subject a TIM3-Fc-OX40L chimeric protein, in which the Fc represents a linker that comprises at least a portion of an Fc domain of an antibody and which comprises at least one cysteine residue capable of forming a disulfide bond. In embodiments, the method generates a memory response which may, e.g., be capable of preventing relapse.

In embodiments, the chimeric protein comprises the extracellular domain of the immune inhibitory agent BTLA and is paired with an immune stimulatory agent as follows: BTLA/OX-40L; BTLA/LIGHT; BTLA/GITRL; BTLA/CD70; BTLA/CD30L; BTLA/CD40L; BTLA/CD137L; BTLA/TL1A; and BTLA/OX40L.

In embodiments, the chimeric protein comprises the extracellular domain of the immune inhibitory agent CD172a(SIRP1α) and is paired with an immune stimulatory agent as follows: CD172a(SIRP1α)/OX-40L; CD172a(SIRP1α)/LIGHT; CD172a(SIRP1α)/CD70; CD172a(SIRP1α)/CD30L; CD172a(SIRP1α)/CD40L; CD172a(SIRP1α)/CD137L; CD172a(SIRP1α)/TL1A; and CD172a(SIRP1α)/OX40L. In embodiments the chimeric protein is CD172a(SIRP1α)-Fc-CD40L or CD172a(SIRP1α)-Fc-LIGHT, in which the Fc represents a linker that comprises at least a portion of an Fc domain of an antibody and which comprises at least one cysteine residue capable of forming a disulfide bond.

In embodiments, there is provided a method of treating a cancer or an inflammatory disease (e.g., any one of those described elsewhere herein) by administering to a subject a CD172a(SIRPα)-Fc-CD40L chimeric protein, in which the Fc represents a linker that comprises at least a portion of an Fc domain of an antibody and which comprises at least one cysteine residue capable of forming a disulfide bond. In embodiments, the method generates a memory response which may, e.g., be capable of preventing relapse. In embodiments, the method includes a sustained therapeutic effect of the CD172a(SIRPα)-Fc-CD40L, e.g., due to binding of the extracellular domain components to their respective binding partners with slow off rates ($K_d$ or $K_{off}$) to optionally provide sustained negative signal masking effect and/or a longer positive signal effect, e.g., to allow an effector cell to be adequately stimulated for an anti-tumor effect.

In embodiments, the chimeric protein comprises the extracellular domain of the immune inhibitory agent CD115 and is paired with an immune stimulatory agent as follows: CD115/OX-40L; CD115/LIGHT; CD115/CD70; CD115/CD30L; CD115/CD40L; CD115/CD137L; CD115/TL1A; and CD115/OX40L.

In embodiments, the chimeric protein comprises the extracellular domain of the immune inhibitory agent TMIGD2 and is paired with an immune stimulatory agent as follows: TMIGD2/OX-40L; TMIGD2/LIGHT; TMIGD2/GITRL; TMIGD2/CD70; TMIGD2/CD30L; TMIGD2/CD40L; TMIGD2/CD137L; TMIGD2/TL1A; and TMIGD2/OX40L.

In embodiments, the chimeric protein comprises the extracellular domain of the immune inhibitory agent CD200 and is paired with an immune stimulatory agent as follows: CD200/OX-40L; CD200/LIGHT; CD200/GITRL; CD200/CD70; CD200/CD30L; CD200/CD40L; CD200/CD137L; CD200/TL1A; and CD200/OX40L.

In embodiments, the present chimeric proteins may comprises variants of the extracellular domains described herein, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequence of the extracellular domains, e.g., human extracellular domains, e.g., one or more of SEQ IDs NOs: 2, 4, 7, 10, 12, 15, 18, 21, 24, 29, 32, 34, 36, 42, and 44.

In embodiments, the chimeric protein of the present invention comprises an extracellular domain of TIM3 (SEQ ID NO: 2).

In embodiments, the chimeric protein of the present invention comprises an extracellular domain of PD-1 (SEQ ID NO: 7).

In embodiments, the chimeric protein of the present invention comprises an extracellular domain of CD172a (SIRP1α) (SEQ ID NO: 10).

In embodiments, the chimeric protein of the present invention comprises an extracellular domain of OX40L (SEQ ID NO: 4).

In embodiments, the chimeric protein of the present invention comprises an extracellular domain of CD40L (SEQ ID NO: 12).

In embodiments, the chimeric protein of the present invention comprises an extracellular domain of TIM3 (SEQ ID NO: 2) and the extracellular domain of OX40L (SEQ ID NO: 4).

In embodiments, the chimeric protein of the present invention comprises an extracellular domain of PD-1 (SEQ ID NO: 7) and the extracellular domain of OX40L (SEQ ID NO: 4).

In embodiments, the chimeric protein of the present invention comprises an extracellular domain of CD172a (SIRP1α) (SEQ ID NO: 10) and the extracellular domain of CD40L (SEQ ID NO: 12).

In embodiments, the chimeric protein of the present invention comprises the hinge-CH2-CH3 domain from a human IgG4 antibody sequence (SEQ ID NO: 45, 46, or 47).

In embodiments, a chimeric protein comprises a modular linker as shown in FIG. 39.

In embodiments, the chimeric protein of the present invention comprises an extracellular domain of TIM3 and the extracellular domain of OX40L, using the hinge-CH2-CH3 domain from a human IgG4 antibody sequence as a linker (this TIM3-Fc-OX40L chimera is SEQ ID NO: 5).

In embodiments, the chimeric protein of the present invention comprises an extracellular domain of PD-1 (SEQ ID NO: 7) and the extracellular domain of OX40L, using the hinge-CH2-CH3 domain from a human IgG4 antibody sequence as a linker (this PD-1-Fc-OX40L chimera is SEQ ID NO: 8).

In embodiments, the chimeric protein of the present invention comprises an extracellular domain of CD172a (SIRP1α) (SEQ ID NO: 10) and the extracellular domain of CD40L, using the hinge-CH2-CH3 domain from a human IgG4 antibody sequence as a linker (this CD172a(SIRP1α)-Fc-CD40L chimera is SEQ ID NO: 13).

In another embodiment, the chimeric protein of the present invention comprises the extracellular domain of PD-1 and the extracellular domain of TL1A (SEQ ID NO: 15).

Additional examples include a chimeric protein encoding the extracellular domain of BTLA, linked through an Fc to OX40L (SEQ ID NO: 19).

Another example is a chimeric protein incorporating the extracellular domain of TMIGD2 adjoined with an Fc linker sequence to the extracellular domain of human OX40L (SEQ ID NO: 22).

Another example is a chimeric protein incorporating the extracellular domain of CD172a(SIRPα) adjoined with an Fc linker sequence to the extracellular domain of human OX40L (SEQ ID NO: 26).

In embodiments, the chimeric protein of the present invention comprises an extracellular domain of CSF1R (SEQ ID NO: 29).

In embodiments, the chimeric protein of the present invention comprises an extracellular domain of CSF1R (SEQ ID NO: 29) and an extracellular domain of CD40L (SEQ ID NO: 12).

In embodiments, the chimeric protein of the present invention comprises an extracellular domain of CSF1R (SEQ ID NO: 29) and an extracellular domain of CD40L (SEQ ID NO: 12), using the hinge-CH2-CH3 domain from a human IgG4 antibody sequence as a linker (this CSF1R-Fc-CD40L chimera is SEQ ID NO: 30)

In embodiments, a chimeric protein can comprise an extracellular domain from a sequence identified herein combined with an extracellular domain from another sequence identified herein.

In embodiments, the present chimeric proteins may be variants described herein, for instance, the present chimeric proteins may have a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the present chimeric proteins, e.g. one or more of SEQ IDs Nos 5, 5, 8, 13, 16, 19, 22, 25, 26, 27, or 30.

In embodiments, the present chimeric proteins comprise an extracellular domain of a human Type I transmembrane protein as recited in TABLE 1 of PCT/US2016/054598, or a functional fragment thereof. In embodiments, the present chimeric proteins comprise an extracellular domain of a human Type II transmembrane protein as recited in TABLE 2 of PCT/US2016/054598, or a functional fragment thereof. In embodiments, the present chimeric proteins comprise an extracellular domain of a Type I transmembrane protein as recited in TABLE 1 of PCT/US2016/054598, or a functional fragment thereof, and an extracellular domain of a Type II transmembrane protein as recited in TABLE 2 of PCT/US2016/054598, or a functional fragment thereof. The entire contents of PCT/US2016/054598 are hereby incorporated by reference.

In embodiments, the chimeric protein may comprise an amino acid sequence having one or more amino acid mutations relative to any of the protein sequences described herein. In embodiments, the one or more amino acid mutations may be independently selected from substitutions, insertions, deletions, and truncations.

In embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the chimeric proteins by reference to the genetic code, including taking into account codon degeneracy.

In embodiments, the chimeric protein comprises a linker. In embodiments, the linker comprising at least one cysteine residue capable of forming a disulfide bond. As described elsewhere herein, such at least one cysteine residue capable of forming a disulfide bond is, without wishing to be bound by theory, responsible for maintain a proper multimeric state of the chimeric protein and allowing for efficient production.

In embodiments, there is provided a method of making a stable chimeric protein comprising adjoining a Type I and Type II transmembrane protein extracellular domain with a linker comprising at least one cysteine residue capable of forming a disulfide bond such that the resultant chimeric protein is properly folded and/or forms into a stable multimeric state.

In embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In embodiments, the linker is a synthetic linker such as PEG.

In embodiments, the linker is a polypeptide. In embodiments, the linker is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In embodiments, the linker is flexible. In another embodiment, the linker is rigid.

In embodiments, the linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100% glycines and serines).

In embodiments, the linker is a hinge region of an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In embodiments, the present linker comprises, one, or two, or three of the upper hinge region, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In embodiments, the linker of the present invention comprises one or more glycosylation sites.

In embodiments, the linker comprises an Fc domain of an antibody (e.g., of IgG, IgA, IgD, and IgE, inclusive of subclasses (e.g., IgG1, IgG2, IgG3, and IgG4, and IgA1 and IgA2)). In embodiments, the linker comprises a hinge-CH2-CH3 Fc domain derived from a human IgG4 antibody. In embodiments, the linker comprises a hinge-CH2-CH3 Fc domain derived from a human IgG1 antibody. In embodiments, the Fc domain exhibits increased affinity for and enhanced binding to the neonatal Fc receptor (FcRn). In embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In embodiments, the Fc domain linker contains one or more amino acid substitutions at amino acid residue 250, 252, 254, 256, 308, 309, 311, 416, 428, 433 or 434 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference), or equivalents thereof. In an embodiment, the amino acid substitution at amino acid residue 250 is a substitution with glutamine. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 308 is a substitution with threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 416 is a substitution with serine. In an embodiment, the amino acid substitution at amino acid residue 428 is a substitution with leucine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In embodiments, the Fc domain linker (e.g., comprising an IgG constant region) comprises one or more mutations such as substitutions at amino acid residue 252, 254, 256, 433, 434, or 436 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In embodiments, the modified humanized antibodies of the invention comprise an IgG constant region that contains one or more mutations at amino acid residues 250, 253, 307, 310, 380, 416, 428, 433, 434, and 435. Illustrative mutations include T250Q, M428L, T307A, E380A, I253A, H310A, R416S, M428L, H433K, N434A, N434F, N434S, and H435A. In an embodiment, the IgG constant region comprises a M428L/N434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or AAA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

Additional illustrative mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al., Nature (2014) 514:642-645, Grevys et al., Journal of Immunology. (2015), 194(11):5497-508, and U.S. Pat. No. 7,083,784, the entire contents of which are hereby incorporated by reference.

In embodiments, the linker comprises the amino acid sequence of SEQ ID NO: 45, or at least 90%, or 93%, or 95%, or 97%, or 98%, or 99% identity thereto. In embodiments, mutations are made to SEQ ID NO: 45 to increase stability and/or half-life. For instance, in embodiments, the linker has the amino acid sequence of SEQ ID NO: 46, or at least 90%, or 93%, or 95%, or 97%, or 98%, or 99% identity thereto. In embodiments, the linker comprises the amino acid sequence of SEQ ID NO: 47, or at least 90%, or 93%, or 95%, or 97%, or 98%, or 99% identity thereto.

Without wishing to be bound by theory, including a linker comprising at least a part of an Fc domain in a chimeric protein, helps avoid formation of insoluble and, likely, non-functional protein concatamers and/or aggregates. This is in part due to the presence of cysteines in the Fc domain which are capable of forming disulfide bonds between chimeric proteins.

An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants.

Further, one or more joining linkers may be employed to connect an Fc domain in a linker (e.g., one of SEQ ID NO: 45, SEQ ID NO: 46, or SEQ ID NO: 47 or at least 90%, or 93%, or 95%, or 97%, or 98%, or 99% identity thereto) and the extracellular domains. For example, any one of SEQ ID NO: 48, SEQ ID NO: 49, SEQ ID NO: 50, SEQ ID NO: 51, SEQ ID NO: 52, SEQ ID NO: 53, or variants thereof may connect an extracellular domain as described herein and a linker as described herein. Optionally, any one of SEQ ID NO: 48, SEQ ID NO: 49, SEQ ID NO: 50, SEQ ID NO: 51, SEQ ID NO: 52, SEQ ID NO: 53, or variants thereof are displaced between an extracellular domain as described herein and a linker as described herein. Optionally, any one of SEQ ID NOs: 45 to 94, or variants thereof are located between an extracellular domain as described herein and an Fc domain as described herein. In embodiments, a chimeric protein comprises one joining linker preceding an Fc domain and a second joining linker following the Fc domain; thus, a chimeric protein may comprise the following structure:

ECD 1-Joining Linker 1-Fc Domain-Joining Linker 2-ECD 2.

In embodiments, the first and second joining linkers may be different or they may be the same.

The amino acid sequences of illustrative linkers are provided in Table 1 below:

TABLE 1

Illustrative linkers
(Fc domain linkers and joining linkers)

| SEQ ID NO. | Sequence |
|---|---|
| 45 | APEFLGGPSVFLFPPKPKDTLMISRTPEVTCVVVDVSQED PEVQFNWYVDGVEVHNAKTKPREEQFNSTYRVVSVLTVLH QDWLSGKEYKCKVSSKGLPSSIEKTISNATGQPREPQVYT LPPSQEEMTKNQVSLTCLVKGFYPSDIAVEWESNGQPENN YKTTPPVLDSDGSFFLYSRLTVDKSSWQEGNVFSCSVMHE ALHNHYTQKSLSLSLGK |

TABLE 1-continued

Illustrative linkers
(Fc domain linkers and joining linkers)

| SEQ ID NO. | Sequence |
|---|---|
| 46 | APEFLGGPSVFLFPPKPKDQLMISRTPEVTCVVVDVSQED PEVQFNWYVDGVEVHNAKTKPREEQFNSTYRVVSVLTTPH SDWLSGKEYKCKVSSKGLPSSIEKTISNATGQPREPQVYT LPPSQEEMTKNQVSLTCLVKGFYPSDIAVEWESNGQPENN YKTTPPVLDSDGSFFLYSRLTVDKSSWQEGNVFSCSVLHE ALHNHYTQKSLSLSLGK |
| 47 | APEFLGGPSVFLFPPKPKDQLMISRTPEVTCVVVDVSQED PEVQFNWYVDGVEVHNAKTKPREEQFNSTYRVVSVLTVLH QDWLSGKEYKCKVSSKGLPSSIEKTISNATGQPREPQVYT LPPSQEEMTKNQVSLTCLVKGFYPSDIAVEWESNGQPENN YKTTPPVLDSDGSFFLYSRLTVDKSRWQEGNVFSCSVLHE ALHNHYTQKSLSLSLGK |
| 48 | SKYGPPCPSCP |
| 49 | SKYGPPCPPCP |
| 50 | SKYGPP |
| 51 | IEGRMD |
| 52 | GGGVPRDCG |
| 53 | IEGRMDGGGGAGGGG |
| 54 | GGGSGGGS |
| 55 | GGGSGGGSGGG |
| 56 | EGKSSGSGSESKST |
| 57 | GGSG |
| 58 | GGSGGGSGGGSG |
| 59 | EAAAKEAAAKEAAAK |
| 60 | EAAAREAAAREAAAREAAAR |
| 61 | GGGGSGGGGSGGGGSAS |
| 62 | GGGGAGGGG |
| 63 | GS or GGS or LE |
| 64 | GSGSGS |
| 65 | GSGSGSGSGS |
| 66 | GGGGSAS |
| 67 | APAPAPAPAPAPAPAPAPAP |
| 68 | CPPC |
| 69 | GGGGS |
| 70 | GGGGSGGGS |
| 71 | GGGGSGGGGSGGGGS |
| 72 | GGGGSGGGGSGGGGSGGGGS |
| 73 | GGGGSGGGGSGGGGSGGGGSGGGGS |
| 74 | GGGGSGGGGSGGGGSGGGGSGGGGSGGGGS |
| 75 | GGGGSGGGGSGGGGSGGGGSGGGGSGGGGSGGGGS |
| 76 | GGGGSGGGGSGGGGSGGGGSGGGGSGGGGSGGGGSGGGGS |
| 77 | GGSGGSGGGSGGGS |

TABLE 1-continued

Illustrative linkers
(Fc domain linkers and joining linkers)

| SEQ ID NO. | Sequence |
|---|---|
| 78 | GGGGGGGG |
| 79 | GGGGGG |
| 80 | EAAAK |
| 81 | EAAAKEAAAK |
| 82 | EAAAKEAAAKEAAAK |
| 83 | AEAAAKEAAAKA |
| 84 | AEAAAKEAAAKEAAAKA |
| 85 | AEAAAKEAAAKEAAAKEAAAKA |
| 86 | AEAAAKEAAAKEAAAKEAAAKEAAAKA |
| 87 | AEAAAKEAAAKEAAAKEAAAKALEAEAAAKEAAAKEAAAKEAAAKA |
| 88 | PAPAP |
| 89 | KESGSVSSEQLAQFRSLD |
| 90 | GSAGSAAGSGEF |
| 91 | GGGSE |
| 92 | GSESG |
| 93 | GSEGS |
| 94 | GEGGSGEGSSGEGSSSEGGGSEGGGSEGGGSEGGS |

Additional illustrative joining linkers include, but are not limited to, linkers having the sequence LE, GGGGS (SEQ ID NO: 69), (GGGGS)$_n$ (n=1-4) (SEQ ID NO: 69-72), (Gly)$_6$ (SEQ ID NO: 78), (Gly)$_6$ (SEQ ID NO: 79), (EAAAK)$_n$ (n=1-3) (SEQ ID NO: 80-82), A(EAAAK)$_n$A (n=2-5) (SEQ ID NO: 83-86), AEAAAKEAAAKA (SEQ ID NO: 83), A(EAAAK)$_4$ALEA(EAAAK)$_4$A (SEQ ID NO: 87), PAPAP (SEQ ID NO: 88), KESGSVSSEQLAQFRSLD (SEQ ID NO: 89), EGKSSGSGSESKST (SEQ ID NO: 56), GSAGSAAGSGEF (SEQ ID NO: 90), and (XP)$_n$, with X designating any amino acid, e.g., Ala, Lys, or Glu.

In embodiments, the joining linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100%) glycines and serines). For example, in embodiments, the joining linker is (Gly$_4$Ser)$_n$, where n is from about 1 to about 8, e.g., 1, 2, 3, 4, 5, 6, 7, or 8 (SEQ ID NO: 69 to SEQ ID NO: 76, respectively). In embodiments, the joining linker sequence is GGSGGSGGGGSGGGGS (SEQ ID NO: 77). Additional illustrative joining linkers include, but are not limited to, linkers having the sequence LE, (Gly)$_8$ (SEQ ID NO: 78), (Gly)$_6$ (SEQ ID NO: 79), (EAAAK)$_n$ (n=1-3) (SEQ ID NO: 80—SEQ ID NO: 82), A(EAAAK)$_n$A (n=2-5) (SEQ ID NO: 83-SEQ ID NO: 86), A(EAAAK)$_4$ALEA(EAAAK)$_4$A (SEQ ID NO: 43), PAPAP (SEQ ID NO: 44), KESGSVSSE-QLAQFRSLD (SEQ ID NO: 45), GSAGSAAGSGEF (SEQ ID NO: 87), and (XP)$_n$, with X designating any amino acid, e.g., Ala, Lys, or Glu. In embodiments, the joining linker is GGS.

In embodiments, the joining linker is one or more of GGGSE (SEQ ID NO: 91), GSESG (SEQ ID NO: 92), GSEGS (SEQ ID NO: 93), GEGGSGEGSSGEGSSSEGGGSEGGGSEGGGSEGGS (SEQ ID NO: 94), and a joining linker of randomly placed G, S, and E every 4 amino acid intervals.

In embodiments, a chimeric protein comprises a modular linker as shown in FIG. 39.

In embodiments, the linker may be flexible, including without limitation highly flexible. In embodiments, the linker may be rigid, including without limitation a rigid alpha helix.

In embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In embodiments, the present chimeric proteins are capable of, and can be used in methods comprising, promoting immune activation (e.g., against tumors). In embodiments, the present chimeric proteins are capable of, and can be used in methods comprising, suppressing immune inhibition (e.g., that allows tumors to survive). In embodiments, the present chimeric proteins provide improved immune activation and/or improved suppression of immune inhibition due to the proximity of signaling that is provided by the chimeric nature of the constructs.

In embodiments, the present chimeric proteins are capable of, or can be used in methods comprising, modulating the amplitude of an immune response, e.g., modulating the level of effector output. In embodiments, e.g., when used for the treatment of cancer, the present chimeric proteins alter the extent of immune stimulation as compared to immune inhibition to increase the amplitude of a T cell response, including, without limitation, stimulating increased levels of cytokine production, proliferation or target killing potential.

In embodiments the present chimeric proteins, in embodiments are capable of, or find use in methods involving, masking an inhibitory ligand on the surface of a tumor cell and replacing that immune inhibitory ligand with an immune stimulatory ligand. Accordingly, the present chimeric proteins, in embodiments are capable of, or find use in methods involving, reducing or eliminating an inhibitory immune signal and/or increasing or activating an immune stimulatory signal. For example, a tumor cell bearing an inhibitory signal (and thus evading an immune response) may be substituted for a positive signal binding on a T cell that can then attack a tumor cell. Accordingly, in embodiments, an inhibitory immune signal is masked by the present constructs and a stimulatory immune signal is activated. Such beneficial properties are enhanced by the single construct approach of the present chimeric proteins. For instance, the signal replacement can be effected nearly simultaneously and the signal replacement is tailored to be local at a site of clinical importance (e.g., the tumor microenvironment). Further embodiments apply the same principle to other chimeric protein constructs, such as, for example, (i) the extracellular domain of PD-1 and (ii) extracellular domain of GITRL; (i) the extracellular domain of BTLA and (ii) extracellular domain of OX40L; (i) the extracellular domain of TIGIT and (ii) extracellular domain of OX40L; (i) the extracellular domain of TIM3 and (ii) extracellular domain of OX40L; and (i) the extracellular domain of CD172a (SIRP1α) and (ii) extracellular domain of CD40L; and (i) the extracellular domain of CD115 and (ii) extracellular domain of CD40L; and (i) the extracellular domain of TIM3 and (ii) extracellular domain of OX40L; and (i) the extracellular domain of TIGIT and (ii) extracellular domain of OX40L; among others.

In embodiments, the present chimeric proteins are capable of, or find use in methods comprising, stimulating or enhancing the binding of immune stimulatory receptor/ligand pairs. Illustrative T cell costimulatory receptors and their ligands include OX-40:OX40-L, CD27:CD70, CD30:CD30-L, CD40:CD40-L; CD137:CD137-L, HVEM:LIGHT, GITR:GITR-L, TNFRSF25:TL1A, DR5:TRAIL, and BTLA:HVEM. In embodiments, the present chimeric proteins are capable of, or find use in methods comprising, inhibiting or reducing the binding of immune inhibitory receptor/ligand pairs. Illustrative T cell coinhibitory receptors and their ligands include, for example, CTLA-4:CD80/CD86, PD-1:PD-L1/PD-L2, BTLA:HVEM, TIM-3:galectin-9/phosphatidylserine, TIGIT/CD155 or CD112, VISTA/VSIG8, CD172a(SIRPα)/CD47, B7H3R/B7H3, B7H4R/B7H4, CD244/CD48, TMIGD2/HHLA2, among others.

In embodiments, the present chimeric protein blocks, reduces and/or inhibits PD-1 and PD-L1 or PD-L2 and/or the binding of PD-1 with PD-L1 or PD-L2. In embodiments, the present chimeric protein blocks, reduces and/or inhibits the activity of CTLA-4 and/or the binding of CTLA-4 with one or more of AP2M1, CD80, CD86, SHP-2, and PPP2R5A. In embodiments, the present chimeric protein increases and/or stimulates GITR and/or the binding of GITR with one or more of GITR ligand. In embodiments, the present chimeric protein increases and/or stimulates OX40 and/or the binding of OX40 with one or more of OX40 ligand.

In embodiments, the present chimeric proteins are capable of, or find use in methods involving, enhancing, restoring, promoting and/or stimulating immune modulation. In embodiments, the present chimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g., M1 macrophages), B cells, and dendritic cells. In embodiments, the present chimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In embodiments, the present chimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g., one or more of M1 and M2) into a tumor or the tumor microenvironment. In embodiments, the present chimeric proteins are capable of, or find use in methods involving, inhibiting and/or causing a decrease in recruitment of immunosuppressive cells (e.g., myeloid-derived suppressor cells (MDSCs), regulatory T cells (Tregs), tumor associated neutrophils (TANs), M2 macrophages, and tumor associated macrophages (TAMs)) to the tumor and/or tumor microenvironment (TME). In embodiments, the present therapies may alter the ratio of M1 versus M2 macrophages in the tumor site and/or TME to favor M1 macrophages.

In embodiments, the present chimeric proteins are capable of, and can be used in methods comprising, inhibiting and/or reducing T cell inactivation and/or immune tolerance to a tumor, comprising administering an effective amount of a chimeric protein described herein to a subject. In embodiments, the present chimeric proteins are able to increase the serum levels of various cytokines including, but not limited to, one or more of IFNγ, TNFα, IL-2, IL-4, IL-5, IL-6, IL-9, IL-10, IL-13, IL-17A, IL-17F, and IL-22. In embodiments, the present chimeric proteins are capable of enhancing IL-2, IL-4, IL-5, IL-10, IL-13, IL-17A, IL-22, TNFα or IFNγ in the serum of a treated subject. In embodiments, administration of the present chimeric protein is capable of enhancing TNFα secretion. In a specific embodiment, administration of the present chimeric protein is capable of enhancing superantigen mediated TNFα secretion by leukocytes. Detection of such a cytokine response may provide a method to determine the optimal dosing regimen for the indicated chimeric protein.

In embodiments, the present chimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. In addition, an anti-tumor CD8+ and/or CD4+ T cell refers to T cells that can mount an immune response to a tumor. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refers to receptors (e.g., CTLA-4, B7-H3, B7-H4, TIM-3) expressed on immune cells that prevent or inhibit uncontrolled immune responses.

In embodiments, the present chimeric proteins are capable of, and can be used in methods comprising, increasing a ratio of effector T cells to regulatory T cells. Illustrative effector T cells include ICOS$^+$ effector T cells; cytotoxic T cells (e.g., αβ TCR, CD3$^+$, CD8$^+$, CD45RO$^+$); CD4$^+$ effector T cells (e.g., αβ TCR, CD3$^+$, CD4$^+$, CCR7$^+$, CD62Lhi, IL-7R/CD127$^+$); CD8$^+$ effector T cells (e.g., αβ TCR, CD3$^+$, CD8$^+$, CCR7$^+$, CD62Lhi, IL-7R/CD127$^+$); effector memory T cells (e.g., CD62Llow, CD44$^+$, TCR, CD3$^+$, IL-7R/CD127$^+$, IL-15R$^+$, CCR7low); central memory T cells (e.g., CCR7$^+$, CD62L$^+$, CD27$^+$; or CCR7hi, CD44$^+$, CD62Lhi, TCR, CD3$^+$, IL-7R/CD127$^+$, IL-15R$^+$); CD62L$^+$ effector T cells; CD8$^+$ effector memory T cells (TEM) including early effector memory T cells (CD27$^+$CD62L$^-$) and late effector memory T cells (CD27$^-$ CD62L$^-$) (TemE and TemL, respectively); CD127($^+$)CD25(low/–) effector T cells; CD127($^-$)CD25(–) effector T cells; CD8$^+$ stem cell memory effector cells (TSCM) (e.g., CD44(low)CD62L(high)CD122(high) sca($^+$)); TH1 effector T-cells (e.g., CXCR3$^+$, CXCR6$^+$ and CCR5$^+$; or αβ TCR, CD3$^+$, CD4$^+$, IL-12R$^+$, IFNγR$^+$, CXCR3$^+$), TH2 effector T cells (e.g., CCR3$^+$, CCR4$^+$ and CCR8$^+$; or αβ TCR, CD3$^+$, CD4$^+$, IL-4R$^+$, IL-33R$^+$, CCR4$^+$, IL-17RB$^+$, CRTH2$^+$); TH9 effector T cells (e.g., αβ TCR, CD3$^+$, CD4$^+$); TH17 effector T cells (e.g., αβ TCR, CD3$^+$, CD4+, IL-23R$^+$, CCR6$^+$, IL-1R$^+$); CD4$^+$CD45RO$^+$ CCR7⁺ effector T cells, CD4⁺CD45RO⁺CCR7(⁻) effector T cells; and effector T cells secreting IL-2, IL-4 and/or IFN-γ. Illustrative regulatory T cells include ICOS⁺ regulatory T cells, CD4⁺CD25⁺FOXP3⁺ regulatory T cells, CD4⁺CD25⁺ regulatory T cells, CD4⁺CD25⁻ regulatory T cells, CD4⁺ CD25high regulatory T cells, TIM-3⁺PD-1⁺ regulatory T cells, lymphocyte activation gene-3 (LAG-3)⁺ regulatory T cells, CTLA-4/CD152⁺ regulatory T cells, neuropilin-1 (Nrp-1)⁺ regulatory T cells, CCR4⁺CCR8⁺ regulatory T cells, CD62L (L-selectin)⁺ regulatory T cells, CD45RBlow regulatory T cells, CD127low regulatory T cells, LRRC32/GARP⁺ regulatory T cells, CD39⁺ regulatory T cells, GITR⁺ regulatory T cells, LAP⁺ regulatory T cells, 1B11⁺ regulatory T cells, BTLA⁺ regulatory T cells, type 1 regulatory T cells (Tr1 cells),T helper type 3 (Th3) cells, regulatory cell of natural killer T cell phenotype (NKTregs), CD8⁺ regulatory T cells, CD8⁺CD28⁻ regulatory T cells and/or regulatory T-cells secreting IL-10, IL-35, TGF-β, TNF-α, Galectin-1, IFN-γ and/or MCP1.

In embodiments, the chimeric protein generates a memory response which may, e.g., be capable of preventing relapse or protecting the animal from a recurrence and/or preventing, or reducing the likelihood of, metastasis. Thus, an animal treated with the chimeric protein is later able to attack tumor cells and/or prevent development of tumors when exposed to the relevant antigen after an initial treatment with the chimeric protein. Accordingly, a chimeric protein of the present invention stimulates both active tumor destruction and also immune recognition of tumor antigens, which are essential in programming a memory response capable of preventing relapse.

In embodiments, the present chimeric proteins are capable of, and can be used in methods comprising, transiently stimulating effector T cells for no longer than about 12 hours, about 24 hours, about 48 hours, about 72 hours or about 96 hours or about 1 week or about 2 weeks. In embodiments, the present chimeric proteins are capable of, and can be used in methods comprising, transiently depleting or inhibiting regulatory T cells for no longer than about 12 hours, about 24 hours, about 48 hours, about 72 hours or about 96 hours or about 1 week or about 2 weeks. In embodiments, the transient stimulation of effector T cells and/or transient depletion or inhibition of regulatory T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In embodiments, the present chimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance. Further, in contrast to, for example, monoclonal antibodies, which are large multimeric proteins containing numerous disulfide bonds and post-translational modifications such as glycosylation, the present chimeric proteins are easier and more cost effective to manufacture.

In embodiments, the present chimeric protein is producible in a mammalian host cell as a secretable and fully functional single polypeptide chain.

In embodiments, the present chimeric protein unexpectedly provides binding of the extracellular domain components to their respective binding partners with slow off rates ($K_d$ or $K_{off}$). In embodiments, this provides an unexpectedly long interaction of the receptor to ligand and vice versa. Such an effect allows for a sustained negative signal masking effect. Further, in embodiments, this delivers a longer positive signal effect, e.g., to allow an effector cell to be adequately stimulated for an anti-tumor effect. For example, the present chimeric protein, e.g., via the long off rate binding allows sufficient signal transmission to provide T cell proliferation and allow for anti-tumor attack. By way of further example, the present chimeric protein, e.g., via the long off rate binding allows sufficient signal transmission to provide release of stimulatory signals, such as, for example, cytokines.

The stable synapse of cells promoted by the present agents (e.g., a tumor cell bearing negative signals and a T cell which could attack the tumor) provides spatial orientation to favor tumor reduction—such as positioning the T cells to attack tumor cells and/or sterically preventing the tumor cell from delivering negative signals, including negative signals beyond those masked by the chimeric protein of the invention.

In embodiments, this provides longer on-target (e.g., intra-tumoral) half-life ($t_{1/2}$) as compared to serum $t_{1/2}$ of the chimeric proteins. Such properties could have the combined advantage of reducing off-target toxicities which may be associated with systemic distribution of the chimeric proteins.

Further, in embodiments, the present chimeric proteins provide synergistic therapeutic effects as it allows for improved site-specific interplay of two immunotherapy agents.

In embodiments, the present chimeric proteins provide the potential for reducing off-site and/or systemic toxicity.

In embodiments, the present chimeric proteins provide reduced side-effects, e.g., GI complications, relative to current immunotherapies, e.g., antibodies directed to checkpoint molecules as described herein. Illustrative GI complications include abdominal pain, appetite loss, autoimmune effects, constipation, cramping, dehydration, diarrhea, eating problems, fatigue, flatulence, fluid in the abdomen or ascites, gastrointestinal (GI) dysbiosis, GI mucositis, inflammatory bowel disease, irritable bowel syndrome (IBS-D and IBS-C), nausea, pain, stool or urine changes, ulcerative colitis, vomiting, weight gain from retaining fluid, and/or weakness Diseases; Methods of Treatment, and Patient Selections In embodiments, the present invention pertains to cancers and/or tumors; for example, the treatment or prevention of cancers and/or tumors. As described elsewhere herein, the treatment of cancer may involve in embodiments, modulating the immune system with the present chimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In embodiments, the chimeric protein is used to treat a subject that has a treatment-refractory cancer. In embodiments, the chimeric protein is used to treat a subject that is refractory to one or more immune-modulating agents. For example, in embodiments, the chimeric protein is used to treat a subject that presents no response to treatment, or even progress, after 12 weeks or so of treatment. For instance, in embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL3280A (ROCHE)-refractory patients. For instance, in embodiments, the subject is refractory to an anti-CTLA-4 agent, e.g., ipilimumab (YERVOY)-refractory patients (e.g., melanoma patients). Accordingly, in embodiments the present invention provides methods of cancer treatment that rescue patients that are non-responsive to various therapies, including monotherapy of one or more immune-modulating agents.

In embodiments, the present invention provides chimeric proteins which target a cell or tissue within the tumor microenvironment. In embodiments, the cell or tissue within the tumor microenvironment expresses one or more targets or binding partners of the chimeric protein. The tumor microenvironment refers to the cellular milieu, including cells, secreted proteins, physiological small molecules, and blood vessels in which the tumor exists. In embodiments, the cells or tissue within the tumor microenvironment are one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor. In embodiments, the present chimeric protein targets a cancer cell. In embodiments, the cancer cell expresses one or more of targets or binding partners of the chimeric protein.

In an illustrative embodiment, the chimeric protein of the invention may target a cell (e.g., cancer cell or immune cell) that expresses PD-L1 and/or PD-L2. In an illustrative embodiment, the chimeric protein may target a cell (e.g., cancer cell or immune cell) that expresses OX-40. In an illustrative embodiment, the chimeric protein may target a cell (e.g., cancer cell or immune cell) that expresses GITR. In an illustrative embodiment, the chimeric protein may target a cell (e.g., cancer cell or immune cell) that expresses 4-1BB. In an illustrative embodiment, the chimeric protein may target a cell (e.g., cancer cell or immune cell) that expresses CD40. In an illustrative embodiment, the chimeric protein may target a cell (e.g., cancer cell or immune cell) that expresses VISTA. In an illustrative embodiment, the chimeric protein may target a cell (e.g., cancer cell or immune cell) that expresses CSF1. In an illustrative embodiment, the chimeric protein may target a cell (e.g., cancer cell or immune cell) that expresses IL-34. In an illustrative embodiment, the chimeric protein may target a cell (e.g., cancer cell or immune cell) that expresses CD47. In an illustrative embodiment, the chimeric protein may target a cell (e.g., cancer cell, stromal cell or immune cell) that expresses galectin-9 and/or phosphatidylserine.

In embodiments, the present methods provide treatment with the chimeric protein in a patient who is refractory to an additional agent, such "additional agents" being described elsewhere herein, inclusive, without limitation, of the various chemotherapeutic agents described herein.

In embodiments, the chimeric proteins are used to treat, control or prevent one or more inflammatory diseases or conditions. Non-limiting examples of inflammatory diseases include acne vulgaris, acute inflammation, allergic rhinitis, asthma, atherosclerosis, atopic dermatitis, autoimmune disease, autoinflammatory diseases, autosomal recessive spastic ataxia, bronchiectasis, celiac disease, chronic cholecystitis, chronic inflammation, chronic prostatitis, colitis, diverticulitis, familial eosinophilia (fe), glomerulonephritis, glycerol kinase deficiency, hidradenitis suppurativa, hypersensitivities, inflammation, inflammatory bowel diseases, inflammatory pelvic disease, interstitial cystitis, laryngeal inflammatory disease, Leigh syndrome, lichen planus, mast cell activation syndrome, mastocytosis, ocular inflammatory disease, otitis, pain, pelvic inflammatory disease, reperfusion injury, respiratory disease, restenosis, rheumatic fever, rheumatoid arthritis, rhinitis, sarcoidosis, septic shock, silicosis and other pneumoconioses, transplant rejection, tuberculosis, and vasculitis.

In embodiments, the inflammatory disease is an autoimmune disease or condition, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In some aspects, the present chimeric agents are used to eliminate intracellular pathogens. In some aspects, the present chimeric agents are used to treat one or more infections. In embodiments, the present chimeric proteins are used in methods of treating viral infections (including, for example, HIV and HCV), parasitic infections (including, for example, malaria), and bacterial infections. In embodiments, the infections induce immunosuppression. For example, HIV infections often result in immunosuppression in the infected subjects. Accordingly, as described elsewhere herein, the treatment of such infections may involve, in embodiments, modulating the immune system with the present chimeric proteins to favor immune stimulation over immune inhibition. Alternatively, the present invention provides methods for treating infections that induce immunoactivation. For example, intestinal helminth infections have been associated with chronic immune activation. In these embodiments, the treatment of such infections may involve modulating the immune system with the present chimeric proteins to favor immune inhibition over immune stimulation.

In embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In embodiments, the viral infection is caused by a virus of family Flaviviridae. In embodiments, the virus of family Flaviviridae is selected from Yellow Fever Virus, West Nile virus, Dengue virus, Japanese Encephalitis Virus, St. Louis Encephalitis Virus, and Hepatitis C Virus. In embodiments, the viral infection is caused by a virus of family Picornaviridae, e.g., poliovirus, rhinovirus, coxsackievirus. In embodiments, the viral infection is caused by a member of Orthomyxoviridae, e.g., an influenza virus. In embodiments, the viral infection is caused by a member of Retroviridae, e.g., a lentivirus. In embodiments, the viral infection is caused by a member of Paramyxoviridae, e.g., respiratory syncytial virus, a human parainfluenza virus, rubulavirus (e.g., mumps virus), measles virus, and human metapneumovirus. In embodiments, the viral infection is caused by a member of Bunyaviridae, e.g., hantavirus. In embodiments, the viral infection is caused by a member of Reoviridae, e.g., a rotavirus.

In embodiments, the present invention provides methods of treating parasitic infections such as protozoan or helminths infections. In embodiments, the parasitic infection is by a protozoan parasite. In embodiments, the oritiziab parasite is selected from intestinal protozoa, tissue protozoa, or blood protozoa. Illustrative protozoan parasites include, but are not limited to, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis,* and *Histomonas meleagridis*. In embodiments, the parasitic infection is by a helminthic parasite such as nematodes (e.g., Adenophorea). In embodiments, the parasite is selected from Secementea (e.g., *Trichuris trichiura, Ascaris lumbricoides, Enterobius vermicularis, Ancylostoma duodenale, Necator americanus, Strongyloides stercoralis, Wuchereria bancrofti, Dracunculus medinensis*). In embodiments, the parasite is selected from trematodes (e.g., blood flukes, liver flukes, intestinal flukes, and lung flukes). In embodiments, the parasite is selected from: *Schistosoma mansoni, Schistosoma haematobium, Schistosoma japonicum, Fasciola hepatica, Fasciola gigantica, Heterophyes heterophyes, Paragonimus westermani*. In embodiments, the parasite is selected from cestodes (e.g., *Taenia solium, Taenia saginata, Hymenolepis nana, Echinococcus granulosus*).

In embodiments, the present invention provides methods of treating bacterial infections. In embodiments, the bacterial infection is by gram-positive bacteria, gram-negative bacteria, aerobic and/or anaerobic bacteria. In embodiments, the bacteria is selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms. In embodiments, the bacteria is selected from, but not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bor-*

*detella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis,* or *Staphylococcus saccharolyticus.*

In some aspects, the present chimeric agents are used to treat one or more autoimmune diseases or disorders. In embodiments, the treatment of an autoimmune disease or disorder may involve modulating the immune system with the present chimeric proteins to favor immune inhibition over immune stimulation. Illustrative autoimmune diseases or disorders treatable with the present chimeric proteins include those in which the body's own antigens become targets for an immune response, such as, for example, rheumatoid arthritis, systemic lupus erythematosus, diabetes mellitus, ankylosing spondylitis, Sjögren's syndrome, inflammatory bowel diseases (e.g., colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause Type I hypersensitivity reactions), and vasculitis.

In still another other aspect, the present invention is directed toward methods of treating and preventing T cell-mediated diseases and disorders, such as, but not limited to diseases or disorders described elsewhere herein and inflammatory disease or disorder, graft-versus-host disease (GVHD), transplant rejection, and T cell proliferative disorder. Specific examples of Type I ECD domains with utility in this method of use include but are not limited to: TNFRSF1b, BTNL2, PD-L1, PD-L2, CTLA-4, B7-H3, B7-H4, CD40, OX40, CD137, among others.

In some aspects, the present chimeric agents are used in methods of activating a T cell, e.g., via the extracellular domain having an immune stimulatory signal.

In some aspects, the present chimeric agents are used in methods of preventing the cellular transmission of an immunosuppressive signal.

Combination Therapies and Conjugation

In embodiments, the invention provides for chimeric proteins and methods that further comprise administering an additional agent to a subject. In embodiments, the invention pertains to co-administration and/or co-formulation. Any of the compositions described herein may be co-formulated and/or co-administered.

In embodiments, any chimeric protein described herein acts synergistically when co-administered with another agent and is administered at doses that are lower than the doses commonly employed when such agents are used as monotherapy. In embodiments, any agent referenced herein may be used in combination with any of the chimeric proteins described herein.

In embodiments, any of the chimeric proteins disclosed herein may be co-administered with another chimeric protein disclosed herein. Without wishing to be bound by theory, it is believed that a combined regimen involving the administration of one or more chimeric proteins which induce an innate immune response and one or more chimeric proteins which induce an adaptive immune response may provide synergistic effects (e.g., synergistic anti-tumor effects).

In some aspects, there is provided a method of treating cancer, comprising administering to a subject in need thereof: (i) a first chimeric protein comprising a general structure of N terminus-(a)-(b)-(c)-C terminus, where: (a) is a first domain comprising an extracellular domain of a Type I transmembrane protein, (b) is a linker comprising at least one cysteine residue capable of forming a disulfide bond, and (c) is a second domain comprising an extracellular domain of a Type II transmembrane protein, and the first chimeric protein modulates the innate immune system; and (ii) a second chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the second chimeric protein modulates the adaptive immune system.

In some aspects, there is provided a method of treating cancer, comprising administering to a subject in need thereof: a second chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the second chimeric protein modulates the adaptive immune system, where the subject is undergoing or has undergone treatment with a first chimeric protein comprising a general structure of N terminus-(a)-(b)-(c)-C terminus, where (a) is a first domain comprising an extracellular domain of a Type I transmembrane protein, (b) is a linker comprising at least one cysteine residue capable of forming a disulfide bond, and (c) is a second domain comprising an extracellular domain of Type II transmembrane protein, and the first chimeric protein modulates the innate immune system.

In embodiments, first chimeric protein is administered before the second chimeric protein.

In embodiments, the first chimeric protein is administered after the second chimeric protein.

In embodiments, the first chimeric protein comprises at least one of: TIGIT, CSF1R, CD172a(SIRP1α), VSIG8, TIM3, 41BBL, CD40L, SIGLEC7, SIGLEC9 LIGHT.

In embodiments, the second chimeric protein comprises at least one of: PD-1, TIM3, VSIG8, CD172a(SIRP1α), OX40L, GITRL, TL1A, IL-2

In embodiments, the first chimeric protein and the second chimeric protein are independently selected from TIM3-Fc-OX40L, CD172a(SIRP1α)-Fc-CD40L, and CSF1R-Fc-CD40L.

In embodiments, TIM3-Fc-OX40L is administered before CD172a(SIRP1α)-Fc-CD40L. In embodiments, TIM3-Fc-OX40L is administered before CSF1R-Fc-CD40L. In embodiments, CD172a(SIRP1α)-Fc-CD40L is administered before TIM3-Fc-OX40L. In embodiments, CSF1R-Fc-CD40L is administered before TIM3-Fc-OX40L.

In embodiments, the first chimeric protein and/or the second chimeric protein causes activation of antigen presenting cells.

In embodiments, the first chimeric protein and/or the second chimeric protein enhances the ability of antigen presenting cells to present antigen.

In embodiments, the first chimeric protein and/or the second chimeric protein provides a sustained immunomodulatory effect.

In embodiments, the first chimeric protein and/or the second chimeric protein prevents a tumor cell from transmitting an immunosuppressive signal.

In embodiments, the second chimeric protein enhances tumor killing activity by T cells.

In embodiments, any chimeric protein which induces an innate immune response may be utilized in the present invention. In embodiments, any chimeric protein which induces an adaptive immune response may be utilized in the present invention. In an illustrative embodiment, a chimeric protein which induce an innate immune response is a chimeric protein comprising the extracellular domain of CSF1R at the N-terminus and the extracellular domain of CD40L at the C-terminus. In another embodiment, a chimeric protein which induces an innate immune response is a chimeric protein comprising the extracellular domain of SIRPα at the N-terminus and the extracellular domain of CD40L at the C-terminus. In an illustrative embodiment, a chimeric protein which induce an adaptive immune response is a chimeric protein comprising the extracellular domain of PD-1 at the N-terminus and the extracellular domain of OX40L at the C-terminus. In another embodiment, a chimeric protein which induces an adaptive immune response is a chimeric protein comprising the extracellular domain of VSIG8 at the N-terminus and the extracellular domain of OX40L at the C-terminus.

In embodiments, the present invention relates to the co-administration of a first chimeric protein, e.g., which induces an innate immune response, and a second chimeric protein, e.g., which induces an adaptive immune response. In such embodiments, the first chimeric protein may be administered before, concurrently with, or subsequent to administration of the second chimeric protein. For example, the chimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an illustrative embodiment, the first chimeric protein and the second chimeric protein are administered 1 week apart, or administered on alternate weeks (i.e., administration of the first chimeric i.e., protein is followed 1 week later with administration of the second chimeric protein and so forth).

Any chimeric protein disclosed herein can be a first chimeric protein, as described herein; any chimeric protein disclosed herein can be a second chimeric protein, as described herein.

In embodiments, a chimeric protein comprising an extracellular domain of TIM3 and an extracellular domain of OX40L is co-administered with a chimeric protein comprising an extracellular domain of CD172a(SIRPα) and an extracellular domain of CD40L. In embodiments the chimeric protein comprising an extracellular domain of TIM3 and an extracellular domain of OX40L is administered before the chimeric protein comprising an extracellular domain of CD172a(SIRPα) and an extracellular domain of CD40L. In embodiments the chimeric protein comprising an extracellular domain of TIM3 and an extracellular domain of OX40L is administered after the chimeric protein comprising an extracellular domain of CD172a(SIRPα) and an extracellular domain of CD40L.

In embodiments, a chimeric protein comprising an extracellular domain of TIM3 and an extracellular domain of OX40L is co-administered with a chimeric protein comprising an extracellular domain of CSF1R and an extracellular domain of CD40L. In embodiments the chimeric protein comprising an extracellular domain of TIM3 and an extracellular domain of OX40L is administered before the chimeric protein comprising an extracellular domain of CSF1R and an extracellular domain of CD40L. In embodiments the chimeric protein comprising an extracellular domain of TIM3 and an extracellular domain of OX40L is administered after the chimeric protein comprising an extracellular domain of CSF1R and an extracellular domain of CD40L. In embodiments, co-administration includes twice administering the same chimeric protein with the first administering and the second administering separated in time. For example, the first administering and the second administering may be 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MED16469 (MEDIMMUNE).

In embodiments, inclusive of, without limitation, infectious disease applications, the present invention pertains to anti-infectives as additional agents. In embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In embodiments, inclusive, without limitation, of autoimmune applications, the additional agent is an immunosuppressive agent. In embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In embodiments, the chimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still other embodiments, the chimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

The chimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In embodiments, the compositions described herein are in the form of a pharmaceutically acceptable salt.

Further, any chimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In embodiments, the compositions described herein are resuspended in a saline buffer (including, without limitation TBS, PBS, and the like).

In embodiments, the chimeric proteins may by conjugated and/or fused with another agent to extend half-life or otherwise improve pharmacodynamic and pharmacokinetic properties. In embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In embodiments, each of the individual chimeric proteins is fused to one or more of the agents described in BioDrugs (2015) 29:215-239, the entire contents of which are hereby incorporated by reference.

Administration, Dosing, and Treatment Regimens

The present invention includes the described chimeric protein (and/or additional agents) in various formulations. Any chimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the formulations comprising the chimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the chimeric protein (and/or additional agents) of the present invention may conveniently be presented in unit dosage forms and may be prepared by any of the methods well known in the art of pharmacy. Such methods generally include the step of bringing therapeutic agents into association with a carrier, which constitutes one or more accessory ingredients. Typically, the formulations are prepared by uniformly and intimately bringing therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any chimeric protein (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In embodiments, the administering is effected orally or by parenteral injection. In most instances, administration results in the release of any agent described herein into the bloodstream.

Any chimeric protein (and/or additional agents) described herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the chimeric protein (and/or additional agents) are administered in the tumor microenvironment (e.g., cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In embodiments, for instance in the treatment of cancer, the chimeric protein (and/or additional agents) are administered intratumorally.

In the various embodiments, the present chimeric protein allows for a dual effect that provides less side effects than are seen in conventional immunotherapy (e.g., treatments with one or more of OPDIVO, KEYTRUDA, YERVOY, and TECENTRIQ). For example, the present chimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g., intratumorally, obviate adverse event seen with standard systemic administration, e.g., IV infusions, as are used with conventional immunotherapy (e.g., treatments with one or more of OPDIVO, KEYTRUDA, YERVOY, and TECENTRIQ).

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any chimeric protein (and/or additional agents) described herein as well as the dosing schedule can depend on various parameters, including, but not limited to, the disease being treated, the subject's general health, and the administering physician's discretion. Any chimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In embodiments any chimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In embodiments, the present invention relates to the co-administration of a chimeric protein which induces an innate immune response and another chimeric protein which induces an adaptive immune response. In such embodiments, the chimeric protein which induces an innate immune response may be administered before, concurrently with, or subsequent to administration of the chimeric protein which induces an adaptive immune response. For example, the chimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an illustrative embodiment, the chimeric protein which induces an innate immune response and the chimeric protein which induces an adaptive response are administered 1 week apart, or administered on alternate weeks (i.e., administration of the chimeric protein inducing an innate immune response is followed 1 week later with administration of the chimeric protein which induces an adaptive immune response and so forth).

The dosage of any chimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any chimeric protein (and/or additional agents) described herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent described herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In embodiments, administration of the chimeric protein (and/or additional agents) described herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In embodiments, a suitable dosage of the chimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween.

In another embodiment, delivery can be in a vesicle, in particular a liposome (see Langer, 1990, *Science* 249:1527-1533; Treat et al., in *Liposomes in therapy of Infectious Disease and Cancer*, Lopez-Berestein and Fidler (eds.), Liss, N.Y., pp. 353-365 (1989).

Any chimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any chimeric protein (and/or additional agents) described herein can be administered in a single daily dose, or the total daily dosage can be administered in divided doses of two, three or four times daily. Furthermore, any chimeric protein (and/or additional agents) described herein can be administered continuously rather than intermittently throughout the dosage regimen.

Cells and Nucleic Acids

In embodiments, the present invention provides an expression vector, comprising a nucleic acid encoding the chimeric protein described herein. In embodiments, the expression vector comprises DNA or RNA. In embodiments, the expression vector is a mammalian expression vector.

Both prokaryotic and eukaryotic vectors can be used for expression of the chimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the chimeric proteins in recombinant host cells.

In embodiments, expression vectors of the invention comprise a nucleic acid encoding the chimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the cell is a tumor cell. In another embodiment, the cell is a non-tumor cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present invention contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In one aspect, the invention provides expression vectors for the expression of the chimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (MV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In embodiments, the present invention provides a host cell, comprising the expression vector comprising the chimeric protein described herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse Sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the chimeric proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Production and purification of Fc-containing macromolecules (such as monoclonal antibodies) has become a standardized process, with minor modifications between products. For example, many Fc containing macromolecules are produced by human embryonic kidney (HEK) cells (or variants thereof) or Chinese Hamster Ovary (CHO) cells (or variants thereof) or in some cases by bacterial or synthetic methods. Following production, the Fc containing macromolecules that are secreted by HEK or CHO cells are purified through binding to Protein A columns and subsequently 'polished' using various methods. Generally speaking, purified Fc containing macromolecules are stored in liquid form for some period of time, frozen for extended periods of time or in some cases lyophilized. In embodiments, production of the chimeric proteins contemplated herein may have unique characteristics as compared to traditional Fc containing macromolecules. In certain examples, the chimeric proteins may be purified using specific chromatography resins, or using chromatography methods that do not depend upon Protein A capture. In embodiments, the chimeric proteins may be purified in an oligomeric state, or in multiple oligomeric states, and enriched for a specific oligomeric state using specific methods. Without being bound by theory, these methods could include treatment with specific buffers including specified salt concentrations, pH and additive compositions. In other examples, such methods could include treatments that favor one oligomeric state over another. The chimeric proteins obtained herein may be additionally 'polished' using methods that are specified in the art. In embodiments, the chimeric proteins are highly stable and able to tolerate a wide range of pH exposure (between pH 3-12), are able to tolerate a large number of freeze/thaw stresses (greater than 3 freeze/thaw cycles) and are able to tolerate extended incubation at high temperatures (longer than 2 weeks at 40 degrees C.). In embodiments, the chimeric proteins are shown to remain intact, without evidence of degradation, deamidation, etc. under such stress conditions.

Subjects and/or Animals

In embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In embodiments, the subject and/or animal is a non-mammal, such, for example, a zebrafish. In embodiments, the subject and/or animal may comprise fluorescently-tagged cells (with e.g., GFP). In embodiments, the subject and/or animal is a transgenic animal comprising a fluorescent cell.

In embodiments, the subject and/or animal is a human. In embodiments, the human is a pediatric human. In embodiments, the human is an adult human. In embodiments, the human is a geriatric human. In embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Any aspect or embodiment described herein can be combined with any other aspect or embodiment as disclosed herein The invention will be further described in the following examples, which do not limit the scope of the invention described in the claims.

EXAMPLES

Figure 2:
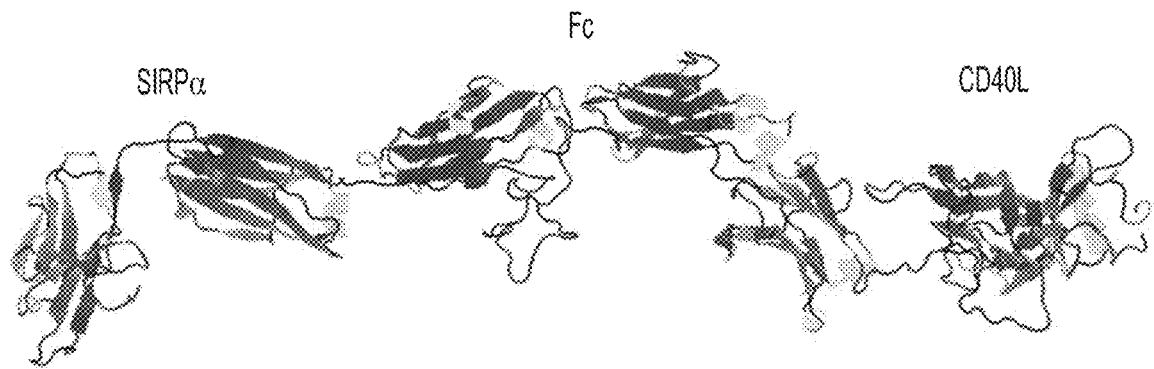
FIG. 2 shows, without wishing to be bound by theory, an in silico predicted structure of a monomeric CD172a (SIRPα)-Fc-CD40L chimeric protein (SL-172154).

Example 1: In Silico Predicted Structure of Monomeric Human CD172a(SIRPα)-Fc-CD40L Chimeric Protein An in silico structure prediction of the monomeric human CD172a(SIRPα)-Fc-CD40L chimeric protein (SL-172154) having 792 amino acid residues was generated, with a p-value $1.14 \times 10^{-21}$. The molecular weight of the monomeric protein was predicted to be 88.1 kDa. A structure of the chimeric protein is provided in FIG. 2.

Specifically, the structure prediction revealed that 48 positions (6%) may be disordered. Secondary structure prediction of the entire sequence of the chimeric protein showed that the protein has the composition of 2% α-helix (H), 50% β-sheet (E), and 47% coil (C). The GDT (global distance test) and uGDT (un-normalized GDT) for the absolute global quality were also calculated for the chimeric protein to give an overall uGDT(GDT) of 429(54). The three-state prediction for solvent accessibility of the protein residues were 33% exposed (E), 48% intermediate (M), and 17% buried (B).

Figure 3A:
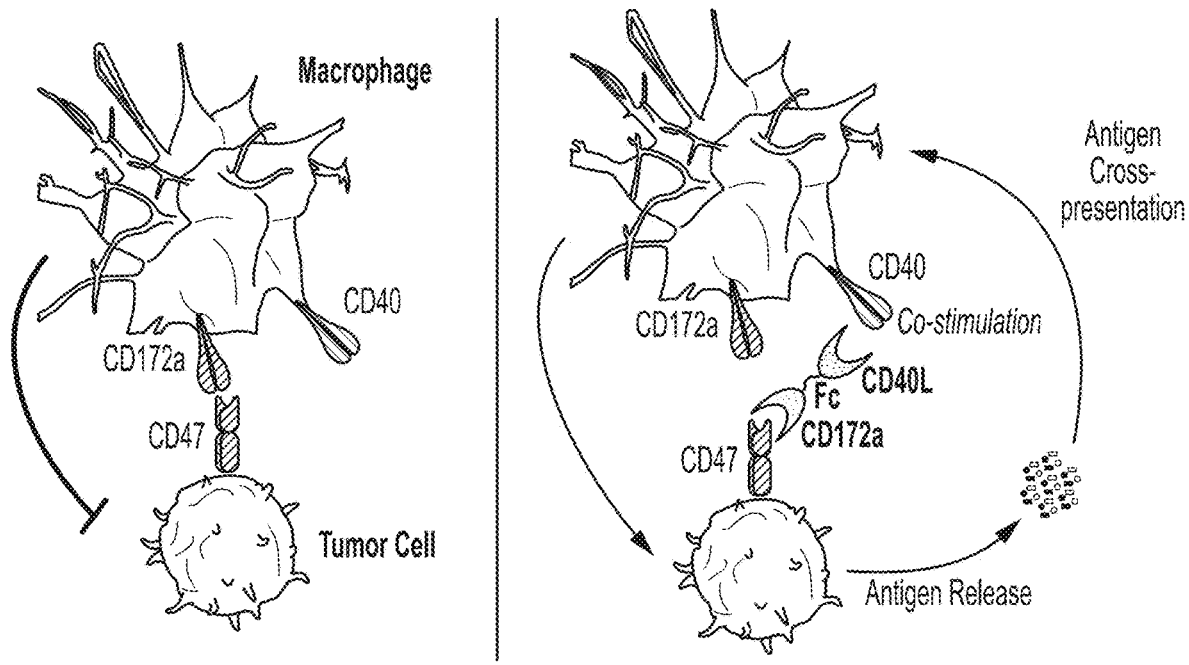
FIG. 3A shows, without wishing to be bound by theory, a schematic diagram illustrating a mechanism of action of the hCD172a(SIRPα)-Fc-CD40L chimeric protein for stimulating active tumor destruction. The chimeric protein may then "dangle" from the surface of the tumor cell, and the CD40L portion of the chimeric protein may then bind to CD40 expressed on the surface of the T cell. This would result in replacement of an inhibitory hCD172a(SIRPα) signal with a co-stimulatory CD40L signal to enhance the anti-tumor activity of T cells.
Figure 3B:
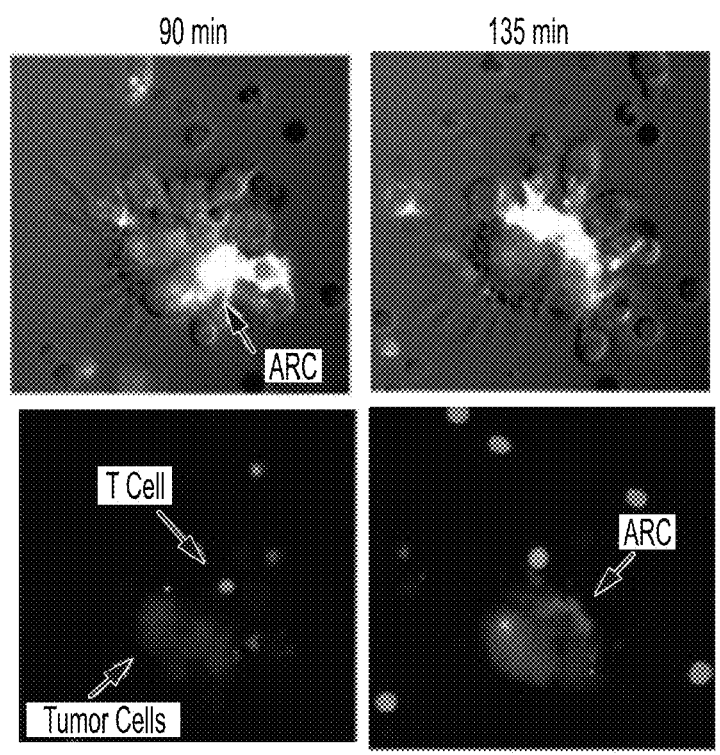
FIG. 3B shows a synapse that has formed by a chimeric protein between a tumor cell and a T cell.

A schematic diagram illustrating a mechanism of action of the hCD172a(SIRPα)-Fc-CD40L chimeric protein for stimulating active tumor destruction is shown in FIG. 3. The chimeric protein may then "dangle" from the surface of the tumor cell, and the CD40L portion of the chimeric protein may then bind to CD40 expressed on the surface of the T cell. This would result in replacement of an inhibitory hCD172a(SIRPα) signal with a co-stimulatory CD40L signal to enhance the anti-tumor activity of T cells.

Many tumor types express high levels of membrane-bound CD47, which can bind to CD172a(SIRPα) on the surface of a macrophage, thereby inducing a 'don't eat me' signal that inhibits macrophage engulfment or phagocytosis of the tumor cell. Without wishing to be bound by theory, it is believed that the CD172a(SIRPα)-Fc-CD40L chimeric protein (SL-172154) binds tumor that express CD47, blocking its interaction with macrophages, thereby allowing macrophage maturation and phagocytosis-mediated destruction of the tumor cells. This in turn results in enhanced tumor-antigen release and cross-presentation back to other macrophages. Interestingly, the cross-presentation of antigens occurs at the same time and in the same tumor microenvironmental context as co-stimulation between macrophage/APC bound CD40 and CD40L from the chimeric protein. The CD172a(SIRPα)-Fc-CD40L chimeric protein therefore stimulates both active tumor destruction, and also immune recognition of tumor antigens, which are essential in programming a memory response capable of preventing relapse (FIG. 3).

Example 2: Characterization of Human CD172a(SIRPα)-Fc-CD40L Chimeric Protein

A human CD172a(SIRPα)-Fc-CD40L chimeric protein was constructed. The chimeric protein was characterized by performing a Western blot analysis against each individual domain of the chimeric protein, i.e., via anti-CD172a (SIRPα), anti-Fc, and anti-CD40L antibodies.

Figure 4:
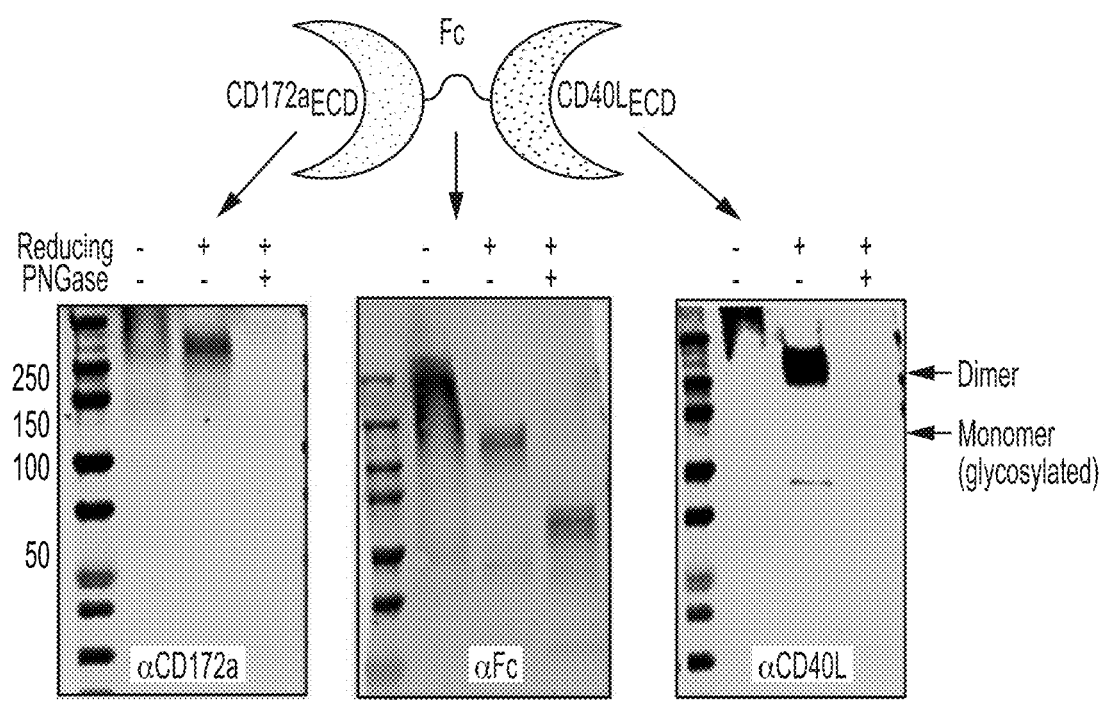
FIG. 4 shows characterization of human CD172a (SIRPα)-Fc-CD40L chimeric protein (SL-172154) by Western blot. Specifically, each individual domain of the chimeric protein was probed using an anti-CD172a, anti-Fc, or anti-CD40L antibody. Untreated samples of the hCD172a (SIRPα)-Fc-CD40L chimeric protein, e.g., control, were loaded into lane 2 in all the blots (no β-mercaptoethanol or PNGase). Samples in lane 3 were treated with the reducing agent, β-mercaptoethanol, while samples in lane 4 were treated with PNGase.

The Western blots indicated the presence of a dominant dimer band in the non-reduced lanes (FIG. 4, lane 2 in each blot), which was reduced to a glycosylated monomeric band in the presence of the reducing agent, β-mercaptoethanol (FIG. 4, lane 3 in each blot). As shown in FIG. 4, lane 4 in each blot, the chimeric protein ran as a monomer at the predicted molecular weight of 88.1 kDa in the presence of both a reducing agent (β-mercaptoethanol) and an endoglycosidase (PNGase).

Example 3: Characterization of the Binding Affinity of the Different Domains of the CD172a(SIRPα)-Fc-CD40L Chimeric Protein Using ELISA Functional ELISA (enzyme-linked immunosorbent assay) assays were developed to demonstrate the binding affinity of the different domains of the human CD172a(SIRPα)-Fc- CD40L chimeric protein to their respective binding partners. The CD172a(SIRPα) domain of the hCD172a(SIRPα)-Fc-CD40L chimeric protein was detected by capturing to a plate-bound recombinant human CD47 protein and detected via an HRP conjugated anti-human IgG antibody. Recombinant hCD172a(SIRPα)-Fc protein was used to generate a standard curve. The Fc portion of the hCD172a(SIRPα)-Fc-CD40L chimeric protein was detected by capturing to a plate-bound human IgG and detected via an HRP conjugated anti-human IgG antibody (hIg). Recombinant hIg protein was used to generate a standard curve. The CD40L domain of the hCD172a(SIRPα)-Fc-CD40L chimeric protein was detected by capturing to a plate-bound recombinant human CD40 protein and detected via a CD40L-specific antibody. Recombinant hCD40L protein was used to generate a standard curve.

Figure 6:
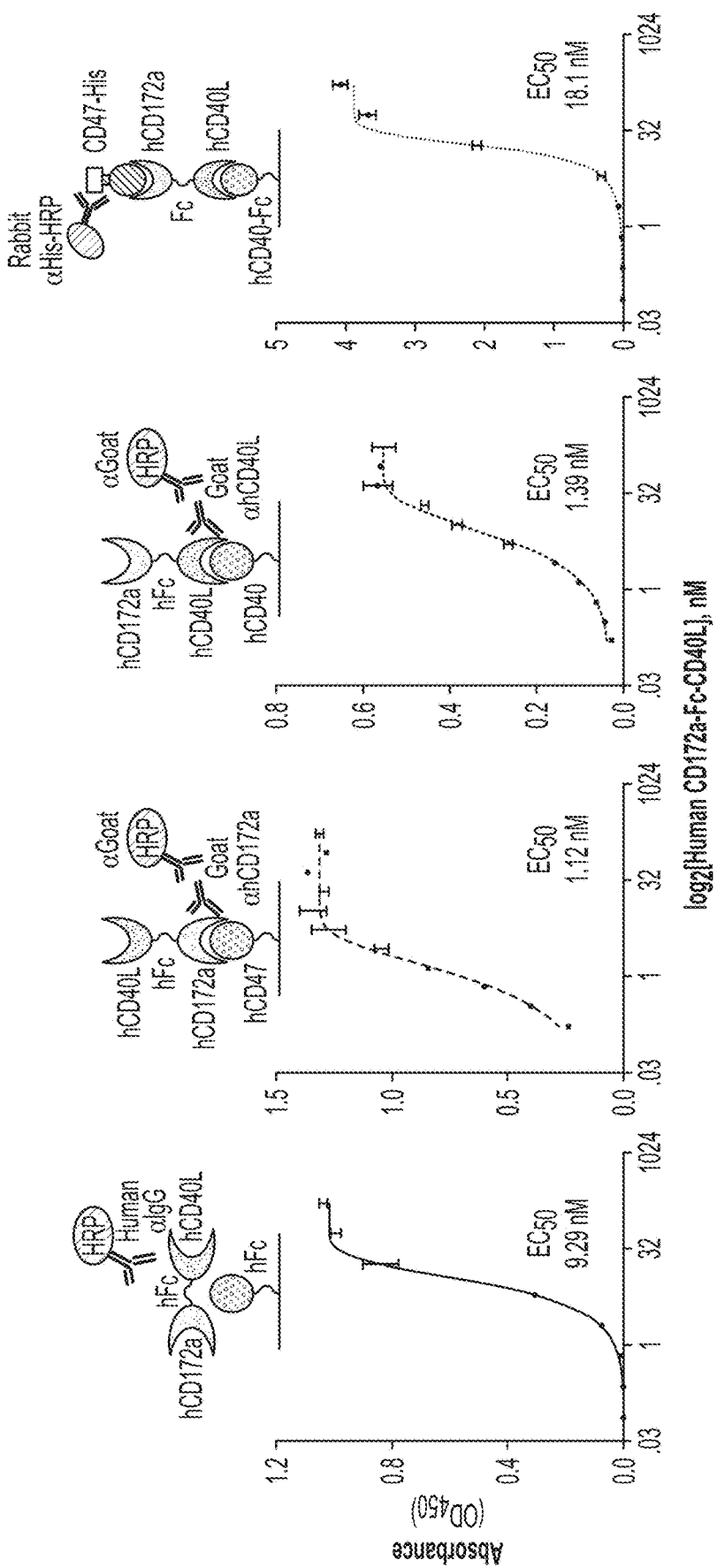
FIG. 6 shows ELISA assays demonstrating the binding affinity of the different domains of human CD172a(SIRPα)-Fc-CD40L chimeric protein for their respective binding partners. The first (left-most) panel shows the binding and detection of hCD172a(SIRPα)-Fc-CD40L chimeric protein to human IgG, the binding partner for Fc. Human Ig (hIg) was used as a standard. The second panel from the left shows the binding and detection of hCD172a(SIRPα)-Fc-CD40L chimeric protein to CD47, the binding partner for CD172a. The third panel from the left shows the binding and detection of hCD172a(SIRPα)-Fc-CD40L chimeric protein to the receptor CD40, the binding partner for CD40L. The last (right-most) panel demonstrates a dual-binding functional ELISA assay where recombinant human CD40 was used to capture the CD40L domain and recombinant human CD47 was used to detect the CD172a(SIRPα) domain, demonstrating contemporaneous binding of CD172a(SIRPα)-Fc-CD40L to both of its binding partners.

As shown in FIG. 6, the different domains of the hCD172a(SIRPα)-Fc-CD40L chimeric protein effectively interacted with their respective binding partners in a concentration-dependent manner and with high affinity. Moreover, as shown in the right panel of FIG. 6, the hCD172a(SIRPα)-Fc-CD40L chimeric protein is able to contemporaneously bind to both CD40 and CD47. Nevertheless, it was observed that in ELISA assays, using the central Fc region to detect chimeric proteins tended to underestimate the actual protein content in a sample. Therefore, low level of the hCD172a(SIRPα)-Fc-CD40L chimeric protein was detected compared to standard in this assay. Based on this data an $EC_{50}$ value for CD47 of 1.39 nM, for mCD172a(SIRPα) of 1.12 nM, and for contemporaneous CD47 and CD40 of 18.1 nm were calculated for the hCD172a(SIRPα)-Fc-CD40L chimeric protein.

Ex vivo cell binding assays were also utilized to assess the ability of the different domains of the CD172a(SIRPα)-Fc-CD40L chimeric protein to bind their respective binding partners. Here, a cell line was engineered to overexpress human CD47 (i.e., HeLa/hCD47) and a cell line was engineered to overexpress murine CD40 (i.e., CHOK1/mCD40).

Figure 7A:
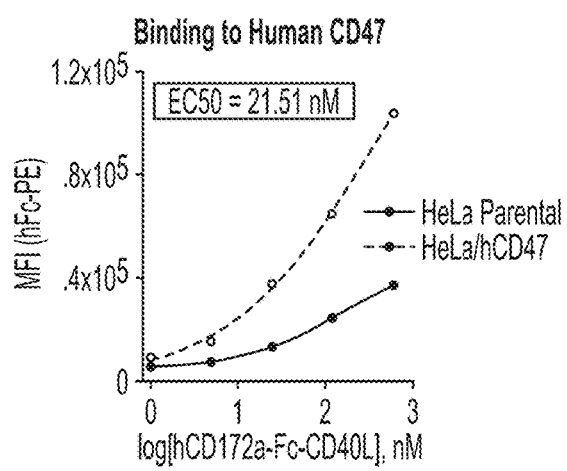
FIG. 7A and FIG. 7B show ex vivo cell binding assays demonstrating the ability of different domains of the CD172a(SIRPα)-Fc-CD40L chimeric protein to bind their respectively binding partners (e.g., receptor or ligand) on the surface of a mammalian cell membrane.
Figure 7B:
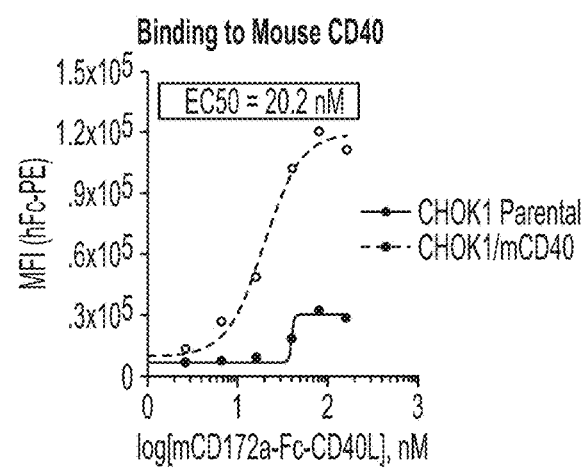

Human CD172a(SIRPα)-Fc-CD40L chimeric protein or murine CD172a(SIRPα)-Fc-CD40L chimeric protein was incubated with the parental and over-expressing cell lines for 2 hours. Cells were collected, washed, and stained with antibodies for the detection of the chimeric protein binding by flow cytometry. As shown in FIG. 7A and FIG. 7B, and as expected, the chimeric proteins did not significantly bind the parental cell lines. However, the hCD172a(SIRPα)-Fc-CD40L bound the HeLa/hCD47 engineered cell line in a concentration-dependent manner; based on this data an $EC_{50}$ value of 21.51 nM was calculated (FIG. 7A). Similarly, the mCD172a(SIRPα)-Fc-CD40L bound the CHOK1/mCD40engineered cell line in a concentration-dependent manner; based on this data an $EC_{50}$ value of 20.2 nM was calculated.

Example 4: Characterization of the Binding Affinity of the CD172a(SIRPα)-Fc-CD40L Chimeric Protein by Surface Plasmon Resonance (SPR)

Figure 8A:
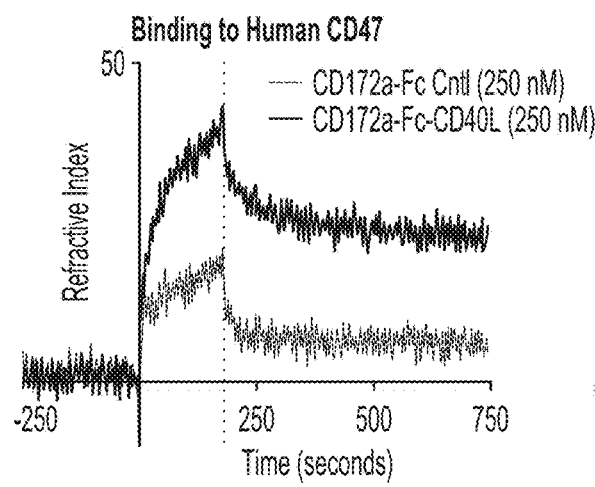
FIG. 8A to FIG. 8E show the binding affinity of the human CD172a(SIRPα)-Fc-CD40L chimeric protein by surface plasmon resonance (SPR).

The binding affinity of the different domains of the hCD172a(SIRPα)-Fc-CD40L chimeric protein was measured by surface plasmon resonance (SPR) using the BioRad ProteOn XPR 360 system. Specifically, the affinity of the chimeric protein for CD47, FcγR1A, and FcRn was determined and compared to recombinant control proteins, and the results are shown in FIG. 8A. to FIG. 8C, respectively. Kinetic data collected is summarized in the table shown in FIG. 8D.

Figure 8B:
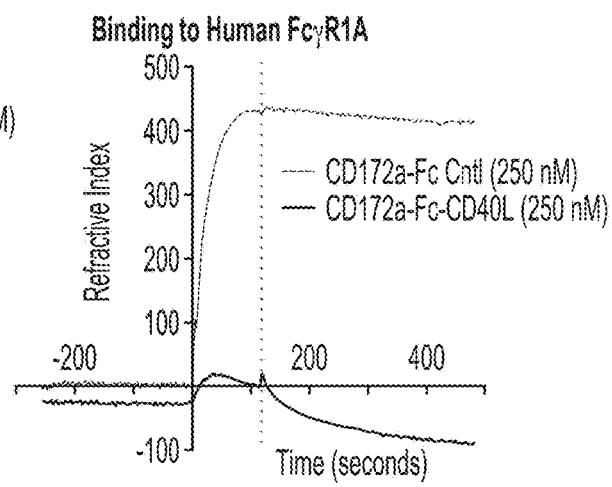
Figures 8C, 8D, 8E:
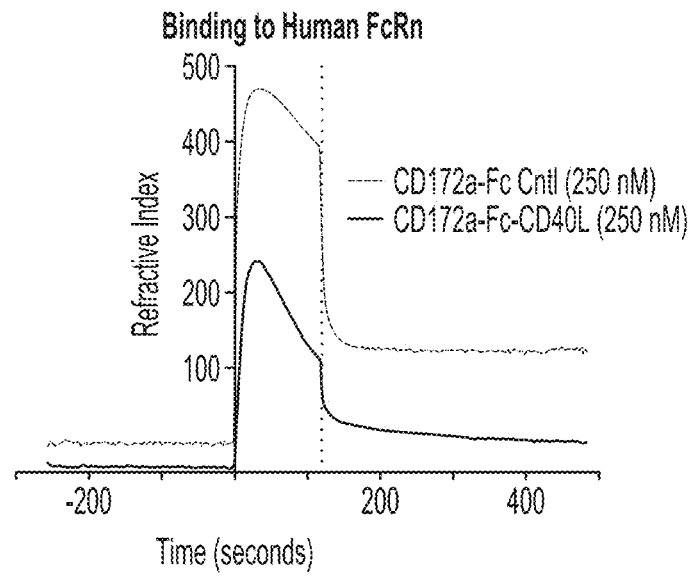

As shown in FIG. 8A, the CD172a(SIRPα)-Fc-CD40L chimeric protein bound to CD47 and with high affinity. The 'on-rate' of CD172a(SIRPα)-Fc-OX40L to human CD47 was rapid, however the 'off-rate' was much lower, in fact ~40-fold slower than the 'off-rate' of recombinant CD47-Fc, indicating that CD172a(SIRPα)-Fc-OX40L bound quickly and stably, with long on-target residence time. The KD of CD172a(SIRPα)-Fc-OX40L binding to human CD47 was calculated to be 3.59 nM. The affinity measurements demonstrated high-affinity binding to the chimeric protein, except against Fc receptors with effector function (FIG. 8B and FIG. 8C). Importantly, the off-rates of the chimeric protein were much slower than those of benchmark control proteins; the chimeric protein dissociation from CD47 was 2.78 fold longer than CD172a(SIRPα)-Fc.

Additionally, the binding affinity of murine CD172a(SIRPα)-Fc-CD40L to mCD40 was assessed by SPR. It was determined that the chimeric protein bound to mCD40 tightly at a Kd of 0.756 nM, as shown in the in FIG. 8E.

Example 5: Functional Assays of the CD172a(SIRPα)-Fc-CD40L Chimeric Protein

Figure 9A:
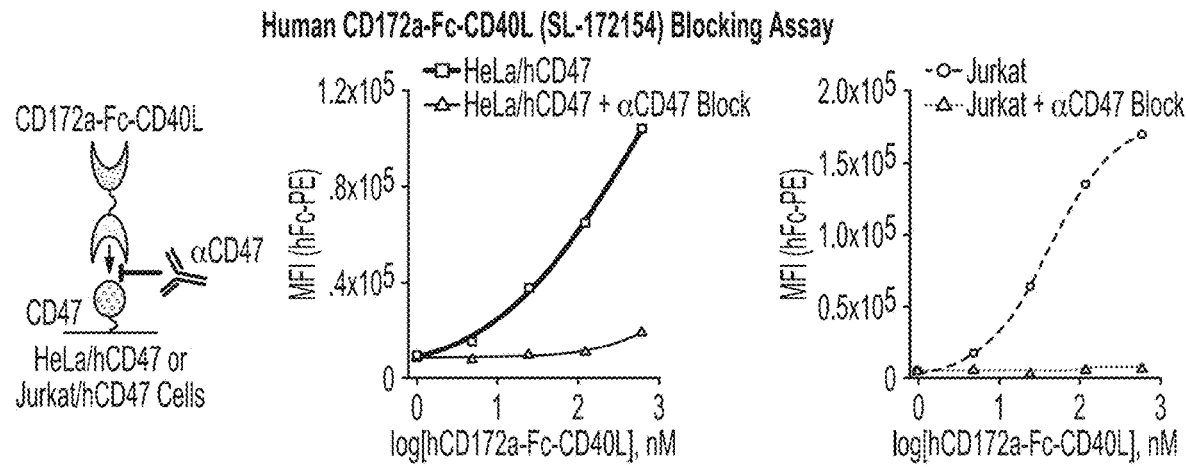
FIG. 9A to FIG. 9C show ex vivo functional assays of the human CD172a(SIRPα)-Fc-CD40L chimeric protein.

Functional assays, ELISA-based blocking assay and macrophage engulfment assays, were performed to demonstrate functional activity of the human CD172a(SIRPα)-Fc-CD40L chimeric protein. ELISA-based blocking assay was performed to demonstrate that hCD172a(SIRPα)-Fc-CD40L chimeric protein binding to cells over-expressing human CD47 (HeLa/hCD47 and Jurkat/endogenous-CD47) can be disrupted by pre-incubating cells with a human CD47 blocking antibody. HeLa cells stably transfected with a human CD47-expressing plasmid, were incubated with increasing concentrations of the human CD172a(SIRPα)-Fc-CD40L chimeric protein, alone, or after HeLa/hCD47 cells were pre-incubated with a human CD47 blocking antibody (FIG. 9A, middle panel). HeLa/hCD47 bound the hCD172a(SIRPα)-Fc-CD40L chimeric protein in a concentration-dependent manner (FIG. 9A, middle panel, top curve). The binding was blocked when HeLa/hCD47 cells were pre-treated with the CD47 blocking antibody (FIG. 9A, middle panel, bottom curve).

Jurkat cells, which expressed high levels of human CD47 endogenously, bound the hCD172a(SIRPα)-Fc-CD40L chimeric protein in a concentration-dependent manner (FIG. 9A, right panel, top curve). Similarly, this binding was blocked when Jurkat cells were pre-treated with the same CD47 blocking antibody (FIG. 9A, right panel, bottom curve).

Together, these data indicated that the binding of the CD172a(SIRPα) component of hCD172a(SIRPα)-Fc-CD40L chimeric protein was highly specific to both overexpressed and endogenous CD47, since binding of the hCD172a(SIRPα)-Fc-CD40L chimeric protein was impeded when CD47 access is blocked.

Figure 9B:
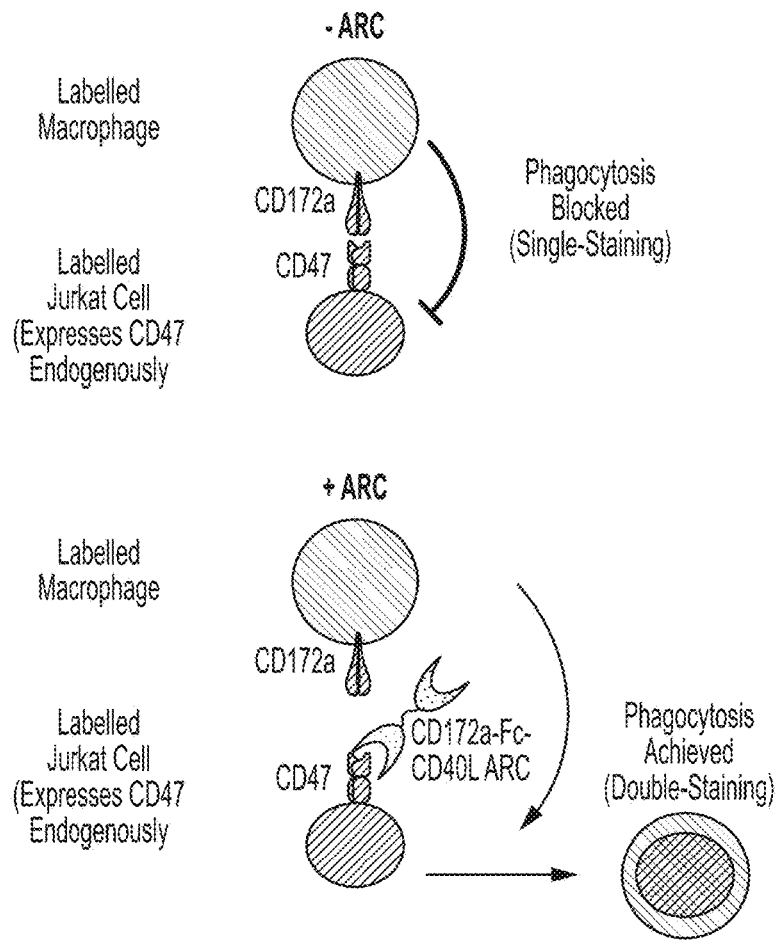
Figure 9C:
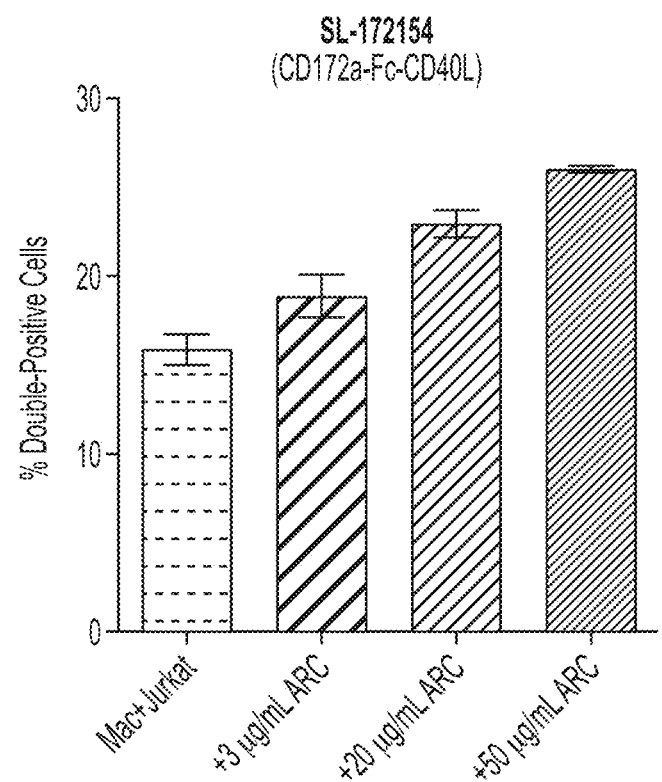

In a macrophage engulfment assay, primary derived human macrophages were incubated with CD47-expressing cells in the presence or absence of the hCD172a(SIRPα)-Fc-CD40L chimeric protein, in order to assess suppression of the 'don't eat me' signal produced when macrophage bound CD172a(SIRPα) was freely able to interact with CD47. A schematic showing the basic principles of the macrophage engulfment assay is shown in FIG. 9B. Primary human monocytes were isolated and differentiated in vitro into macrophages. As the donor of CD47, the suspension cell line Jurkat was identified as expressing high levels of membrane bound CD47. Macrophages and Jurkat cells were incubated with different cell trace dyes, and co-cultured, in the presence or absence of the CD172a(SIRPα)-Fc-CD40L chimeric protein (FIG. 9B). In the absence of the chimeric protein, Jurkat-CD47 interacted with macrophage-CD172a (SIRPα), blocking phagocytosis, resulting in baseline levels of cells which were double positive for both cell trace dyes (FIG. 9C, left bar). When the chimeric protein was added to the Jurkat/macrophage co-culture, increased levels of double positive cells were detected, which increased in a concentration-dependent manner (FIG. 9C, right three bars). The results of the macrophage engulfment assay indicated that the CD172a(SIRPα)-Fc-CD40L chimeric protein was able to promote macrophage phagocytosis of CD47+ cells.

Figure 10A:
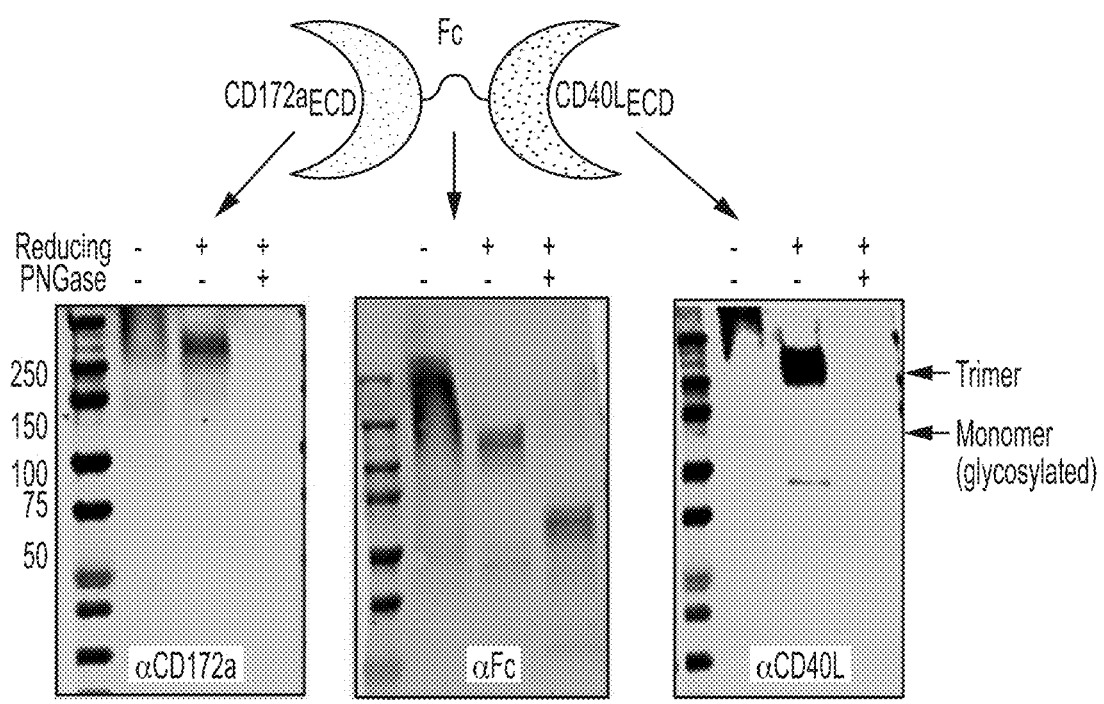
FIG. 10A and FIG. 10B show characterization of murine CD172a(SIRPα)-Fc-CD40L chimeric protein by Western blot analysis and ELISA assays.

Example 6: Characterization of the Murine CD172a(SIRPα)-Fc-CD40L Chimeric Protein The murine CD172a(SIRPα)-Fc-CD40L chimeric protein was characterized by performing a Western blot analysis against each individual domain of the chimeric protein, i.e., via anti-CD172a(SIRPα), anti-Fc, and anti-CD40L antibodies. As shown in FIG. 10A, all three domains of the mCD172a(SIRPα)-Fc-CD40L chimeric protein were detected under non-reduced (Lane 2), reduced (Lane 3) and reduced+PNGase treatments (Lane 4). The reduced, glycosylated form of the chimeric protein migrated at the expected molecular weight of approximately 110 kDa. The reduced, deglycosylated form was not detected by any of the antibodies, which could be due to its dependence on the protein being glycosylated.

Figure 10B:
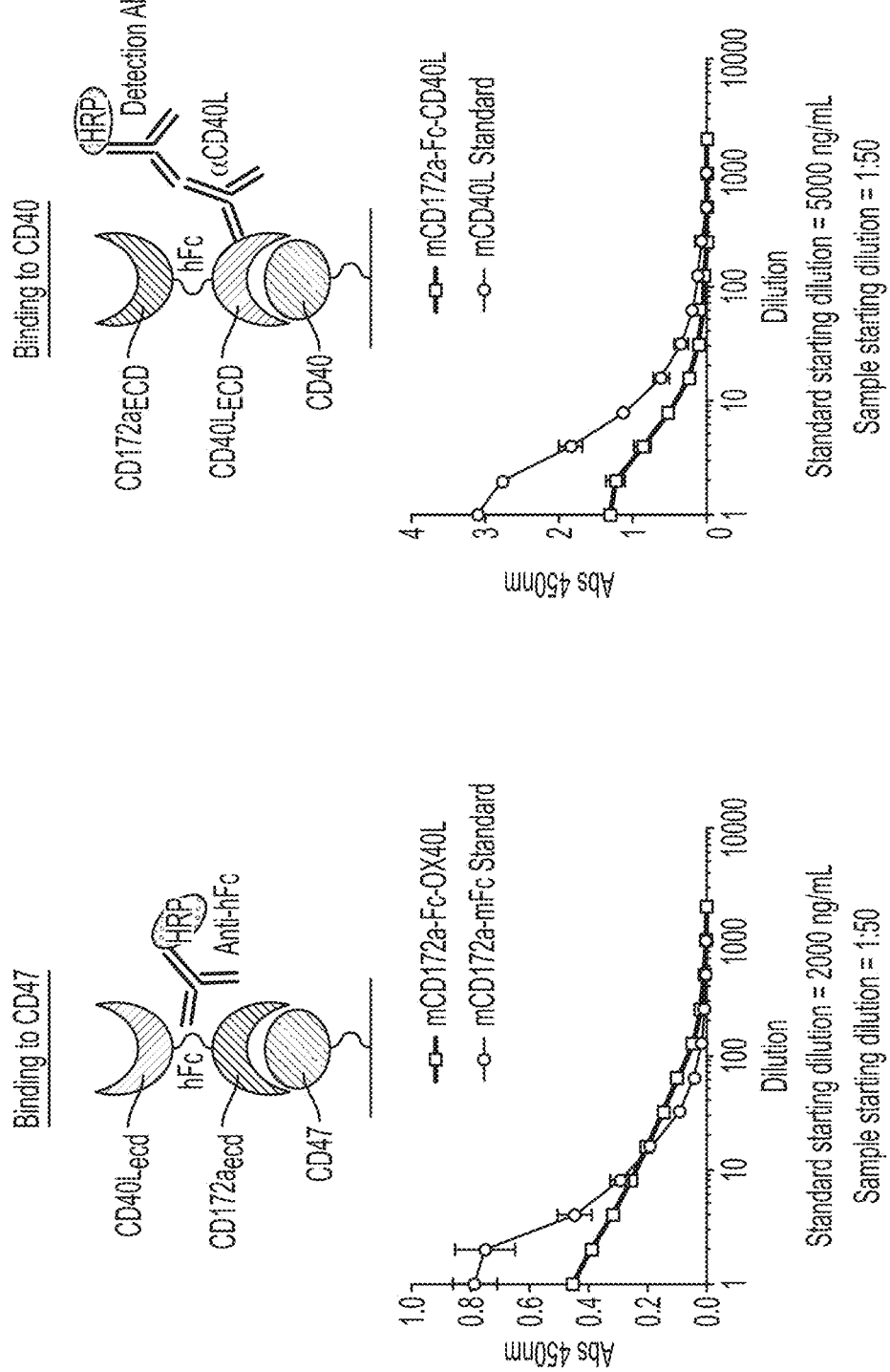

ELISA assays were performed to demonstrate the binding affinity of the different domains of the mCD172a(SIRPα)-Fc-CD40L chimeric protein to interact with their predicted binding partners (i.e., CD47 or CD40). Specifically, the CD172a(SIRPα) domain of the mCD172a(SIRPα)-Fc-CD40L chimeric protein was detected by capturing to a plate-bound recombinant CD47 protein and detecting via an HRP-conjugated anti-Fc antibody (FIG. 10B, left panel, square symbols). Recombinant mCD172a(SIRPα)-mFc was used to generate a standard curve (FIG. 10B, left panel, circle symbols). The CD40L domain of the chimeric protein was detected by capturing to a plate-bound recombinant murine CD40 protein and detecting via a CD40L-specific antibody (FIG. 10B, right panel, square symbols). Recombinant mCD40L was used to generate a standard curve (FIG. 10B, right panel, circle symbols). As shown in FIG. 10B, the different domains of the mCD172a(SIRPα)-Fc-CD40L chimeric protein effectively interacted with their respective binding partners and with high affinity.

The in vivo anti-tumor activity of the mCD172a(SIRPα)-Fc-CD40L chimeric protein was analyzed using the CT26 mouse colorectal tumor model. In one set of experiments, Balb/c mice were inoculated with CT26 tumor cells on day 0 and/or rechallenged with a second inoculation of CT26 tumor cells at day 30. Following 4 days of tumor growth, when tumors reached a diameter of 4-5 mm, mice were treated with anti-CD47, anti-CD40, a combination of the two antibodies, or with mCD172a(SIRPα)-Fc-CD40L chimeric protein.

Figure 11A:
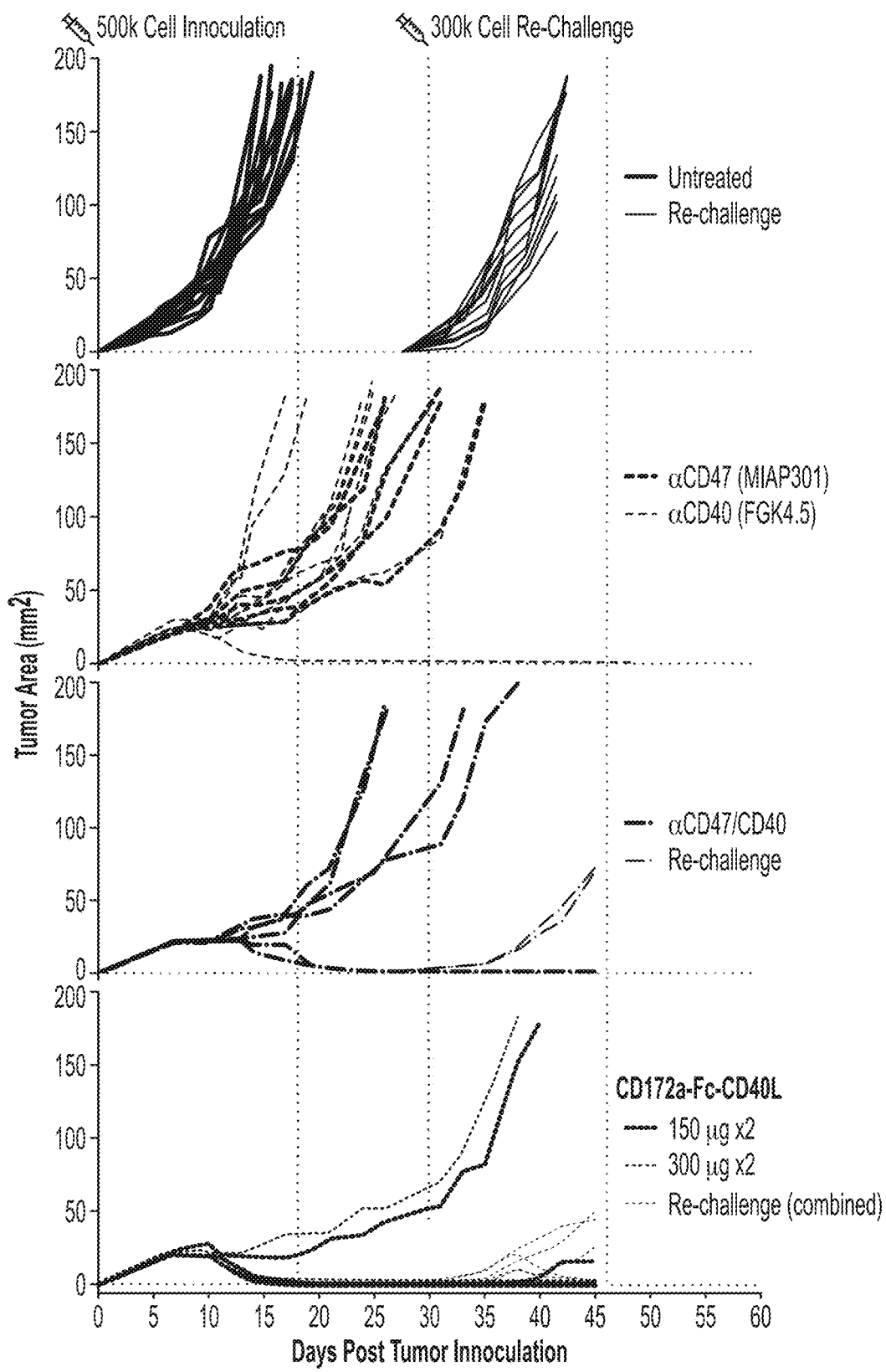
FIG. 11A to FIG. 11C shows results from in vivo tumor studies demonstrating the anti-tumor efficacy of mCD172a (SIRPα)-Fc-CD40L chimeric protein. A CT26 tumor was implanted into Balb/c mice prior to treatment with anti-CD47, anti-CD40, a combination of the two antibodies, with mCD172a(SIRPα)-Fc-CD40L, or with control antibodies.

The tumor growth for each treatment group was assessed as shown in FIG. 11A. Specifically, the untreated mice developed tumors quickly. Treatment with the anti-CD47, anti-CD40, or the combination of those two antibodies appeared to slightly delay the development of tumors. In comparison, treating mice with the mCD172a(SIRPα)-Fc-CD40L chimeric protein significantly prevented and/or delayed the development of tumors. Importantly, the CD172a(SIRPα)-Fc-CD40L chimeric protein is effectively able to kill tumor cells and/or reduce tumor growth when rechallenged (which illustrates a cancer relapse). Thus, the CD172a(SIRPα)-Fc-CD40L chimeric protein appears to generate a memory response which may be capable of preventing relapse.

The overall survival percentage of mice through forty-five days after tumor inoculation was also assessed. All of the untreated mice died within twenty-one days after tumor inoculation. Most of the mice treated with a single antibody died around day 30. The mice receiving a combination of anti-CD40 and anti-CD47 antibodies demonstrated only about a 30% survival at day 50. Significantly, all the mice treated with the mCD172a(SIRPα)-Fc-CD40L chimeric protein survived past fifty days after tumor inoculation as shown in FIG. 11B.

Figures 11B, 11C:
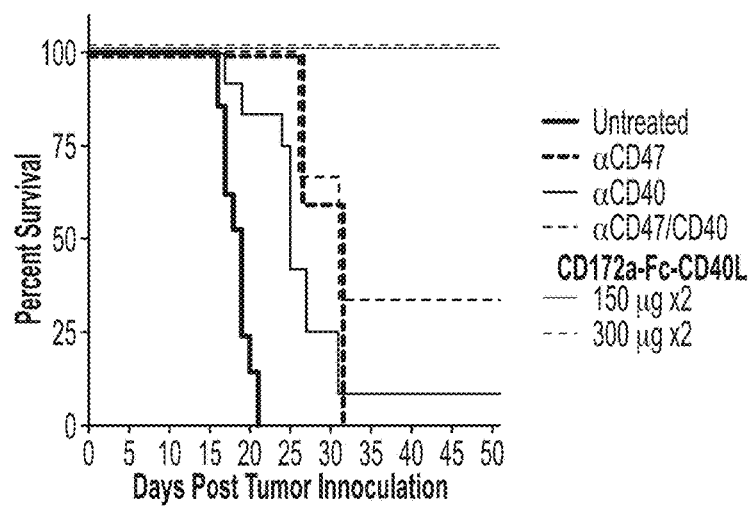

As shown in FIG. 11C, monotherapy with either anti-CD40 or anti-CD47 led to moderate extensions in the tumor growth rates for most mice, with one animal completely rejected the tumor (anti-CD40 group, out of twelve total mice treated). When the two antibodies were administered in combination, there was a synergistic effect, with two out six mice in the long-term follow-up group having complete tumor rejection. For mice treated with mCD172a(SIRPα)-Fc-CD40L, there was significantly superior activity in both the 150 and 300 µg dose levels as compared to the antibody combinations, with a slightly improved rejection rate in the 150 versus the 300 µg group. In comparison to the antibody combination treatment, there was an 80% complete rejection rate observed with treatment using the mCD172a(SIRPα)-Fc-CD40L chimeric protein.

Immune phenotyping was also performed by analyzing splenocytes, lymph node cells, and tumor infiltrating lymphocytes on day thirteen post tumor inoculation. As shown in FIG. 12A, FIG. 12C, and FIG. 12D, mice treated with the mCD172a(SIRPα)-Fc-CD40L chimeric protein exhibited higher percentages of total CD4+ T cells in the spleen, peripheral lymph nodes and tumor as compared to the control or the combination antibody treatment group (anti-CD40 and anti-CD47). Within the spleen, this increase mostly comprised an increase in CD4+CD25– T cells, which would be consistent with the notion that activation of non-regulatory T cells was involved (FIG. 12B). There was also an increase in CD8+ T cells in mice treated with mCD172a(SIRPα)-Fc-CD40L in the peripheral lymph nodes, but this increase was not observed in the spleen or tumor (FIG. 12A, FIG. 12C, and FIG. 12D).

The ability of the mCD172a(SIRPα)-Fc-CD40L chimeric protein to stimulate the recognition of tumor antigens by CD8+ T cells was also analyzed. Specifically, FIG. 12E shows tetramer staining analysis for determining the fraction of CD8+ T cells that recognized the AH1 tumor antigen natively expressed by CT26 tumors. Within the spleen and tumor infiltrated lymphocytes (TIL), a higher proportion of CD8+ T cells was found to recognize the AH1 tumor antigen in mice treated with the chimeric protein as compared to the untreated mice.

One of the indicators of CD40 activation was the proportion of cells which upregulated IL-15 receptor alpha. Amongst the treatment groups, there was a significant increase in the mice treated with the 150 µg dose of the mCD172a(SIRPα)-Fc-CD40L chimeric protein, but not in the anti-CD40/CD47 treatment group (FIG. 12F).

Together, these data demonstrate that mCD172a(SIRPα)-Fc-CD40L was effective at eliminating established tumors and generating a memory immune response capable of preventing tumor growth upon re-challenge. Moreover, mCD172a(SIRPα)-Fc-CD40L outperformed the benchmark antibody combinations (anti-CD47+anti-CD40) when administered at the optimal dose. Notably, the 150 μg dose of mCD172a(SIRPα)-Fc-CD40L appeared to be more efficacious and with a better defined immune signature than the 300 μg dose.

The above data clearly demonstrate, inter alia, functional activity of mCD172a(SIRPα)-Fc-CD40L in vivo, at least, in treating cancer.

Figure 13:
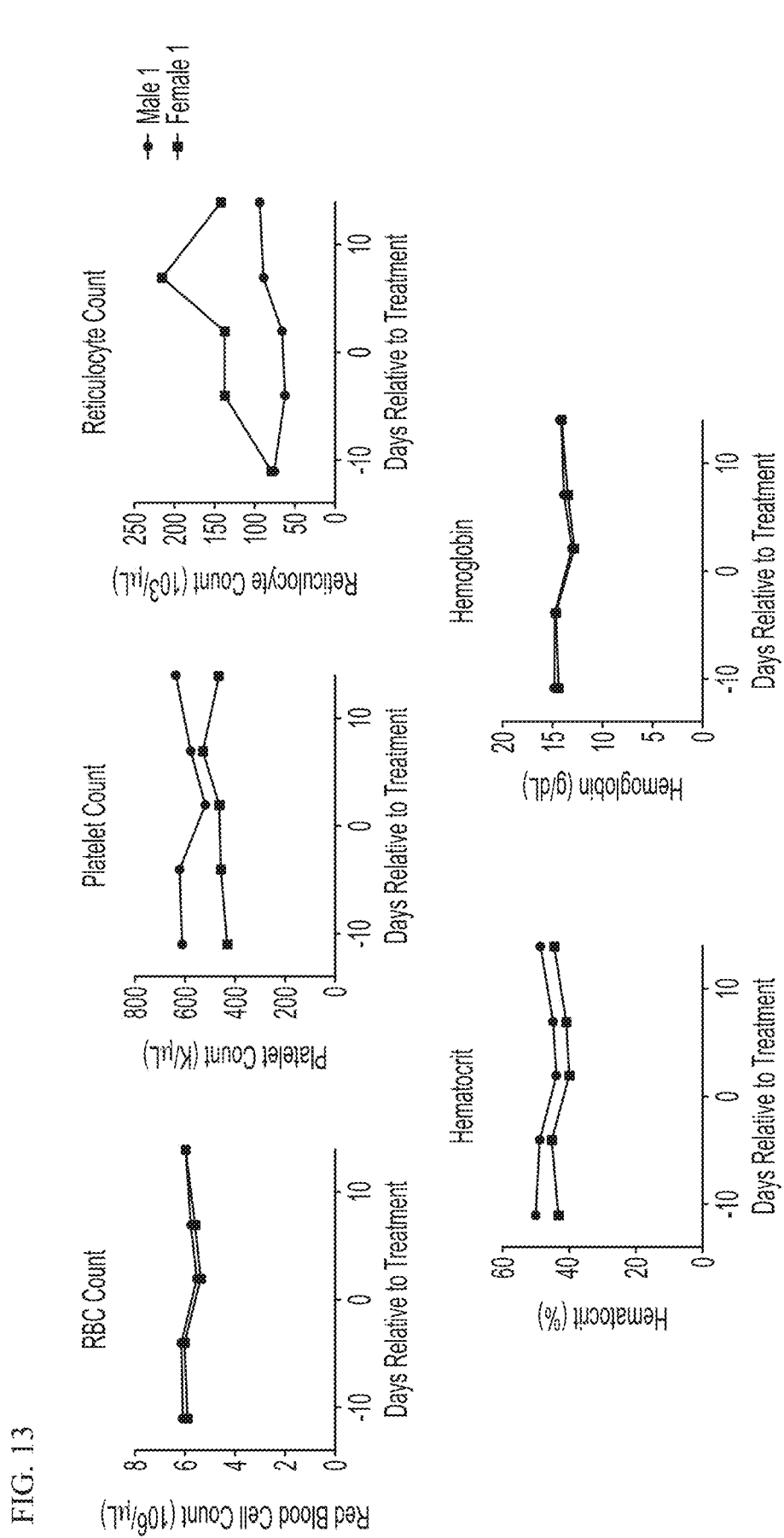
FIG. 13 shows data from cynomolgus macaques treated with human CD172a(SIRPα)-Fc-CD40L. 1 male and 1 female cynomolgus macaque were treated with a single dose of hCD172a(SIRPα)-Fc-CD40L at 1 mg/kg. Serum was collected at multiple time points from pre-treatment to fourteen days after treatment to evaluate pharmacokinetics and safety. CBC/CMPs were performed at five time points for safety and specific evaluation of hemolysis and thrombocytopenia. No evidence of red blood cell lysis or platelet depletion were observed following treatment with hCD172a (SIRPα)-Fc-CD40L. Gross safety assessments were made multiple times daily, and no additional safety signals were observed.

Example 7: Characterization of the Human CD172a(SIRPα)-Fc-CD40L Chimeric Protein In Vivo The inability of the human CD172a(SIRPα)-Fc-CD40L chimeric protein to bind to red blood cells and, thereby, causing hemolysis was then tested. Here, hCD172a(SIRPα)-Fc-CD40L was contacted with cynomolgus macaque red blood cells (RBCs; FIG. 13 left top panel). No significant change in RBC counts was detected in the two monkeys; thus, the chimeric protein did not cause significant lysis of cynomolgus macaque RBCs in vivo. The hCD172a(SIRPα)-Fc-CD40L chimeric protein likewise did not appear to significantly affect indicators hemolysis (See FIG. 13, remaining panels). No evidence of RBC lysis or platelet depletion was observed following treatment with hCD172a(SIRPα)-Fc-CD40L. Gross safety assessments were made multiple times daily, and no additional safety signals were observed. These data indicate that hCD172a(SIRPα)-Fc-CD40L does not cause hemolysis of RBCs as an unwanted side effect.

Example 8: Characterization of Combination Treatments with a Plurality of Chimeric Proteins In this example, anti-tumor potency and/or synergistic effects were determined for treatments comprising combinations of chimeric proteins. Specifically, murine models of colorectal cancer (MC38 or CT26) or of melanoma (B16.F10) were used to assess the effects of these treatments on tumor growth and overall survival.

Figure 14:
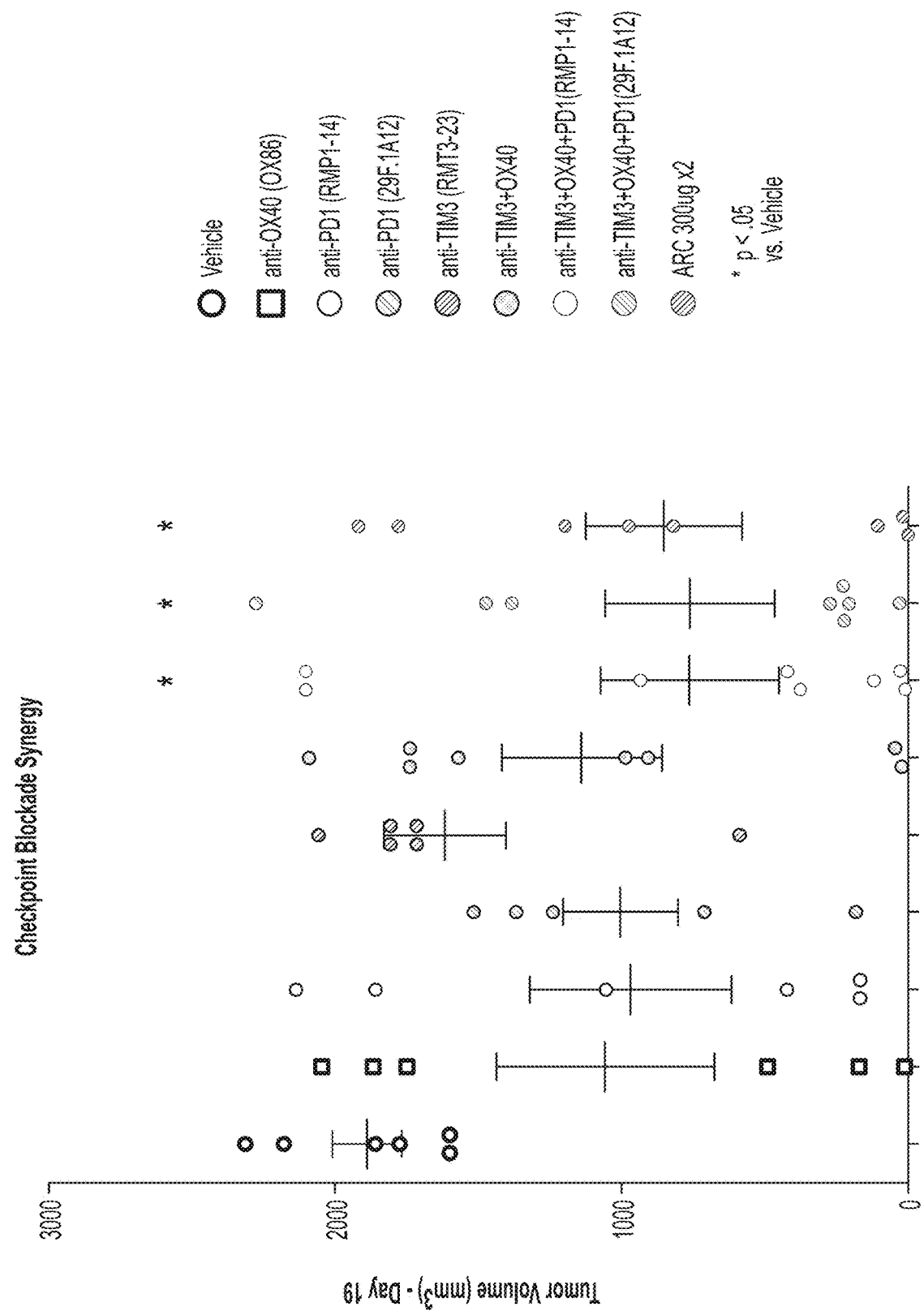
FIG. 14 shows in vivo synergy in reducing tumor volumes of treatments with antibodies (as monotherapies or in combinations) directed to checkpoint proteins or treatments with chimeric proteins. The conditions are, left to right: vehicle, anti-OX40 (OX86), anti-PD-1 (RMP1-14), anti-PD-1 (29F.1A12), anti-TIM3 (RMT3-23), anti-TIM3+OX40, anti-TIM3+OX40+PD-1 (RMP1-14), anti-TIM3+OX40+PD-1 (29F.1A12), ARC 300 μg×2 ("ARC" is the TIM3-Fc-OX40L chimeric protein).

Balb/c mice (n=6, 8, or 9) described in FIG. 14 were inoculated in the hind flank with $2.5 \times 10^5$ MC38-ova tumor cells. On days 5 and 8, mice were treated with the OX86 (anti-OX40) antibody; the RMP1-14 or 29F.1.A12 (anti-PD-1) antibody; the RMT3-32 (anti-TIM3) antibody; the anti-TIM3 and the anti-OX40 antibodies; the anti-TIM3, the anti-OX40, and the anti-PD-1 (RMP1-14) antibodies; the anti-OX40, the anti-TIM3, and the 29F.1.A12/anti-PD-1 antibodies; or the TIM3-Fc-OX40L chimeric protein. When provided, 100 μg of each antibody was administered via intraperitoneal injection. When provided, 300 μg of the TIM3-Fc-OX40L chimeric protein was administered via intraperitoneal injection on day 5 and again on day 7. Tumor area was calculated on the 19th day after inoculation by taking perpendicular tumor diameter measurements using electronic calipers. Neither the mice treated with a single antibody nor the mice treated with both the anti-TIM3 and the anti-OX40 antibodies had a statistically-significant reduction in tumor size relative to control treatments. However, when compared to control treatments, a statistically-significant ($p<0.05$) reduction in tumor size was observed in mice treated with either combination of three antibodies and in mice treated with two sequential doses of the TIM3-Fc-OX40L chimeric protein.

Figure 15A:
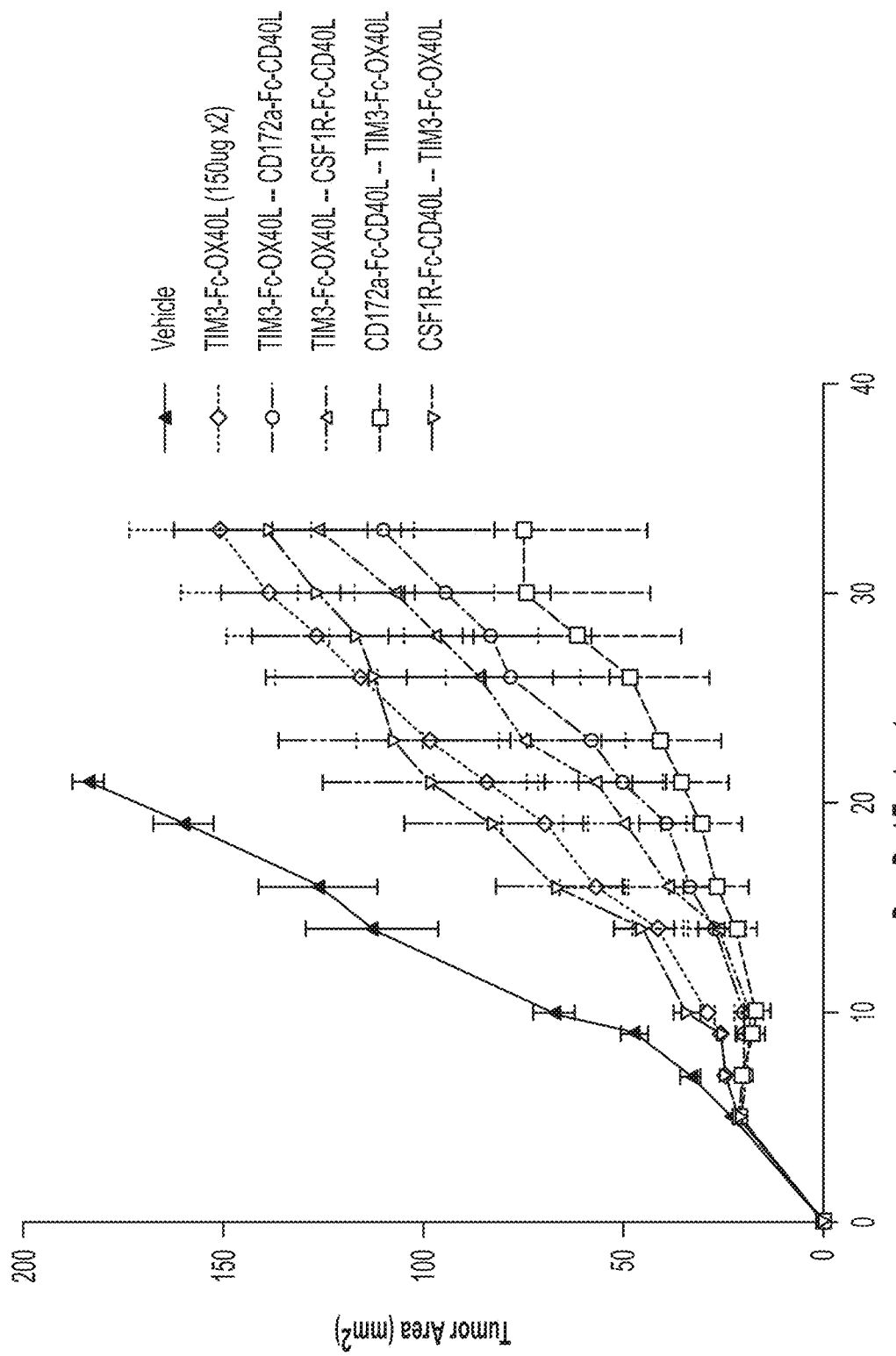
FIG. 15A shows in vivo reduction in tumor volume from sequential treatments of chimeric proteins, either two sequential treatments with the same chimeric protein or treatments with two different chimeric proteins.
Figure 15B:
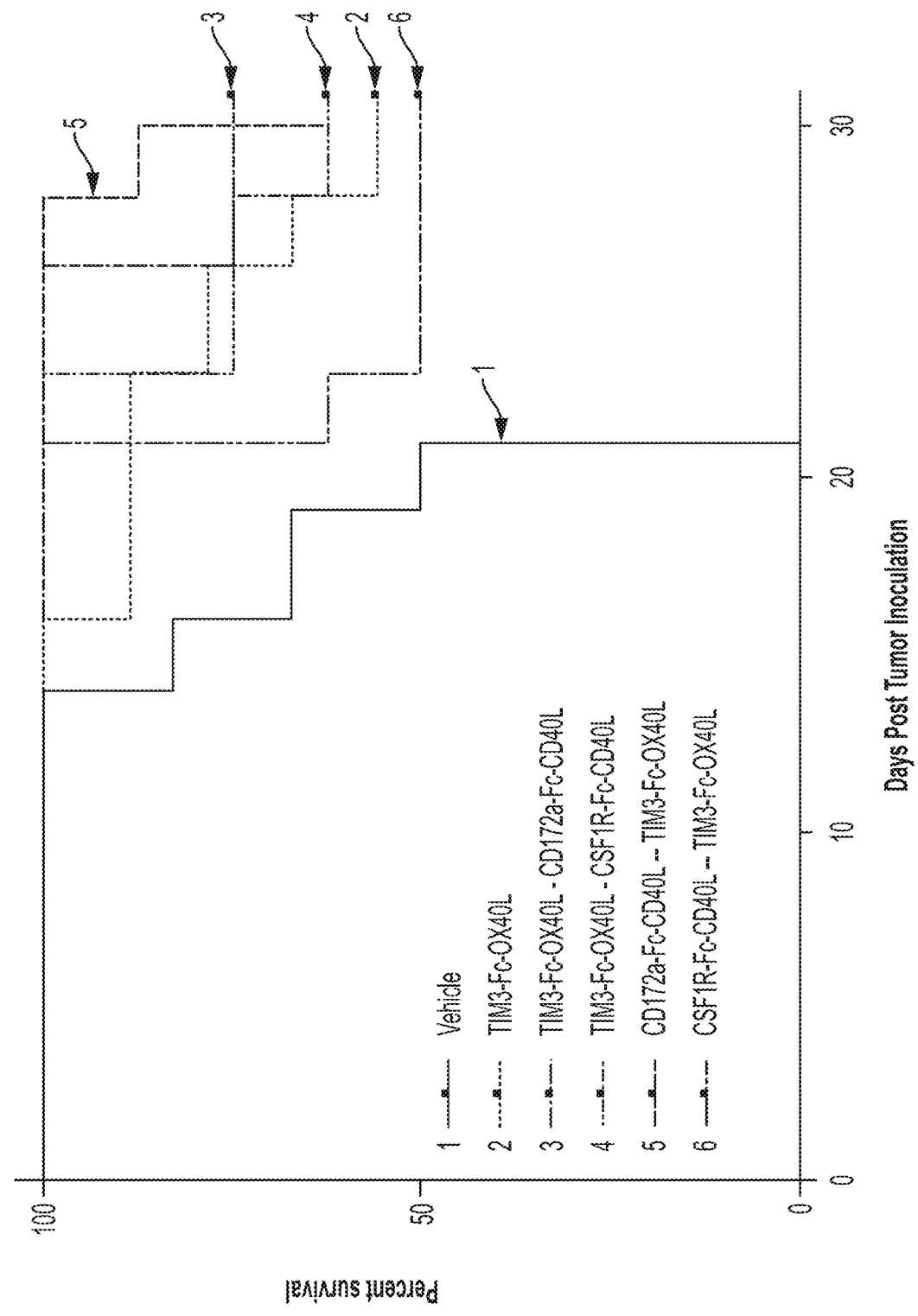
FIG. 15B shows percent survival over time for the mice shown in FIG. 15A. For clarity, in FIG. 15A, the conditions at point 20 days on the x axis are (top to bottom): vehicle, CSF1R-Fc-CD40L—TIM3-Fc-OX40L, TIM3-Fc-OX40L (150 μg×2), TIM3-Fc-OX40L—CSF1R-Fc-CD40L, TIM3-Fc-OX40L—CD172a-Fc-CD40L, and CD172a-Fc-CD40L—TIM3-Fc-OX40L. For clarity, in FIG. 15B, the conditions are identified as: vehicle: "1"; TIM3-Fc-OX40L (150 μg×2): "2"; TIM3-Fc-OX40L—CD172a-Fc-CD40L: "3"; TIM3-Fc-OX40L—CSF1R-Fc-CD40L: "4"; CD172a-Fc-CD40L—TIM3-Fc-OX40L: "5"; and CSF1R-Fc-CD40L—TIM3-Fc-OX40L: "6".

Balb/c mice (n=8 or 9) described in FIG. 15A and FIG. 15B were inoculated in the hind flank with CT26 tumor cells. Mice in a first treatment group, on days 5 and 7, were treated with 150 μg of the TIM3-Fc-OX40L chimeric protein. Mice in a second treatment group were treated on day 5 and 7 with 150 μg of the TIM3-Fc-OX40L chimeric protein and then treated on day 7 and 9 with 150 μg of the CD172a(SIRPα)-Fc-CD40L chimeric protein. Mice in a third treatment group were treated on day 5 and 7 with 150 μg of the TIM3-Fc-OX40L chimeric protein and then treated on day 7 and 9 with 150 μg of the CSF1R-Fc-CD40L chimeric protein. Mice in a fourth treatment group were treated on day 5 and 7 with 150 μg of the CD172a(SIRPα)-Fc-CD40L chimeric protein and then treated on day 7 and 9 with 150 μg of TIM3-Fc-OX40L chimeric protein. Mice in a fifth treatment group were treated on day 5 and 7 with 150 μg of the CSF1R-Fc-CD40L chimeric protein and then treated on day 7 and 9 with 150 μg of the TIM3-Fc-OX40L chimeric protein. Tumor areas were calculated periodically. Of the mice in the first, second, third, and fifth treatment groups, only one mouse in each treatment group rejected the tumor inoculation and two mice in the fourth group rejected the tumor inoculation.

As shown in FIG. 15A, mice in each of the treatment groups showed reductions in tumor size (relative to control treatments) over the course of the test period, with the greatest reduction observed for mice of the fourth treatment group, which were first treated with CD172a(SIRPα)-Fc-CD40L chimeric protein and then treated with the TIM3-Fc-OX40L chimeric protein. The next greatest tumor reduction was for the same CD172a(SIRPα)-Fc-CD40L pairing TIM3-Fc-OX40L yet in a reversed order. Thus, for this paring, treating with the TIM3-Fc-OX40L chimeric protein second provided the greater reduction in tumor size. Surprisingly, an opposite pattern was observed for the other pairing of chimeric proteins. Indeed, a greater reduction in tumor size resulted when the TIM3-Fc-OX40L chimeric protein is treated before the CSF1R-Fc-CD40L when compared to a treatment with the CSF1R-Fc-CD40L chimeric protein first. Thus, for this paring, treating with the TIM3-Fc-OX40L chimeric protein first provides the greater reduction in tumor size. Finally, for the treatment groups in which TIM3-Fc-OX40L was treated first, a greater reduction in tumor size was observed when a different chimeric protein was provided second relative to the mice who receive TIM3-Fc-OX40L as both a first and a second treatment. Thus, for certain chimeric proteins, there may be an advantage from administering different first and second chimeric proteins.

Similarly, as shown in FIG. 15B, mice in each of the treatment group had improved survival relative to the control treated mice; with survival at about 30 days of between about 50% and 75%. Again, for the treatment groups in which TIM3-Fc-OX40L was treated first, improved survival was observed when a different chimeric protein was provided second relative to the mice who receive TIM3-Fc-OX40L as both a first and a second treatment. Again, for certain chimeric proteins, there may be an advantage from administering different first and second chimeric proteins.

These data demonstrate that treatments including sequential treatments two chimeric proteins (either identical or different chimeric proteins) provides enhanced anti-tumor efficacy and improved survival. Moreover, for certain chimeric proteins, efficacy and survival may be affected by the order that two different chimeric proteins are administered. Furthermore, for certain chimeric proteins, efficacy and survival may be affected when the second chimeric protein administered differs from the first-administered chimeric protein. These data support the understanding that a combined regimen involving the administration of one or more chimeric proteins which induce an innate immune response before, concurrently with, or subsequent to administration of one or more chimeric proteins which induce an adaptive immune response may provide synergistic effects (e.g., synergistic anti-tumor effects).

Example 9: Characterization of the Contribution of an Fc Domain in a Linker to Functionality of Chimeric Proteins In this example, the contribution of an Fc domain in a linker to functionality of chimeric proteins of the present invention was assayed. Here, a PD-1-Fc-OX40L was used as a model for Fc-containing chimeric proteins. Thus, the data presented below is relevant to chimeric proteins of the present invention.

Figure 16:
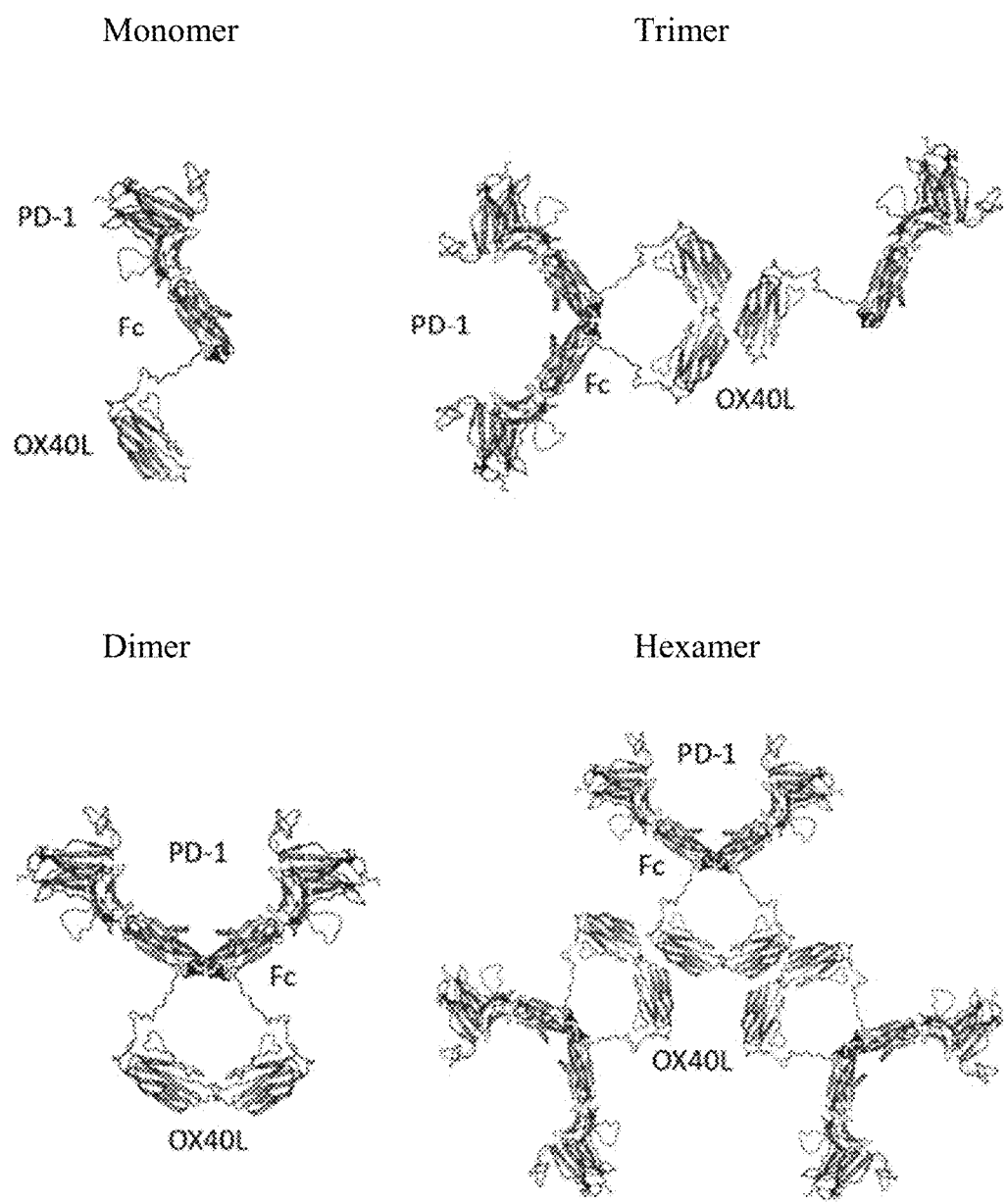
FIG. 16 shows, without wishing to be bound by theory, four potential configurations of PD-1-Fc-OX40L chimeric proteins.

In its native state, PD-1 exists as monomer whereas OX40Ls tend to dimerize due to electrostatic interactions between the OX40L domains; Fc domains associate with each other via disulfide bonds, e.g., via their cysteine residue(s). Together, several inter-molecular interactions may contribute to the quaternary structure of PD-1-Fc-OX40L. There are, at least, four potential configurations of PD-1-Fc-OX40L, with the chimeric protein existing as a monomer, a dimer, a trimer, or a hexamer. See, FIG. 16.

Figure 17:
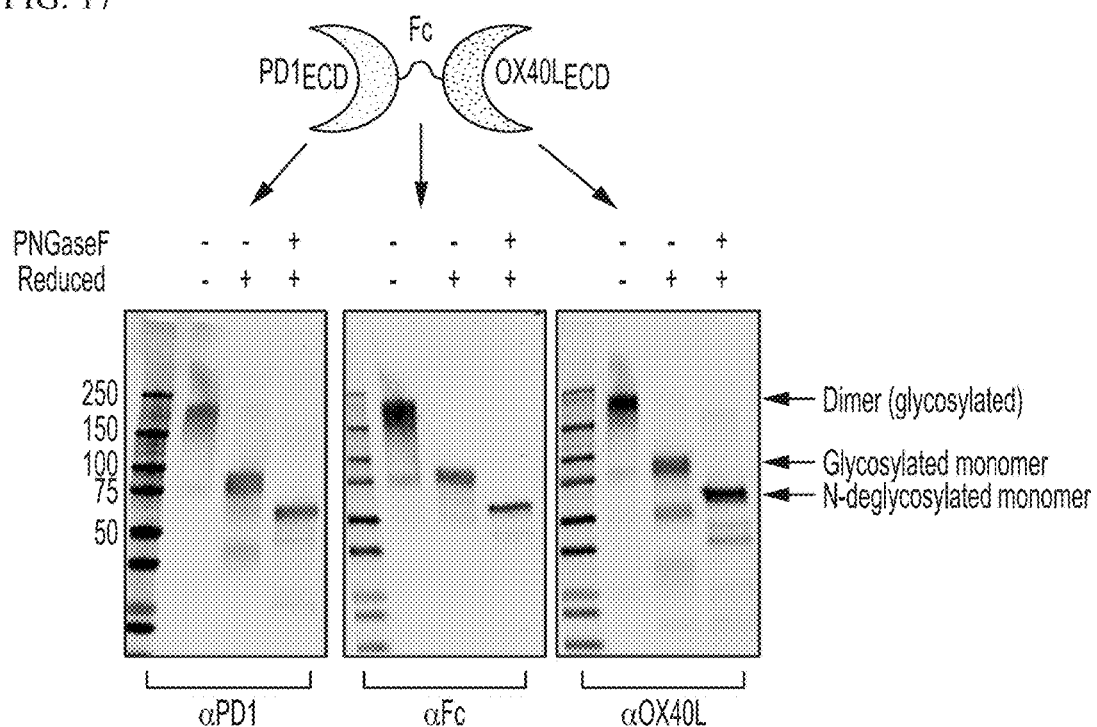
FIG. 17 shows Western blots of PD-1-Fc-OX40L chimeric proteins run on SDS-PAGE under a non-reducing condition, a reducing condition, and a reducing condition and following treatment with Peptide-N-Glycosidase F (PNGaseF).

The existence of monomeric and dimeric configurations of the chimeric protein was tested by exposing chimeric proteins to reducing and non-reducing conditions and then running the proteins on SDS-PAGE. Under non-reducing conditions (Reduced: "−"), the chimeric protein migrated in SDS-PAGE at about 200 kDa. Here, Western blots were probed with antibodies directed against PD-1, Fc, or OX40L in, respectively, the left, middle, and right blots shown in FIG. 17. Since, the predicted monomeric molecular weight of the chimeric protein is 57.6 kDa, the 200 kDa species was expected to be, at least a dimer. However, under reduced conditions (Reduced: "+"), which reduces disulfide bonds (e.g., between Fc domains), the chimeric protein migrated in SDS-PAGE at about 100 kDa. Since the 100 kDa species was heavier than expected, it was predicted that the extra mass was due to glycosylation. Finally, chimeric proteins were treated with Peptide-N-Glycosidase F (PNGaseF "+") and run on SDS-PAGE under reduced conditions. Under these conditions, the chimeric protein migrated at about 57.6 kDa. These data suggest that the chimeric protein is glycosylated and exists naturally, at least, as a dimer; with dimerization likely due to disulfide bonding between Fc domains e.g., via their cysteine residue(s).

Figure 18:
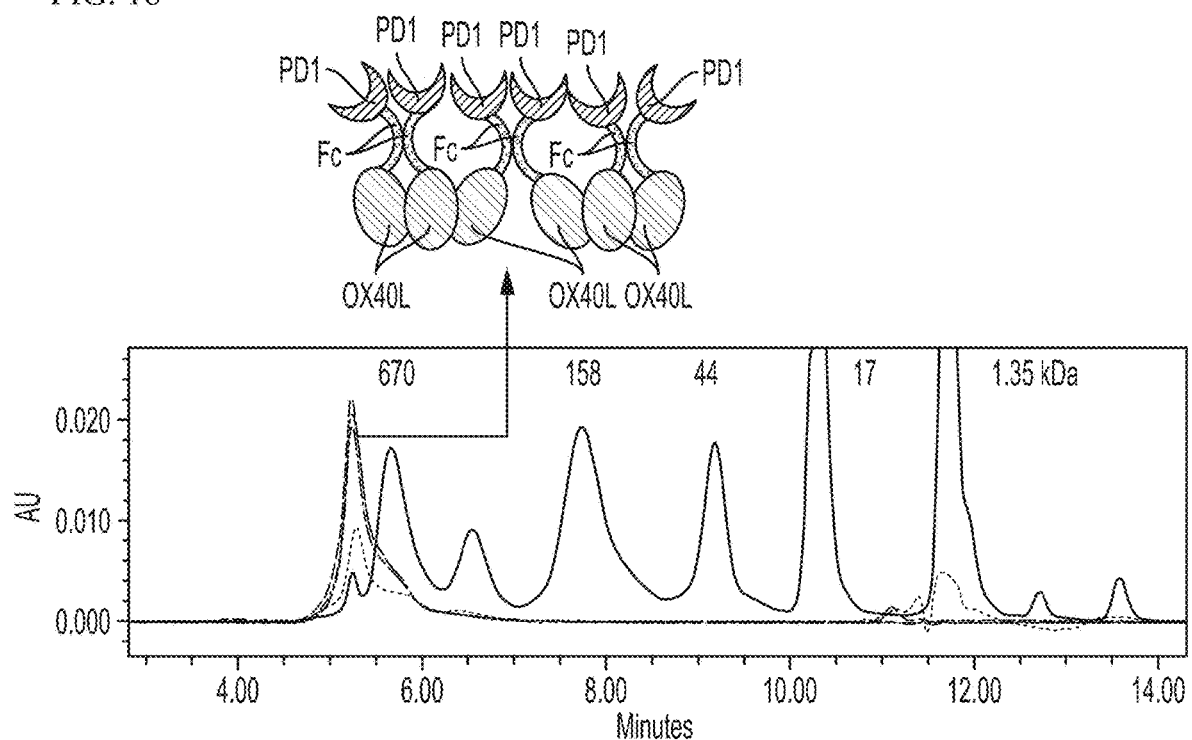
FIG. 18 shows a chromatograph for PD-1-Fc-OX40L chimeric proteins run on Size Exclusion Chromatography (SEC).

SDS-PAGE gel methods do not accurately predict the molecular weight for highly charged and/or large molecular weight proteins. Thus, chimeric proteins were next characterized using Size Exclusion Chromatography (SEC). Unlike SDS-PAGE, in which the negatively-charged SDS reduces charge-based interactions between peptides, SEC does not use detergents or reducing agents. When the PD-1-Fc-OX40L chimeric protein was run on SEC, none of the peaks were around 200 kDa. This suggests, that natively, the chimeric protein does not exist as a dimer. Instead, a peak having a size greater than 670 kDa was detected. See, FIG. 18. This and the prior data suggests that the PD-1-Fc-OX40L chimeric protein exists as a hexamer in its native state.

Figure 19:
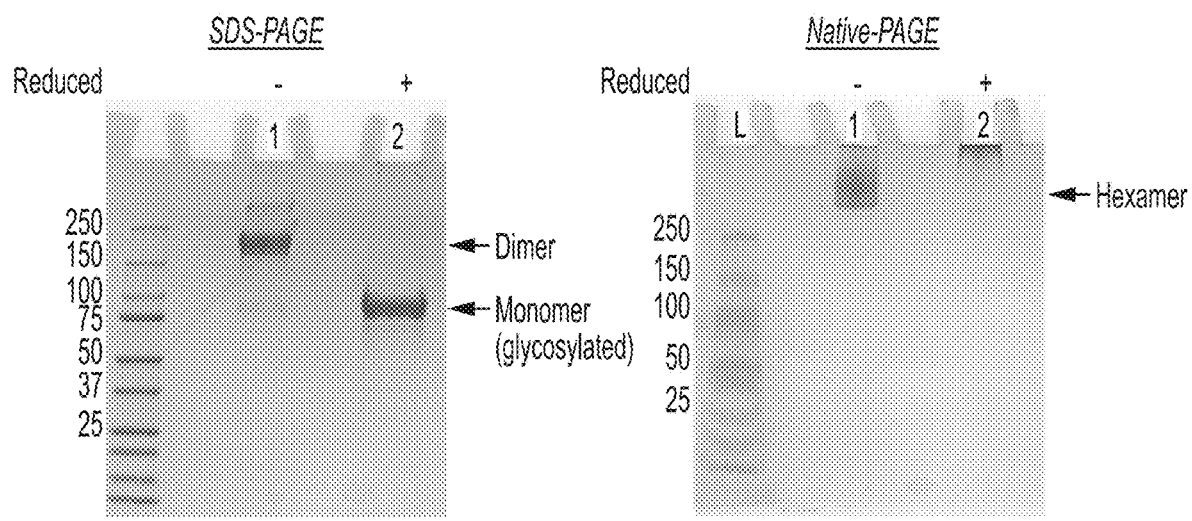
FIG. 19 shows SDS-PAGE and native (non-SDS) PAGE gels for PD-1-Fc-OX40L chimeric proteins run under a non-reducing condition ("−") or a reducing condition ("+").

As shown above, when run on SDS-PAGE under non-reducing conditions or under reducing conditions, SDS in the sample and/or running buffer converts the hexameric PD-1-Fc-OX40L chimeric protein into a predominant dimer or monomer, respectively, in the absence and presence of a reducing agent. See, FIG. 19 (left gel). When run on native PAGE, which lacks SDS, and in the absence of a reducing agent, the chimeric protein exists as a hexamer. However, when run on native PAGE and in the presence of a reducing agent (which reduces disulfide bonds) the chimeric protein migrated heavier than expected; as shown in FIG. 19 (right gel, lane 2), with the chimeric protein failed to substantially migrate out of the loading well. This data suggests that the chimeric protein oligomerized into a higher-order protein. Thus, in chimeric proteins, disulfide bonding appears to be important for controlling higher-order oligomerization.

Figure 20:
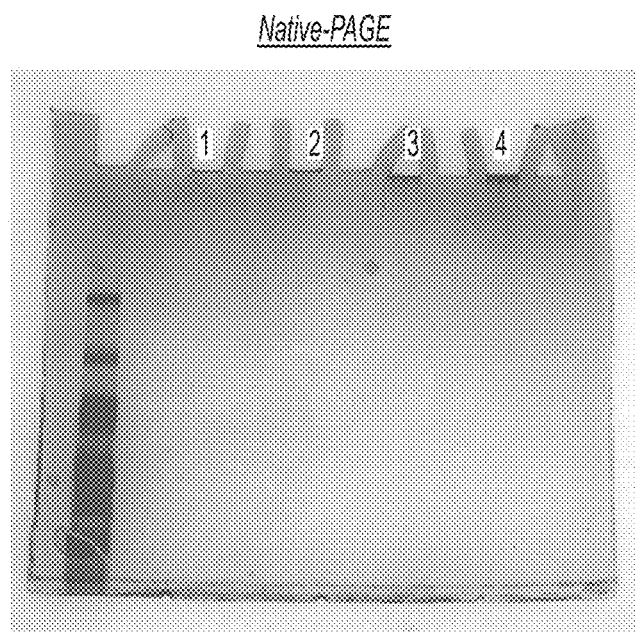
FIG. 20 shows a native (non-SDS) PAGE gel for PD-1-No Fc-OX40L chimeric proteins which lack a Fc domain.
Figure 21:
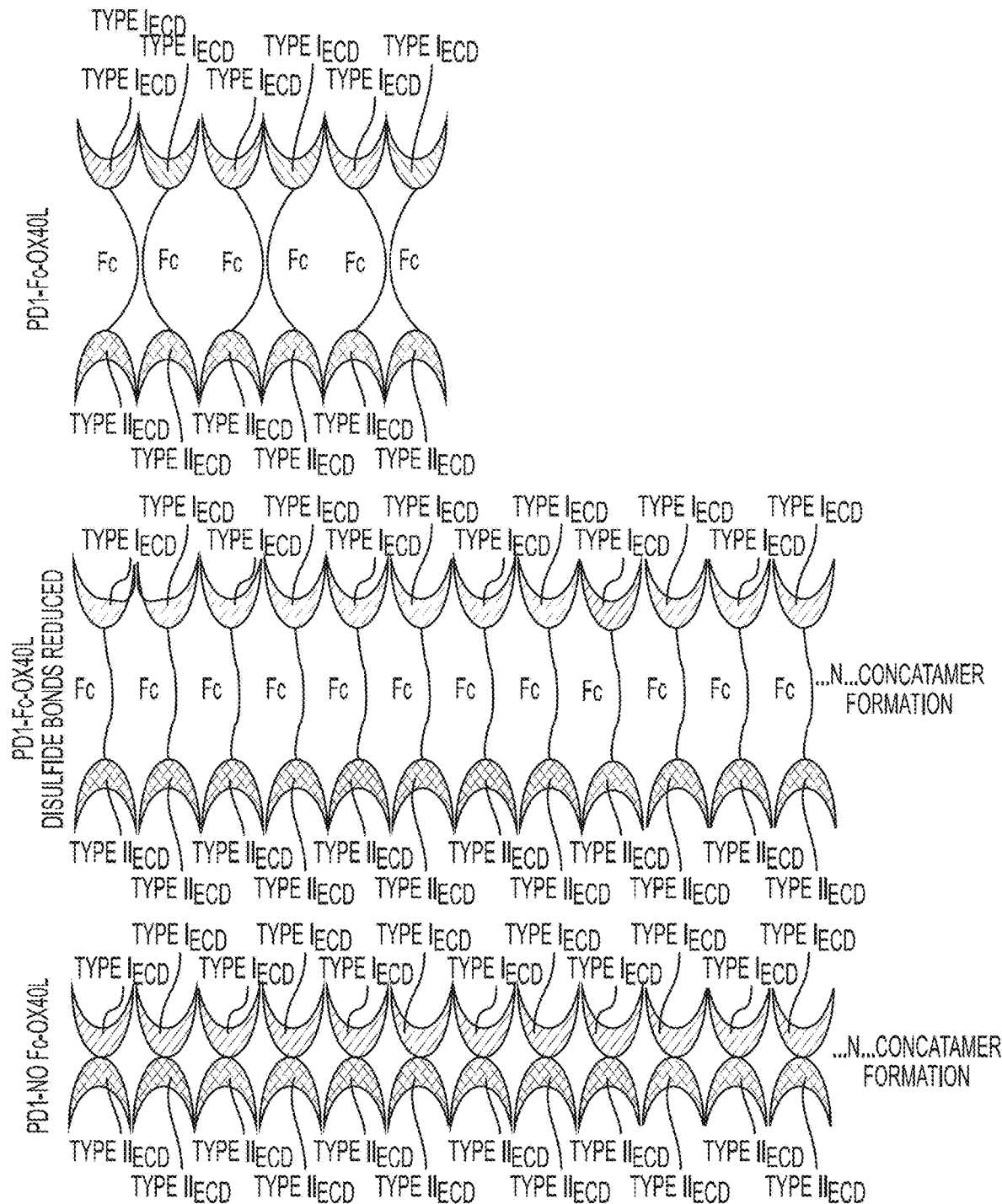
FIG. 21 shows, without wishing to be bound by theory, a model for how a hexamer and concatemers form from chimeric proteins of the present invention.

To further confirm this, chimeric proteins lacking an Fc domain were constructed, e.g., "PD-1-No Fc-OX40L". Such chimeric proteins will not have the disulfide bonding which occurs between Fc domains in the chimeric proteins described previously. As shown in FIG. 20, when chimeric proteins lacking Fc domains are run on native PAGE, none of the protein substantially migrated out of its loading well; again, suggesting that the "No Fc" chimeric proteins have formed a concatemer-like complex comprising numerous proteins. Thus, omission of the Fc domain in a chimeric protein leads to formation of protein aggregates. These data indicate that disulfide bonding, e.g., between Fc domains on different chimeric proteins, stabilizes the chimeric proteins and ensures that they each exist as a hexamer and not as a higher-order protein/concatemer. In other words, the Fc domain surprisingly puts order to chimeric protein complexes. Lanes 1 to 4 respectively include 2.5 µg, of PD-1-No Fc-OX40L, 5 µg of PD-1-No Fc-OX40L, 2.5 µg of PD-1-No Fc-OX40L, and 5 µg of PD-1-No Fc-OX40L Shown in FIG. 21 is a model summarizing the above data and showing how a hexamer and concatemers form from chimeric proteins of the present invention. The illustrative chimeric protein (PD-1-Fc-OX40L) naturally forms into a hexamer (due to electrostatic interactions between the OX40L domains and dimerization by Fc domains). However, in the absence of the controlling effects off disulfide bonding between Fc domains, under reduced conditions for the PD-1-Fc-OX40L protein and due to the absence of Fc domains in the PD-1-No Fc-OX40L, these latter chimeric proteins form concatemers.

Additionally, chimeric proteins were constructed in which the Fc domain (as described herein) was replaced with Ficolin (which lacks cysteine residues necessary for disulfide bonding between chimeric proteins). As with the No Fc chimeric proteins and chimeric proteins comprising an Fc and run on native PAGE and in the presence of a reducing agent (both of which formed aggregates that do not migrate into a gel) chimeric proteins comprising Ficolin appear to also form higher-order lattices which did not migrate into a gel. These data reinforce the conclusion that disulfide binding is important for proper folding and function of chimeric proteins of the present invention.

Finally, chimeric proteins were prepared using coiled Fc domains (CCDFc). Very little purified protein was delivered under functional evaluation.

Accordingly, including an Fc domain in a linker of a chimeric protein (which is capable of forming disulfide bonds between chimeric proteins), helps avoid formation of insoluble and, likely, non-functional protein concatemers and/or aggregates.

Example 10: Characterization of Different Joining Linker Sequences for the Chimeric Proteins Different unique joining linker sequences (17 linkers) were identified with varying characteristics (length, solubility, charge and flexibility). Constructs were then synthesized incorporating each of those 17 joining linker sequences into the 'linker 2' position, where the configuration of chimeric protein:

ECD 1-Joining Linker 1-Fc-Joining Linker 2-ECD 2

The production levels for those 17 constructs were tested in CHO cells. The following table provides a summary for the different joining linker sequences, characteristics of those joining linkers, the production level (by A280), and the Additionally, each purified protein with different linker sequences was also characterized by binding to PD-L1 or binding values ($EC_{50}$) based on FACS analysis to PD-L1 or OX40. Some variations in production levels and activity between certain joining linker sequences were determined.

Figure 22A:
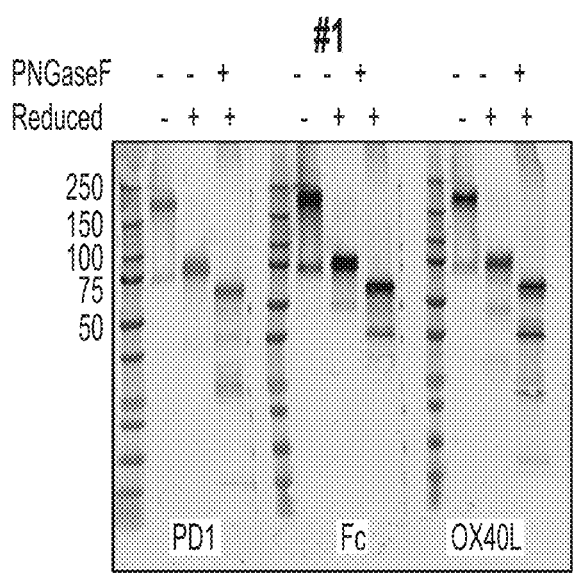
FIG. 22A to FIG. 22Q show characterization of PD-1-Fc-OX40L chimeric proteins with different joining linker sequences by Western blot analysis. Sequences of the different joining linkers are provided below in the Examples section. Specifically, each individual domain of the fusion construct was probed using an α-PD-1, α-Fc, or α-OX40L antibody. In each figure, untreated samples of the PD-1-Fc-OX40L chimeric protein, e.g., control, were loaded into lane 1 in all the blots (no β-mercaptoethanol or PNGase). Samples in lane 2 were treated with the reducing agent, β-mercaptoethanol, while samples in lane 3 were treated with PNGase.
Figure 22B:
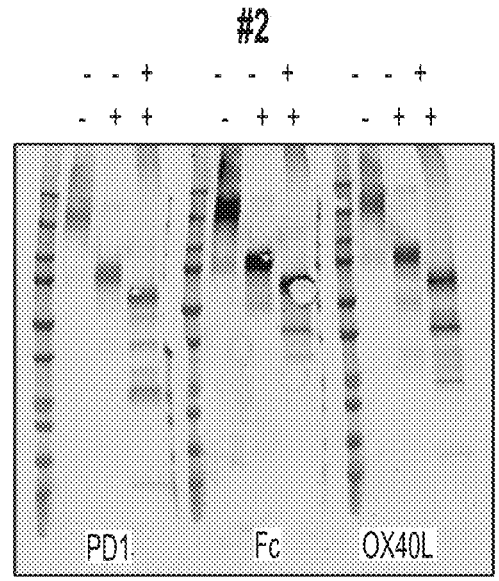
Figure 22C:
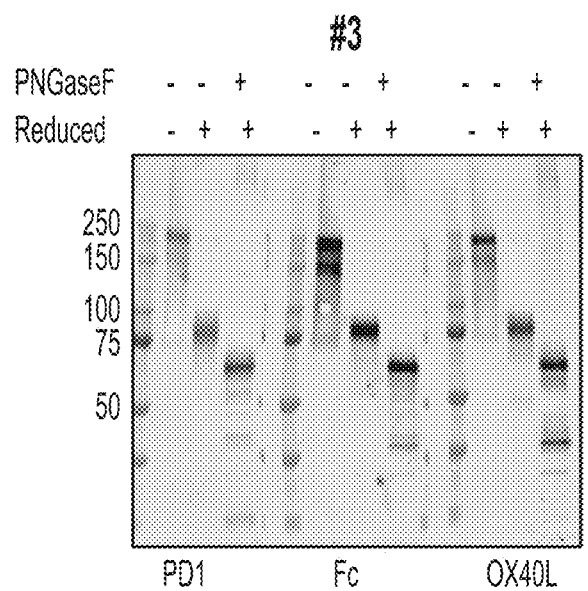
Figure 22D:
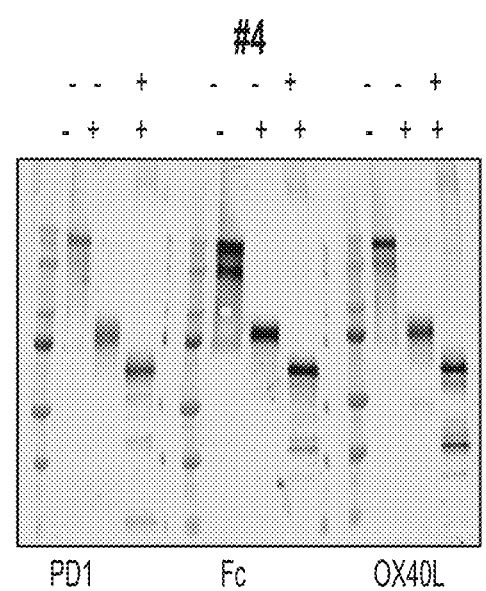
Figure 22E:
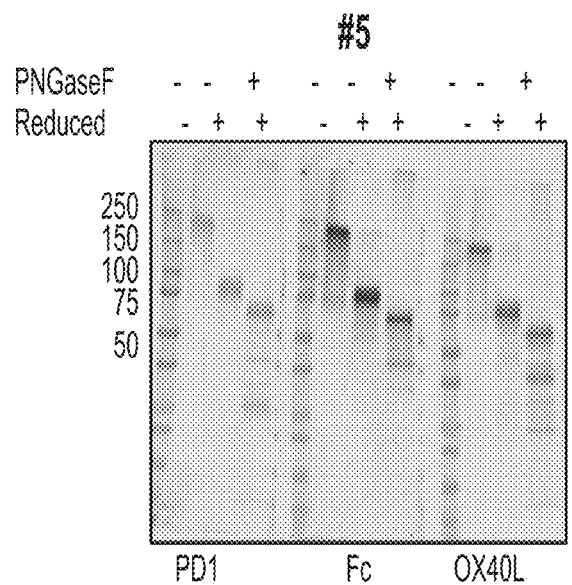
Figure 22F:
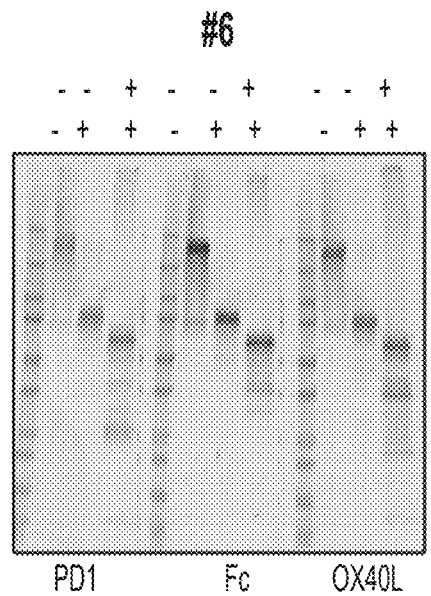
Figure 22G:
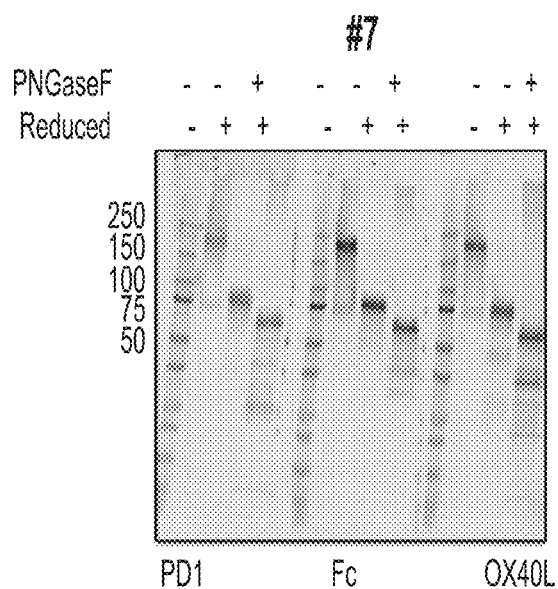
Figure 22H:
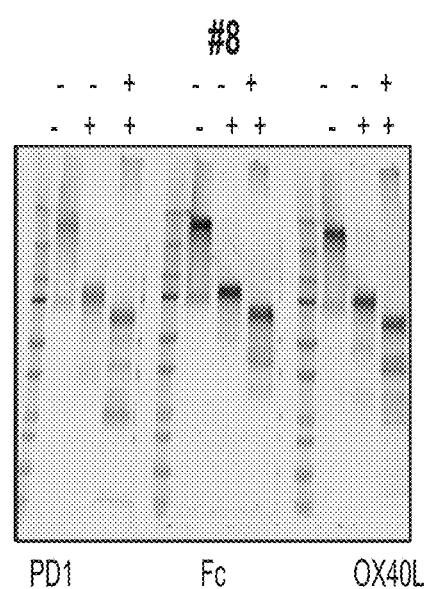
Figure 22I:
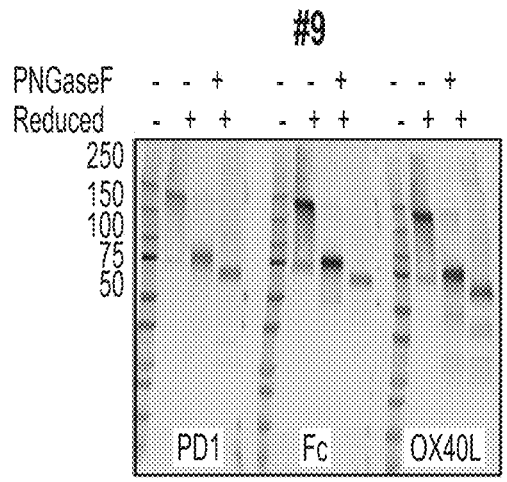
Figure 22J:
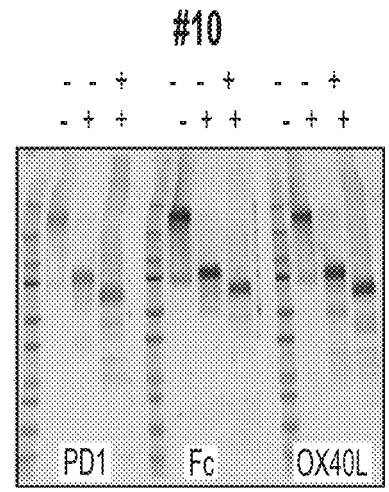
Figure 22K:
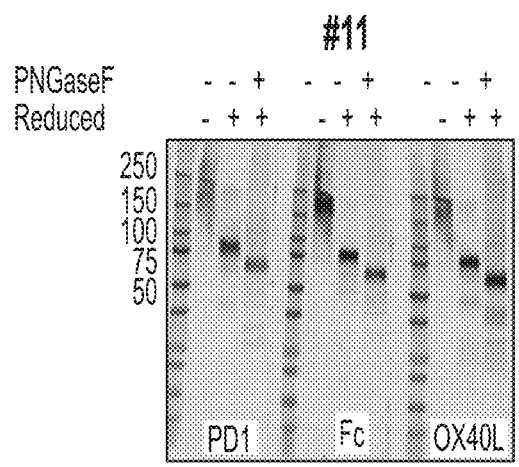
Figure 22L:
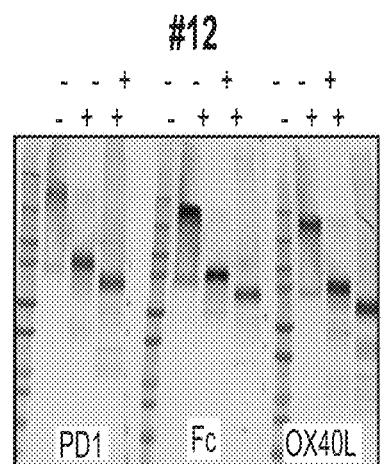
Figure 22M:
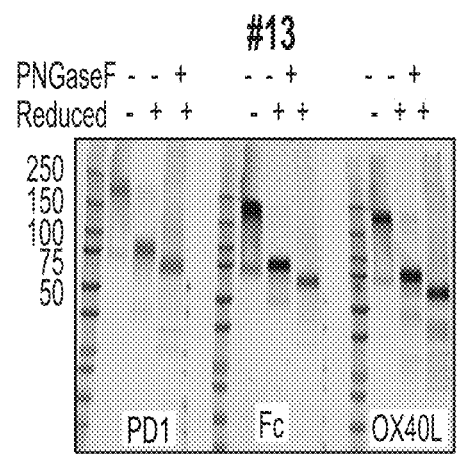
Figure 22N:
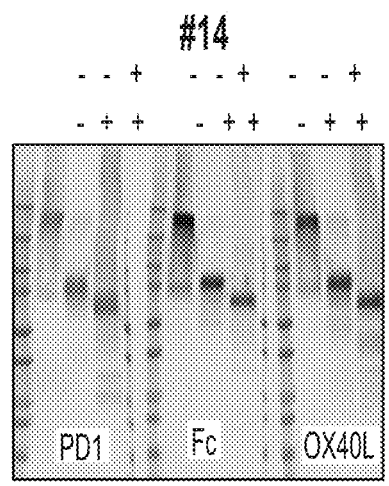
Figure 22O:
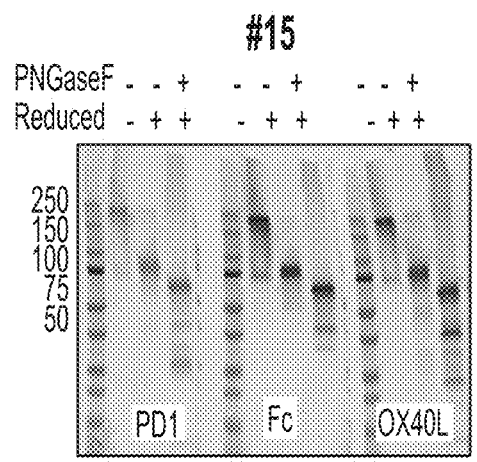
Figure 22P:
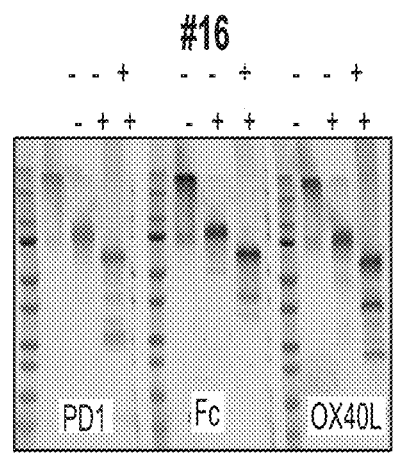
Figure 22Q:
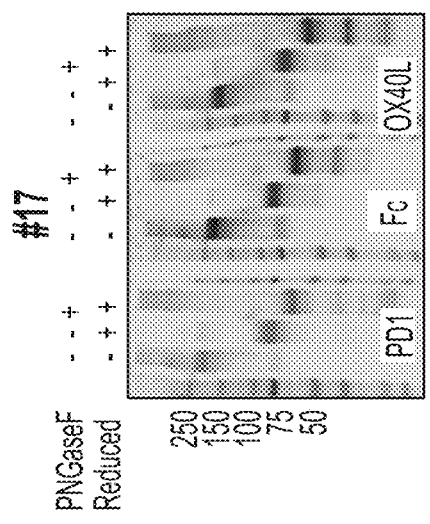
Figure 23:
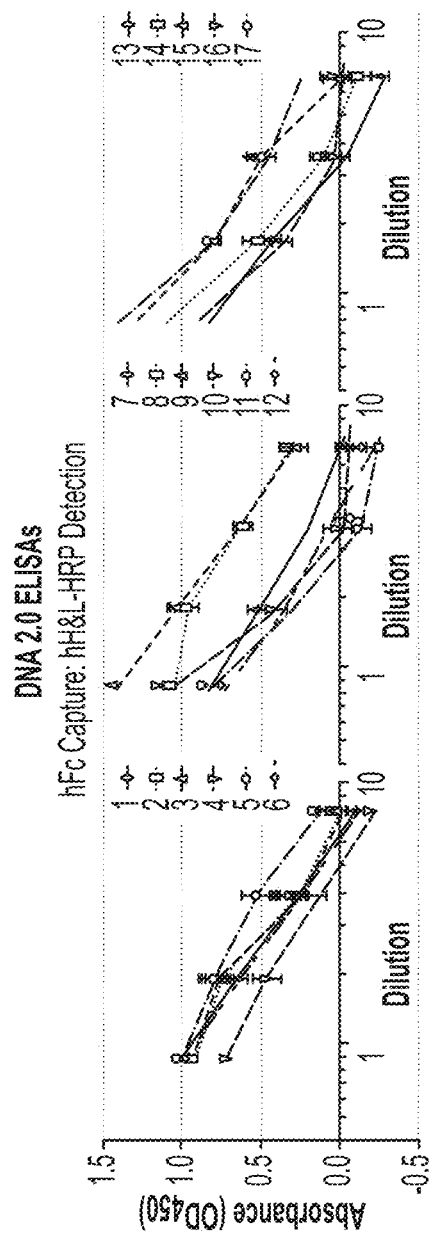
FIG. 23 shows characterization of PD-1-Fc-OX40L chimeric proteins with different joining linker sequences by ELISA-based capture and detection assay against the central Fc region of the protein. The protein concentration of each PD-1-Fc-OX40L chimeric protein with different joining linker sequence (#1 to #17) was determined.
Figure 24A:
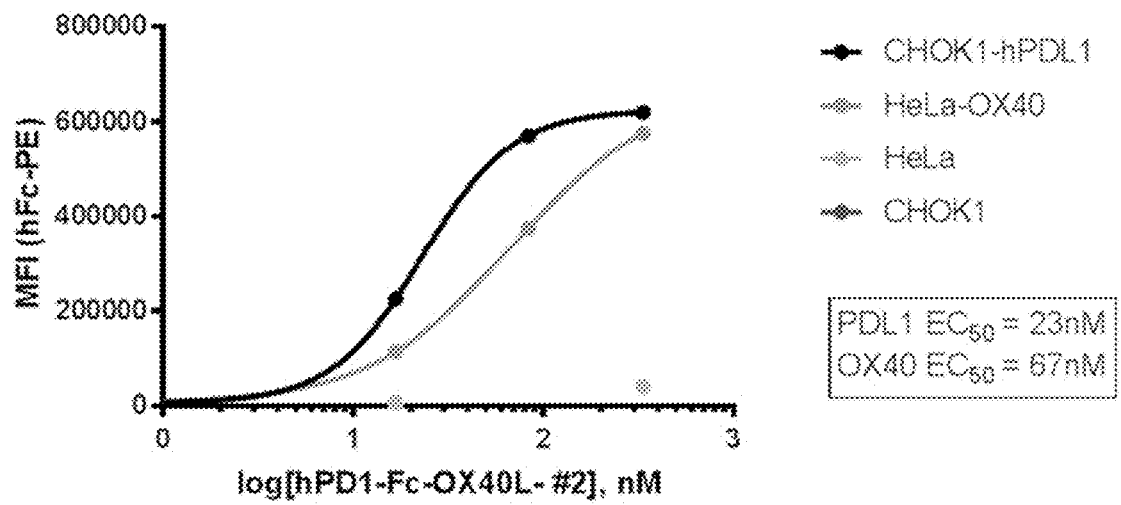
FIG. 24A to FIG. 24P show the flow cytometry profiles of PD-1-Fc-OX40L chimeric proteins with different joining linker sequences by FACS analysis to PD-L1 or OX40. The $EC_{50}$ values were calculated for each PD-1-Fc-OX40L chimeric protein with different joining linker sequence (#2 to #17).
Figure 24B:
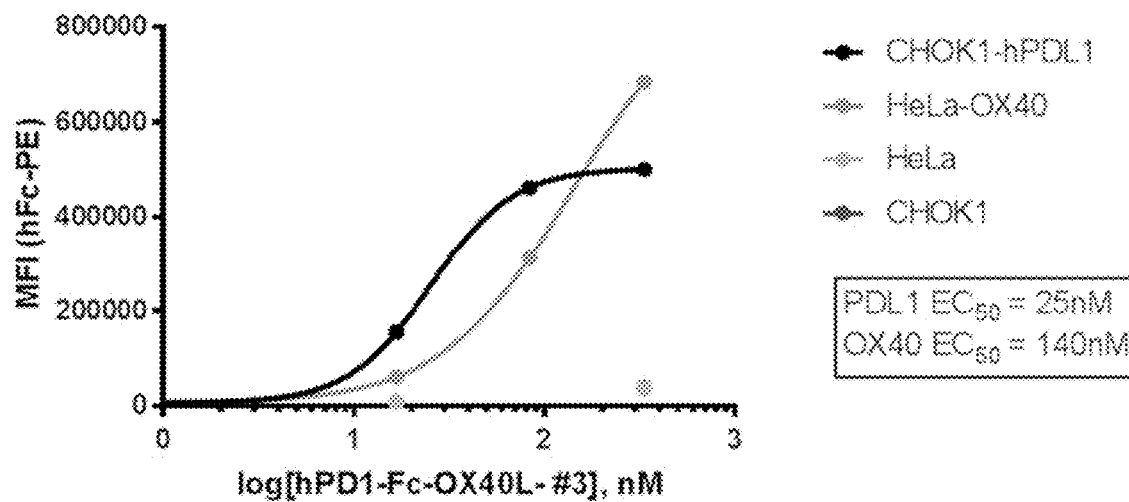
Figure 24C:
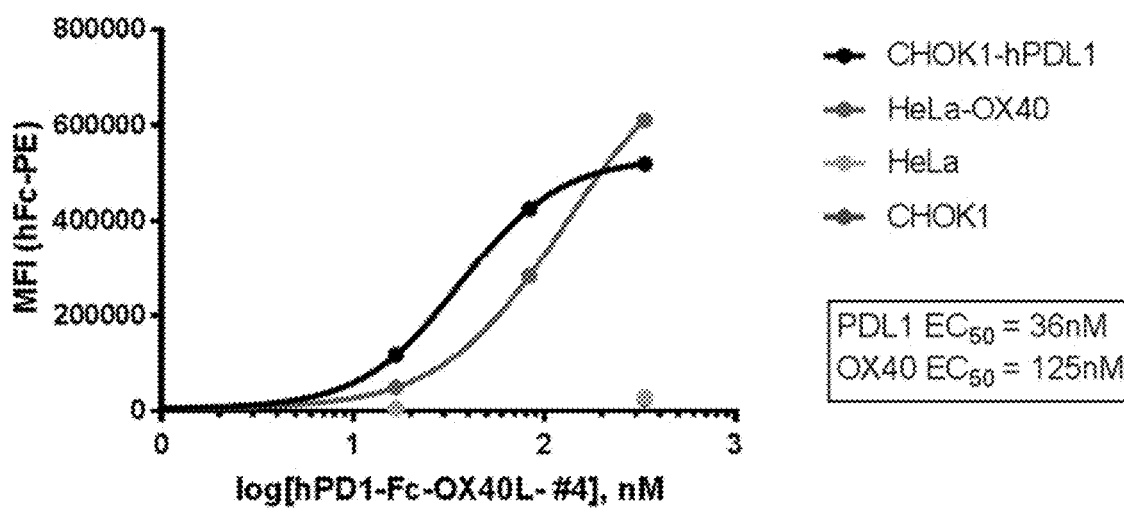
Figure 24D:
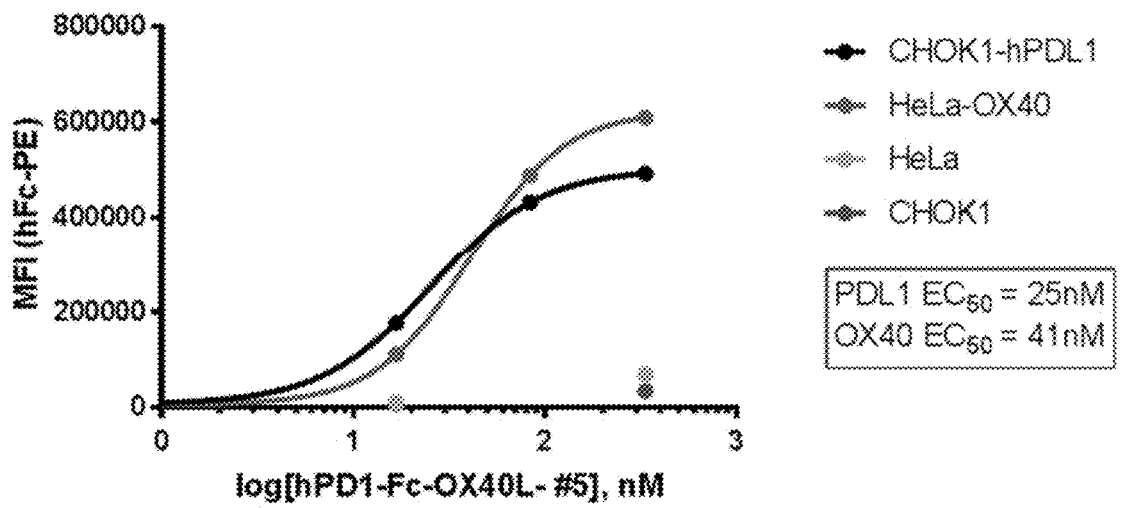
Figure 24E:
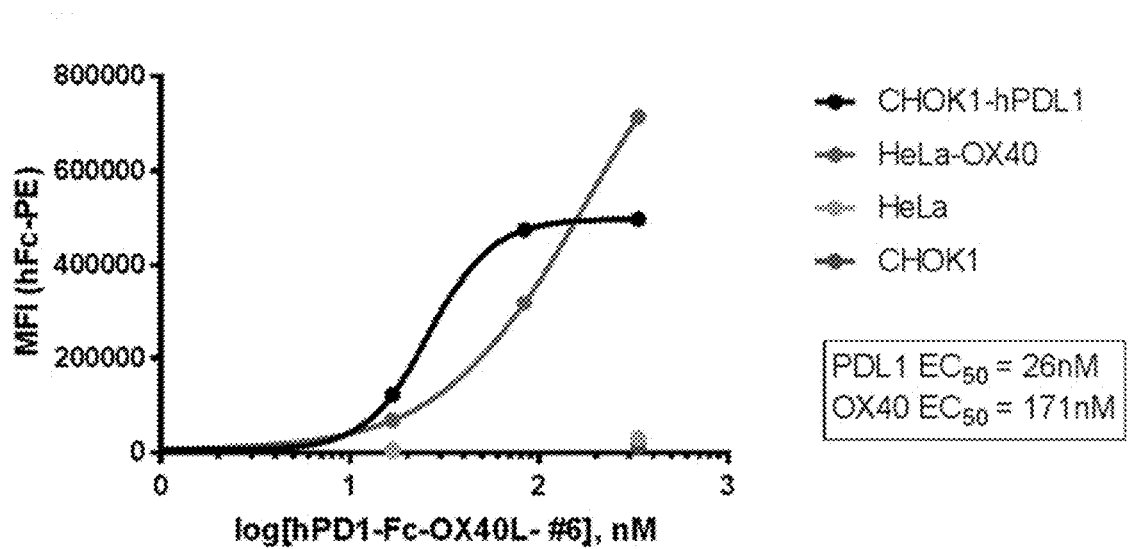
Figure 24F:
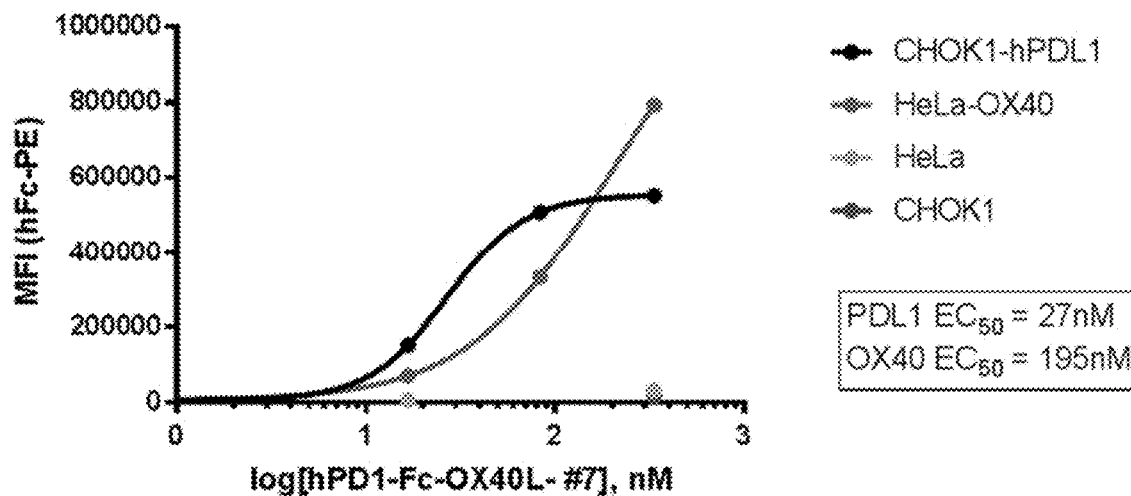
Figure 24G:
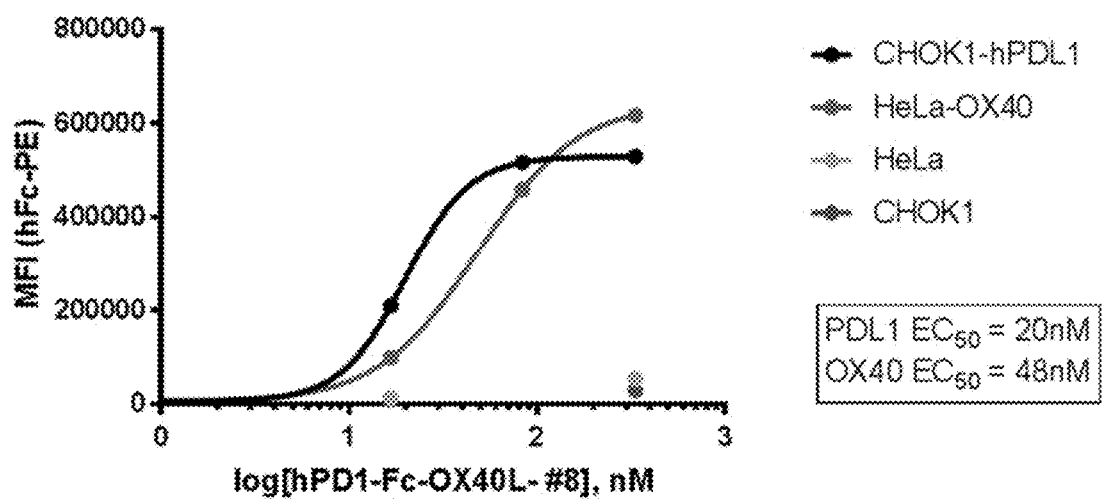
Figure 24H:
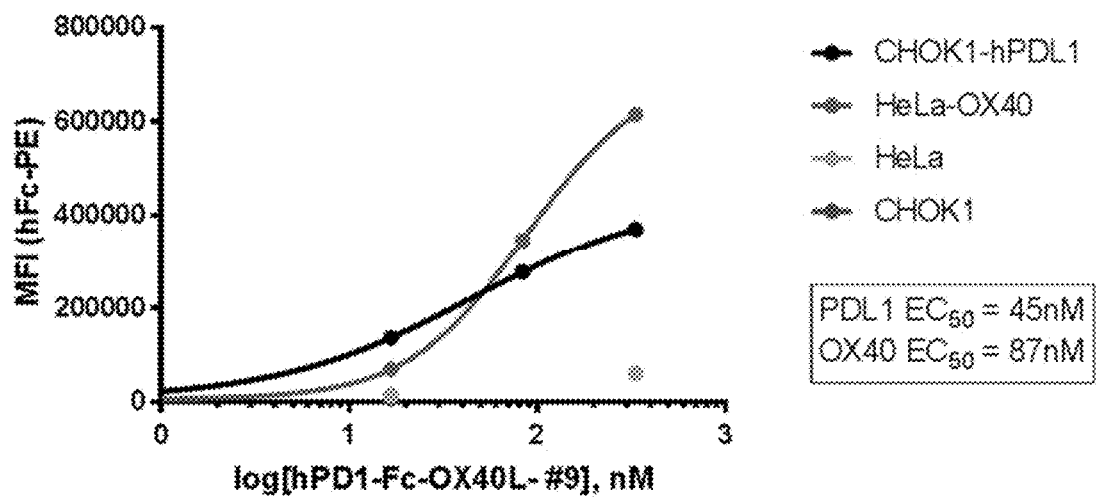
Figure 24I:
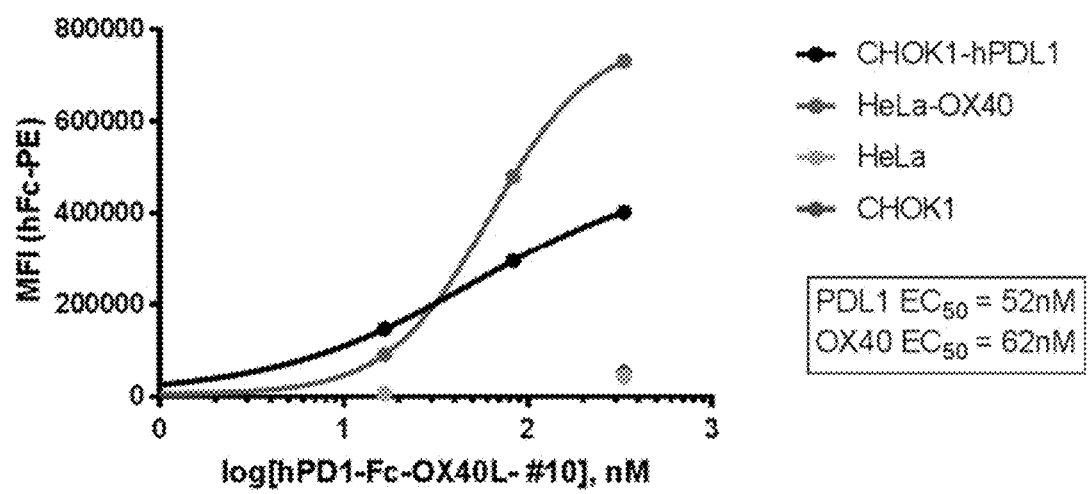
Figure 24J:
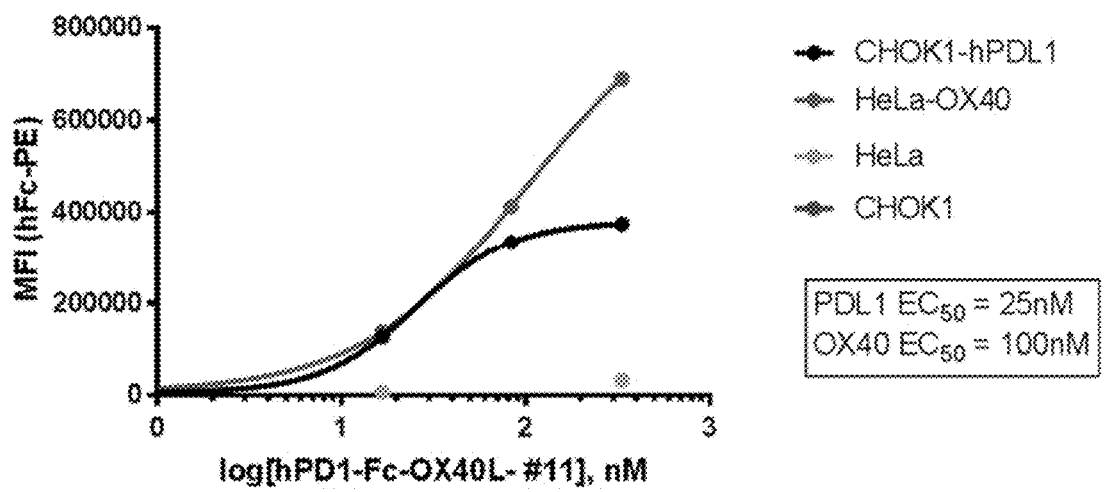
Figure 24K:
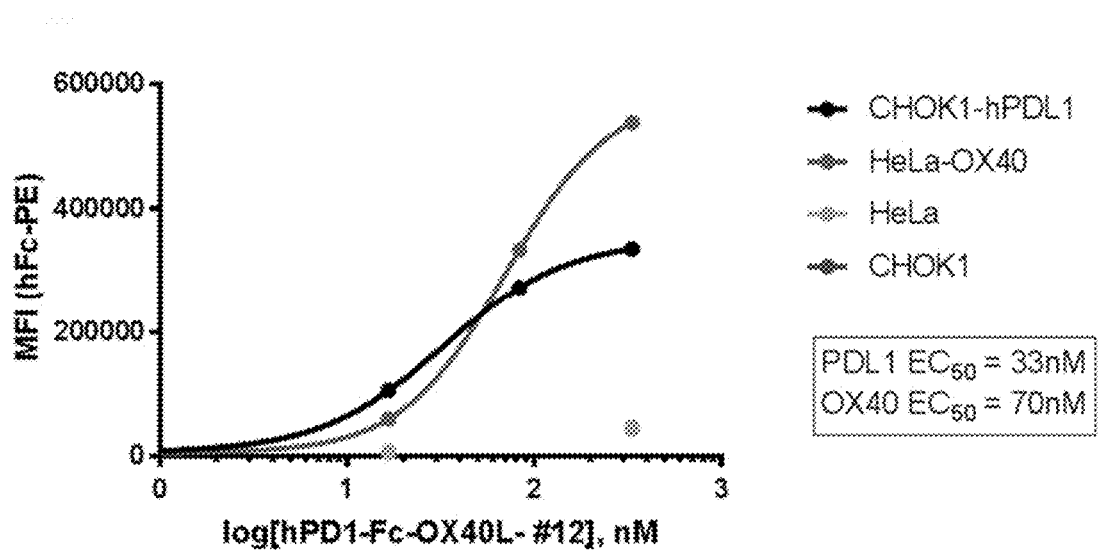
Figure 24L:
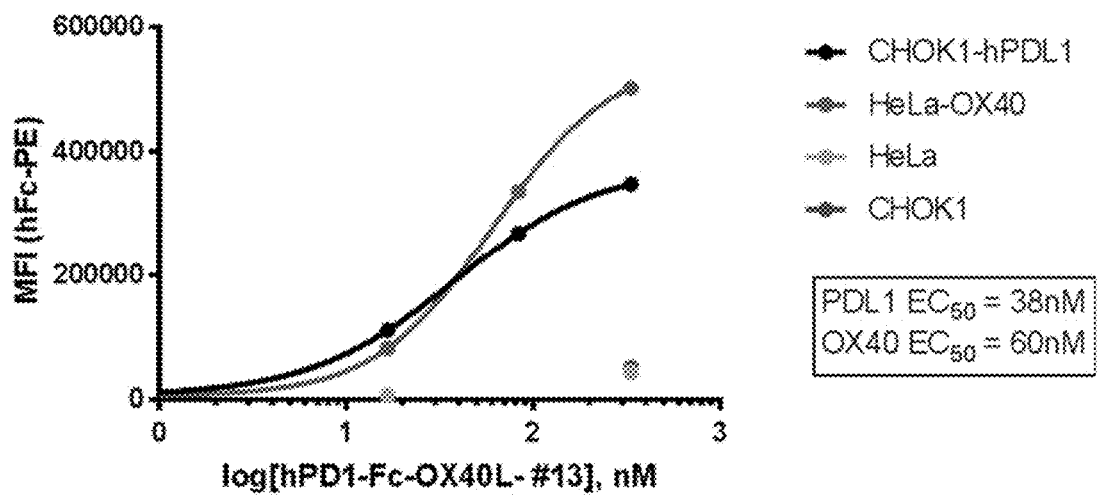
Figure 24M:
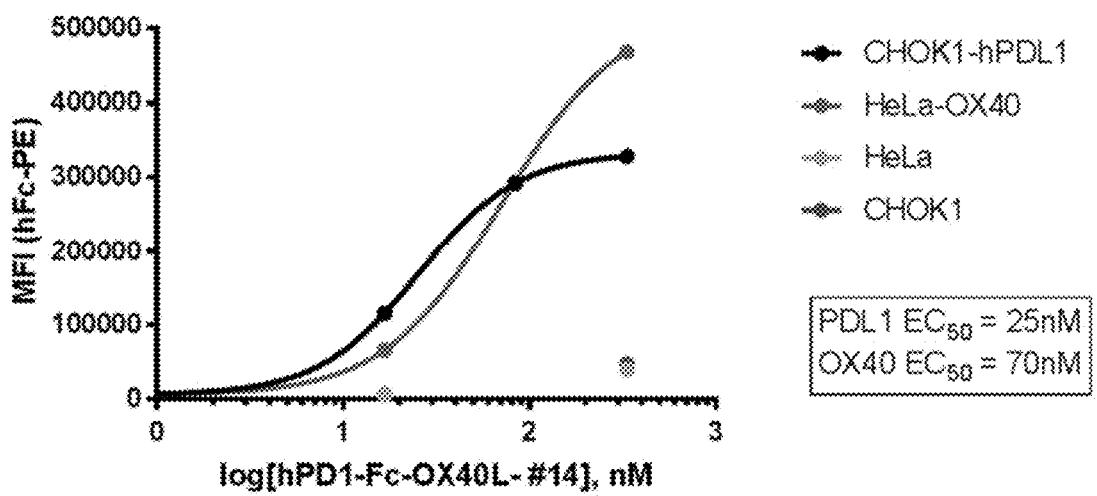
Figure 24N:
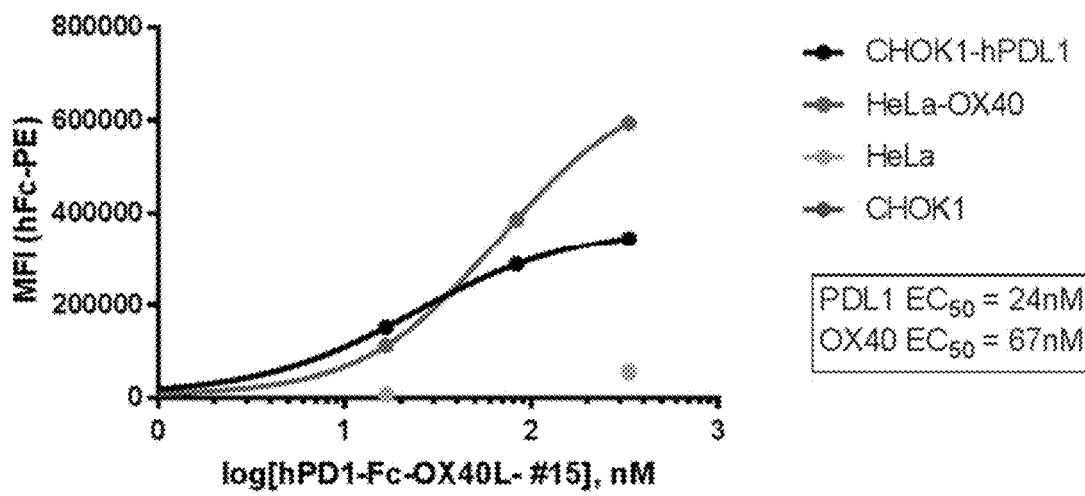
Figure 24O:
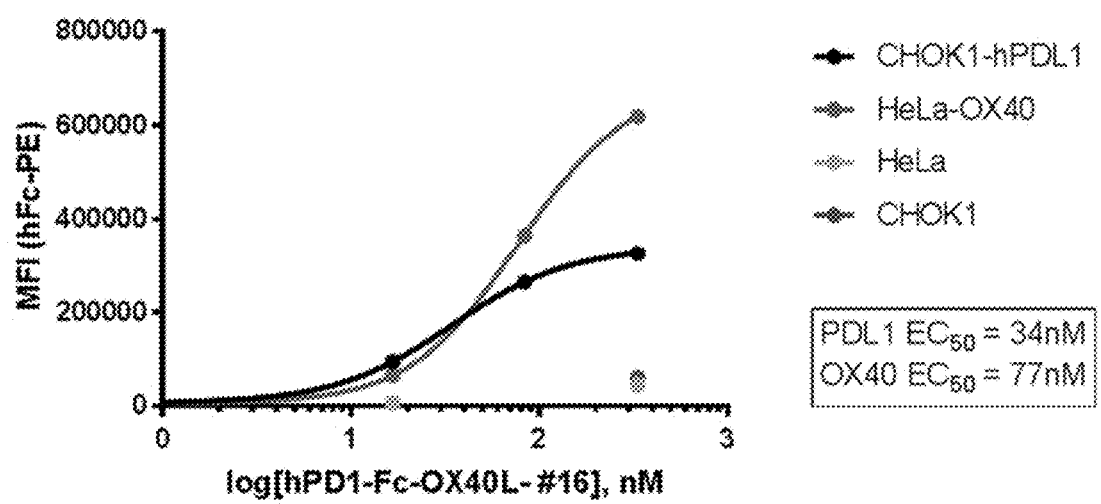
Figure 24P:
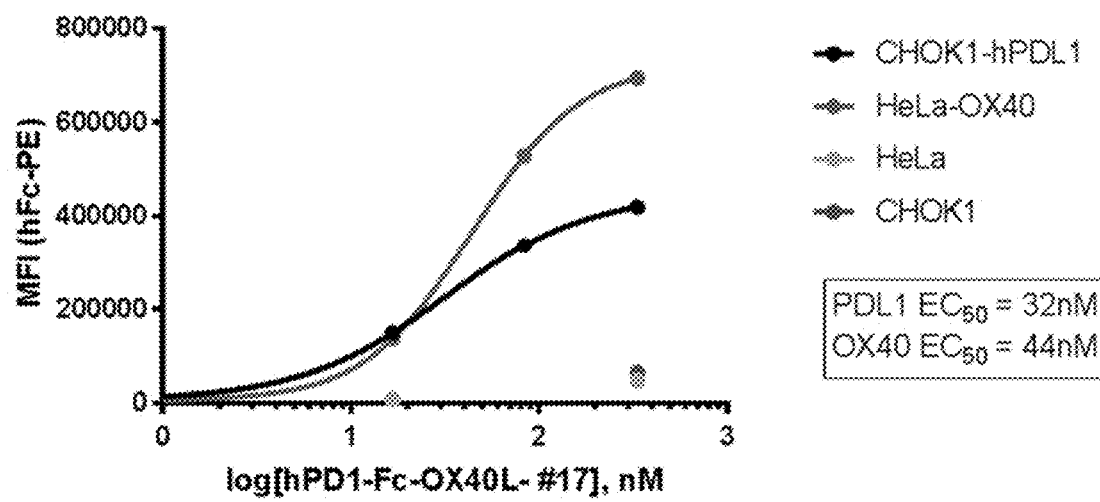

Characterization of PD-1-IgG4-OX40L chimeric proteins with different joining linker sequences (17 linkers) by Western blot analysis is shown in FIG. 22A to FIG. 22Q. Specifically, each individual domain of the fusion construct was probed using an anti-PD-1, anti-Fc, or anti-OX40L antibody. Results showed similar performance across each chimeric protein suggesting that all of the candidate joining linker sequences were functional. OX40 in ELISA assays (FIG. 23), as well as cell-based flow cytometry assays (FIG. 24A to FIG. 24P).

TABLE 2

Summary for optional joining linker sequences

| Protein Name | Protein conc. A280 | CHO-PD-L1 EC50 (nM) | HeLa-OX40 EC50 (nM) | Joining Linker 2 Sequence | Characteristics |
|---|---|---|---|---|---|
| PD-1_IgG4_OX40L (1) | 0.17 | 27 | 6 | IEGRMD (SEQ ID NO: 51) | Linker |
| PD-1_IgG4_OX40L (2) | 0.12 | 23 | 67 | SKYGPPCPPCP (SEQ ID NO: 49) | IgG4Hinge Region |
| PD-1_IgG4_OX40L (3) | 0.15 | 25 | 140 | GGGSGGGS (SEQ ID NO: 54) | Flexible |
| PD-1_IgG4_OX40L (4) | 0.11 | 36 | 125 | GGGSGGGGSGGG (SEQ ID NO: 55) | Flexible |
| PD-1_IgG4_OX40L (5) | 0.22 | 25 | 41 | EGKSSGSGSESKST (SEQ ID NO: 56) | Flexible + soluble |
| PD-1_IgG4_OX40L (6) | 0.12 | 26 | 171 | GGSG (SEQ ID NO: 57) | Flexible |
| PD-1_IgG4_OX40L (7) | 0.11 | 27 | 195 | GGSGGGSGGGSG (SEQ ID NO: 58) | Flexible |
| PD-1_IgG4_OX40L (8) | 0.21 | 20 | 48 | EAAAKEAAAKEAAAK (SEQ ID NO: 59) | RigidAlpha Helix |
| PD-1_IgG4_OX40L (9) | 0.23 | 45 | 87 | EAAAREAAAREAAAR EAAAR (SEQ ID NO: 60) | RigidAlpha Helix |
| PD-1_IgG4_OX40L (10) | 0.13 | 52 | 62 | GGGGSGGGGSGGGGS AS (SEQ ID NO: 61) | Flexible |
| PD-1_IgG4_OX40L (11) | 0.07 | 25 | 100 | GGGVPRDCG (SEQ ID NO: 52) | Flexible |
| PD-1_IgG4_OX40L (12) | 0.11 | 33 | 70 | GGGGAGGGG (SEQ ID NO: 62) | Flexible |
| PD-1_IgG4_OX40L (13) | 0.12 | 38 | 60 | GS (SEQ ID NO: 63) | Highly flexible |
| PD-1_IgG4_OX40L (14) | 0.18 | 25 | 70 | GSGSGS (SEQ ID NO: 64) | Highly flexible |
| PD-1_IgG4_OX40L (15) | 0.19 | 24 | 67 | GSGSGSGSGS (SEQ ID NO: 65) | Highly flexible |
| PD-1_IgG4_OX40L (16) | 0.11 | 34 | 77 | GGGGSAS (SEQ ID NO: 66) | Flexible |
| PD-1_IgG4_OX40L (17) | 0.19 | 32 | 44 | APAPAPAPAPAPAPA PAPAP (SEQ ID NO: 67) | Rigid |

Example 11: Characterization of Murine PD-1-Fc-OX40L Chimeric Proteins

Figure 25A:
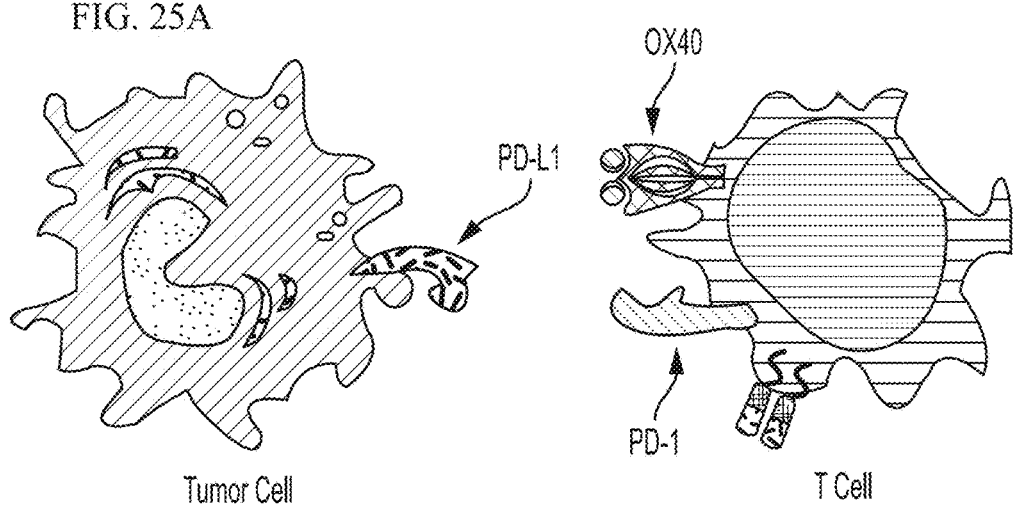
FIG. 25A, using an PD1-Fc-OX40L chimeric protein as a non-limiting example, shows that tumor cells may express PD-L1 on the cell surface, which can bind to PD-1 expressed by a T cell (FIG. 25B). This interaction suppresses activation of T cells. A chimeric protein comprising the extracellular domain of PD-1, adjoined to the extracellular domain of OX40L may bind to PD-L1 on the surface of a tumor cell, preventing binding to PD-1 on the surface of a T cell (FIG. 25C). The chimeric protein may then "dangle" from the surface of the tumor cell, and the OX40L portion of the chimeric protein may then bind to OX40 expressed on the surface of the T cell. This would result in replacement of an inhibitory PD-L1 signal with a co-stimulatory OX40L signal to enhance the anti-tumor activity of T cells.
Figure 25B:
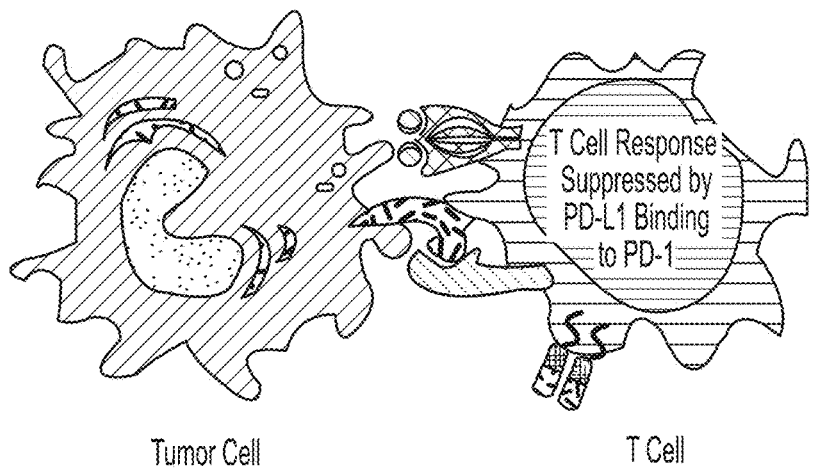
Figure 25C:
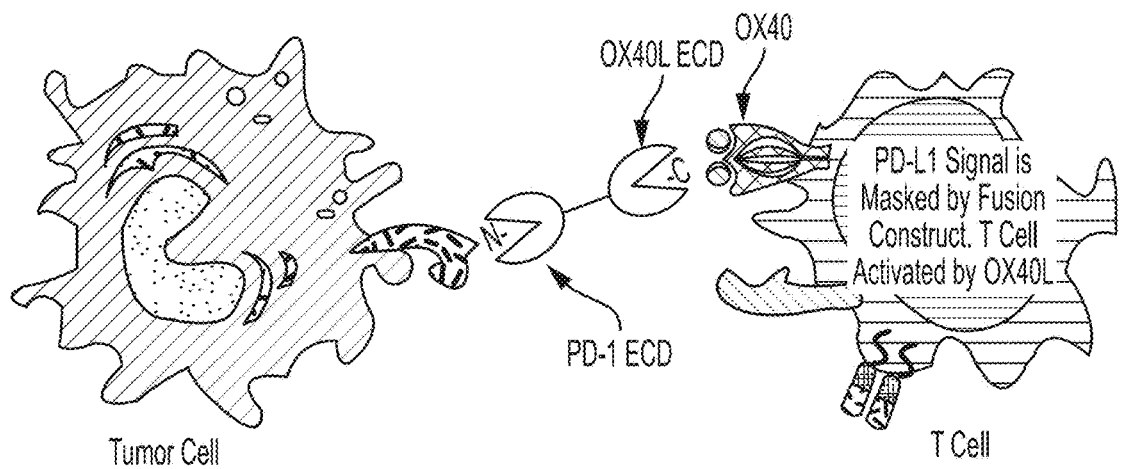

Tumor cells may express PD-L1 on their cell surface, which can bind to PD-1 expressed by a T cell (FIG. 25A and FIG. 25B). This interaction suppresses activation of T cells. A chimeric protein comprising the extracellular domain of PD-1, adjoined to the extracellular domain of OX40L (i.e., PD-1-Fc-OX40L) may bind to PD-L1 on the surface of a tumor cell, preventing binding to PD-1 on the surface of a T cell (FIG. 25C). The chimeric protein may then "dangle" from the surface of the tumor cell, and the OX40L portion of the chimeric protein may then bind to OX40 expressed on the surface of the T cell. This would result in replacement of an inhibitory PD-L1 signal with a co-stimulatory OX40L signal to enhance the anti-tumor activity of T cells.

The binding affinity of the different domains of the murine PD-1-Fc-OX40L chimeric protein was measured by surface plasmon resonance (SPR) using the BioRad ProteOn XPR 360 system. Specifically, the affinity of the chimeric proteins for PD-L1, PD-L2, OX40, and FcRn were determined and compared to recombinant control proteins, and the results are shown in the Table below:

| Binding to: | FcRn | OX40 | PD-L2 | PD-L1 |
|---|---|---|---|---|
| Sample | Ka (on-rate; 1/Ms) | Kd (off-rate; 1/s) | KD (binding; M) | |
| PD1-Fc | $3.24\,E+4$ | $1.08\,E-3$ | 33.3 nM | |
| PD1-Fc-OX40L | $4.97\,E+4$ | $4.87\,E-4$ | 9.8 nM | |
| PD1-Fc | $4.79\,E+4$ | $1.71\,E-3$ | 23.1 nM | |
| PD1-Fc-OX40L | $5.29\,E+4$ | $5.61\,E-4$ | 10.6 nM | |
| OX40L-Fc | $6.74\,E+5$ | $7.12\,E-4$ | 1.06 nM | |
| PD1-Fc-OX40L | $3.19\,E+0$ | $3.07\,E-8$ | 9.62 nM | |
| IgG2A | $3.00\,E+6$ | $2.42\,E-2$ | 8.08 nM | |
| PD1-Fc-OX40L | $4.72\,E+4$ | $2.62\,E-3$ | 55.6 nM | | mPD-1-Fc-OX40L bound to chip-bound mPD-L1-His (9.8 nM), PD-L2-His (10.6 nM), OX40-His (9.62 nM), and FcRn-His (55.6 nM) using SPR. Binding of control proteins (PD-1-Fc, OX40L-Fc, and IgG2A) were also shown. No binding of mPD-1-Fc-OX40L was detected to FcγR1.

Figure 26A:
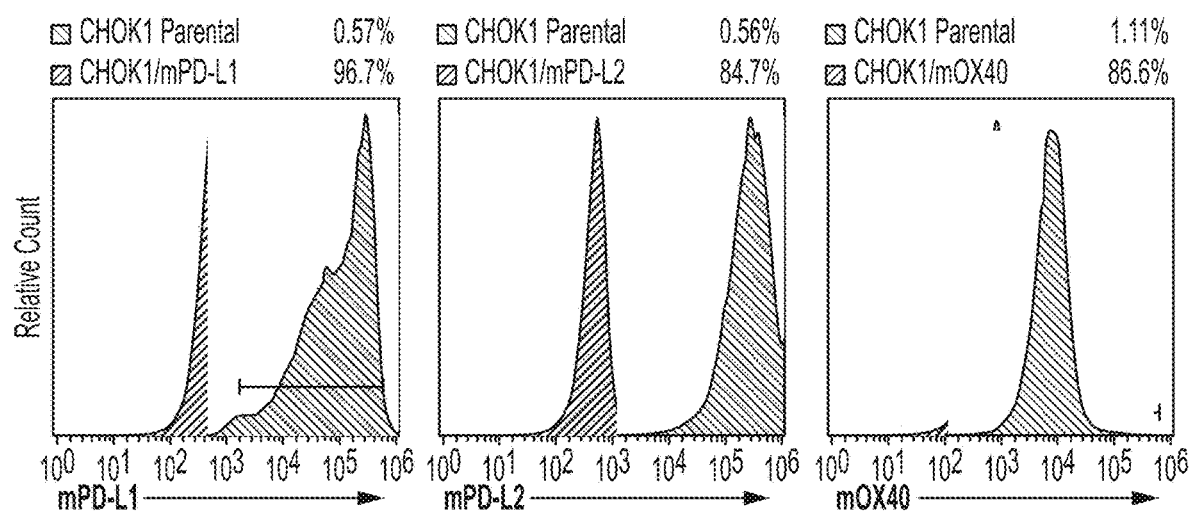
FIG. 26A shows cell lines generated to overexpress murine PD-L1 (CHOK1/mPD-L1), PD-L2 (CHOK1/mPD-L2), or OX40 (CHOK1/mOX40).
Figure 26B:
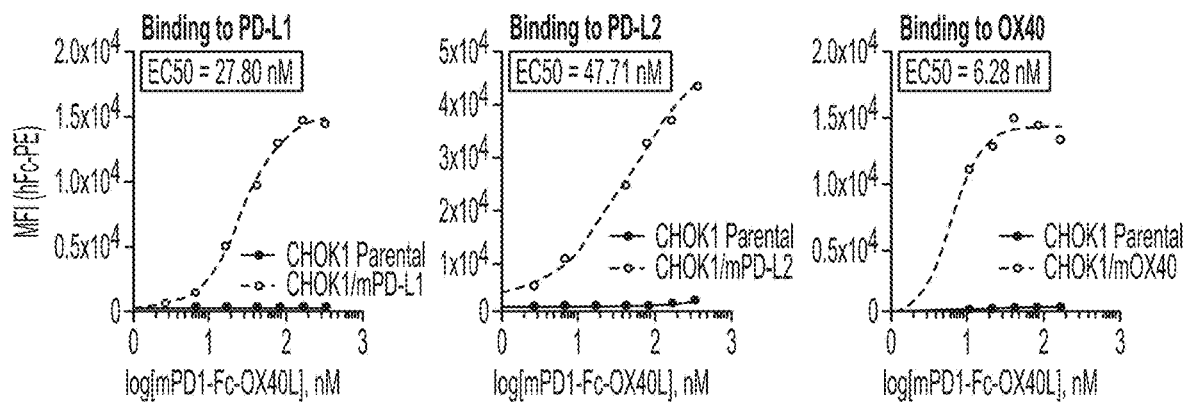
FIG. 26B shows in vitro cell binding to demonstrate the ability of the murine PD-1-Fc-OX40L chimeric protein to bind to the engineered cell lines.

Additional analysis was carried out to determine whether the mPD-1-Fc-OX40L chimeric protein could bind its targets on the surface of living cells. To assess mPD-1-Fc-OX40L binding to murine PD-L1, PD-L2, and OX40, the Chinese hamster ovary cell line, CHOK1, was transfected to stably express murine PD-L1, PD-L2, and OX40 (FIG. 26A). mPD-1-Fc-OX40L chimeric protein was incubated with each parental and over-expressing cell line for 2 hours. Cells were collected, washed, and stained with antibodies for the detection of the chimeric protein binding by flow cytometry. All engineered cell lines (CHOK1/hPD-L1, CHOK1/hPD-L2, and CHOK1/hOX40) bound mPD-1-Fc-OX40L in a concentration-dependent manner at low nM as shown in FIG. 26B. mPD-1-Fc-OX40L did not bind to parental CHOK1 cells since they did not express detectable levels of human PD-L1, OX40, or PD-L2. However, nearly the entire population of CHO-K1-PD-L1, CHOK1-PD-L2, and Jurkat/hOX40 cells shifted significantly, indicating that the different components of the chimeric protein were capable of binding to its respective receptor/ligands on living cells (FIG. 26A and FIG. 26B).

Figure 26C:
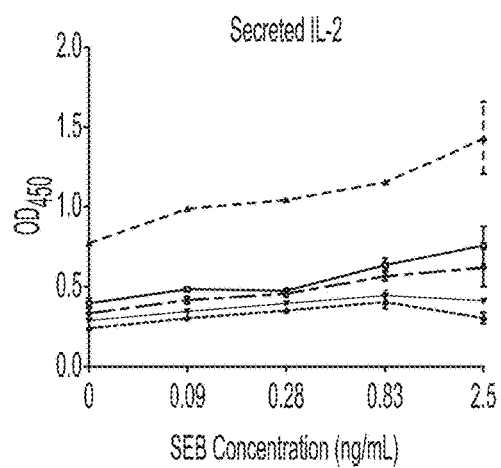
FIG. 26C and FIG. 26D show *Staphylococcus aureas*, Enterotoxin Type B (SEB) superantigen cytokine release assays which demonstrate the effects of the mPD-1-Fc-OX40L chimeric protein on IL-2 (FIG. 26C) and TNFα (FIG. 26D) secretion.
Figure 26D:
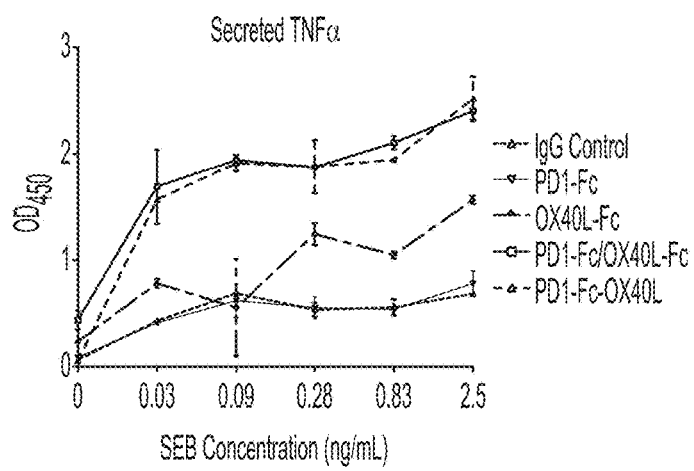

The functional activity of mPD-1-Fc-OX40L chimeric protein was assessed using the superantigen cytokine release assay. In this assay, increasing concentrations of staphylococcus enterotoxin B (SEB) were used to activate human peripheral blood leukocytes in the presence of various test agents. The quantity of TNFα or IL-2 secreted into the culture supernatant was monitored as a functional readout in the ability of test agents to either block suppressive signaling events or co-stimulate immune activating signals. As shown in FIG. 26C, the mPD-1-Fc-OX40L chimeric protein induced secretion of IL2 at higher levels (top curve) in comparison of other test agents i.e., PD-1-Fc, OX40L-Fc, and PD-1-Fc/OX40L-Fc. However, as shown in FIG. 26D, the mPD-1-Fc-OX40L chimeric protein and the PD-1-Fc/OX40L-Fc induced the highest level of secreted TNFα (top two curves) in comparison to other test agents: PD-1-Fc and OX40L-Fc. Media and IgG controls were used. Together, these results suggest that mPD-1-Fc-OX40L chimeric protein functionally activates primary leukocytes to release TNFα and IL2 in vitro.

Figure 27A:
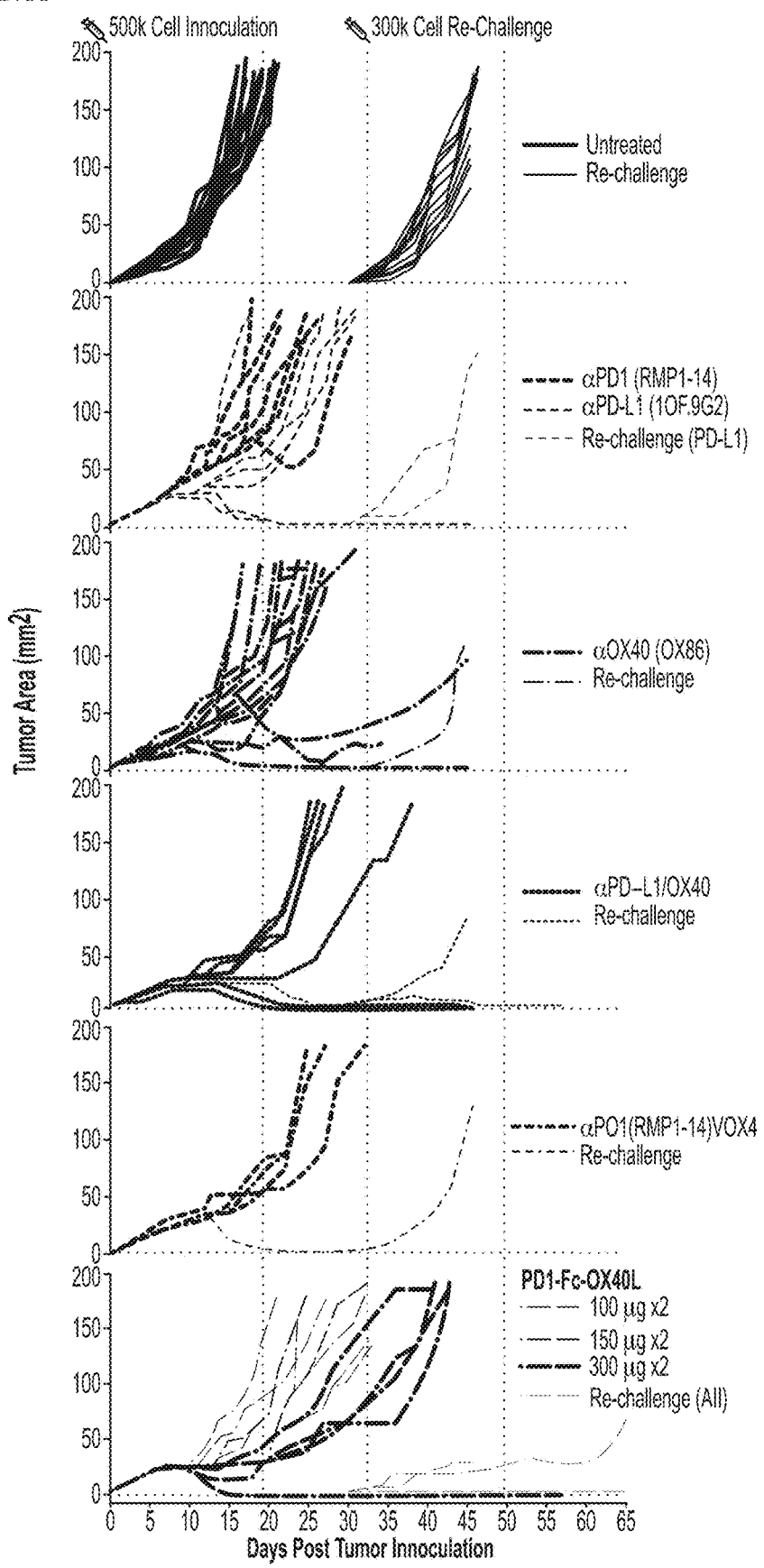
FIG. 27A shows the evolution of in vivo tumor size after CT26 tumor inoculation for each group of mice described in the figure.

FIG. 27A to FIG. 27F show results from in vivo tumor studies demonstrating that the mPD-1-Fc-OX40L chimeric protein has significant anti-tumor activity in a CT26 tumor rechallenge model. Mice inoculated with CT26 tumors were alternately treated with anti-PD-1, anti-PD-L1, anti-OX40, a combination of anti-PD-L1 and OX40 antibodies, a combination of anti-PD-1 and OX40 antibodies, with control antibodies, or with one of three doses of the mPD-1-Fc-OX40L chimeric protein (i.e., 100 μg, 150 μg and 300 μg) and on two occasions (see bottom panel). Specifically, Tumor inoculation occurred on day 0, first treatment on day 5, and second treatment on day 7; tumor re-challenge (implantation of a second tumor on the opposite flank without re-treatment with drug) occurred on day 30 in any mice that rejected the primary tumor. Mice were re-challenged with CT26 tumor cells. FIG. 27A shows the evolution of tumor size over sixty-five days after tumor inoculation for each group. Importantly, the PD-1-Fc-OX40L chimeric protein is effectively able to kill tumor cells and/or reduce tumor growth when rechallenged (which illustrates a cancer relapse). Thus, the PD-1-Fc-OX40L chimeric protein appears to generate a memory response which may be capable of preventing relapse.

Figure 27B:
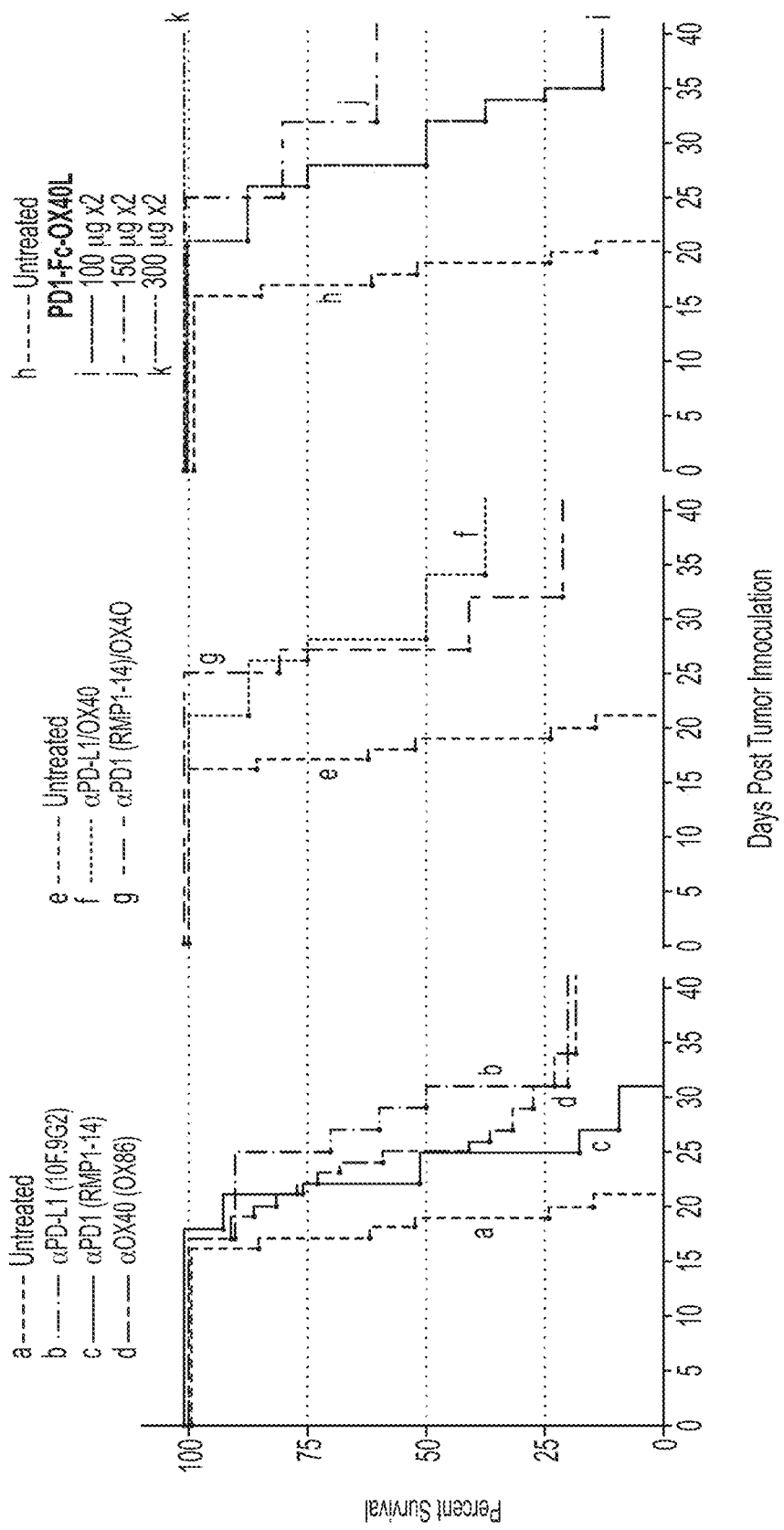
Figure 27D:
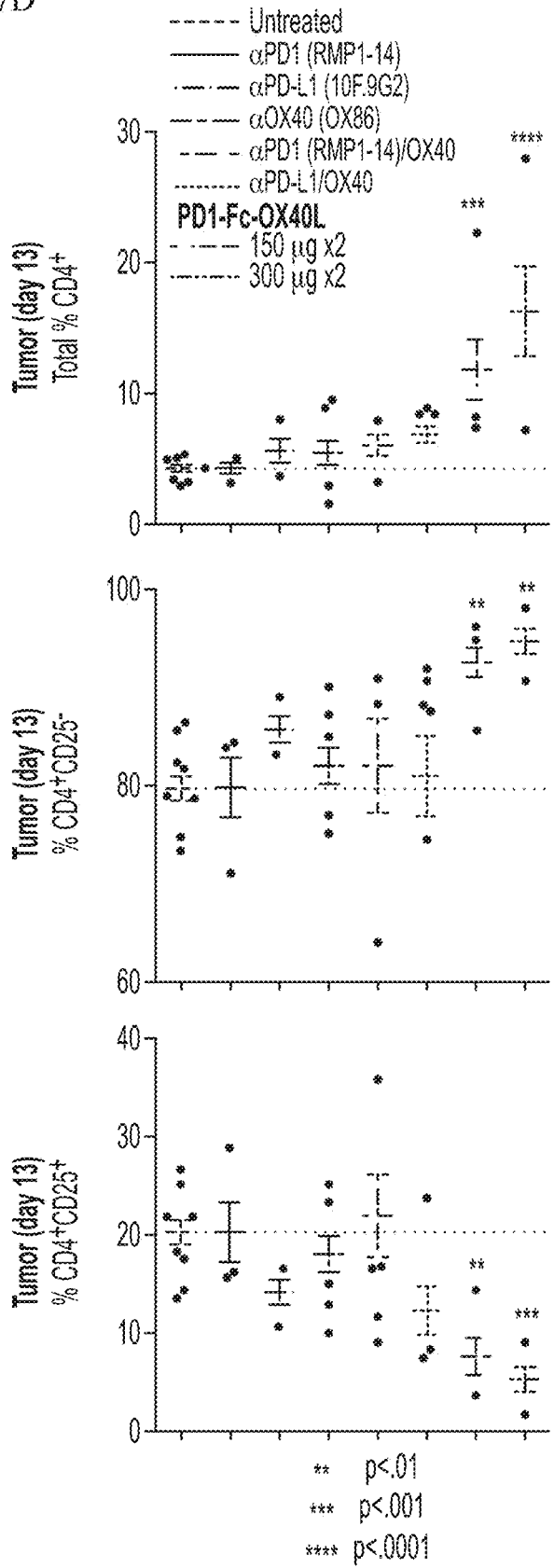
Figures 27F, 27G:
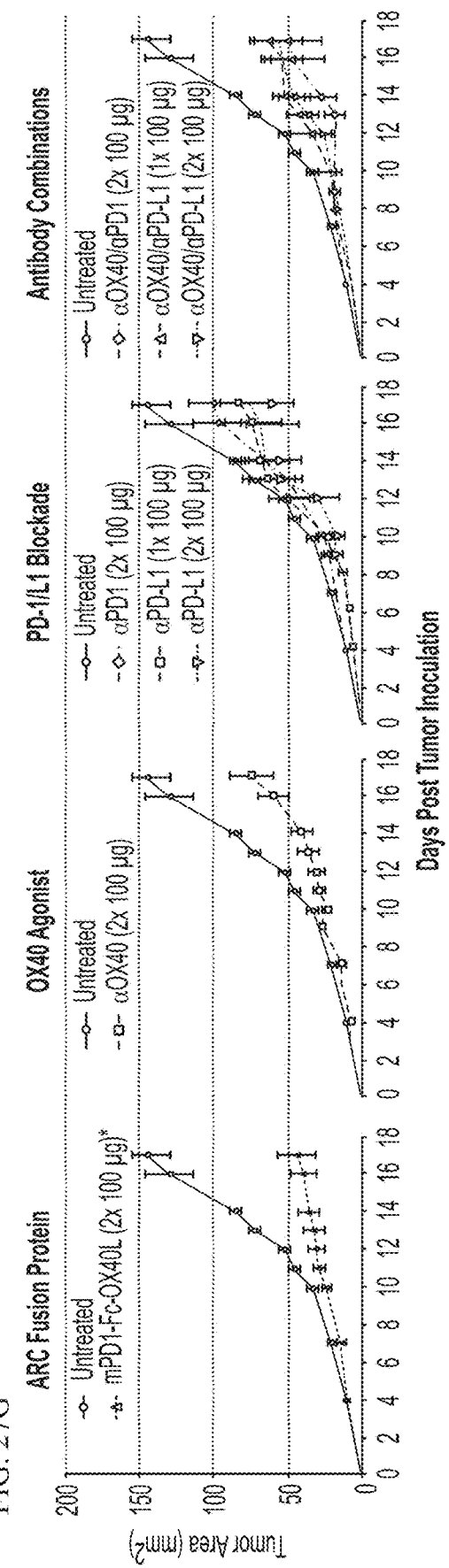
FIG. 27F summarizes the treatment outcomes for each experimental group.
FIG. 27G and FIG. 27H show in vivo anti-tumor activity of the mPD-1-Fc-OX40L chimeric protein in the CT26 tumor model.

FIG. 27B and FIG. 27C shows the overall survival percentage, and statistics, of mice and tumor rejection through forty days after tumor inoculation. FIG. 27D shows changes in CD4+ T-cells, CD4+CD25− effector T cells or CD4+CD25+ regulatory T cells in the tumor of mice treated with the chimeric protein and other benchmark antibodies. FIG. 27E shows changes in CD4+ T-cells, CD4+CD25− effector T cells or CD4+CD25+ regulatory T cells in the spleen of mice treated with the chimeric protein and other benchmark antibodies. FIG. 27F summarizes treatment outcomes for each group. For FIG. 27D and FIG. 27E, cohorts of treated mice were euthanized thirteen days after initial tumor inoculation. Tumors and spleens were isolated, dissociated, and analyzed for proportions of effector and non-effector/Treg populations by flow cytometry.

Figure 27H:
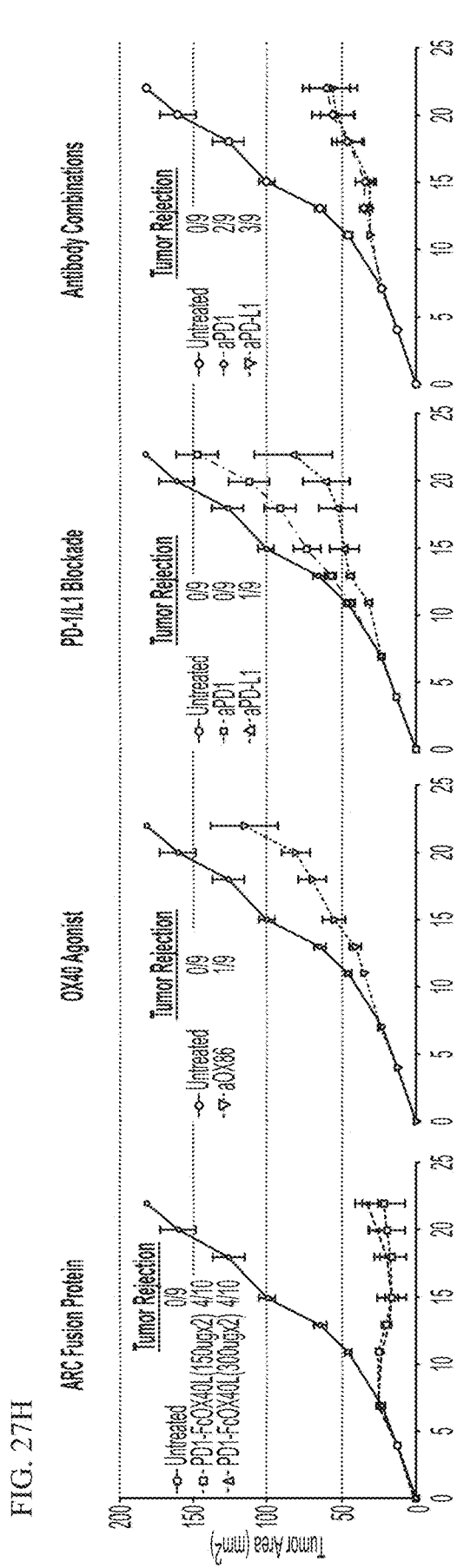

Overall, administration of mPD-1-Fc-OX40L significantly reduced tumor size in the CT26 colorectal cancer model. Particularly, use of mPD-1-Fc-OX40L resulted in greater tumor regression than the OX40 agonist and PD-L1 blocking antibodies (FIG. 27G). mPD-1-Fc-OX40L outperformed anti-OX40, anti-PD-1, or anti-PD-L1 antibodies and antibody combinations at low dose (100 μg, FIG. 27G) and at a higher dose (300 μg, FIG. 27H). Cytokine signature suggests that 100 μg was a sub-optimal dose. At a higher dose (300 μg chimeric protein vs. 2700 μg mAb), mPD-1-Fc-OX40L significantly outperformed anti-PD-1/L1+anti- OX40 mAb combinations. In FIG. 27G and FIG. 27H, data identified as "ARC Fusion Protein" refers to the mPD-1-Fc-OX40L chimeric protein.

The above data clearly demonstrate, inter alia, functional activity of mPD-1-Fc-OX40L in vivo, at least, in treating cancer.

Example 12: Characterization of Human PD-1-Fc-OX40L Chimeric Proteins

Figure 28C:
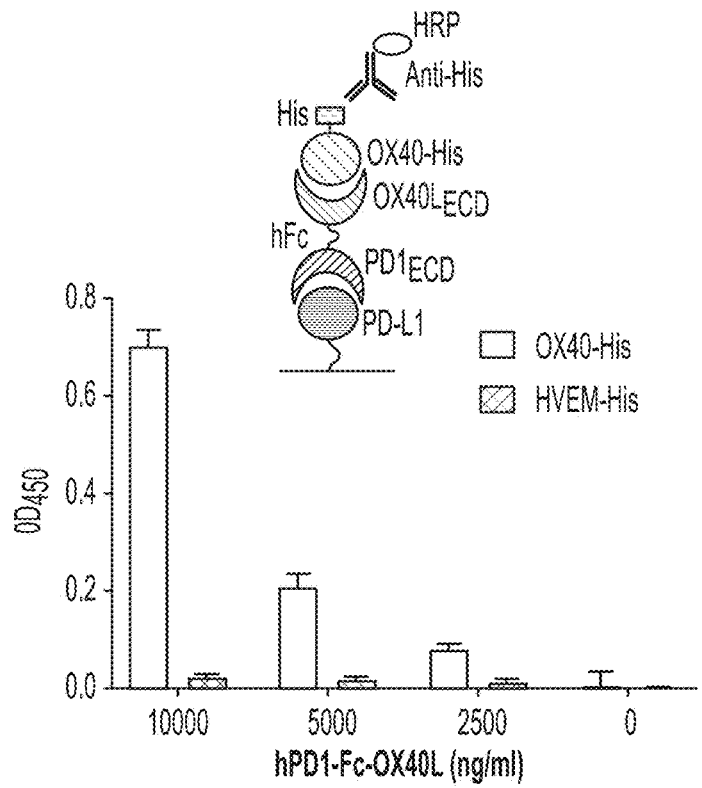

ELISA (enzyme-linked immunosorbent assay) assays were developed to demonstrate the binding affinity of the different domains of the human PD-1-Fc-OX40L chimeric protein (also referred to as SL-279252) to their respective binding partners. FIG. 28A shows the binding and detection of human PD-1-Fc-OX40L chimeric protein to human IgG, the binding partner for Fc (square symbols). Human Ig (hIg) was used as a standard (circle symbols). It was observed that in ELISA assays generally, using the central Fc region to detect chimeric proteins tended to underestimate the actual protein content in a sample. Therefore, low level of the hPD-1-Fc-OX40L chimeric protein was detected compared to standard in this assay. FIG. 28B shows the binding and detection of human PD-1-Fc-OX40L chimeric protein to the receptor OX40, i.e., the binding partner for OX40L (square symbols). Recombinant OX40L-Fc was used to generate a standard curve (circle symbols). FIG. 28C shows dual-binding ELISA assay demonstrating the ability of PD-1-Fc-OX40L to bind and engage both targets (PD-L1 and OX40-His) simultaneously. Increasing concentrations of hPD-1-Fc-OX40L chimeric protein were incubated with a fixed amount of plate-bound recombinant human PD-L1 protein. Thereafter, recombinant OX40-His protein or a control His-tagged protein (HVEM-His) was incubated with the complex and binding was detected via an HRP-conjugated anti-His antibody. The results clearly show that hPD-1-Fc-OX40L binds to PD-L1 and OX40 simultaneously and with high specificity.

Figure 29A:
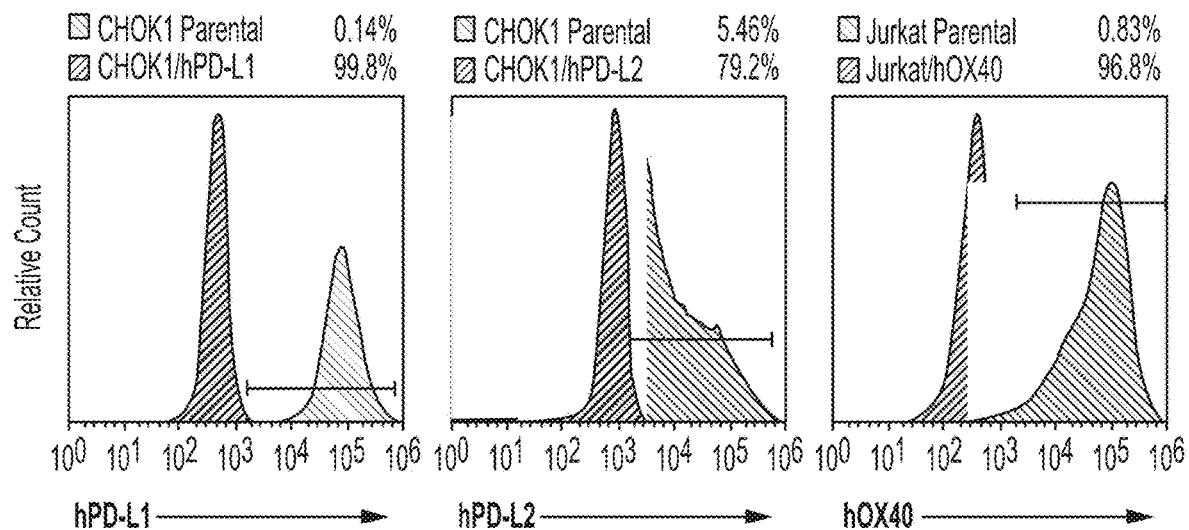
FIG. 29A shows the characterization of human cell lines used for in vitro binding to human PD-1-Fc-OX40L.

Additional analyses were carried out to determine whether hPD-1-Fc-OX40L fusion protein could bind its targets on the surface of living cells in vitro. To assess hPD-1-Fc-OX40L's binding to the human OX40 receptor, the human AML T cell line Jurkat was engineered to overexpress OX40, creating Jurkat/hOX40 cells (verified by flow cytometry; FIG. 29, right panel). To assess binding to PD-L1, the Chinese hamster ovary cell line, CHOK1, which does not express human PD-L1, was transfected to stably express human PD-L1 (FIG. 29A, left panel). To assess binding to human PD-L2, CHOK1 cells were transfected to stably express human PD-L2 (FIG. 29A, middle panel). Human PD-1-Fc-OX40L chimeric protein was incubated with each parental cell line and each of the over-expressing cell lines for two hours. Cells were collected, washed, and stained with antibodies for the detection of chimeric protein binding by flow cytometry. For histograms to the left and in the middle, parental CHOK1 (cell population to the right) and CHOK1/hPD-L1 (cell population to the left) cells were assessed by flow cytometry using an hPD-L1 antibody or an hPD-L2 antibody, respectively. In the right histogram, parental Jurkat cells (cell population to the right) and Jurkat/hOX40 (cell population to the left) were assessed by flow cytometry using a hOX40 antibody. All engineered cell lines (CHOK1/hPD-L1, CHOK1/hPD-L2, and Jurkat/hOX40) bound hPD-1-Fc-OX40L in a concentration-dependent manner at low nM.

Figure 29B:
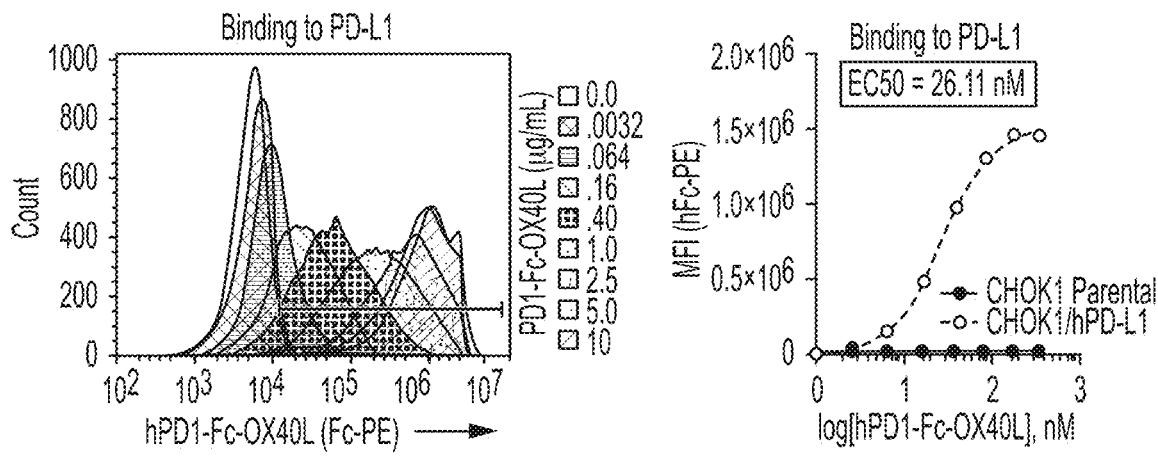
FIG. 29B to FIG. 29D show binding of hPD-1-Fc-OX40L to cells expressing, respectively, PD-L1, PD-L2, or OX40. In each, the right panel shows the titration curve for increasing concentrations of the chimeric protein.
Figure 29C:
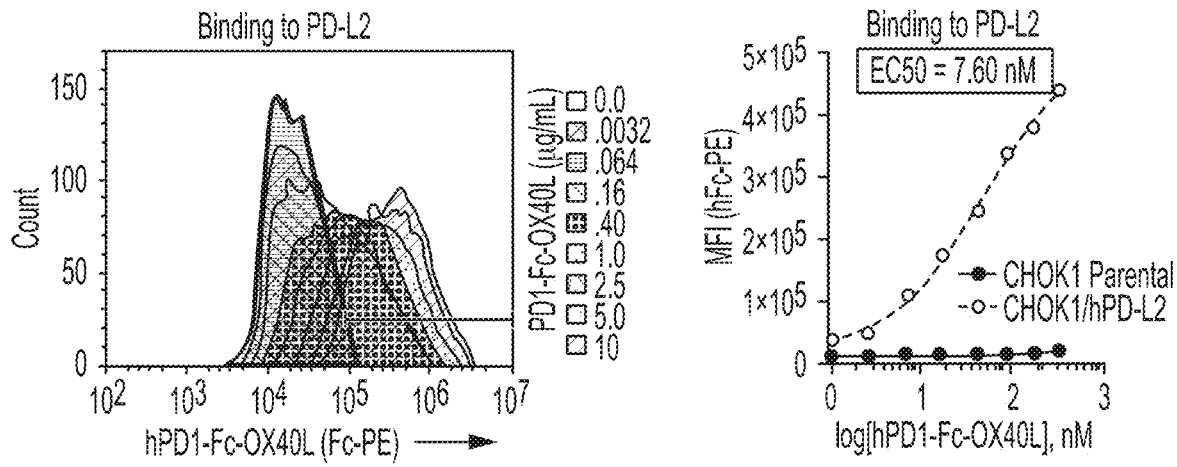
Figure 29D:
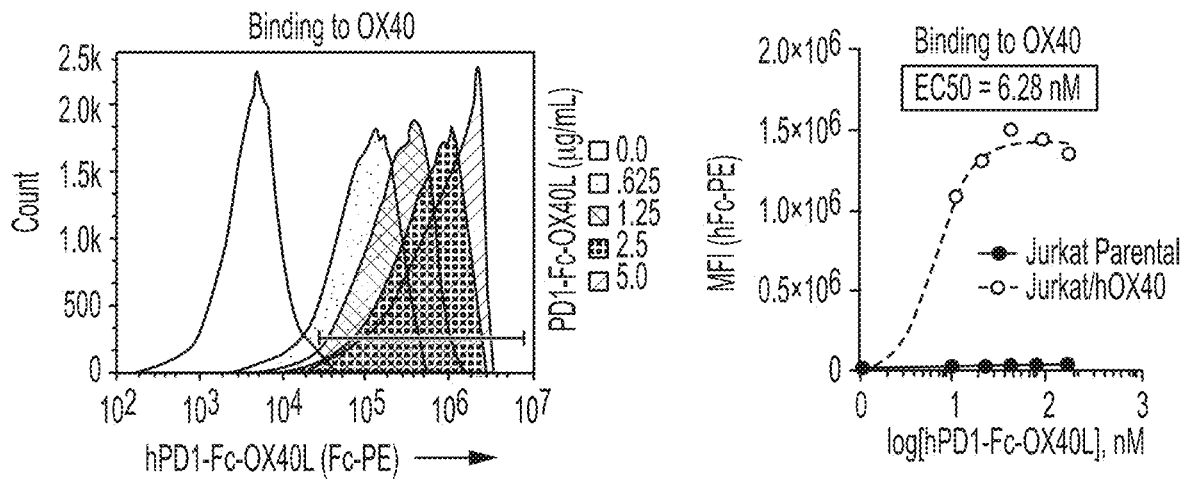

As shown in FIG. 29B to FIG. 29D, hPD-1-Fc-OX40L did not bind to parental CHO-K1 cells since they did not express detectable levels of human PD-L1 or PD-L2. Similarly, hPD-1-Fc-OX40L did not bind to parental Jurkat cells since they did not express detectable levels of OX40. However, nearly the entire population of CHO-K1-PD-L1, CHOK1-PD-L2, and Jurkat/hOX40 cells shifted significantly, indicating that the different components of the chimeric protein were each capable of binding its respective receptor/ligands on living cells. in vitro cell binding affinities of SL-279252-CHOK1/hPD-L1 at 26.11 nM, SL-279252-CHOK1/hPD-L2 at 7.60 nM, and SL-279252-Jurkat/hOX40 at 6.28 nM.

Next, surface plasmon resonance (SPR) analysis was performed to determine the affinity by which SL-279252 bound to hPD-L1, hPD-L2, and hOX40. Specifically, polyhistidine-tagged versions of recombinant human PD-L1, PD-L2, or OX40 was bound to ProteOn HTG tris-NTA chips (BIORAD). SL-279252 was then flowed over the bound ligands over a time course and a relative index of 'on-rate' (Ka) and 'off-rate' (Kd) was generated to calculate binding affinity ($K_D$) of SL-279252 to each partner. Recombinant human PD-1-Fc and OX40L-Fc were used as positive controls for binding. These controls have a relatively fast 'on-rate' and an equally fast 'off-rate', resulting in low nanomolar binding affinities. The results of SPR binding affinity demonstrated high-affinity binding for each portion of the fusion protein (except against Fc receptors with effector function). Importantly, the off-rates of hPD-1-Fc-OX40L were much slower than those of benchmark control proteins: hPD-1-Fc-OX40L dissociation from PD-L1 was 18 fold longer than PD-1-Fc, from PD-L2 was 13.4 fold longer than PD-1-Fc, and from OX40 was 36.32 fold longer OX40L-Fc. Together, these results indicated that the hPD-1-Fc-OX40L fusion protein had a long residence time when bound to PD-L1 or PD-L2.

The above data clearly demonstrates that the different domains of the human PD-1-Fc-OX40L fusion protein (SL-279252) bind their native binding partners (e.g., receptor or ligand; PD-L1, PD-L2, and OX40) on the surface of a mammalian cell membrane.

Figure 30:
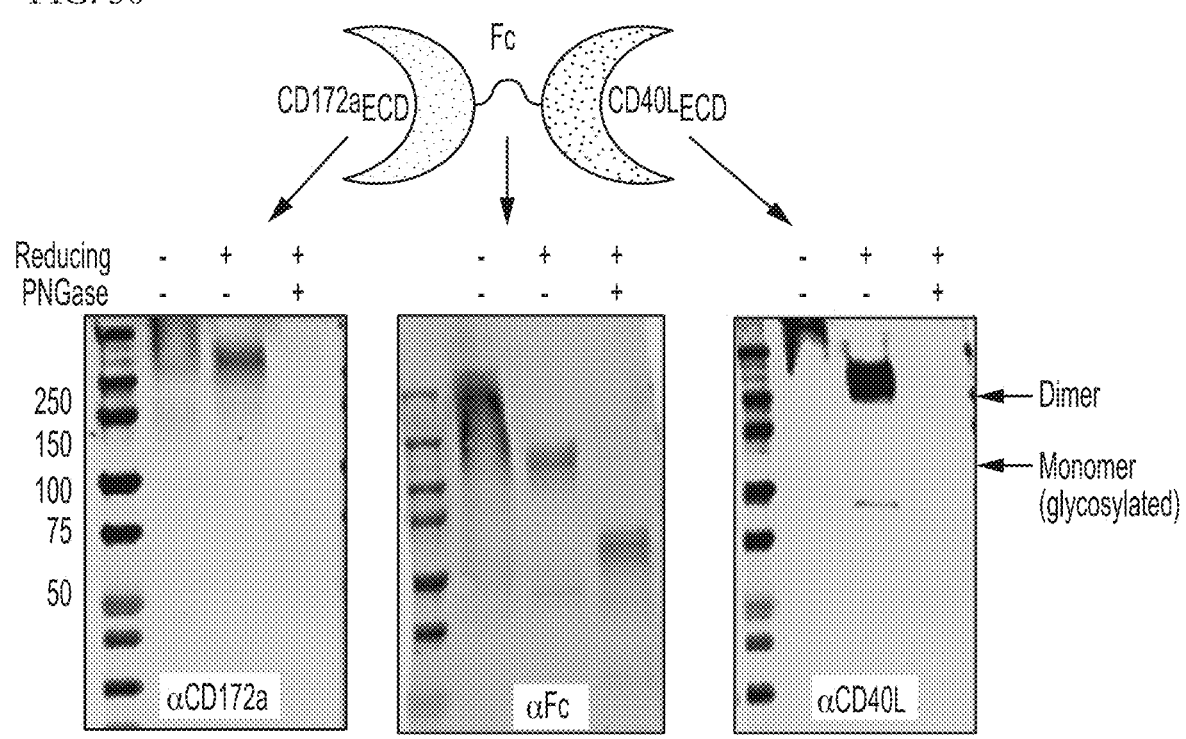
FIG. 30 shows characterization of human PD-1-Fc-OX40L fusion protein (SL-279252) by Western blot analysis. Each of the three domains of the chimeric protein was probed, respectively, with an anti-PD-1, anti-Fc, or anti-OX40L antibody. Untreated samples of the hPD-1-Fc-OX40L fusion protein, e.g., control, were loaded into lane 1 in all the blots (no β-mercaptoethanol or Peptide:N-Glycosidase (PNGase).

To confirm that all three domains of the human PD-1-Fc-OX40L (SL-279252) are intact and recognizable by a protein detection assay, Western blot analysis was performed on purified fusion protein which were probed with human anti-PD-1, anti-Fc, and anti-OX40L (FIG. 30). SL-279252 was detected by all three antibodies and when the protein was run under reducing conditions, migrated at approximately 75 kDa. Approximately 50% of the non-reduced protein ran as a dimer, which was a potential advantage, given the in vivo oligomerization associated with OX40L signaling and function. The predicted molecular weight for SL-279252 was 60.3 kDa. The reduced fraction of SL-279252 was detected at a higher molecular weight, which, without wishing to be bound by theory, may be due to glycosylation. This was verified by treating SL-279252 with a protein deglycosylase, PNGase F. Following deglycosylation, the reduced fraction of SL-279252 migrated exactly at the predicted molecular weight of 60.3 kDa. This provided evidence that SL-279252 was co/post-translationally modified through glycosylation, which plays essential roles in the proper folding and stability of proteins, and cell-to-cell adhesion (Dalziel M, Dwek R A. Science 2014; Maverakis E, Lebrilla C B. J Autoimmun. 2015).

Figure 31A:
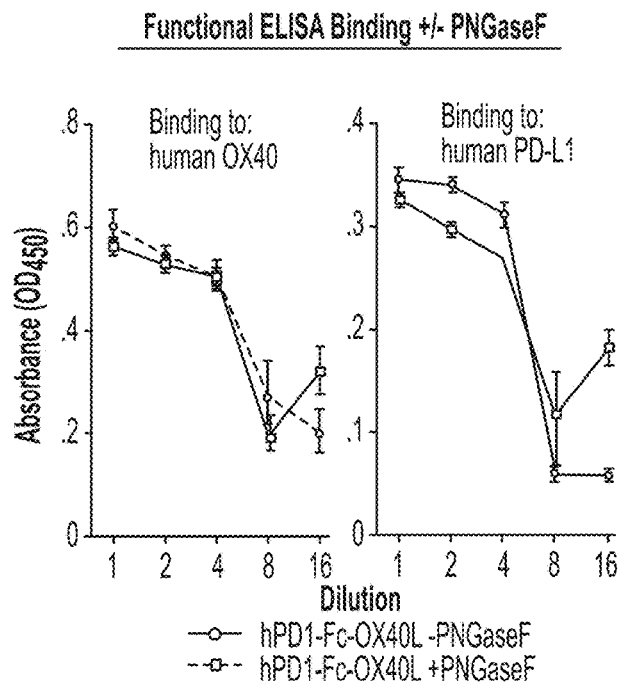
FIG. 31A and FIG. 31B show functional ELISA (FIG. 31A) and cell binding assays (FIG. 31B) which determine whether glycosylation of the PD-1-Fc-OX40L fusion protein (SL-279252) impacts its function.
Figure 31B:
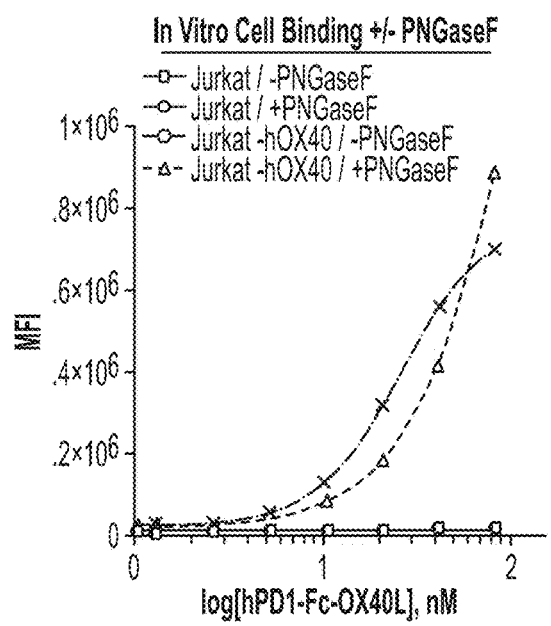

Since the human PD-1-Fc-OX40L chimeric protein retained glycosylase modifications, further analysis was performed to determine whether its glycosylation status impacted its function. hPD-1-Fc-OX40L was treated with the deglycosylase PNGase F, and then its binding to hOX40 was assessed in routine functional ELISA (FIG. 31A) and cell binding assays with Jurkat cells expressing hOX40 (FIG. 31B). Jurkat cell lines that do not express hOX40 were used as control. Results indicated that glycosylation did not play a significant role in hPD-1-Fc-OX40L binding to its interacting partners.

Figure 32A:
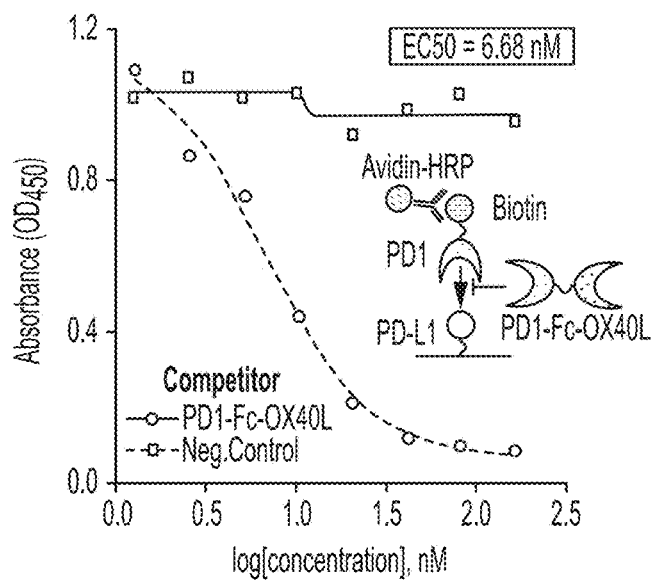

Next, an ELISA-based blocking/competition assay was performed to demonstrate that hPD-1-Fc-OX40L could outcompete human PD-1-biotin for binding to plate-bound recombinant human PD-L1. In this assay, recombinant human PD-L1 was coated on high-binding ELISA plates. Horseradish peroxidase (HRP) signal was produced using detection with recombinant human PD-1-Biotin, followed by an avidin-HRP avidin. As shown in FIG. 32A, in case of a negative control (a chimeric protein that does contain PD-L1 binding domain) the signal for PD-1-biotin was not disrupted (FIG. 32A, top curve/Square symbols). Notably, hPD-1-Fc-OX40L blocked PD-1-Biotin binding to PD-L1 (thereby decreasing HRP signal), in a concentration-dependent manner (FIG. 32A, bottom curve/circle symbols). The results of this assay demonstrated that hPD-1-Fc-OX40L strongly competes with PD-1-biotin for binding to recombinant human PD-L1, with a calculated $IC_{50}$ of 6.68 nM.

Figure 32D:
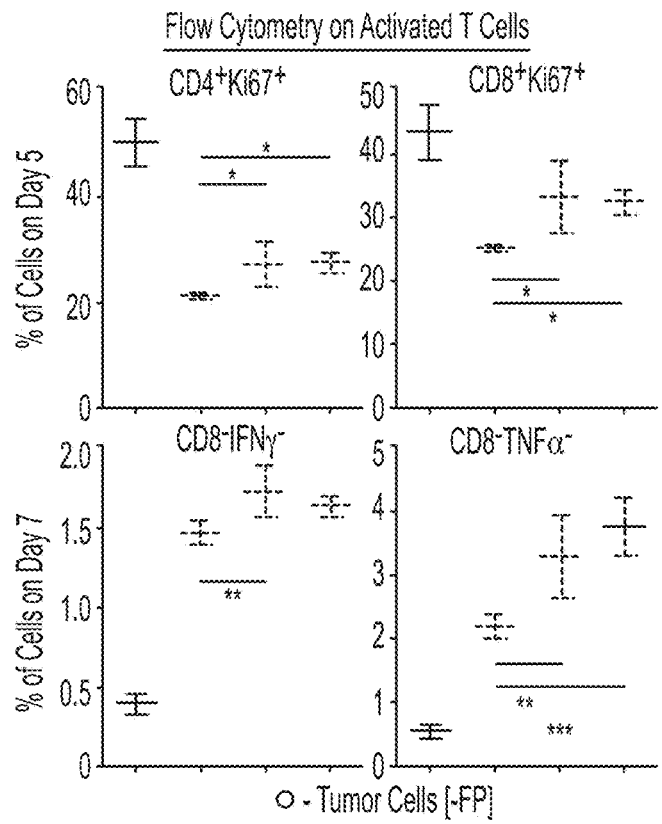

A cytokine release, tumor co-culture assay was performed to demonstrate that the hPD-1-Fc-OX40L chimeric protein was capable of inducing the expression of IL-2 in T cells. As shown in FIG. 32B, primary human CD3+ T cells, in the presence or absence of hPD-1-Fc-OX40L, were incubated with $PD-L1_{low}$ or $PD-L1_{high}$ human tumor cells; thus, allowing assessment of the effector function and proliferation of T cells using IL2 secretion and flow cytometry-based immune assessment. Specifically, human peripheral blood leukocytes were isolated by density gradient centrifugation, followed by negative enrichment for CD3+ cells, and subsequent activation with CD3/CD28 beads. The activated cells were then co-cultured with either a $PD-L1_{low}$ prostate cancer cell (human PC3) or a $PD-L1_{high}$ lung adenocarcinoma cell (human HCC827) in the presence of absence of hPD-1-Fc-OX40L (500 ng and 5 µg concentrations). The quantity of IL-2 produced and secreted into the cell culture supernatant was then measured by ELISA (FIG. 32C). The hPD-1-Fc-OX40L induced higher levels of secreted IL2 in PC3 cells (FIG. 32C, left bundle) than in HCC827 cells (FIG. 32C, right bundle). As human T cells produced significantly more IL-2 when co-cultured with the PC3 cell line than with the HCC827 cell line, this suggested that the quantity of PD-L1 inhibited IL-2 production (FIG. 32C). When hPD-1-Fc-OX40L was added to the co-cultures, however, increased IL-2 production was observed in both co-culture systems. In addition to measuring the amount of IL-2 secreted, the activated T cells from the co-culture assay were collected and analyzed by intracellular flow cytometry. These data indicated that hPD-1-Fc-OX40L increased Ki67, IFNγ, and TNFα staining in both CD4+ and CD8+ T cells (FIG. 32D).

Figure 32E:
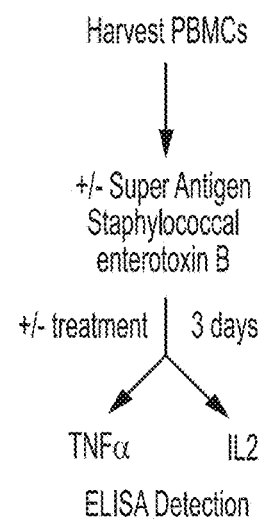
Figure 32F:
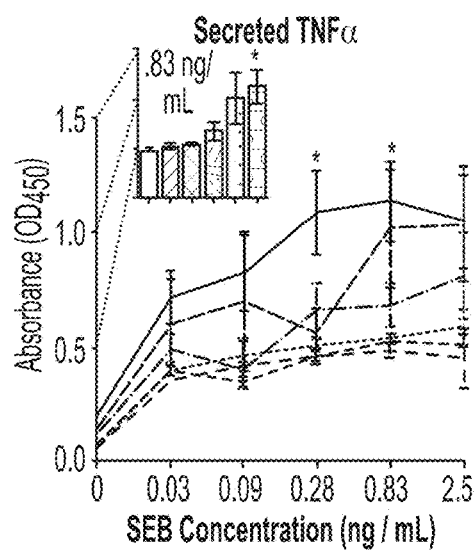
Figure 32G:
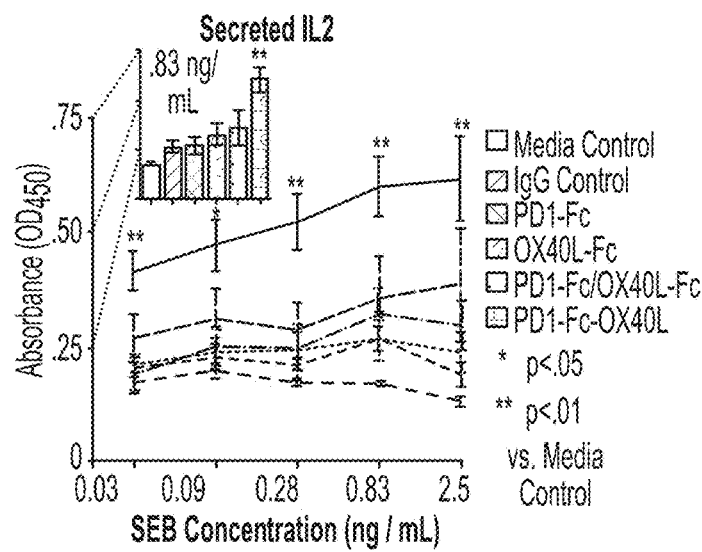

Another functional assay to characterize the functional activity of hPD-1-Fc-OX40L chimeric protein is the superantigen cytokine release assay. In this assay, increasing concentrations of staphylococcus enterotoxin B (SEB) were used to activate human peripheral blood leukocytes in the presence of various test agents; a flow chart of the steps is shown in FIG. 32E. The quantity of TNFα (FIG. 32F) or IL-2 (FIG. 32G) secreted into the culture supernatant was monitored as a functional readout of the ability of test agents to either block suppressive signaling events or co-stimulate immune activating signals. As shown in FIG. 32F and FIG. 32G, the hPD-1-Fc-OX40L chimeric protein induced secretion of TNFα and the secretion of IL2 at higher levels (top curves) in comparison to other test agents PD-1-Fc, OX40L-Fc, and PD-1-Fc/OX40L-Fc. Media and IgG controls were used. Together, these results suggest that hPD-1-Fc-OX40L chimeric protein functionally activated primary human leukocytes cells in vitro.

Figure 33A:
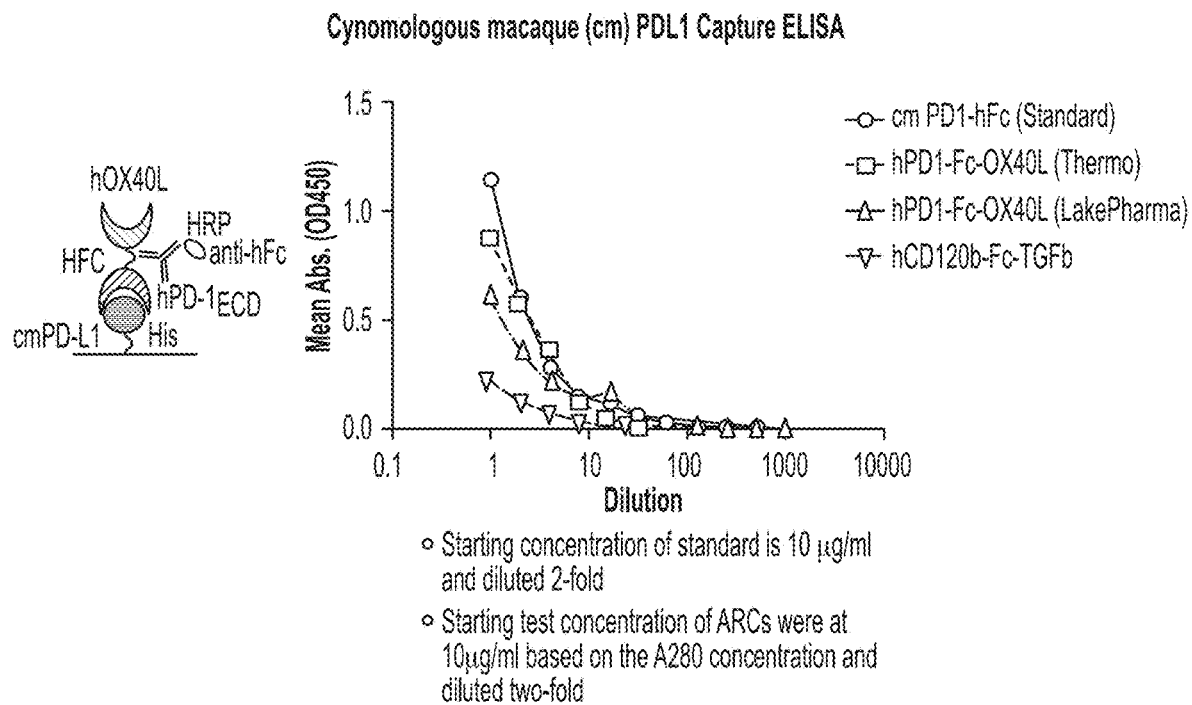
FIG. 33A to FIG. 33C show ELISA assays demonstrating binding affinity and cross-reactivity of the human PD-1-Fc-OX40L fusion protein to PD-L1 (FIG. 33A) and PD-L2 (FIG. 33A) of cynomolgus macaque or to OX40 (FIG. 33C) of rhesus macaque.
Figure 33B:
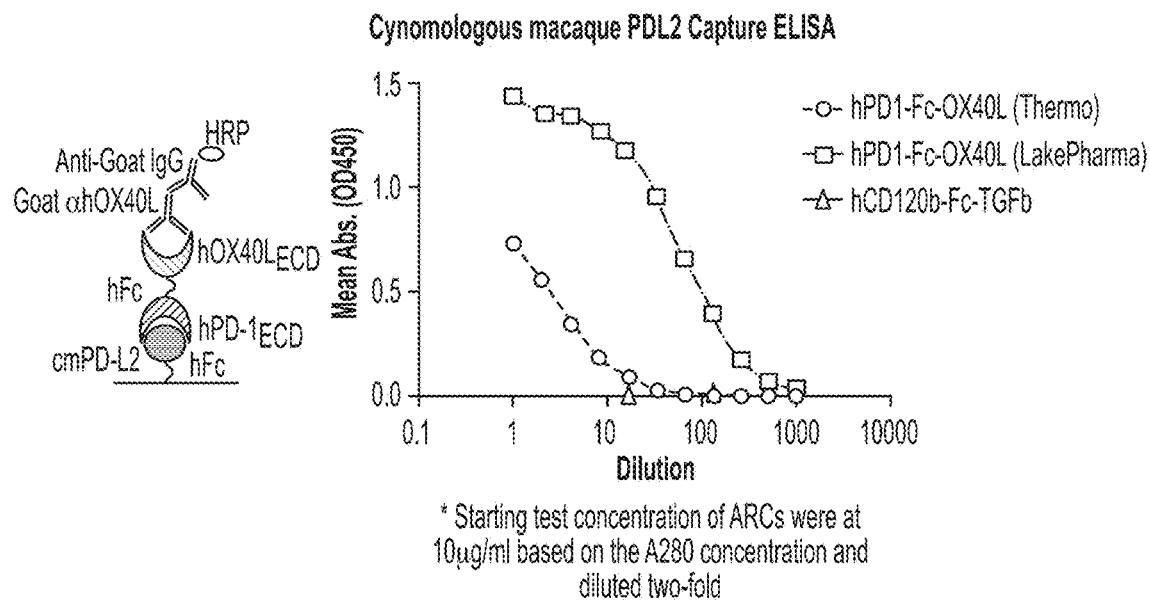
Figure 33C:
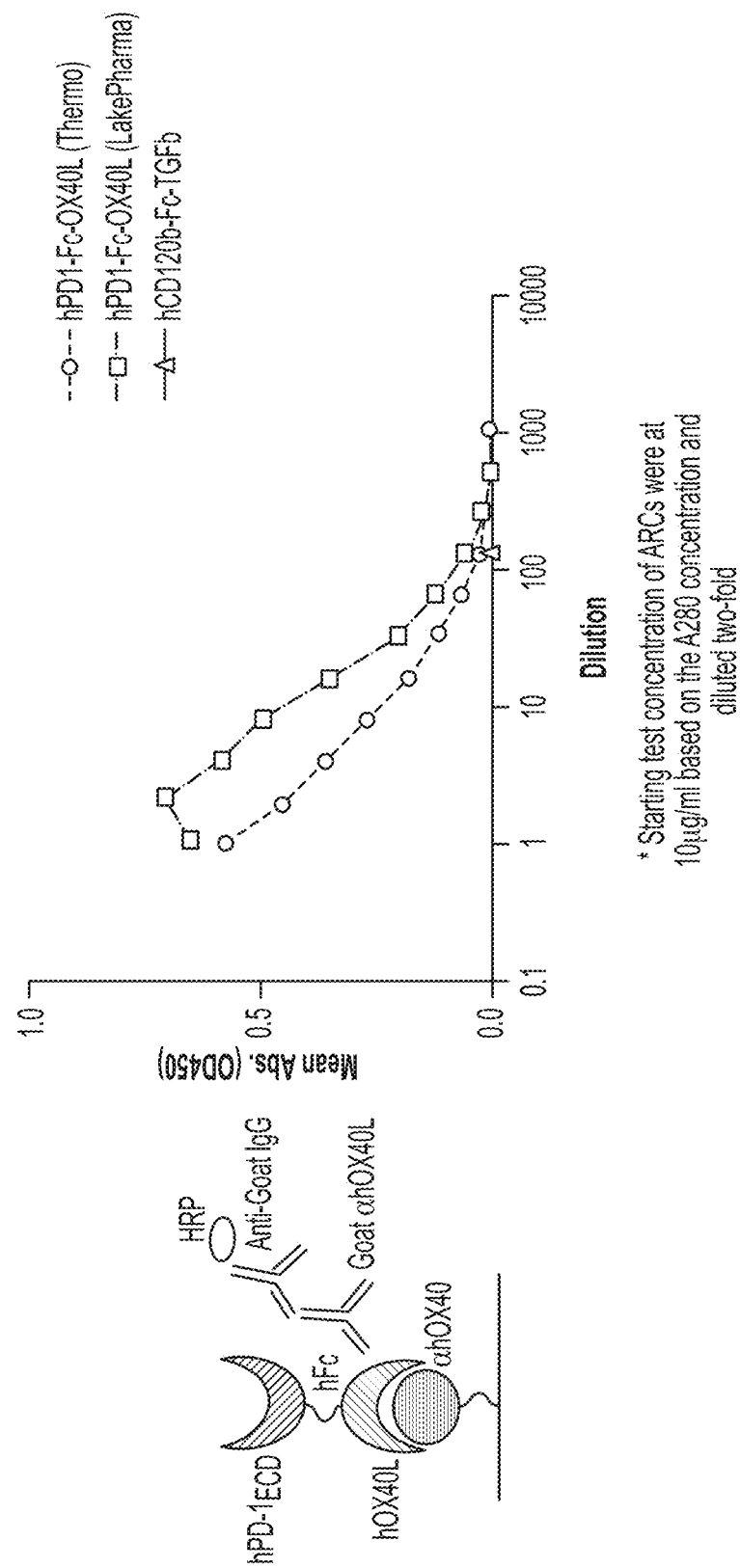

Finally, ELISA assays were performed to demonstrate the binding affinity and cross-reactivity of the human PD-1-Fc-OX40L chimeric protein to OX40 from rhesus macaque and PD-L1 and PD-L2 from cynomolgus macaque. As shown in FIG. 33A, human PD-1-Fc-OX40L chimeric protein specifically bound to plate-bound recombinant cmPD-L1 and the binding was detected by an HRP conjugated anti-hFc antibody. Human PD-1-Fc-OX40L chimeric protein was used from two different sources (square and triangle symbols). Human CD120b-Fc-TGFb chimeric protein (inverted triangle symbols) was used as a control while recombinant cmPD-1-hFc was used to generate a standard curve (circle symbols). These results indicate that hPD-1-Fc-OX40L chimeric protein cross-reacted with cmPD-L1.

hPD-1-Fc-OX40L chimeric protein specifically bound to plate-bound recombinant cmPD-L2 and the binding was detected via an HRP-conjugated anti-Goat IgG binding to Goat anti-hOX40L antibody. Human PD-1-Fc-OX40L chimeric protein was used from two different sources (FIG. 33B, square and circle symbols). Human CD120b-Fc-TGFb chimeric protein (FIG. 33B, triangle symbols) was used as a control. As shown in FIG. 33C, the binding of human PD-1-Fc-OX40L chimeric protein from two different sources (square and circle symbols) and hCD120b-Fc-TGFb chimeric protein (triangle symbols) to a plate-bound rmOX40 was demonstrated. Binding was detected via an HRP-conjugated anti-Goat IgG binding to Goat anti-hOX40L antibody. Accordingly, the above data demonstrates that hPD-1-Fc-OX40L chimeric protein cross-reacted with cmPD-L1, cmPD-L2, and rmOX40.

Example 12: Characterization of the Murine TIM3-Fc-OX40L Chimeric Protein

Figure 34:
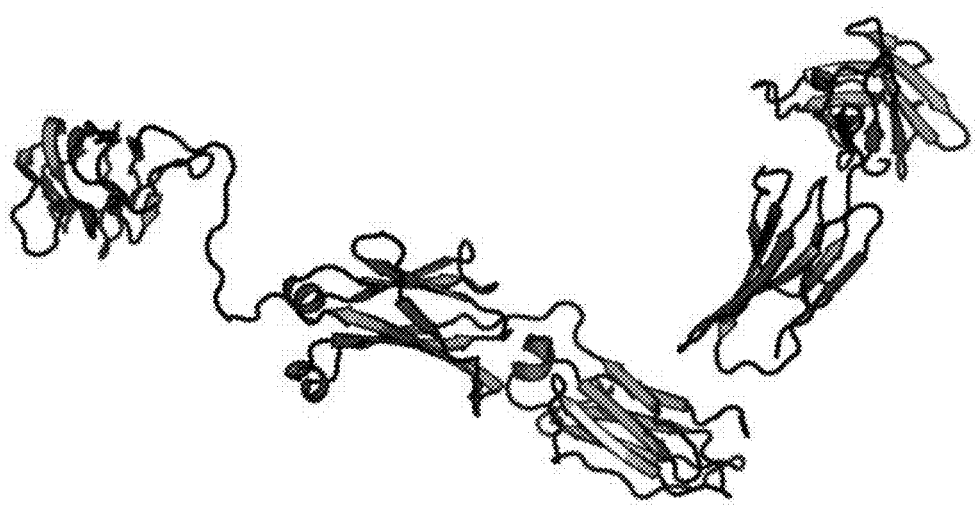
FIG. 34 shows, without wishing to be bound by theory, an in silico predicted structure of monomeric TIM3-Fc-OX40L chimeric protein (SL-366252).

An in silico structure prediction of a monomeric TIM3-Fc-OX40L chimeric protein (SL-366252) having 548 amino acid residues was generated, with a p-value $5.1 \times 10^{-17}$. The molecular weight of the monomeric protein was predicted to be 61.6 kDa. A structure of the chimeric protein is provided in FIG. 34.

Specifically, the structure prediction revealed that six positions (1%) may be disordered. Secondary structure prediction of the entire sequence of the chimeric protein showed that the protein has the composition of 3% α-helix (H), 43% β-sheet (E), and 51% coil (C). The GDT (global distance test) and uGDT (un-normalized GDT) for the absolute global quality were also calculated for the chimeric protein to give an overall uGDT(GDT) of 481(87). The three-state prediction for solvent accessibility of the protein residues were 35% exposed (E), 49% intermediate (M), and 14% buried (B).

Figure 35:
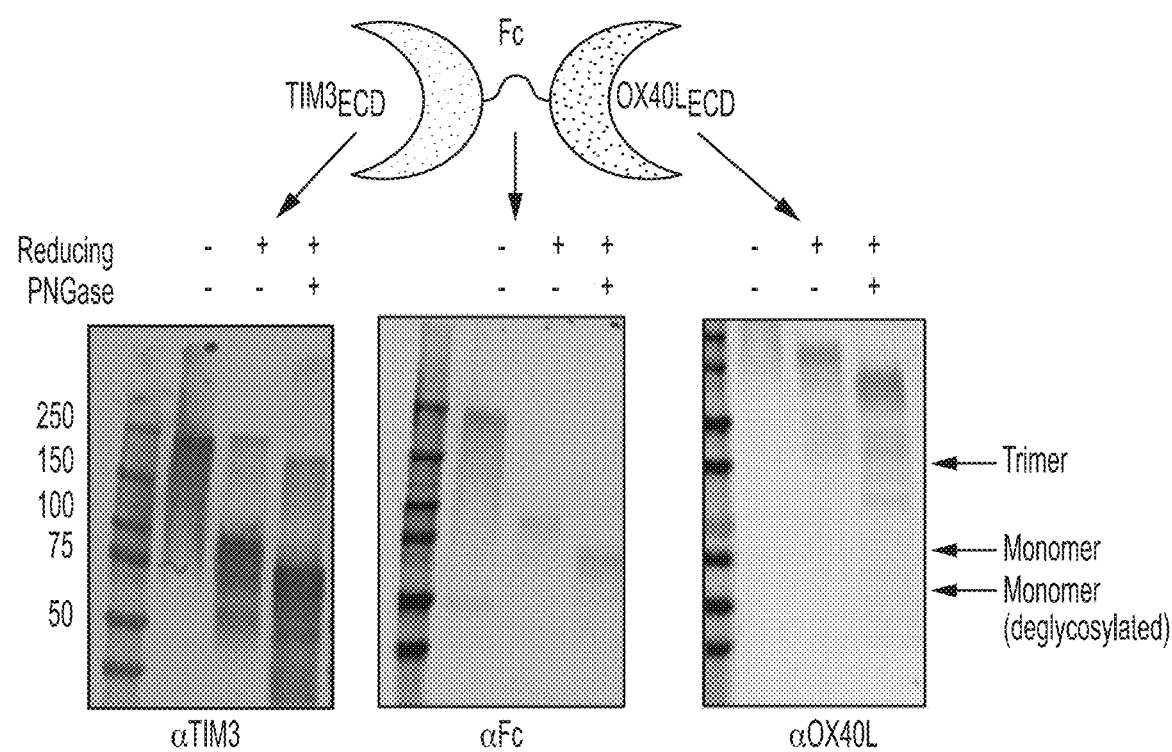
FIG. 35 shows characterization of murine TIM3-Fc-OX40L chimeric protein (SL-366252) by Western blot analysis. Specifically, each individual domain of the fusion construct was probed using an anti-TIM3, anti-Fc, or anti-OX40L antibody. Untreated samples of the mTIM3-Fc-OX40L chimeric protein, e.g., control, were loaded into lane 2 in all the blots (no β-mercaptoethanol or PNGase). Samples in lane 3 were treated with the reducing agent, β-mercaptoethanol, while samples in lane 4 were treated with PNGase.

A murine TIM3-Fc-OX40L chimeric protein was constructed. The chimeric protein was characterized by performing a Western blot analysis against each individual domain of the chimeric protein, i.e., via anti-TIM3, anti-Fc, and anti-OX40L antibodies. The Western blots indicated the presence of a dominant trimeric band in the non-reduced lanes (FIG. 35, lane 2 in each blot), which was reduced to a glycosylated monomeric band in the presence of the reducing agent, β-mercaptoethanol (FIG. 35, lane 3 in each blot). As shown in FIG. 35, lane 4 in each blot, the chimeric protein ran as a monomer at the predicted molecular weight of 61.6 kDa in the presence of both a reducing agent (β-mercaptoethanol) and an endoglycosidase (PNGase).

Figure 36:
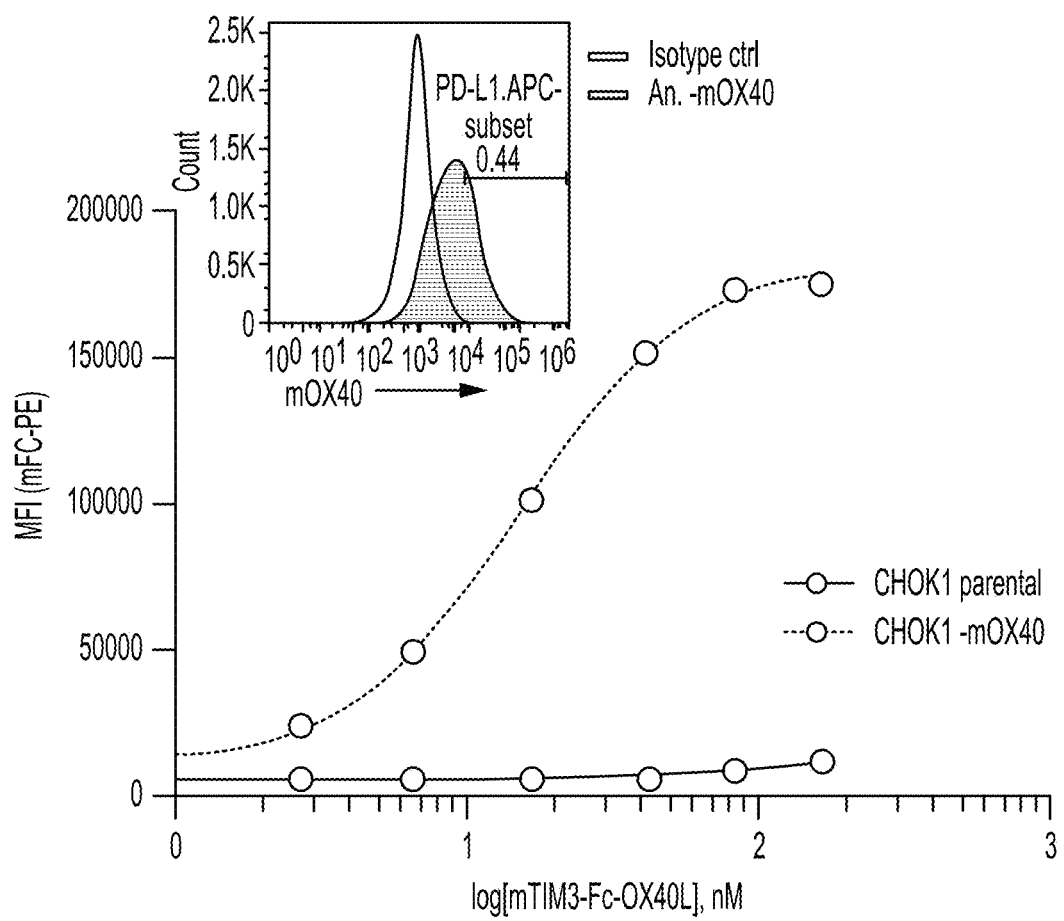
FIG. 36 shows ex vivo cell binding assays demonstrating the ability of the TIM3-Fc-OX40L chimeric protein to bind its binding partners (e.g., receptor or ligand) on the surface of a mammalian cell membrane. Specifically, the graph shows the binding of the TIM3-Fc-OX40L chimeric protein to mOX40 (CHOK1-mOX40 is top curve, CHOK1 parental is bottom).

Cell binding assays were performed to demonstrate the binding affinity of the different domains of the mTIM3-Fc-OX40L chimeric protein towards their respective binding partners on the surface of a mammalian cell membrane. For the cell binding assays, immortalized cell lines were engineered to stably express murine receptor OX40 (CHOK1-mOX40). Increasing concentrations of mTIM3-Fc-OX40L were incubated with each parental (control) and over-expressing cell lines for 2 hours. Cells were collected, washed, and stained with antibodies for the detection of chimeric protein binding by flow cytometry. As shown in FIG. 36, mTIM3-Fc-OX40L bound to the engineered cell line (CHOK1-mOX40) in a concentration-dependent manner with low nM affinity. Specifically, the CHOK1 parental cell line (bottom curve) was not responsive to increasing concentrations of the mTIM3-Fc-OX40L chimeric protein as it did not overexpress mOX40. In comparison, the CHOK1-mOX40 cell line, which overexpressed mOX40, bound to mTIM3-Fc-OX40L in a concentration-dependent manner. The cell binding assay also indicated that mTIM3-Fc-OX40L bound to mOX40 with an affinity of 15.2 nM.

In vivo functional assays were performed to demonstrate the functional activity of the mTIM3-Fc-OX40L chimeric protein. Mice were inoculated with CT26 tumors on day 0. Once the tumors were palpable and at least 4-6 mm in diameter, mice were treated with two doses of 150 μg of the mTIM3-Fc-OX40L chimeric protein. Immunophenotyping was performed on various tissues collected from the mice on day 13 after implantation.

Figure 37A:
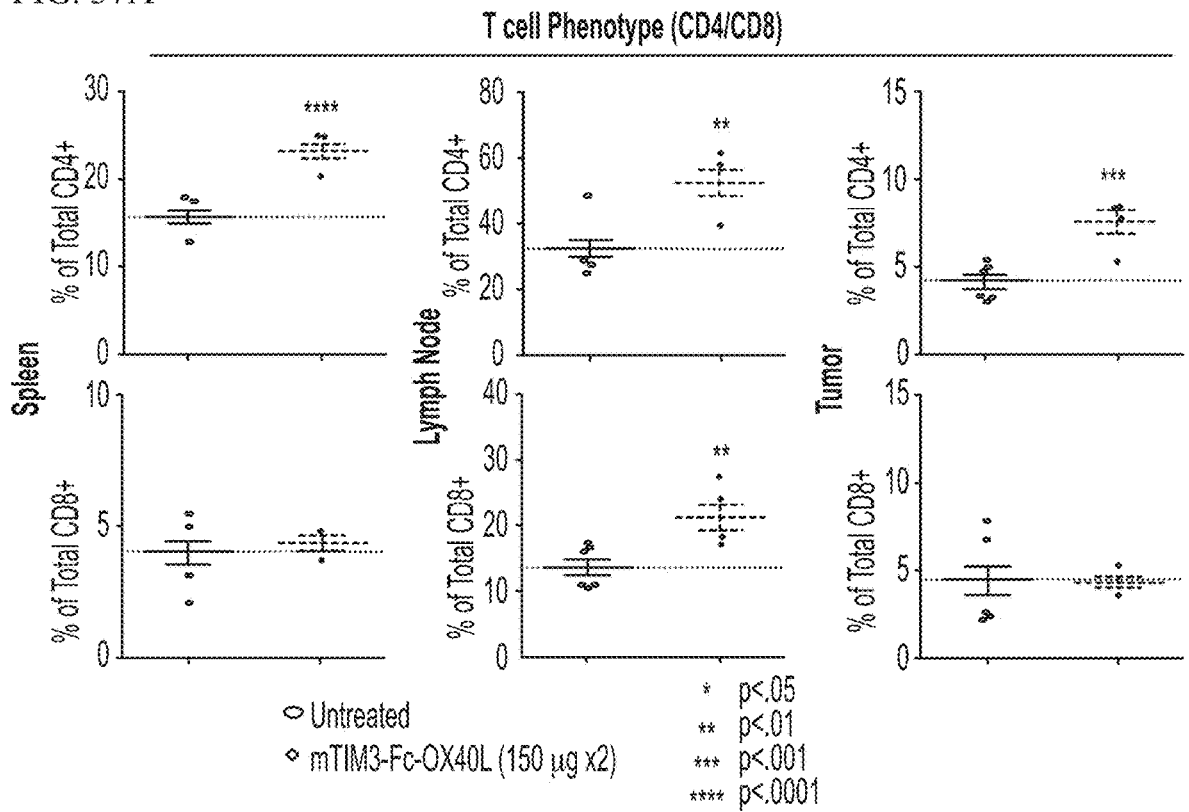
FIG. 37A to FIG. 37C show in vivo functional assays of the murine TIM3-Fc-OX40L chimeric protein. Immune profiling was performed on tumor-bearing mice treated with mTIM3-Fc-OX40L chimeric protein.
Figure 37B:
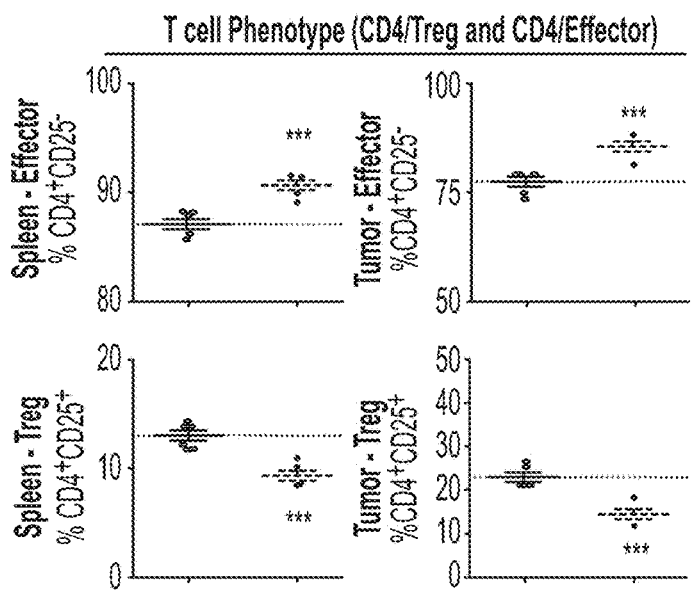

Immune profiling was performed on tumor-bearing mice treated with the murine TIM3-Fc-OX40L chimeric protein. As shown in FIG. 37A, mice treated with the mTIM3-Fc-OX40L chimeric protein exhibited higher percentages of total CD4+ T cells in the spleen, peripheral lymph nodes and tumor (right bundle in FIG. 37A) as compared to the control treatment groups (left bundle in FIG. 37A). Within the spleen and the tumor, this increase in CD4+ T cell population was mostly due to an increase in CD4+CD25− effector T cells, consistent with the notion that activation of non-regulatory T cells was involved (FIG. 37B). The treated mice also exhibited a lower percentage of CD4+CD25+ regulatory T cells, suggesting that regulatory T cells may be suppressed by the chimeric protein (FIG. 37B).

Figure 37C:
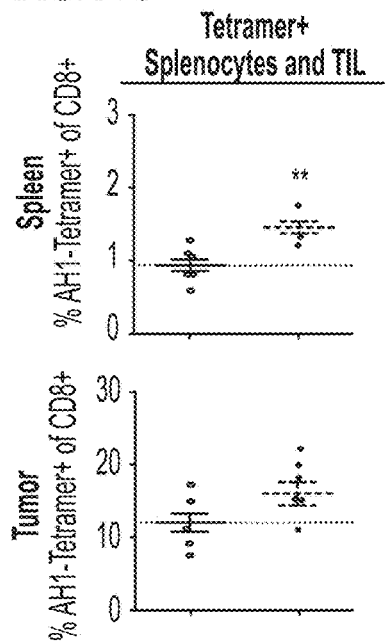

The ability of the chimeric protein to stimulate the recognition of tumor antigens by CD8+ T cells was also analyzed. Specifically, FIG. 37C shows tetramer staining analysis for determining the fraction of CD8+ T cells that recognized the AH1 tumor antigen natively expressed by CT26 tumors. Within the spleen, a higher proportion of CD8+ T cells was found to recognize the AH1 tumor antigen in mice treated with the mTIM3-Fc-OX40L chimeric protein (right bundle in FIG. 37C) as compared to the untreated mice (left bundle in FIG. 37C). Notably, a much higher proportion of the AH1 tetramer positive CD8+ T cells was observed within tumor infiltrated lymphocytes (TIL) for mice treated with the chimeric protein (right bundle in FIG. 37C) as compared to the untreated control mice (right bundle in FIG. 37C).

The in vivo anti-tumor activity of the mTIM3-Fc-OX40L chimeric protein was analyzed using the MC38 and CT26 mouse colorectal tumor models. In one set of experiments, Balb/c mice were inoculated with CT26 tumor cells on day 0 and/or rechallenged with a second inoculation of CT26 tumor cells at day thirty. Following four days of tumor growth, when tumors reached a diameter of 4-5 mm, mice were treated with either control antibodies or 150 μg of the mTIM3-Fc-OX40L chimeric protein. Treatments were repeated on day seven. An analysis of the evolution of tumor size over forty-five days after tumor inoculation was conducted.

As shown in FIG. 38A, the untreated mice developed significant tumors, whereas none of the mice treated with the mTIM3-Fc-OX40L chimeric protein developed tumors of detectable size. Importantly, the mTIM3-Fc-OX40L chimeric protein is effectively able to kill tumor cells and/or reduce tumor growth when rechallenged (which illustrates a cancer relapse). Thus, the mTIM3-Fc-OX40L chimeric protein appears to generate a memory response which may be capable of preventing relapse. The overall survival percentage of mice (FIG. 38B) through fifty days after tumor inoculation shows that all of the untreated mice died within twenty-one days after tumor inoculation, whereas mice treated the mTIM3-Fc-OX40L chimeric protein showed a 100% survival rate at fifty days after tumor inoculation. FIG. 38C summarizes the treatment outcomes for each group.

The above data clearly demonstrate, inter alia, functional activity of mTIM3-Fc-OX40L in vivo, at least, in treating cancer.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method of treating a tumor that expresses CD47, CEACAM1, and/or galectin-9, comprising administering to a subject in need thereof:
   (i) a first chimeric protein of a general structure of N terminus-(a)-(b)-(c)-C terminus, wherein:
      (a) is a first domain comprising an extracellular domain of TIM3, (b) is a linker comprising at least one cysteine residue capable of forming a disulfide bond, and (c) is a second domain comprising an extracellular domain of OX40L, and
   (ii) a second chimeric protein of a general structure of N terminus-(a)-(b)-(c)-C terminus, wherein:
      (a) is a first domain comprising an extracellular domain of CD172a(SIRP1α), (b) is a linker comprising at least one cysteine residue capable of forming a disulfide bond, and (c) is a second domain comprising an extracellular domain of CD40L.

2. The method of claim 1, wherein the first chimeric protein is administered before the second chimeric protein.

3. The method of claim 1, wherein the first chimeric protein is administered after the second chimeric protein.

4. The method of claim 1, wherein the first chimeric protein and the second chimeric protein are TIM3-Fc-OX40L and CD172a(SIRP1α)-Fc-CD40L, respectively.

5. The method of claim 1, wherein the linker is a polypeptide selected from a flexible amino acid sequence, an IgG hinge region, or an antibody sequence.

6. The method of claim 5, wherein the linker comprises hinge-CH2-CH3 Fc domain from IgG4.

7. The method of claim 6, wherein the hinge-CH2-CH3 Fc domain is from human IgG4.

8. The method of claim 7, wherein the linker comprises an amino acid sequence that is at least 95% identical to the amino acid sequence of SEQ ID NO: 45.

9. The method of claim 7, wherein the linker comprises an amino acid sequence that is at least 95% identical to the amino acid sequence of SEQ ID NO: 46.

10. The method of claim 7, wherein the linker comprises an amino acid sequence that is at least 95% identical to the amino acid sequence of SEQ ID NO: 47.

11. The method of claim 7, wherein the linker further comprises at least one joining linker selected from SEQ ID NOs: 48 to 94.

12. The method of claim 11, wherein the linker comprises at least two joining linkers each joining linker independently selected from SEQ ID NOs: 48 to 94; wherein one joining linker is located N terminal to the hinge-CH2-CH3 Fc domain and another joining linker is located C terminal to the hinge-CH2-CH3 Fc domain.

13. The method of claim 1, wherein:
   the extracellular domain of TIM3 comprises an amino acid sequence that is at least 95% identical to the amino acid sequence of SEQ ID NO: 2;
   the extracellular domain of OX40L comprises an amino acid sequence that is at least 95% identical to the amino acid sequence of SEQ ID NO: 4;
   the extracellular domain of CD172a(SIRP1α) comprises an amino acid sequence that is at least 95% identical to the amino acid sequence of SEQ ID NO: 10; and/or
   the extracellular domain of CD40L comprises an amino acid sequence that is at least 95% identical to the amino acid sequence of SEQ ID NO: 12.

14. The method of claim 1, wherein:
   the first chimeric protein comprises an amino acid sequence that is at least 95% identical to the amino acid sequence of SEQ ID NO: 5, and/or
   the second chimeric protein comprises an amino acid sequence that is at least 95% identical to the amino acid sequence of SEQ ID NO: 13.

15. A method of treating colon cancer, comprising administering to a subject in need thereof:
   (i) a first chimeric protein of a general structure of N terminus-(a)-(b)-(c)-C terminus, wherein:

(a) is a first domain comprising an extracellular domain of TIM3, (b) is a linker comprising at least one cysteine residue capable of forming a disulfide bond, and (c) is a second domain comprising an extracellular domain of OX40L, and (ii) a second chimeric protein of a general structure of N terminus-(a)-(b)-(c)-C terminus, wherein:

(a) is a first domain comprising an extracellular domain of CD172a(SIRP1α), (b) is a linker comprising at least one cysteine residue capable of forming a disulfide bond, and (c) is a second domain comprising an extracellular domain of CD40L.

16. The method of claim 15, wherein the first chimeric protein is administered before the second chimeric protein, or the first chimeric protein is administered after the second chimeric protein.

17. The method of claim 15, wherein:
the extracellular domain of TIM3 comprises an amino acid sequence that is at least 95% identical to the amino acid sequence of SEQ ID NO: 2;
the extracellular domain of OX40L comprises an amino acid sequence that is at least 95% identical to the amino acid sequence of SEQ ID NO: 4;
the extracellular domain of CD172a(SIRP1α) comprises an amino acid sequence that is at least 95% identical to the amino acid sequence of SEQ ID NO: 10; and/or
the extracellular domain of CD40L comprises an amino acid sequence that is at least 95% identical to the amino acid sequence of SEQ ID NO: 12.

18. The method of claim 15, wherein the linker comprises an amino acid sequence that is at least 95% identical to the amino acid sequence of SEQ ID NO: 45, SEQ ID NO: 46 or SEQ ID NO: 47.

19. The method of claim 18, wherein the linker further comprises at least one joining linker selected from SEQ ID NOs: 48 to 94.

20. The method of claim 15, wherein:
the first chimeric protein comprises an amino acid sequence that is at least 95% identical to the amino acid sequence of SEQ ID NO: 5, and/or
the second chimeric protein comprises an amino acid sequence that is at least 95% identical to the amino acid sequence of SEQ ID NO: 13.

* * * * *